US006495357B1

(12) United States Patent
Fuglsang et al.

(10) Patent No.: US 6,495,357 B1
(45) Date of Patent: Dec. 17, 2002

(54) LIPOLYTIC ENZYMES

(75) Inventors: Claus Crone Fuglsang, Nivaa; Jens Sigurd Okkels, Frederiksberg; Dorte Aaby Petersen, Birkerod; Shamkant Anant Patkar, Lyngby; Marianne Thellersen, Frederiksberg; Allan Svendsen, Birkeroed; Kim Borch, Copenhagen, all of (DK); John C. Royer, Davis, CA (US); Titus Kretzschmar, Vaerloese (DK); Torben Halkier, Birkeroed (DK); Jesper Vind, Lyngby (DK); Steen Troels Jorgensen, Alleroed (DK)

(73) Assignee: Novozyme A/S, Bagsvaerd (DK)

( * ) Notice: Subject to any disclaimer, the term of this patent is extended or adjusted under 35 U.S.C. 154(b) by 0 days.

(21) Appl. No.: 09/007,288

(22) Filed: Jan. 14, 1998

Related U.S. Application Data

(63) Continuation-in-part of application No. PCT/DK96/00322, filed on Jul. 12, 1996, and a continuation-in-part of application No. PCT/DK96/00341, filed on Aug. 12, 1996.
(60) Provisional application No. 60/011,627, filed on Feb. 14, 1996, provisional application No. 60/011,634, filed on Feb. 14, 1996, provisional application No. 60/016,754, filed on May 7, 1996, and provisional application No. 60/020,461, filed on May 7, 1996.

(30) Foreign Application Priority Data

| | | |
|---|---|---|
| Jul. 14, 1995 | (DK) | 0832/95 |
| Aug. 11, 1995 | (DK) | 0905/95 |
| Sep. 13, 1995 | (DK) | 1013/95 |
| Sep. 29, 1995 | (DK) | 1096/95 |
| Nov. 21, 1995 | (DK) | 1306/95 |
| Apr. 1, 1996 | (DK) | 0372/96 |
| Apr. 1, 1996 | (DK) | 0374/96 |

(51) Int. Cl.$^7$ ................................................ C12N 9/20
(52) U.S. Cl. ...................... 435/198; 435/195; 435/196; 435/197
(58) Field of Search ............................... 435/183, 198, 435/195, 196, 197

(56) References Cited

U.S. PATENT DOCUMENTS 5,892,013 A * 4/1999 Svendsen et al. .......... 536/23.2

FOREIGN PATENT DOCUMENTS

| EP | 0 214 761 | 3/1987 |
| WO | WO 92/05249 | 4/1992 |
| WO | WO 93/01285 | 1/1993 |
| WO | WO 94/03578 | 2/1994 |
| WO | WO 94/14964 | 7/1994 |
| WO | WO 94/25578 | * 11/1994 |

OTHER PUBLICATIONS

Lunn, C. et al., M.in Enzym., vol. 125, pp. 138–149, 1986.*
Japanese Application including translation of Asahi Kasei Kogyo KK, JP 6113845.

* cited by examiner

Primary Examiner—Nashaat T. Nashed
(74) Attorney, Agent, or Firm—Elias J. Lambiris; Jason I. Garbell

(57) ABSTRACT

The present invention relates to a modified enzyme with lipolytic activity, a lipolytic enzyme capable of removing a substantial amount of fatty matter a one cycle wash, a DNA sequence encoding said enzymes, a vector comprising said DNA sequence, a host cell harbouring said DNA sequence or said vector, and a process for producing said enzymes with lipolytic activity.

63 Claims, 22 Drawing Sheets

```
    ATGAGGAGCTCCCTTGTGCTGTTCTTTGTCTCTGCGTGGACGGCCTTGGCCAGTCCTATT
1    M  R  S  S  L  V  L  F  F  V  S  A  W  T  A  L  A  S  P  I   -

CGTCGAGAGGTCTCGCAGGATCTGTTTAACCAGTTCAATCTCTTTGCACAGTATTCTGCA
21   R  R  E  V  S  Q  D  L  F  N  Q  F  N  L  F  A  Q  Y  S  A   -

GCCGCATACTGCGGAAAAAACAATGATGCCCCAGCTGGTACAAACATTACGTGCACGGGA
41   A  A  Y  C  G  K  N  N  D  A  P  A  G  T  N  I  T  C  T  G   -

AATGCCTGCCCCGAGGTAGAGAAGGCGGATGCAACGTTTCTCTACTCGTTTGAAGACTCT
61   N  A  C  P  E  V  E  K  A  D  A  T  F  L  Y  S  F  E  D  S   -

GGAGTGGGCGATGTCACCGGCTTCCTTGCTCTCGACAACACGAACAAATTGATCGTCCTC
81   G  V  G  D  V  T  G  F  L  A  L  D  N  T  N  K  L  I  V  L   -

TCTTTCCGTGGCTCTCGTTCCATAGAGAACTGGATCGGGAATCTTAACTTCGACTTGAAA
101  S  F  R  G  S  R  S  I  E  N  W  I  G  N  L  N  F  D  L  K   -

GAAATAAATGACATTTGCTCCGGCTGCAGGGGACATGACGGCTTCACTTCGTCCTGGAGG
121  E  I  N  D  I  C  S  G  C  R  G  H  D  G  F  T  S  S  W  R   -

TCTGTAGCCGATACGTTAAGGCAGAAGGTGGAGGATGCTGTGAGGGAGCATCCCGACTAT
141  S  V  A  D  T  L  R  Q  K  V  E  D  A  V  R  E  H  P  D  Y   -

CGCGTGGTGTTTACCGGACATAGCTTGGGTGGTGCATTGGCAACTGTTGCCGGAGCAGAC
161  R  V  V  F  T  G  H  S  L  G  G  A  L  A  T  V  A  G  A  D   -

CTGCGTGGAAATGGGTATGATATCGACGTGTTTTCATATGGCGCCCCCGAGTCGGAAAC
181  L  R  G  N  G  Y  D  I  D  V  F  S  Y  G  A  P  R  V  G  N   -

AGGGCTTTTGCAGAATTCCTGACCGTACAGACCGGCGGAACACTCTACCGCATTACCCAC
201  R  A  F  A  E  F  L  T  V  Q  T  G  G  T  L  Y  R  I  T  H   -

ACCAATGATATTGTCCCTAGACTCCCGCCGCGCGAATTCGGTTACAGCCATTCTAGCCCA
221  T  N  D  I  V  P  R  L  P  P  R  E  F  G  Y  S  H  S  S  P   -

GAGTACTGGATCAAATCTGGAACCCTTGTCCCCGTCACCCGAAACGATATCGTGAAGATA
241  E  Y  W  I  K  S  G  T  L  V  P  V  T  R  N  D  I  V  K  I   -

GAAGGCATCGATGCCACCGGCGGCAATAACCAGCCTAACATTCCGGATATCCCTGCGCAC
261  E  G  I  D  A  T  G  G  N  N  Q  P  N  I  P  D  I  P  A  H   -

CTATGGTACTTCGGGTTAATTGGGACATGTCTTTAG
281  L  W  Y  F  G  L  I  G  T  C  L  *
```

Fig. 1

```
     ATGAAACGCATTTGTGGTTCCCTGCTGTTGCTCGGTTTGTCGATCAGCGCCGCGCTCGCT
1     M  K  R  I  C  G  S  L  L  L  L  G  L  S  I  S  A  A  L  A

AGCCCTATACGTAGAGAGGTCTCGCAGGATCTGTTTAACCAGTTCAATCTCTTTGCACAGTATTCTGCA
21    S  P  I  R  R  E  V  S  Q  D  L  F  N  Q  F  N  L  F  A  Q  Y  S  A

GCCGCATACTGCGGAAAAAACAATGATGCCCCAGCTGGTACAAACATTACGTGCACGGGA
44    A  A  Y  C  G  K  N  N  D  A  P  A  G  T  N  I  T  C  T  G   -

AATGCCTGCCCCGAGGTAGAGAAGGCGGATGCAACGTTTCTCTACTCGTTTGAAGACTCT
64    N  A  C  P  E  V  E  K  A  D  A  T  F  L  Y  S  F  E  D  S   -

GGAGTGGGCGATGTCACCGGCTTCCTTGCTCTCGACAACACGAACAAATTGATCGTCCTC
84    G  V  G  D  V  T  G  F  L  A  L  D  N  T  N  K  L  I  V  L   -

TCTTTCCGTGGCTCTCGTTCCATAGAGAACTGGATCGGGAATCTTAACTTCGACTTGAAA
104   S  F  R  G  S  R  S  I  E  N  W  I  G  N  L  N  F  D  L  K   -

GAAATAAATGACATTTGCTCCGGCTGCAGGGGACATGACGGCTTCACTTCGTCCTGGAGG
124   E  I  N  D  I  C  S  G  C  R  G  H  D  G  F  T  S  S  W  R   -

TCTGTAGCCGATACGTTAAGGCAGAAGGTGGAGGATGCTGTGAGGGAGCATCCCGACTAT
144   S  V  A  D  T  L  R  Q  K  V  E  D  A  V  R  E  H  P  D  Y   -

CGCGTGGTGTTTACCGGACATAGCTTGGGTGGTGCATTGGCAACTGTTGCCGGAGCAGAC
164   R  V  V  F  T  G  H  S  L  G  G  A  L  A  T  V  A  G  A  D   -

CTGCGTGGAAATGGGTATGATATCGACGTGTTTTCATATGGCGCCCCCGAGTCGGAAAC
184   L  R  G  N  G  Y  D  I  D  V  F  S  Y  G  A  P  R  V  G  N   -

AGGGCTTTTGCAGAATTCCTGACCGTACAGACCGGCGGAACACTCTACCGCATTACCCAC
204   R  A  F  A  E  F  L  T  V  Q  T  G  G  T  L  Y  R  I  T  H   -

ACCAATGATATTGTCCCTAGACTCCCGCCGCGCGAATTCGGTTACAGCCATTCTAGCCCA
224   T  N  D  I  V  P  R  L  P  P  R  E  F  G  Y  S  H  S  S  P   -

GAGTACTGGATCAAATCTGGAACCCTTGTCCCCGTCACCCGAAACGATATCGTGAAGATA
244   E  Y  W  I  K  S  G  T  L  V  P  V  T  R  N  D  I  V  K  I   -

GAAGGCATCGATGCCACCGGCGGCAATAACCAGCCTAACATTCCGGATATCCCTGCGCAC
264   E  G  I  D  A  T  G  G  N  N  Q  P  N  I  P  D  I  P  A  H   -

CTATGGTACTTCGGGTTAATTGGGACATGTCTTTAG
284   L  W  Y  F  G  L  I  G  T  C  L  *
```

Fig. 2

```
  1  ATGAAACGCATTTGTGGTTCCCTGCTGTTGCTCGGTTTGTCGATCAGCGCCGCGCTCGCC
     M   K   R   I   C   G   S   L   L   L   G   L   S   I   S   A   A   L   A

21  GAGGTCTCGCAGGATCTGTTTAACCAGTTCAATCTCTTTGCACAGTATTCTGCA
     E   V   S   Q   D   L   F   N   Q   F   N   L   F   A   Q   Y   S   A

39  GCCGCATACTGCGGAAAAAACAATGATGCCCCAGCTGGTACAAACATTACGTGCACGGGA
     A   A   Y   C   G   K   N   N   D   A   P   A   G   T   N   I   T   C   T   G   -

59  AATGCCTGCCCCGAGGTAGAGAAGGCGGATGCAACGTTTCTCTACTCGTTTGAAGACTCT
     N   A   C   P   E   V   E   K   A   D   A   T   F   L   Y   S   F   E   D   S   -

79  GGAGTGGGCGATGTCACCGGCTTCCTTGCTCTCGACAACACGAACAAATTGATCGTCCTC
     G   V   G   D   V   T   G   F   L   A   L   D   N   T   N   K   L   I   V   L   -

99  TCTTTCCGTGGCTCTCGTTCCATAGAGAACTGGATCGGGAATCTTAACTTCGACTTGAAA
     S   F   R   G   S   R   S   I   E   N   W   I   G   N   L   N   F   D   L   K   -

119  GAAATAAATGACATTTGCTCCGGCTGCAGGGGACATGACGGCTTCACTTCGTCCTGGAGG
     E   I   N   D   I   C   S   G   C   R   G   H   D   G   F   T   S   S   W   R   -

139  TCTGTAGCCGATACGTTAAGGCAGAAGGTGGAGGATGCTGTGAGGGAGCATCCCGACTAT
     S   V   A   D   T   L   R   Q   K   V   E   D   A   V   R   E   H   P   D   Y   -

159  CGCGTGGTGTTTACCGGACATAGCTTGGGTGGTGCATTGGCAACTGTTGCCGGAGCAGAC
     R   V   V   F   T   G   H   S   L   G   G   A   L   A   T   V   A   G   A   D   -

179  CTGCGTGGAAATGGGTATGATATCGACGTGTTTTCATATGGCGCCCCCGAGTCGGAAAC
     L   R   G   N   G   Y   D   I   D   V   F   S   Y   G   A   P   R   V   G   N   -

199  AGGGCTTTTGCAGAATTCCTGACCGTACAGACCGGCGGAACACTCTACCGCATTACCCAC
     R   A   F   A   E   F   L   T   V   Q   T   G   G   T   L   Y   R   I   T   H   -

219  ACCAATGATATTGTCCCTAGACTCCCGCCGCGCGAATTCGGTTACAGCCATTCTAGCCCA
     T   N   D   I   V   P   R   L   P   P   R   E   F   G   Y   S   H   S   S   P   -

239  GAGTACTGGATCAAATCTGGAACCCTTGTCCCCGTCACCCGAAACGATATCGTGAAGATA
     E   Y   W   I   K   S   G   T   L   V   P   V   T   R   N   D   I   V   K   I   -

259  GAAGGCATCGATGCCACCGGCGGCAATAACCAGCCTAACATTCCGGATATCCCTGCGCAC
     E   G   I   D   A   T   G   G   N   N   Q   P   N   I   P   D   I   P   A   H   -

279  CTATGGTACTTCGGGTTAATTGGGACATGTCTTTAG
     L   W   Y   F   G   L   I   G   T   C   L   *
```

Fig. 3

Construction of pSX578

Length: 1115

```
1    AAAGGCATTC TCATTTTGTA GTCTTATTGC TAGCAGTATT CATCTGCATG
51   TGCTCTGTAT CGGGTGTGCC ACTGCAAATT GATCCACGCG ATGACAAGAG
101  CTATGTTCCT GAACAATATC CTTTGAAGGT GAATGGTCCT TTGCCAGAAG
151  GTGTAAGCGT GATCCAAGGC TATTGTGAAA ACTGTACCAT GTATCCTGAA
201  AAAAATAGTG TATCGGCATT CTCGTCATCA TCCACACAAG ATTATCGTAT
251  TGCAAGCGAG GCAGAGATTA AGGCACACAC ATTTTACACA GCATTGTCAG
301  CCAATGCATA CTGCAGAACT GTCATTCCTG GTGGTCGATG GAGCTGTCCC
351  CACTGTGGTG TTGCATCCAA TTTGCAAATT ACCAAGACTT TCAGCACCTT
401  AATCACTGAT ACTAATGTCT TGGTGGCTGT TGGCGAAAAG GAGAAGACCA
451  TCTATGTAGT TTTTCGTGGT ACAAGCTCAA TTCGCAACGC CATTGCTGAC
501  ATTGTTTTTG TACCAGTGAA TTATCCACCT GTTAATGGAG CCAAAGTACA
551  CAAAGGATTT CTTGATAGCT ATAACGAAGT CCAGGATAAA CTTGTTGCTG
601  AAGTCAAGGC ACAACTTGAT CGTCATCCAG GATACAAGAT CGTCGTCACT
651  GGACATTCCT TGGGAGGTGC AACAGCTGTT CTCAGTGCAC TTGACCTTTA
701  TCACCATGGC CATGCCAATA TCGAAATCTA TACTCAAGGT CAGCCACGTA
751  TAGGTACTCC AGCATTTGCA AACTATGTGA TAGGCACCAA GATTCCATAC
801  CAACGTCTTG TCCATGAGCG TGACATTGTT CCTCACCTTC CACCTGGTGC
851  ATTTGGTTTC TTGCATGCTG GTGAAGAGTT TTGGATCATG AAAGATAGCT
901  CGTTGCGCGT ATGTCCAAAT GGCATTGAAA CTGACAACTG CAGCAACTCC
951  ATTGTTCCCT TCACTAGTGT CATTGACCAT TTAAGCTATC TTGACATGAA
1001 CACTGGTCTC TGTTTATAAT CTTTAGTATC ATCCACTCCT CCTCTTTAAT
1051 GCAATACTTT TTAAGATAAA TCACAAGTAT ACTTTGTACA AAACCAAAAA
1101 AAAAAAAAAA AAAAA
```

Fig. 16

```
            CACATACAGGAATTCATTCAAGAATAGTTCAAACAAGAAGATTACAAACTATCAATTTCA
    4861 --------+---------+---------+---------+---------+---------+ 4920
            GTGTATGTCCTTAAGTAAGTTCTTATCAAGTTTGTTCTTCTAATGTTTGATAGTTAAAGT

H T G I H S R I V Q T R R L Q T I N F I
                            B
                            Bs
                   S N      sp
            N   BB BB    N a ISS   CBi1    B
          BB  IRAAssKasDMMNNIAuBaccS AvaH2S   s
          aa  aslvaapmtpsnccal3slrrm linK8a   e
          en  IawaJJnHYnpliilwAIIFFa uJIA6c   R
          II  VIIIIIIIIIIIVIIIIII IIIII      I
                / IIII / I III /  III / III
            TACACAATATAAACGACGGTACCCGGGGATCCACCATGAGGAGCTCCCTTGTGCTGTTCT
    4921 --------+---------+---------+---------+---------+---------+ 4980
            ATGTGTTATATTTGCTGCCATGGGCCCCTAGGTGGTACTCCTCGAGGGAACACGACAAGA

H N I N D G T R G S T M R S S L V L F F

H
            B     CBa   CC  CB           C C
            s     M vseS vBaNAv c       Mv a   M
            m     w ialt ifchli e       ni c   w
            A     o JJly Ja8euJ f       IR 8   o
            I     I IIII IIIIII I        III I
                        //  //
            TTGTCTCTGCGTGGACGGCCTTGGCTAGCTCCACACAAGATTATCGTATTGCAAGCGAGG
    4981 --------+---------+---------+---------+---------+---------+ 5040
            AACAGAGACGCACCTGCCGGAACCGATCGAGGTGTGTTCTAATAGCATAACGTTCGCTCC c    V S A W T A L A S S T Q D Y R I A S E A
                               I
                      START of the MATURE ATTC 44896
                              C   C   C
                    M         M v   v N S v P
                    s           w i  is f is
                    e         o J   Ri c R t
                    I         I I   II III
            CAGAGATTAAGGCACACACATTTTACACAGCATTGTCAGCCAATGCATACTGCAGAACTG
    5041 --------+---------+---------+---------+---------+---------+ 5100
            GTCTCTAATTCCGTGTGTGTAAAATGTGTCGTAACAGTCGGTTACGTATGACGTCTTGAC c    E I K A H T F Y T A L S A N A Y C R T V
                                              _____
                                         T    T
                E A                      s    s
                c Sc B     C         T   C  p SCp
                o ce s  T  B  Av   F BM s B v 5 fv5
                R rlm   a  c  li   o ssp s i 0 ai0
                I FI F  q  c  uJ   k IIR b R 9 NR9
                IIII I  I  II  I  IIIII  I III
                                    /
```

Fig. 17

```
          TCATTCCTGGTGGTCGATGGAGCTGTCCCCACTGTGGTGTTGCATCCAATTTGCAAATTA
     5101 ---------+---------+---------+---------+---------+---------+ 5160
          AGTAAGGACCACCAGCTACCTCGACAGGGGTGACACCACAACGTAGGTTAAACGTTTAAT c    I P G G R W S C P H C G V A S N L Q I T
                         T             C
                   M     s B           v
                   s     p a           i
                   e     R e           J
                   I     I I           I
          CCAAGACTTTCAGCACCTTAATCACTGATACTAATGTCTTGGTGGCTGTTGGCGAAAAGG
     5161 ---------+---------+---------+---------+---------+---------+ 5220
          GGTTCTGAAAGTCGTGGAATTAGTGACTATGATTACAGAACCACCGACAACCGCTTTTCC c    K T F S T L I T D T N V L V A V G E K E
                              T
                              s
                   M          C p       B
              BB   b          R Av 5 M      s
              cb   o          s li 0 w      r
              cs   I          a uJ 9 o      D
              II   I          I III I       I
                                   /
          AGAAGACCATCTATGTAGTTTTTCGTGGTACAAGCTCAATTCGCAACGCCATTGCTGACA
     5221 ---------+---------+---------+---------+---------+---------+ 5280
          TCTTCTGGTAGATACATCAAAAAGCACCATGTTCGAGTTAAGCGTTGCGGTAACGACTGT c    K T I Y V V F R G T S S I R N A I A D I
                   T
                   s
                   p T            NC B     U
              R B  5 s          M B  Iv s    Rb
              s s  0 p          s s  ai a    sa
              a r  9 R          e I  IJ X    aC
              I I  I I          I I  VI I    I I
                                       /
          TTGTTTTTTGTACCAGTGAATTATCCACCTGTTAATGGAGCCAAAGTACACAAAGGATTTC
     5281 ---------+---------+---------+---------+---------+---------+ 5340
          AACAAAAACATGGTCACTTAATAGGTGGACAATTACCTCGGTTTCATGTGTTTCCTAAAG c    V F V P V N Y P P V N G A K V H K G F L
                          E                   S E
                  C       cBS                 a c
                  Av      osc          F      u Do
                  Ii      Rpr          o      3 p5
                  uJ      IGF          k      A n7
                  II      III          I      I II
                  /                           /
```

Fig. 17 (cont.)

```
TTGATAGCTATAACGAAGTCCAGGATAAACTTGTTGCTGAAGTCAAGGCACAACTTGATC
5341 ---------+---------+---------+---------+---------+---------+ 5400
     AACTATCGATATTGCTTCAGGTCCTATTTGAACAACGACTTCAGTTCCGTGTTGAACTAG c      D S Y N E V Q D K L V A E V K A Q L D R

E          S  BMT                     B M
       B  cS       H C a sas    B T B         C C    sCsP
       s  o c      i CjDu pep   s Bs MsS       vCj  Apvpv  D
       a  R r      n jep3 214   p sp nat       ije  l2iAu  d
       B  l F      4 ePnA 4l5   G rR  lJy      ReP  u4J1l  e
       l  ll       l llll lll   l ll lll       lll  lllll  l
                    // /          / /         /   ////
     GTCATCCAGGATACAAGATCGTCGTCACTGGACATTCCTTGGGAGGTGCAACAGCTGTTC
5401 ---------+---------+---------+---------+---------+---------+ 5460
     CAGTAGGTCCTATGTTCTAGCAGCAGTGACCTGTAAGGAACCCTCCACGTTGTCGACAAG c      H P G Y K I V V T G H S L G G A T A V L B
           Bs
           sp            N H N    B
        A C i1T          B lC a l c
        p v H2s H        sDNEavHeMMaS  e T
        a i K8p p        ascalialsslt  8 a
        L R A6R h        JaoelJelclly  3 q
        l l lll l        llllllllllll  l l
           //             // ////  /
     TCAGTGCACTTGACCTTTATCACCATGGCCATGCCAATATCGAAATCTATACTCAAGGTC
5461 ---------+---------+---------+---------+---------+---------+ 5520
     AGTCACGTGAACTGGAAATAGTGGTACCGGTACGGTTATAGCTTTAGATATGAGTTCCAG c      S A L D L Y H H G H A N I E I Y T Q G Q C  MB          C           N   H
        Bv as  B    R      v       B l   iT
        pi ea  s    s      i       a a   nf
        mJ lA  l    a      R       n l   fi
        ll ll  l    l      l       lV    ll
                                    /
     AGCCACGTATAGGTACTCCAGCATTTGCAAACTATGTGATTGGCACCAAGATTCCATACC
5521 ---------+---------+---------+---------+---------+---------+ 5580
     TCGGTGCATATCCATGAGGTCGTAAACGTTTGATACACTATCCGTGGTTCTAAGGTATGG c      P R I G T P A F A N Y V L G T K I P Y Q N  MT              E  D
        M      l  as             cSS r C         C
        a      aM ep    H         Moec a  v      j
        e      ls l4    p         nRxr l  i      e
        l      ll l5    h         llAF l  R      P
        l      ll ll    l         llll l  l      l
                                   /            /
```

Fig. 17 (cont.)

```
            AACGTCTTGTCCATGAGCGTGACATTGTTCCTCACCTTCCACCTGGTGCATTTGGTTTCT
      5581 ---------+---------+---------+---------+---------+---------+ 5640
            TTGCAGAACAGGTACTCGCACTGTAACAAGGAGTGGAAGGTGGACCACGTAAACCAAAGA c     R L V H E R D I V P H L P P G A F G F L

N       S   N
            C C I       a M  I C    C
            v a aEMNS     Hu DbR aAj   Av  M HT
            i c lassp    p3 poc lle   li  w hh
            R 8 lrlph    hA nla lwP   uJ  o aa
            I I IIIII    II III III   II  I II
              ///         II  /   /    /
            TGCATGCTGGTGAAGAGTTTTGGATCATGAAAGATAGCTCGTTGCGCGTATGTCCAAATG
      5641 ---------+---------+---------+---------+---------+---------+ 5700
            ACGTACGACCACTTCTCAAAACCTAGTACTTTCTATCGAGCAACGCGCATACAGGTTTAC c     H A G E E F W I M K D S S L R V C P N G CB
            S vsPT       B        SB             M
            f ioss       b        pf             s
            c RFte       v        ea             e
            I IIII       I        II             I
                /
            GCATTGAAACTGACAACTGCAGCAACTCCATTGTTCCCTTCACTAGTGTCATTGACCATT
      5701 ---------+---------+---------+---------+---------+---------+ 5760
            CGTAACTTTGACTGTTGACGTCGTTGAGGTAACAAGGGAAGTGATCACAGTAACTGGTAA c     I E T D N C S N S I V P F T S V I D H L T
                N                S H N s
            C   I     T  B     a C Ba I p
            Av  a     Bs Bs  M XB  u vAseT a 5
            li  I     sp sm  n bf  9 icola I 0
            uJ  I     rR aA  I aa  6 JiFlu I 9
            II  I     II II  I II  I IIIII I I
             /         /  /               ///
            TAAGCTATCTTGACATGAACACTGGTCTCTGTTTATAGTCTAGAGGGCCGCATGATGTAA
      5761 ---------+---------+---------+---------+---------+---------+ 5820
            ATTCGATAGAACTGTACTTGTGACCAGAGACAAATATCAGATCTCCCGGCGTACTACATT c     S Y L D M N T G L C L * S R G P H D V I
                            STOP of ATTC 44896
            MT
            as            C              B    R C
            ep            j F           M As   I j
            I4            e o           n cr   e e
            I5            P k           I iB   A P
            II            I I           I II   I I
             /
            TTAGTTATGTCACGCTTACATTCACGCCCTCCCCCCACATCCGCTCTAACCGAAAAGGAA
```

Fig. 17 (cont.)

```
                5821 ---------+---------+---------+---------+---------+---------+ 5880
                     AATCAATACAGTGCGAATGTAAGTGCGGGAGGGGGGTGTAGGCGAGATTGGCTTTTCCTT c      S Y V T L F T P S P H I R S N R K G R

E
                                    c
                                  o PS   E
                              B    AONsa    c
                              s    B v1lpu   o              M
                              m    f a0a59   5              s
                              F    a  l9ll6   7              e
                              I    I  IIVII  I               I
                                    / //
                     GGAGTTAGACAACCTGAAGTCTAGGTCCCTATTTATTTTTTTATAGTTATGTTAGTATTA
                5881 ---------+---------+---------+---------+---------+---------+ 5940
                     CCTCAATCTGTTGGACTTCAGATCCAGGGATAAATAAAAAAATATCAATACAATCATAAT
c      S * T T * S L G P Y L F F Y S Y V S I K
```

Fig. 17 (cont.)

```
                     B         BC
         B          Ts   B B MA     MAsvMT
         b          so   b p wc    nloiws
         v          eF   v m oi    luFJoe
         |          ||   | | ||    ||||||
                                     ///
   ATGAGATTTCCTTCTATTTTTACTGCTGTTTTATTCGCTGCTTCCTCCGCTTTAGCTGCT
1  ---------+---------+---------+---------+---------+---------+ 60
   TACTCTAAAGGAAGATAAAAATGACGACAAAATAAGCGACGAAGGAGGCGAAATCGACGA a   M R F P S I F T A V L F A A S S A L A A -

T
         H              s E    M       M
         i        T     CM p c BCsP  C       a
    B  n B        s     vb A5 o Acvpv Av     e
    s  c s        p     io p0 5 leiAu li     |
    r  l b        R     Jl o9 7 ufJ1l uJ     |
    |  | |        |     || || | ||||| ||     |
                                / /  /// /
   CCAGTCAACACTACCACTGAAGATGAAACGGCTCAAATTCCAGCTGAAGCTGTCATCGGT
61 ---------+---------+---------+---------+---------+---------+ 120
   GGTCAGTTGTGATGGTGACTTCTACTTTGCCGAGTTTAAGGTCGACTTCGACAGTAGCCA a   P V N T T T E D E T A Q I P A E A V I G -

E                         H
         c                         g
         o        T  H        C       i
         5        a  p        j    E
         7        q  h        e    |
         |        |  |        |    |
   TACCTTGATTTAGAAGGTGATTTCGATGTTGCTGTTTTGCCATTTTCCAACTCCACCAAT
121 ---------+---------+---------+---------+---------+---------+ 180
   ATGAGACTAAATCTTCCACTAAAGCTACAACGACAAAACGGTAAAAGGTTGAGGTGGTTA a   Y L D L E G D F D V A V L P F S N S T N -

T
         s                B    B
         p       M    C   B  s M  TsM
         4       m    j   b  r w  son
         C       e    e   v  D o  eFl
         |       |    |   |  | |  |||
   AACGGTTTATTGTTTATCAATACTACTATTGCCTCCATTGCTGCTAAAGAAGAAGGTGTT
181 ---------+---------+---------+---------+---------+---------+ 240
   TTGCCAAATAACAAATAGTTATGATGATAACGGAGGTAACGACGATTTCTTCTTCCACAA a   N G L L F I N T T I A S I A A K E E G V -

M          H
         b          iT
         o          nf
         |          fi
         |          ||
                    /
   TCTTTGGATAAAAGA
241 ---------+----- 255
   AGAAACCTATTTTCT a   S L D K R -
```

Fig. 18

LIPOLYTIC ENZYMES

CROSS-REFERENCE TO RELATED APPLICATIONS

This application is a continuation-in-part of application serial nos. PCT/DK96/00322 and PCT/DK9600341 filed Jul. 12, 1996 and Aug. 12, 1996, respectively, which claim priority of U.S. application Nos. 60/011,627, 60/011,634, 60/016,754 and 60/020,461 filed on Feb. 14, 1996 and May 7, 1996, and Danish application nos. 0832/95, 0905/95, 1013/95, 1096/95, 1306/95, 0372/96 and 0374/96 filed on Jul. 14, 1995, Aug. 11, 1995, September 13,1995, Sept. 29, 1995, Nov. 21, 1995 and Apr. 1, 1996, respectively, the contents of which are fully incorporated herein by reference.

FIELD OF THE INVENTION

The present invention relates to a modified enzyme with lipolytic activity, a lipolytic enzyme capable of removing a substantial amount of fatty matter during a one cycle wash, a DNA sequence encoding said enzymes, a vector comprising said DNA sequence, a host cell harbouring said DNA sequence or said vector, and a process for producing said enzymes with lipolytic activity.

Further the invention relates to a method for applying a peptide addition to a parent enzyme with lipolytic activity, a composition comprising an enzyme with lipolytic activity of the invention, the advantageous use of the enzyme of the invention in detergent compositions, and further a method for improving the washing performance of detergent compositions.

BACKGROUND OF THE INVENTION

Detergent enzymes have been marketed for more than 20 years and are today well established as normal detergent ingredients in both powder and liquid detergent all over the world.

Detergent compositions may comprise many different enzymes, of which proteases, amylases, cellulases, lipases, cutinases are the most important today. In this context lipolytic enzymes serve to remove lipid or faty stains from clothes and other textiles.

Lipolytic Enzymes

Lipolytic enzymes (i.e. enzymes classified under the Enzyme Classification number E.C. 3.1.1 (Carboxylic Ester Hydrolases) in accordance with the Recommendations (1992) of the International Union of Biochemistry and Molecular Biology (IUBMB)) are enzymes which can be used for removing lipid or fatty stains from clothes and other textiles.

Various microbial lipases have been suggested as detergent enzymes. Examples of such lipases include a *Humicola lanuginosa* lipase, e.g. described in EP 258 068 and EP 305 216, a Rhizomucor miehei lipase, e.g. as described in EP 238 023 and Boel et al., Lipids 23, 701–706, 1988, Absidia sp. lipolytic enzymes (WO 96/13578), a Candida lipase, such as a *C. antarctica* lipase, e.g. the *C. antarctica* lipase A or B described in EP 214 761, a Pseudomonas lipase such as a *P. alcaligenes* and *P. pseudoalcaligenes* lipase, e.g. as described in EP 218 272, a *P. cepacia* lipase, e.g. as described in EP 331 376, a Pseudomonas sp. lipase as disclosed in WO95/14783, a Bacillus lipase, e.g. a *B. subtilis* lipase (Dartois et al., (1993) Biochemica et Biophysica acta 1131, 253–260), a *B. stearothermophilus* lipase (JP 64/744992) and a *B. pumilus* lipase (WO 91/16422).

Furthermore, a number of cloned lipases have been described, including the *Penicillium camembertii* lipase described by Yamaguchi et al., (1991), Gene 103, 61–67), the *Geotricum candidum* lipase (Schimada, Y. et al., (1989), J. Biochem., 106, 383–388), and various Rhizopus lipases such as *a R. delemar* (R. D. Joerger and M. J. Hass (1993), Lipids 28 p. 81–88), a *R. niveus* lipase (W. Kugimiya et al. (1992), Biosci. Biotech. Biochem. 5, p. 716–719), *R. javinicus* (W. Uyttenbroeck et al. (1993) Biol. chem. Hoppe-Seyler 374, p.245–254) and a *R. oryzae* (Haas, M. J., Allen, J. and Berka, T. R. (1991) Gene 109, p.107–113) which has a substantially identical sequence to the other Rhizopus lipases.

Other types of lipolytic enzymes having been suggested as detergent enzymes include cutinases, e.g. derived from *Pseudomonas mendocina* as described in WO 88/09367, or a cutinase derived from *Fusarium solani pisi* (e.g. described in WO 90/09446).

In recent years attempts have been made to prepare modified lipolytic enzymes, such as variants and mutants having improved properties for detergent purposes.

For instance, WO 92/05249 discloses lipase variants with improved properties, in which certain characteristics of wild-type lipase enzymes have been changed by specific, i.e. site-directed modifications of their amino acid sequences. More specifically, lipase variants are described, in which one or more amino acid residues of the so-called lipid contact zone of the parent lipase has been modified.

WO 94/01541 describes lipase variants with improved properties, in which an amino acid residue occupying a critical position vis a vis the active site of the lipase has been modified.

EP 407 225 discloses lipase variants with improved resistance towards proteolytic enzymes, which have been prepared by specifically defined amino acid modifications.

EP 260 105 describes hydrolases in which an amino acid residue within 15 Å from the active site has been substituted.

WO 95/35381 discloses Pseudomonas sp. lipase variants, in particular *B. pumilus* and *P. pseudoalcaligenes* lipase variants which have been modified so as to increase the hydrophobicity at the surface of the enzyme.

WO 96/00292 discloses Pseudomonas sp. lipase variants, in particular *B. pumilus* and *P. pseudoalcaligenes* lipase variants which have been modified so as to improve the enzyme's compatibility to anionic surfactants.

WO 95/30744 discloses mutant lipases such as Pseudomonas sp. lipases which have been modified to an increased surfactant resistance.

WO 94/25578 discloses mutant lipases comprising at least a substitution of the methionine corresponding to position 21 in the *P. pseudoalcaligenes* lipase, in particular to leucine, serine or alanine.

All of the above mentioned lipase variants have been constructed by use of site-directed mutagenesis resulting in a modification of specific amino acid residues which have been chosen either on the basis of their type or on the basis of their location in the secondary or tertiary structure of the parent lipase.

An alternative approach for constructing mutants or variants of a given protein has been based on random mutagenesis. For instance, U.S. Pat. No. 4,898,331 and WO 93/01285 disclose such techniques.

WO 95/22615 discloses variants of lipolytic enzymes having an improved washing performance, the variants having been prepared by a method involving subjecting a DNA sequence encoding the parent lipolytic enzyme to random mutagenesis and screening for variants having a decreased dependence to calcium and/or an improved tolerance towards a detergent or one or more detergent components as compared to the parent lipolytic enzyme.

WO 95/09909 discloses, inter alia, chemically modified lipases or lipase mutants which has a higher pI than the corresponding modified enzyme.

Comments to Prior Art

It is known from prior art to modify lipolytic enzymes by site-directed mutagenesis to obtain an improved performance, in particular washing performance of lipolytic enzymes. The generally used concept has been to insert, delete or substitute amino acids within the structural part of the amino acid chain of the parent lipolytic enzyme in question. Lipolytic enzymes with a significantly improved washing performance have been achieved this way.

However, there is a need for providing lipolytic enzymes with an even further improved performance, such as washing performance and/or even further improved dishwashing properties than the lipolytic enzymes prepared by these prior art methods.

Furthermore, a drawback of all detergent lipolytic enzymes described until now is that they exert the best fat removing effect after more than one wash cycle, presumably because the known lipolytic enzymes, when deposited on the fatty stain to be removed, are more active during a certain period of the drying process than during the wash process itself (Gormsen et al., in Proceedings of the 3rd World Conference on Detergents, AOCS press, 1993, pp 198–203). This has the practical consequence that at least two wash cycles (separated by a sufficient drying period) are required to obtain a substantial removal of fatty stains.

Some lipolytic enzymes have been described as allegedly being capable of removing fatty matter during the first wash cycle. Thus, WO 94/03578 discloses a detergent composition which in addition to various detergent components an enzyme which is alleged to be capable of exhibiting a substantial lipolytic activity during the main cycle of a wash process. Examples of lipolytic enzymes allegedly exhibiting the above activity include stem-specific cutinases such as the cutinase from Fusarium solani pisi, Fusarium roseum culmorum, Rhizoctonia solani and Alternaria brassicicola. However, when tested under realistic washing conditions none of these enzymes are capable of removing substantial amounts of a fatty stain during a one cycle wash process (cf the examples hereinafter).

Thus, a need exists for lipolytic enzymes which under realistic wash conditions are capable of removing substantial amounts of fatty matter during one wash cycle.

SUMMARY OF THE INVENTION

Thus, one object of the present invention is to improve properties of enzymes with lipolytic activity, in particular to improve the washing performance of such enzymes. Another object of the invention is to provide lipolytic enzymes which are capable of removing a substantial amount of fatty matter during one wash cycle.

It has surprisingly been found that it is possible to significantly enhance the washing performance of a lipolytic enzyme by applying a peptide addition to the N- and/or C-terminal of the enzyme.

Consequently, in a first aspect the invention relates to a modified enzyme with lipolytic activity which as compared to its parent enzyme has one or more peptide additions in its C-terminal and/or N-terminal end.

Furthermore, the present inventors have now surprisingly identified and constructed a novel class of lipolytic enzymes which are capable of removing substantial amounts of a fatty material during a one cycle wash performed under realistic washing conditions.

Accordingly, in a second aspect the invention relates to a lipolytic enzyme which, when present in detergent composition A and/or B defined herein, is capable of removing at least 15% more lard from a lard stained swatch than the same detergent composition without the enzyme, in a one cycle wash assay comprising subjecting 7 lard-stained cotton swatches (9×9 cm) per beaker to a one cycle wash in a thermostated Terg-O-to-Meter (TOM), each beaker containing 1000 ml of water comprising 3.2 mM $Ca^{2+}/Mg^{2+}$ (in a ratio of 5:1) and 5 g/l of said detergent composition, pH 10, and comprising 12500 LU/l of the lipolytic enzyme, the wash treatment being carried out for 20 minutes at a temperature of 30° C., followed by rinsing for 15 minutes in running tap water and overnight linedrying at room temperature, subsequent extraction and quantification of fatty matter on the swatches by Soxhlet extraction.

The Detergent Composition A and/or B and the one cycle wash assay are further described in the Materials and Methods section herein.

The present invention constitutes the first true demonstration of the surprising fact that it is possible to develop (identify and/or create) first wash lipolytic enzymes. Thus, what hitherto has been considered impossible (based on several years of intensive research by a number of research teams throughout the world (as reflected by the number of hopeful patent applications filed in this field as mentioned above)) has now been shown to be possible.

The present inventors have developed very convenient and successful methods for creating first wash lipolytic enzymes.

Accordingly, in a third important aspect the invention relates to a method of preparing a first wash mutated lipolytic enzyme, which method comprises at least the following steps:

(a) subjecting a DNA sequence encoding a parent lipolytic enzyme to mutagenesis, conveniently random mutagenesis to form a variety of mutated DNA sequences;

(b) expressing the mutated DNA sequences in host cells;

(c) screening for host cells expressing a mutated lipolytic enzyme which has a decreased dependence on calcium and/or an improved tolerance towards a detergent or a detergent component as compared to the parent lipolytic enzyme; and selecting a mutated lipolytic enzyme among those resulting from step (c) which, when present in the detergent composition A and/or B in a concentration of 12500 LU/l, is capable of removing at least 15% more lard from a lard stained swatch, than the same detergent composition without the enzyme, in the one cycle wash assay described above.

In a fourth aspect the invention relates to a method of preparing a first wash mutated lipolytic enzyme which method comprises at least the following steps: constructing mutated DNA sequences by combining a DNA sequence encoding a first parent lipolytic enzyme and a DNA sequence encoding a second parent lipolytic enzyme and optionally further DNA sequences encoding a third (and optionally further) parent lipolytic enzymes, the DNA sequences being sufficiently homologous to allow for recombination between parts of or the entire DNA sequences to take place, expressing the resulting mutated DNA sequences in host cells, and selecting a mutated lipolytic enzyme encoded by a mutated DNA sequence which, when present in detergent composition A or B in a concentration of 12500 LU/l, is capable of removing at least 15% more lard from a lard stained swatch than the same detergent composition without the enzyme, in the one cycle wash described above.

In a preferred embodiment the methods according to the third and fourth aspects of the invention are combined, i.e. a mutated lipolytic enzyme resulting from the method of the third aspect is used as a parent enzyme in the method according to the fourth aspect.

In a further aspect the invention relates to a DNA construct comprising a DNA sequence encoding a modified lipase or a first wash lipolytic enzyme as defined above.

In a still further aspect the invention relates to a recombinant expression vector carrying the DNA construct, a cell which is transformed with the DNA construct or the vector as well as a method of producing a modified or a first wash lipolytic enzyme by culturing said cell under conditions conducive to the production of the enzyme, after which the enzyme is recovered from the culture.

In final aspects the invention relates to the use of a modified or first wash lipolytic enzyme as a detergent enzyme, in particular for washing or dishwashing, and to a detergent additive and a detergent composition comprising the enzyme.

BRIEF DESCRIPTION OF THE DRAWING

FIG. 1 shows the nucleotide and amino acid sequence of the coding region of the *Humicola lanuginosa* lipase gene as present in the yeast expression vector pJSO37. The signal sequence (amino acids 1 to 17) is the original signal sequence from *Humicola lanuginosa*. The SPIRR (SEQ ID NO:29) peptide addition is located at amino acid residue 18 to 22. Amino acid residue 23 (E) is the first amino acid residue of the parent lipase expressed in *Aspergillus oryzae*.

FIG. 2 shows the nucleotide and amino acid sequence of the coding region of the *Humicola lanuginosa* lipase gene as present in the *E. coli* expression vector pJSO215. The signal sequence (amino acids 1 to 20) is the *A. lyticus* protease I signal (WO 96/17943). The SPIRR (SEQ ID NO:29) peptide is added after amino acid residue 20, Amino acid residue 26 (E) is the first amino acid residue of the parent lipase expressed in *Aspergillus oryzae*.

FIG. 3 shows the nucleotide and amino acid sequence of the coding region of the *Humicola lanuginosa* lipase gene as present in the *E coli* expression vector pSX581. The signal sequence (amino acids 1 to 20) is the *A. lyticus* protease I signal sequence (WO 96/17943). Amino acid residue 21 (E) is the first amino acid residue of the parent lipase.

FIG. 16 shows the original sequence of the *Absidia reflexa* ATTC 44896 lipase. The triplett coding for the first amino acid serine of the mature NL127 as well as the stop codon are underlined;

FIGS. 17A–17E shows the *Absidia reflexa* ATTC 44896 sequence in the context of the yeast expression vector pTiK05;

FIG. 18 shows the mating factor α1 signal sequence.

DEFINITIONS AND BACKGROUND ON LIPASE STRUCTURE

Figure 4:
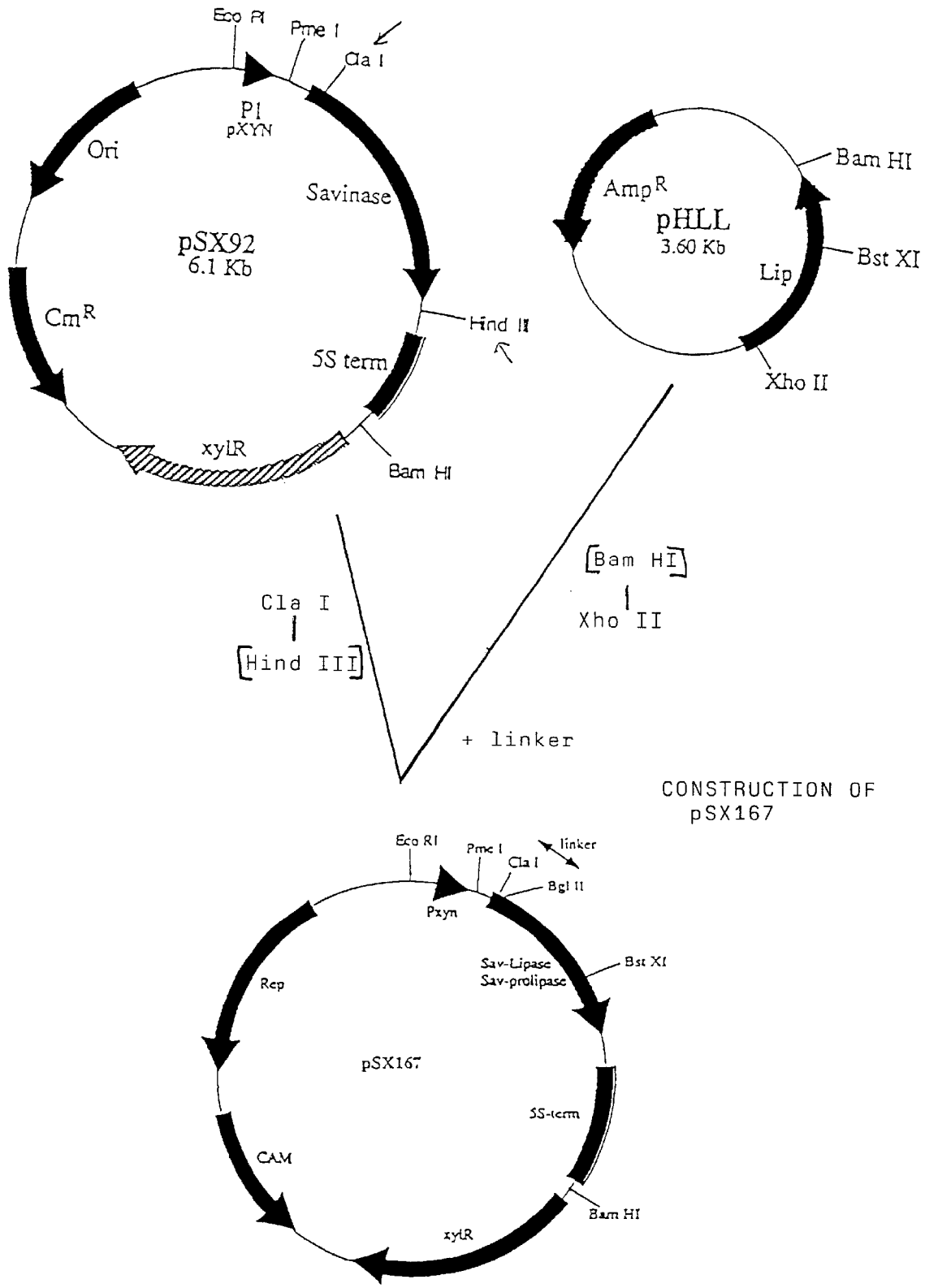
FIG. 4 shows the construction of pSX164.

Definitions of Terms Used in the Present Application

In the present context the term "lipolytic enzyme" is intended to indicate an enzyme classified under the Enzyme Classification number E.C. 3.1.1 (Carboxylic Ester Hydrolases) in accordance with the Recommendations (1992) of the International Union of Biochemistry and Molecular Biology (IUBMB)). Lipolytic enzymes thus exhibit hydrolytic activity towards at least one of the types of ester bonds present in at least one of the following lipids: mono-, di- and triglycerides, phospholipids (all classes), thioesters, cholesterol esters, wax-esters, cutin, suberin, synthetic esters, etc. (cf. the different types of esterbonds mentioned in the context of E.C. 3.1.1).

Thus, the lipolytic enzyme may, e.g., be what has conventionally been termed a lipase, a phospholipase, an esterase or a cutinase. The term "lipolytic enzyme" is intended to embrace naturally-occurring enzymes as well as enzymes, which as compared to a naturally-occurring enzyme, have been modified, e.g. by modification of one or more amino acid residues of the enzyme or by chemical modification. In the present context the latter type of a lipolytic enzyme is termed a variant.

In the present context the term "modified enzyme" is intended to indicate a derivative or variant of a parent enzyme, which derivative or variant as compared to the parent enzyme comprises a peptide addition at the C-terminal and/or N-terminal end (fused to the first and/or last amino acid residue of the parent enzyme) and/or within the non-structural part of the C- and/or N-terminal end of the parent enzyme. In particular, the term "modified" is intended to indicate that i) an appropriate peptide addition has been applied to the parent enzyme or ii) one or more amino acid residues within the non-structural part of the C-terminal and/or N-terminal part of the parent mature enzyme has/have been deleted or replaced by other amino acid residues, or iii) the parent enzyme has been modified by a combination of i) or ii). In the present context first wash lipolytic enzymes of the invention which have been modified in this way may be termed a modified enzyme of the invention.

In the present context the term "peptide addition" is intended to indicate that a stretch of one or more consecutive amino acid residues has been added to either or both of the N- and/or C-terminal end(s) of the parent enzyme (i.e. fused to the first and/or last amino acid residue of the parent enzyme) or inserted within the non-structural part of the N- and/or C-terminal end(s) of the parent enzyme.

The term "an appropriate peptide addition" is used to indicate that the peptide addition to be used is one which is capable of effecting an improved wash performance or a first wash performance. The "appropriateness" of the peptide addition may be checked by a comparative analysis of the wash performance or first wash performance of a modified enzyme to which the peptide addition has been applied and of the corresponding parent enzyme, respectively. The wash performance may, e.g., be determined by any suitable technique such as any of the wash performance assays described in the present application. The first wash performance may, e.g., be determined by the one cycle wash assay described in the Materials and Methods section.

The term "non-strucural part" is intended to indicate the part of the N- and C-terminal end, respectively, which is outside the first or last, respectively, structural element, such as an a-helix or β-sheet structure, of the folded mature enzyme. The non-structural part may easily be identified in a three-dimensional structure or model of the enzyme in question. Typically, the non-structural part comprises the first or the last about 1–20 amino acid residues of the amino acid sequence constituting the enzyme.

The non-structural part of the *H. lanuginosa* lipolytic enzyme normally comprises the first or the last about 1–20 amino acid residues of the mature enzyme.

The term "mature enzyme" is used in its conventional meaning, i.e. to indicate the active form of the enzyme resulting after expression and posttranslational processing (to remove pro and/or pre-sequences) by the producer organism in question. When the enzyme is a secreted enzyme, the mature enzyme will normally be the form of the enzyme resulting after secretion. More specifically this means that the pre- and pro-peptide sequences, if present, have been removed from the initially translated enzyme, i.e. the unprocessed enzyme.

The term "parent enzyme" in intended to indicate the enzyme to be modified according to the invention. The parent enzyme may be a naturally-occuring (or wild type) enzyme or may be a variant thereof prepared by any suitable means. For instance, the parent enzyme may be a variant of a naturally-occurring enzyme which has been modified by substitution, deletion or truncation of one or more amino acid residues or by addition or insertion of one or more amino acid residues to the amino acid sequence of a naturally-occurring enzyme, typically in the structural part of the enzyme. Accordingly, the term is used to identify the starting material to be modified in accordance with a method of the invention for preparing modified or first wash lipolytic enzymes, irrespectively of whether said starting material is a naturally-occurring enzyme or a variant of such enzyme.

In the present context the capability of the enzyme in removing a substantial amount of fatty matter during a one cycle wash is also referred to as a first wash effect, a one cycle wash effect, a through-the-wash effect, and the like. Analogously, lipolytic enzymes of the invention, which are capable of effecting removal of a substantial amount of a fatty material during a one cycle wash, are called first wash lipolytic enzymes, through-the-wash lipolytic enzymes, one cycle wash lipolytic enzymes, and the like.

In the present context the term "Detergent Composition A and/or B" as used to define the lard removing capability of a given first wash lipolytic enzyme of the invention is intended to indicate that the lipolytic enzyme has the indicated lard removing capability when present in either or both of Detergent Compositions A and B.

The term "a variety of mutated sequences" as used about the method according to the third aspect is intended to be understood to indicate that at least two, but preferably a much higher number of different sequences, such as at least 10, at least 50 at least 100, at least 1000 sequences have resulted from the mutagenesis.

The term "random mutagenesis" is intended to be understood in a conventional manner, i.e. to indicate an introduction of one or more mutations at random positions of the parent enzyme or introduction of random amino acid residues in selected positions or regions of the parent enzyme. The random mutagenesis is normally accompanied by a screening which allows the selection of mutated lipolytic enzymes which, as compared with the parent enzyme, have improved properties. Suitable techniques for introducing random mutations and screening for improved properties are discussed in detail below.

The term "satisfactory wash performance" as used about lipolytic enzymes disclosed herein is intended to indicate that the enzyme has an improved performance when tested in a suitable wash assay or a wash related assay (such as the assays described in the Materials and Methods and Example 12 below) as compared to the commercially available lipolytic enzymes (Lumafast and Lipomax from Genencor, Lipolase and Lipolase Ultra from Novo Nordisk and Liposam (from Showa Denko). The improved performance may be in terms of lipid stain removing capability and/or a decreased calcium dependency, an improved tolerance towards a detergent or detergent component, an increased hydrophobicity, an interesting substrate specificity, or the like.

In the present context, the term "decreased dependence on calcium" as used in connection with the screening for mutated lipolytic enzymes, in particular lipolytic enzymes exhibiting enzymatic activity towards lipase substrates having hydrocarbon chains (ffa-part) of a length exceeding approx. 6–8 C-atomes, is intended to mean that the mutated lipolytic enzyme requires lower amounts of $Ca^{2+}$ for exhibiting the same degree of activity and/or stability as the parent enzyme when tested under similar conditions. In other words the stability and/or activity of the enzyme is/are increased in the absence of calcium as compared to that of the parent enzyme. The stability may, e.g., be assayed by a determination of residual activity upon preincubation under Ca-free conditions and/or DSC (Differential Scanning Calorimetry) in the absence/presence of free Ca2+. Preferably, the mutated lipolytic enzyme of the invention is substantially independent of the presence of calcium for exhibiting enzymatic activity, in particular at a pH higher than 8.

The term "improved tolerance towards a detergent or detergent component" as used in connection with the screening for mutated lipolytic enzymes is intended to mean that the mutated lipolytic enzyme is active at higher concentrations of the detergent or detergent component than the parent lipolytic enzyme.

In the present context the term "detergent" is intended to indicate a mixture of detergent ingredients normally used for washing or dishwashing. Analogously, a "detergent component" is intended to indicate a component or ingredient normally found in detergent or dishwashing compositions, specific examples of which are given in the section further below entitled "Detergent compositions".

Background on Lipolytic Enzyme Structure and Definition of Structure Terminology The 3D structure of a number of lipolytic enzymes has been determined. It has been found that the structures have a common motif in the core of the protein consisting of a central β-sheet, one of the strands ending in a nucleophil elbow including the active serine residue (Ollis et al, 1992). Lipolytic enzymes comprise a lipid contact zone which is a surface with increased surface hydrophobicity which interacts with the lipid substrate at or during hydrolysis. For lipolytic enzymes containing a lid the lipid contact zone is typically formed when the enzyme is activated by substrate (and the lid thereby displaced). For lipolytic enzymes which do not contain a lid there is generally little or no corresponding substantial movement leading to the creation of the lipid contact zone. The lipid substrate is a conglomerate of single lipid substrate molecules. The lipid contact zone contains a binding area to which a single lipid substrate molecule binds before hydrolysis. This binding area contains an acyl-binding hydrophobic cleft and a so-called hydrolysis pocket, which is situated around the active site Ser, and in which the hydrolysis of the lipid substrate is believed to take place. The lipid contact zone includes one or more protein secondary structure elements, i.e., loop sequences, the amino acid residues of which contact, bind to and/or interact with the substrate during hydrolysis when the lipolytic enzyme is activated.

The lipid contact zone may be recognized, e.g. from a three-dimensional structure of the lipolytic enzyme in question created by suitable computer programs. The lipid contact zone may be identified by searching the structure for the relevant features defining the zone, including a zone positioned on top of the active site residues and containing a lid structure (for lipolytic enzymes containing a lid) which when opened creates a hydrophobic surface containing a narrow hydrophobic binding pocket. The conformation of the inactive and activated *H. lanuginosa* lipolytic enzyme, respectively, is shown in FIGS. 1 and 2 of WO 92/05249.

In terms of amino acid residues the lipid contact zone of the *H. lanuginosa* lipolytic enzyme is defined by amino acid residues 21–25, 36–38, 56–62, 81–98, 110–116, 144–147, 172–174, 199–213 and 248–269. These residues have been identified on the basis of computer model simulations of the interaction between the lipolytic enzyme and a lipid substrate. For lipolytic enzymes having substantially the same structure as the *H. lanuginosa* lipolytic enzyme, e.g. the lipolytic enzymes produced by *Rhizomucor miehei*, by the *Rhizopus oryzae*, by *Penicillium camembertii* and by *Absidia* sp. (cf the "Background of the Invention" section above) the lipid contact zone is constituted by amino acid residues occupying homologous positions to those given above for the *H. lanuginosa* enzyme. The homologous positions may be identified by an alignment of the relevant amino acid sequences (e.g. using the UWGCG GAP programme) looking for groups of sequence similarity, but may more conveniently be done by comparing the structures or structure models of the relevant enzymes. More specifically, the lipid contact zone of these enzymes is constituted of the following residues (the numbering used refers to the amino acid residue in the mature enzyme, the sequence of which is apparent from the references disclosed in the Background of the Invention section above unless otherwise indicated):

*Penicillium camembertii*: 21–25, 36–38, 56–62, 81–98, 109–115, 143–146, 172–174, 198–212, 247–280;

*Rhizopus oryzae*: 29–33, 39–41, 57–62, 81–98, 109–115, 143–146, 175–177, 202–216, 245–269.

*Rhizomucor miehei*: 29–33, 39–41, 56–61, 80–97, 108–114, 142–145, 174–176, 201–215, 245–10 269;

*Absidia sp. lipase:* 29–33, 39–41, 56–61, 80–97, 108–114, 142–145, 171–173, 198–212, and 239–263, the numbering based on that the mature enzyme has the following N-terminal sequence: SSKQDYR (SEQ ID NO:104). The entire sequence is apparent from (SEQ ID NO:122).

As an alternative or in addition to the homology based identification of the lipid contact zone, the lipid contact zone may be identified by a) calculating the hydrophobic vector of the 3-D molecular structure of the activated enzyme;

b) making a cut perpendicular to the vector through the CA-atom (Cα-atom) of the second amino acid residue after the active site serine in the linear sequence;

c) including all residues with at least one atom on that side of the cut to which the vector points; and selecting from those residues, those which have at least one atom within 5 Ångström of the surface of the protein.

The hydrophobic vector is calculated from the protein structure by summing up all residue vectors for residues having a surface accessibility (Lee et al., *Mol. Biol*, 55, pp.379–400 (1971)) of at least 15%. The starting point of the residue vector is defined as the CA-atom of the residue and its direction is through the mass centre of the sidechain. The magnitude of each residue vector is defined as the residues relative free energy of transfer between water and a more hydrophobic solvent (see, e.g., Creighton, Protein, W. Freeman & Co., p.151 (1984)). The surface accessibility of each residue is calculated using the Connolly program (Lee et al., op. cit.).

Using the above method and/or the alignment of the various sequences, which is apparent from Svendsen et al, Biochimica et Biophysica Acta, 1259 (1995) 9–17, the following lipid contact zones of lipolytic enzymes isolated from various Pseudomonas sp. have been identified (the numbering used refers to the amino acid residues of the mature enzyme as presented in the above mentioned publication (Svendsen et al. (1995))):

*Pseudomonas cepacia* lipase: 15–36, 110–167, 209–266, 281–304;

*Pseudomonas pseudoalcaligenes* lipase: 15–35, 106–163, 200–232, 250–271;

*Pseudomonas glumae*: 15–36, 110–167, 209–266, 281–304;

*Pseudomonas mendocina* (SD702) lipase: 19–39, 111–166, 213–244, 258–279 (the sequence is apparent from WO 95/14783);

Pseudomonas sp. (Liposam®) lipase: 17–37, 109–161, 208–239, 253–274 (SEQ ID NO:91);

*Pseudomonas wisconsinensis* lipase: 13–34, 106–161, 200–242, 250–270 (the sequence is apparent from WO 96/12012).

The lipid contact zone for lipolytic enzymes which do not contain a lid structure may be determined from the topology of the core as evaluated in a structure or model of the three-dimensional structure of the lipolytic enzyme. In this manner the lipid contact zone of the *Fusarium solani pisi* lipolytic enzyme has been determined to amino acid residues 40–50, 78–91, 119–121, 147–154, 171–193 (as evaluated on the basis of the mature enzyme).

Some lipolytic enzymes also comprise a surface loop structure, i.e., a lid, which is part of the lipid contact zone. The surface loop structure covers the active serine when the lipolytic enzyme is in inactive form. When the enzyme is activated, the surface loop structure shifts to expose the active serine residue. The surface loop structure has a predominantly hydrophobic inner surface facing the binding pocket and a predominantly hydrophilic outer surface.

Examples of lipolytic enzymes which have a surface loop structure are those produced by *Humicola lanuginosa, Rhizomucor miehei*, Rhizopus sp., *Penicillium camembertii* and Absidia sp., a number of Pseudomonas sp., such as *Ps. cepacia, Ps. aeroginosa, Ps. fragi* (cf. the "Background of the Invention" section above), *Candida rugosa* (Grochulski,P et al (1993) J. Biol. Chem. 268, p. 12843) and the human pancreatic lipase described in Winkler et al., *Nature* 343, pp. 771–74 (1990).

The surface loop structure of the lipolytic enzyme produced by *Humicola lanuginosa* DSM 4109 is defined by amino acid residues at positions 82–96. The surface loop structure of lipolytic enzymes with substantially the same three-dimensional structure (cf above) is defined by the amino acid residues occupying homologous positions to those of the *H. lanuginosa* lipolytic enzyme, i.e.81–98 (for the *Penicillium camembertii* lipase), 82–99 (for *Rhizopus oryzae*), 80–97 (for *Rhizomucor miehei*), 80–97 (for *Absidae* sp. lipase).

The surface loop structure of a representative number of lipolytic enzymes produced by Pseudomonas sp. are: *Ps. glumae*: 135–155, *Ps. cepacia* 135–155, *Ps pseudoalcaligenes* 132–152), Pseudomonas sp. lipase (SD705) (Liposam®) 129–149 shown in SEQ ID NO:91.

DETAILED DESCRIPTION OF THE INVENTION

Peptide Addition

As stated above it has surprisingly been found that a significantly improved wash performance of lipolytic enzymes may be achieved when an appropriate peptide addition is applied to a non-structural part of the enzyme in its mature form or at the C-terminal and/or N-terminal end of the mature enzyme.

The term "improved wash performance" is intended to indicate that the modified enzyme of the invention has a better lipid soil removing capability than the unmodified parent enzyme when tested under wash like conditions. The improvement is often indicated in terms of "an improvement factor" ($f_{improve}$) (further reference vide the Materials and Methods section further below). Dependent on the peptide addition and the mature enzyme an improvement factor ($f_{improve}$) in the range of 1–5, or even up to 10 (such as in the range of 1–10) has been obtained. It is presently believed that even higher improvement factors such as up to 20, even up 30, or even up to 50, such as between 30 and 50, or even higher may be achieved in accordance with the present invention.

It is presently contemplated that the improved wash performance effected by the peptide addition is, at least in part, due to an increased affinity of the modified lipolytic enzyme towards its lipid substrate (although this may not be the only reason).

The present invention is not limited to improving the wash performance of a parent lipolytic enzyme. It is contemplated that also other properties of parent lipolytic enzymes may be improved in accordance with the first aspect of the present invention, i.e. by applying an appropriate peptide addition at or within a non-structural part of the C-terminal and/or N-terminal end of the parent enzyme. More specifically, it is contemplated that the activity of a parent lipolytic enzyme, e.g., in removing pitch in the paper and pulp industry, in degreasing hides in the leather industry, in acting as a catalyst in organic syntheses, etc., may be significantly improved by applying an appropriate peptide addition at or within the N-terminal or C-terminal end of a lipolytic enzyme, i.e. a peptide addition which is capable of exerting the desired function. Also in these connections it is believed that the improved activity may be at least partly due to an improved affinity for the substrate in question.

As a consequence of the improved activity it may be possible to reduce the dosage of the enzyme required for a given purpose considerably, as compared to the dosage of needed dosage of the unmodified parent enzyme.

It is presently believed that the capability of the peptide addition of providing the desired effect (such as improved wash performance, improved performance in degreasing of hides, Esc, depends on, e.g., the identity of the parent enzyme to be modified, the structure (including length) of the peptide addition, the impact of the peptide addition on the structure of the entire lipolytic enzyme, the nature or functionality of amino acid residues of the peptide addition, etc. A prerequisite for the peptide addition being capable of providing the desired effect is, of course, that the modified enzyme containing the peptide addition is expressible in a suitable host organism. The following general considerations are of relevance for the design of a suitable peptide addition:

Length of peptide addition: It has been found that peptide additions containing varying numbers of amino acid residues are capable of providing the desired effect and thus, it is not possible to specify an exact number of amino acid residues to be present in the peptide addition to be used in accordance with the present invention. It is contemplated that the upper limit of the number of amino acid residues is determined, inter alia, on the basis of the impact of the peptide addition on the expression, the structure and/or the activity of the resulting modified enzyme. It is believed that the peptide addition may comprise a substantial number of amino acid residues, however, without all of these amino acid residues need to contributing to the desired effect (even if the peptide addition contains a substantial number of amino acid residues only a small number of these need to providing the desired function, this small number may be termed the functional part of the peptide addition). The main consideration in relation to the lower limit of the number of amino acid residues of the peptide addition will normally be that the number should be sufficient to provide the desired effect.

The peptide addition may thus comprise a single amino acid residue or an amino acid chain of from 2 and 500 amino acids, such as from 1 to 200, or from 2 to 100, preferably from 2 to 50, such as 3 to 50, even more preferably from 7–45 and still more preferably between 1 and 15, such as between 1 and 10 or 1 and 7, especially between 4 and 10, such as 4 and 7 amino acids.

Stability: The peptide addition should preferably be chosen so as to provide a modified lipolytic enzyme with an acceptable stability (e.g. structural stability and/or expression stability) or so as to not significantly reduce the structural stability of the parent enzyme. Although many peptide additions are not believed to confer any substantial structural instability to the resulting modified enzyme, it may in certain instances and with certain parent enzymes be relevant to choose a peptide addition which in itself can confer a structural stability to the modified lipolytic enzyme. For instance, a peptide addition which in itself forms a structural element, such as an α-helix or β-sheet, may stabilize the resulting modified enzyme and thus be used in the context of the present invention. Peptide sequences capable of forming such structures are known in the art. Alternatively, an improved structural stability may be provided by introduction of cystein bridges in the modified lipolytic enzyme of the invention. For instance, a cystein bridge between the peptide addition and the mature part of the enzyme may be established if at least one of the amino acid residues of the peptide addition is a cystein residue which is located so as to be able to form a covalent binding to a cystein residue in the mature part of the enzyme. The positive effect of introducing a cystein bridge is illustrated in Example 24. If no suitable cystein is present in the mature enzyme, a cystein may be inserted at a suitable location of said parent enzyme, conveniently by replacing an amino acid of the parent enzyme, which is considered unimportant for the activity.

In addition, it may be desirable that at least one of the amino acid residues of the peptide addition is chosen so as to make the peptide addition less susceptibility to proteolytic degradation by proteolytic enzymes of the host cell used for expressing the modified lipolytic enzyme. For instance, the peptide addition may comprise at least one, and preferably at least two proline residues. Preferably, the peptide addition comprises 1–5, such as 1–4 or 1–3 or two or one proline residues. The proline residue(s) is (are) preferably placed at the proteolytic cleavage site or close thereto. Alternatively, the peptide addition may be one which provides a protease stable loop to the modified lipase, e.g. as described in EP 407 225 or WO 93/11254.

Nature of amino acid residues of the peptide addition: As stated above and without being limited to any theory, it is presently believed that the improved performance may at least partly be due to an increased affinity of the modified lipolytic enzyme toward the substrate provided by the peptide addition. In particular in relation to wash performance, it is believed that favourable electrostatic interactions may be obtained between the negatively charged lipid surface and positively charged and/or hydrophobic amino acid residues present in the modified enzyme. Accordingly, it is particularly preferred that the modified enzyme of the invention comprises a peptide addition with at least one positive charge, such as at least 2, 3, 4 or more positive charges or expressed differently, in which a substantial number of the amino acid residues of the peptide addition is positively charged and/or hydrophobic.

Analogously, and in order to reduce the negative charge in a non-structural end of the parent enzyme it is preferred to remove at least one such as two or more negatively charged amino acid residues from a non-structural N-terminal or C-terminal part of the parent enzyme of choice, in particular from the part of the parent lipase being constructed of the 1–5 first or last N-terminal or C-terminal amino acid residues, such as 1–4, or 1–3 or 1–2. The negatively charged amino acid residue may either be removed or replaced by a neutral, a positively charged or a hydrophobic amino acid residue. For instance, the negatively charged amino acid residue to be removed may be an E or D which may be replaced with either of the positively charged amino acid residues R, K or H, the neutral amino acid residues S, T, G or Q, or the hydrophobic amino acid residues A, I, W, F or L. Similarly, a neutral amino acid residue of a non-structural N-terminal or C-terminal part of the parent enzyme may be replaced with a positively charged or hydrophobic amino acid residue as defined above.

Accordingly, the modified lipolytic enzyme of the invention in addition or as an alternative to a N-terminal and/or C-terminal extension may comprise a mutation in the non-structural C-terminal and/or N-terminal end of the parent enzyme, which mutation has involved deleting or replacing a negatively charged amino acid residue of said non-structural part with a positively charged or neutral amino acid residue or with a hydrophobic amino acid residue.

If a peptide addition is present in both the N- and the C-terminal of the parent enzyme, the peptide addition at or within each of the terminals may have the same or a different amino acid sequence.

Test of suitability of peptide addition: the effect of using a given peptide addition, e.g., designed on the basis of the above principles may be tested by constructing a modified lipolytic enzyme containing the peptide addition and testing the properties of the resulting enzyme for the desired enzyme application such as wash, pitch removal, degreasing of leather, Esc either in a full scale test or in an assay which correlates well with the enzyme application in question.

The peptide addition can be generalised in the following way.

The first residue (counted from the outer residue) is named "a", the second is named "b", the third "c" etc. Thus, in case of an N-terminal addition the first amino acid residue is termed "a", in case of a C-terminal addition the last amino acid residue is termed "a".

In an important embodiment of the invention the peptide addition consists of from 1 to 7 amino acids. Such peptide addition, which can be applied to both the N- and/or C-terminal of the parent enzyme, can be referred to as:

a (one amino acid peptide addition)
a-b (two amino acids peptide addition)
a-b-c (three amino acids peptide addition)
a-b-c-d (four amino acids peptide addition)
a-b-c-d-e (five amino acids peptide addition)
a-b-c-d-e-f (six amino acids peptide addition)
a-b-c-d-e-f-g (seven amino acids peptide addition)

Each letter defines an amino acid residue.

a, b, c, d, e, f and g may independently be any amino acid including Alanine (A), Valine (V), Leucine (L), Isoleucine (I), Proline (P), Phenylalanine (F), Tryptophan (W), Methionine (M), Glycine (G), Serine (S), Threonine (T), Cysteine (C), Tyrosine (Y), Asparagine (N), Glutamine (Q), Aspartic acid (D), Glutamic acid (E), Lysine (K), Arginine (R), and Histidine (H).

In specific embodiments a, b, c, d, e, f, and g are independently one of the following amino acids:

a: Leu, Ile, Val, Trp, Phe, Ser, Arg, Cys, or Lys,
b: Leu, Ile, Val, Trp, Phe Ser, Pro, Arg, Lys, Cys or His,
c: Leu, Ile, Val, Trp, Phe, Ser, Pro, Arg, Cys, or Lys.
d: Leu, Ile, Val, Trp, Phe, Ser, Pro, Arg, Cys, or Lys.
e: Leu, Ile, Val, Trp, Phe, Pro, Arg, Lys, Ala, Glu, Cys, or Asp,
f: Leu, Ile, Val, Trp, Phe, Pro, Arg, Lys, Ala, Glu, Cys, or Asp,
g: Leu, Ile, Val, Trp, Phe, Pro, Arg, Lys, Cys, or Met.

In a preferred embodiment at least one such as one, two, three or four of a, b, c, d, e, f, or g is a positively charged amino acid, i.e. Arg (R) or Lys (K) or a hydrophobic amino acid, i.e. Leu, Ile, Val, Trp or Phe.

As stated further above, and dependent on the host cell of choice it is generally believed that it is important that the peptide addition comprises at least one proline residue in order to protect the modified lipolytic enzyme against proteolytic degradation during the processing of the enzyme by the host cell of choice. It may be desirable that the proline residue occupies position two (i.e. b) and/or three (i.e. c) of the peptide addition or a position close to the desired cleavage point (i.e. the point where processing by the host cell in question is believed to occur). Accordingly, in one embodiment b and optionally c of the peptide addition is Pro.

In another embodiment of the invention a-b is SP (Ser-Pro), A-P or Q-P. If the peptide addition contains more amino acid residues, e.g. between 4 and 7 amino acids the peptide addition has the general formula (SEQ ID NO:123) SPcd, SPcde, SPcdef, SPcdefg or APcd, APcde, APcdef, Apcdefg or QPcd, QPcde, QPcdef, QPcdefg. In each of these formulae c, d, e, f, and g may be any amino acid. However, preferred are the above mentioned group of amino acids.

In another embodiment a-b comprise at least one positive amino acids (i.e. Arg and Lys) or hydrophobic amino acid residue (i.e. Leu, Ile, Val, Trp and Phe).

Specifically, the peptide addition applied to the parent lipolytic enzyme may advantageously be one of the following amino acid residues or peptides:

Arg (R), or Lys (K), or Leu (L), or Ile (I), or
Val (V), or Trp (W) or Phe (F), or
Arg-Pro (RP), or
Lys-Lys (KK), or
Arg-Lys (RK), or
Lys-Arg (KR), or
Arg-Arg (RR), or
Arg-Arg-Pro (RRP), or
Arg-Pro-Val-Ser-Gln-Asp (RPVSQD) (SEQ ID NO:17)
Ser-Pro-Ile-Arg-Met (SPIRM) (SEQ ID NO:18), or
Ser-Pro-Ile-Arg-Ala-Arg (SPIRAR) (SEQ ID NO:19), or
Ser-Pro-Ile-Arg-Pro-Arg (SPIRPR) (SEQ ID NO:20) or
Ser-Pro-Ile-Arg-Glu-Arg (SPIRER) (SEQ ID NO:21), or
Ser-Pro-Ile-Arg-Lys (SPIRK) (SEQ ID NO:22), or
Ser-Pro-Ile-Lys-Lys (SPIKK) (SEQ ID NO:23), or
Ser-Pro-Ile-Arg-Arg-Pro (SPIRRP) (SEQ ID NO:24), or
Ser-Pro-Pro-Arg-Arg (SPPRR) (SEQ ID NO:25), or
Ser-Pro-Iso-Pro-Arg (SPIPR) (SEQ ID NO:26), or
Ser-Pro-Arg-Pro-Arg (SPRPR) (SEQ ID NO:27), or
Ser-Pro-Ile-Arg (SPIR) (SEQ ID NO:28), or
Ser-Pro-Ile-Arg-Arg (SPIRR) (SEQ ID NO:29), or
Ser-Cys-Ile-Arg-Arg, (SCIRR) (SEQ ID NO:30), or
Ser-Pro-Ile-Arg-Pro-Arg-Pro (SPIRPRP) (SEQ ID NO:31), or
Ser-Cys-Ile-Arg-Pro-Arg-Pro (SCPIRPRP) (SEQ ID NO:32), or
Ser-Pro-Arg-Arg-Pro-Arg-Thr (SPRRPRT) (SEQ ID NO:33), or
Ser-Pro-Phe-Arg-Pro-Lys-Leu (SPFRPKL) (SEQ ID NO:34), or
Ser-Pro-Pro-Arg-Arg-Pro (SPPRRP) (SEQ ID NO:35), or
Ser-Pro-Ile-Arg-Arg-Glu (SPIRRE) (SEQ ID NO:36), or
Ser-Pro-Pro-Arg-Pro-Pro (SPPRPP) (SEQ ID NO:37), or
Ser-Pro-Pro-Arg-Pro-Arg (SPPRPR) (SEQ ID NO:38), or
Ser-Pro-Pro-Trp-Trp-Pro (SPPWWP) (SEQ ID NO:39), or
Ser-Pro-Pro-Trp-Arg-Pro (SPPWRP) (SEQ ID NO:40), or
Ser-Pro-Pro-Arg-Trp-Pro (SPPRWP) (SEQ ID NO:41), or
Ser-His-Trp-Arg-Arg-Trp (SHWRRW)(SEQ ID NO:43), or
Ser-His-Trp-Arg-Lys (SHWRK) (SEQ ID NO:44), or
Ser-His-Trp-Arg-Arg (SHWRR) (SEQ ID NO:45), or
Thr-Ala-Ile-Arg-Pro-Arg-Lys (TAIRPRK) (SEQ ID NO:46),
Ser-Thr-Arg-Arg-Pro-Arg-Pro (STRRPRP) (SEQ ID NO:47),
Gly-Pro-Ile-Arg-Pro-Arg-Pro (GPIRPRP) (SEQ ID NO:48), or
Leu-Pro-Phe-Arg-Glu-Arg-Pro (LPFRQRP) SEQ ID NO:49), or
Ser-Arg-Ser-Arg-His-Asp-Ala (SRSRHNA) (SEQ ID NO:50), or
Ile-Pro-Ile-Arg-Pro-Arg-Arg (IPIRPRR) (SEQ ID NO:51), or
Ser-Thr-Arg-Arg-Pro-Arg-Pro (STRRPRP) (SEQ ID NO:52), or
Thr-Ala-Ile-Arg-Pro-Arg-Lys (TAIRPRK) (SEQ ID NO:53), or
Trp-Arg-Trp-Arg-Trp-Arg (WRWRWR) (SEQ ID NO:54), or
Glu-Pro-Ile-Arg-Arg (QPIRR) (SEQ ID NO:55), or
Ser-His-Trp-Glu-Glu (SHWQQ) (SEQ ID NO:56), or
Ser-Ala-Leu-Arg-Pro-Arg-Lys (SALRPRK) (SEQ ID NO:87).

Also contemplated according to the invention are additions comprising more than 7 amino acids, such as from 8 to 15 amino acids.

Such peptides can be generalised as:
a-b-c-d-e-f-g-h (8 amino acid peptide)
a-b-c-d-e-f-g-h-i (9 amino acid peptide)
a-b-c-d-e-f-g-h-i-j (10 amino acid peptide)
a-b-c-d-e-f-g-h-i-j-k (11 amino acid peptide)
a-b-c-d-e-f-g-h-i-j-k-l (12 amino acid peptide)
a-b-c-d-e-f-g-h-i-j-k-l-m (13 amino acid peptide)
a-b-c-d-e-f-g-h-i-j-k-l-m-n (14 amino acid peptide)
a-b-c-d-e-f-g-h-i-j-k-l-m-n-o (15 amino acid peptide).
a to o may be any of the twenty amino acids mentioned above.

The a–g stretch may be as defined above in relation to a peptide addition comprising 1 to 7 amino acid residues.

h, i, j, k, l, m, n, o may as mentioned above be any amino acid, preferably any of the following amino acids: Arg, Lys, Ala, Val, Trp, Ile, Phe, Ser or Pro.

Specific examples of such additions are listed below:
Arg-Pro-Arg-Pro-Arg-Pro-Arg-Pro (RPRPRPRP) (SEQ ID NO:57), or
Ser-Ser-Thr-Arg-Arg-Ala-Ser-Pro-Ile-Lys-Lys (SSTRRASPIKK) (SEQ ID NO:58), or
Ala-Trp-Trp-Pro-Ser-Pro-Ile-Arg-Pro-Arg-Pro (AWWPSPIRPRP) (SEQ ID NO:59), or
Ala-Pro-Pro-Pro-Arg-Pro-Arg-Pro-Arg-Pro-Arg-Pro (APPPRPRPRPRP) (SEQ ID NO:60), or
Ala-Pro-Pro-Pro-Arg-Thr-Arg-Pro-Arg-Pro-Arg-Ser (APPPRTRPRPRS) (SEQ ID NO:61), or
Ser-Pro-Lys-Arg-Lys-Pro-Arg-Pro (SPKRKPRP) (SEQ ID NO:62), or
Ser-Gln-Arg-Ile-Lys-Gln-Arg-Ile-Lys (SQRIKQRIK) (SEQ ID NO:63), or
Ser-Pro-Pro-Pro-Arg-Pro-Arg-Pro (SPPPRPRP) (SEQ ID NO:64), or
Ser-Pro-Ile-Arg-Pro-Arg-Pro-Arg-Pro-Arg (SPIRPRPRPR) (SEQ ID NO:65), or
Ser-Pro-Ile-Arg-Lys-Ala-Trp-Trp-Pro (SPIRKAWWP) (SEQ ID NO:66), or
Ala-Pro-Pro-Pro-Lys-Ala-Ser-Pro-Arg-Gln-Pro (APPPKASPRQRP) (SEQ ID NO:67), or
Ser-Pro-Ile-Arg-Pro-Arg-Pro-Ser-Pro-Ile-Arg-Pro-Arg-Pro-Arg(SPIRPRPSPIRPRP) (SEQ ID NO:68), or
Ser-Pro-Pro-Arg-Trp-Pro-Arg-Arg (SPPRWPRR) (SEQ ID NO:69), or
Ser-Pro-Pro-Arg-Trp-Pro-Arg-Trp (SPPRWPRW) (SEQ ID NO:70), or
Ser-Pro-Pro-Arg-Trp-Pro-Trp-Arg (SPPRWPWR) (SEQ ID NO:71), or
Ser-Pro-Pro-Trp-Arg-Pro-Arg-Arg (SPPWRPRR) (SEQ ID NO:72), or
Ser-Pro-Pro-Trp-Trp-Pro-Arg-Trp (SPPWWPRW) (SEQ ID NO:73), or
Ser-Pro-Pro-Trp-Trp-Pro-Trp-Arg (SPPWWPWR) (SEQ ID NO:74), or
Ser-Pro-Pro-Trp-Trp-Pro-Trp-Trp (SPPWWPWW) SEQ ID NO:75), or Ser-Pro-Pro-Trp-Pro-Arg-pro-Arg-Pro (SPPWPRPRP) (SEQ ID NO:76), or Ala-Pro-Pro-Pro-Arg-Pro-Arg-Leu-Leu-Pro-Ile-Ser (APPPRPRLLPIS) (SEQ ID NO:88), or Ala-Pro-Pro-Pro-Thr-Arg-Gln-Arg-Gln-Ser-Pro (APPPTRQRQSP) (SEQ ID NO:89), or Ala-Pro-Pro-Pro-Arg-Thr-Ile-Pro-Arg-Ser-Ser-Pro (APPPRTIPRSSP) (SEQ ID NO:90).

In any of the above specified peptide additions (whether comprising 1 to 7 or 1 to 15 amino acid residues) in which the position "a" is a Ser, Ala, Arg, Lys or Pro, the Ser may be replaced with an Ala, Arg, Lys or Pro, the Ala with a Ser, Arg, Lys or Pro and the Arg, Lys or Pro with a Ala or Ser.

It is to be emphasized that the above peptide addition may be at either the N-terminal and/or the C-terminal. Examples of modified lipolytic enzymes with both a N- and a C-terminal peptide addition include all combinations of the peptide additions specifically mentioned above. Two specific examples of such are the N-terminal addition SPIRPRP (SEQ ID NO:31) together with the C-terminal addition RRP or RR.

If the peptide addition is inserted into the non-structural part of the parent enzyme, it may replace one or more of the amino acid residues of said non-structural part. For instance, the peptide addition may replace one or more amino acid residues occupying the first, e.g. 1–5, amino acid residues of the N-terminal end and/or the last, e.g. 1–5, amino acids of the enzyme (i.e. the 1–5 amino acid residues of the C-terminal end). For instance, the peptide addition may replace amino acid residue(s) 1 and/or 2 and/or 3 and/or 4, and/or 5, etc. from either end of the parent enzyme. When the parent enzyme is *H. lanuginosa* lipase it has been of particular interest to combine any of the above peptide additions (applied in the N-terminal) with a deletion of the parent first (1E).

In accordance with the invention, it is also contemplated to apply, to the modified enzyme, one or more charged amino acids which permit effective purification of the modified enzyme. Techniques for doing this is well known by a person skilled in the art of molecular biology.

The First Wash Lipolytic Enzyme of the Invention

Preferably, the first wash lipolytic enzyme of the invention is capable of effecting an even higher lard removing capability than that stated above in "Summary of the Invention". Accordingly, in a preferred embodiment Detergent Composition A and/or B comprising the first wash lipolytic enzyme of the invention is capable of removing at least 15%, such as at least 20% more lard, than Detergent Composition A and/or B, respectively, which does not comprise the lipolytic enzyme, when tested in the one cycle wash assay described herein in a concentration of 12500 LU/l. In a more preferred embodiment the lipolytic enzyme is one, which, when present in Detergent Composition A and/or B allows the detergent composition to remove at least 25% such as at least 30% or 35% or 40% or 50% more lard than Detergent Composition A and/or B without the lipolytic enzyme, when tested in the one cycle wash assay as described herein.

The concentration of lipolytic enzyme used in the above described one cycle wash assay (i.e. 12500 LU/l) may be considered high for practical applications, but has been chosen for assay purposes in order to minimize the analytical variation. A more realistic concentration is 1250 LU/l which in an alternative embodiment may be used to define the lard removing capability of a lipolytic enzyme of the invention. Accordingly, in a further embodiment the first wash lipolytic enzyme is one which is capable of removing at least 15%, such as at least 20% more lard, than Detergent Composition A and/or Detergent Composition B which does not comprise the lipolytic enzyme, when used in the one cycle wash assay described herein in a concentration of 1250 LU/l. In an even more preferred embodiment the first wash lipolytic enzyme, when present in Detergent Composition A and/or B in a concentration of 1250 LU/l, allows the detergent composition to remove at least 25% such as at least 30% or 35% more lard than Detergent Composition A and/or B without the lipolytic enzyme, when used in a one cycle wash assay as described herein.

In preferred embodiments the first wash lipolytic enzyme of the invention is capable of removing:

(a) when present in Detergent composition A in a concentration of 1250 LU/l at least 15% more lard from a lard stained swatch than Detergent composition A without the enzyme, (b) when present in Detergent A in a concentration of 12500 LU/l at least 40% more lard from a lard stained swatch than Detergent Composition A without the enzyme, (c) when present in Detergent composition B in a concentration of 1250 LU/l at least 15% more lard from a lard stained swatch than Detergent composition B without the enzyme, (d) when present in Detergent B in a concentration of 12500 LU/l at least 15% more lard from a lard stained swatch than Detergent Composition B without the enzyme, when tested in a one cycle wash assay as described herein.

In Example 12 herein a comparison is shown between the fat removing capability of lipolytic enzymes of the invention and that of lipolytic enzymes described in WO 94/03578 alleged to have a through-the-wash-effect. It is seen that the enzymes of the invention removed substantially more lard in a one cycle wash than the prior art enzymes. The comparison between the enzymes has been done by use of the same assay.

While the first wash lipolytic enzyme of the invention may be of any of the above mentioned types of lipolytic enzymes such as a hydrolase exhibiting activity towards ester and/or phospholipid bonds, it is particularly preferred that the enzyme is a lipolytic enzyme which exhibits activity towards esterbonds in mono-, di- and/or tri-glycerides and/or which exhibits activity towards cutin. Such enzymes are generally considered to be of high interest as detergent enzymes.

In the Materials and Methods section and in Example 12 below suitable assays for identifying first wash lipolytic enzymes are given. These assays may be used to identify naturally-occurring first wash lipolytic enzymes. More specifically, in order to identify a naturally-occurring first wash lipolytic enzyme according to the invention candidate enzymes are recovered from suitable organisms expected to produce lipolytic enzymes, such as organisms which are taxonomically related to the ones given in the "Background of the Invention" section above or discussed later on in the "Parent Lipolytic Enzymes" section, or organisms which are found in an environment which require the organism to produce lipolytic enzymes in order to prevail. Subsequently, the recovered enzymes are subjected to the first wash lipolytic enzyme assays disclosed herein.

Although the first wash lipolytic enzyme of the invention may be a novel naturally-occurring enzyme (identified on the basis of its first wash performance) it is presently preferred that the enzyme is a mutated enzyme, i.e. an enzyme which has been prepared by subjecting a parent lipolytic enzyme to mutagenesis and/or to chemical modification so as to result in a modified lipolytic enzyme which has a first wash activity. The parent lipolytic enzyme may be one which has a first wash activity (which may thus be improved by the mutagenesis or chemical modification) or may be without any first wash activity as defined herein. In one embodiment it is considered advantageous that the parent enzyme has a satisfactory wash performance itself or even a first wash performance, the latter property then being improved by the mutation(s). Parent enzymes with a satisfactory (but not necessarily a first wash performance) may be selected using the assay described in Example 13 hereinafter.

The chemical modification of amino acid residues of the parent enzyme may e.g. be performed in accordance with the principles disclosed in WO 95/09909 the content of which is incorporated herein by reference. For instance, the chemical modification may be accomplished by coupling an amine ligand (such as an aminated sugar, aminated alcohol or aminated glucosamine or isomeric forms thereof) to the carboxyl group of glutamic acid or aspartic acid residues in the enzyme. The chemical modification may be performed by methods known in the art, such as those described in WO 95/09909. The chemical modification may be done on acid groups so as to remove negative charges.

The mutagenesis of the parent lipolytic enzyme is preferably done so as to improve the substrate binding affinity of the parent enzyme. More specifically, it has been found that an improved substrate binding affinity may result in a first wash activity being obtained. It is presently contemplated that an improved substrate binding affinity may be achieved by making the surface of the parent enzyme less negative. Accordingly, the mutagenesis may be performed so as to replace at least one neutral amino acid residue located at the surface of the parent enzyme with a positively charged amino acid residue, deleting a negatively charged amino acid residue located at the surface of the parent enzyme or replacing a negatively charged amino acid residue located at the surface of the parent enzyme with a neutral (including hydrophobic) or positively charged amino acid residue. Amino acid residues located at the surface of the enzyme may be identified by use of the Conolly program referred to in the Definitions section above. In a preferred embodiment the mutagenesis is performed so as to remove the amino acid residue D and/or E, and/or to insert, conveniently by replacement, of R, K, W, F, Y, I or L. A suitable test for an improved substrate binding affinity is described in Example 27 hereinafter.

The 1 st wash effect of the above changes from negative towards positive surface may be improved and/or stabilized by introduction of exchanges optimizing the structure or stability. Thus, for instance introduction of a proline residue into the enzyme surface may lead to an increased proteolytic and/or thermal stability; introduction of hydrophilic amino acid residues, e.g. Glu and/or Asp, may increase the anionic detergent stability, and the introduction of hydrophobic amino acid residues may increase the adsorption/affinity of the enzyme. The introduction of the above type of amino acid residues may either be accomplished by simply inserting the amino acid residues into a suitable location at the surface of the enzyme or by replacing amino acid residue(s) located at such position(s).

It is presently believed that a first wash lipolytic enzyme of the invention is a variant of a parent lipolytic enzyme which comprises at least one mutation, but typically more mutations, preferably located at the surface of the enzyme. The variant may comprise more mutations such as at least 2, 3, 4 or 5 mutations, e.g. in the range of 1–20, 1–15, 1–12, 1–10, 1–9, 1–8, 1–4 mutations, or any number of mutations which does not impair the enzymatic activity of the enzyme.

It has been found that mutations within as well as outside the lipid contact zone of the parent *H. lanuginosa* lipase disclosed herein may be of importance for achieving a first wash activity. Accordingly, the first wash lipolytic enzyme of the invention carrying a mutation may be constructed from a parent lipolytic enzyme by modification of at least one amino acid residue outside the lipid contact zone of the parent enzyme and/or by addition of at least one amino acid residue outside said zone, and/or by modification of at least one amino acid residue within the lipid contact zone of the parent enzyme and/or by addition of at least one amino acid residue within said zone.

Accordingly, in another embodiment the first wash lipolytic enzyme of the invention is one, which has been prepared from the parent enzyme by modification, deletion or substitution of at least one amino acid residue in the lipid contact zone of the parent enzyme or addition of at least one amino acid residue to said zone. In a still further embodiment the first wash lipolytic enzyme is one which has been prepared from the parent enzyme by modification, deletion or substitution of at least one amino acid residue outside the lipid contact zone or addition of at least one amino acid residue to said zone,the amino acid residue preferably being located at the surface of the parent enzyme. The mutations within or outside the lipid contact zone are preferably conducted to as to improve the substrate binding affinity of the resulting modified enzyme, conveniently be removal of negative charges as described above.

Although site-directed mutagenesis following the above principles (and combined with testing of the resulting enzyme variants for first wash activity) may be used for the creation of first wash lipolytic enzymes it is presently preferred to use other methods of creating first wash lipolytic enzymes. Random mutagenesis, in particular localized random mutagenesis, as well as in vivo recombination of homologous genes have been found to be of particular interest for that purpose—these methods are described in detail further below.

First Wash Lipolytic Enzyme Modified in a Non-structural Part of its C- or N-terminus It has surprisingly been found that it is possible to confer a first wash effect to a parent lipolytic enzyme or to significantly enhance the first wash effect of a parent lipolytic enzyme by applying at least one N-terminal and/or C-terminal peptide addition at or within a non-structural part of the parent enzyme in its mature form or by introducing other changes in a non-structural part of the C-terminal and/or N-terminal end of the parent mature enzyme.

Accordingly, in a further highly preferred embodiment the first wash lipolytic enzyme of the invention is a variant of a parent lipolytic enzyme which, as compared to the parent enzyme, has been modified at or within a non-structural part of the N- and/or C-terminal end of the parent enzyme.

The modified enzyme may comprise a peptide addition at either the N-terminal or the C-terminal end or both in the N- and the C-terminal ends of the parent lipolytic enzyme. If a peptide addition is applied to both the N- and the C-terminus of the parent enzyme, the peptide addition at either terminus may have the same amino acid sequence or different amino acid sequence. Multiple copies of the same or different peptide additions may be inserted or added.

It is presently contemplated that the improved first wash performance effected by the peptide addition is, at least in part, due to an increased affinity of the modified lipolytic enzyme towards its lipid substrate (although this may not be the only reason). Accordingly, in a preferred embodiment the peptide addition is one which confer an increased affinity of the modified enzyme towards its lipid substrate.

For enzymes having a similar three-dimensional structure to that of the *H. lanuginosa* lipolytic enzyme the insertion may be made in the part of said enzyme which corresponds to a "non-structural part" of the *H. lanuginosa* lipolytic enzyme.

It is presently believed that the capability of the peptide addition of providing the desired first wash effect depends on, e.g., the identity of the parent enzyme to be modified, the structure (including length) of the peptide addition, the impact of the peptide addition on the structure of the entire lipolytic enzyme, the nature or functionality of amino acid residues of the peptide addition, etc. A prerequisite for the peptide addition being capable of providing the desired effect is, of course, that the modified enzyme containing the peptide addition is expressible in a suitable host organism. The peptide addition to be used in accordance with this aspect of the invention may be as described in the above section entitled "Peptide addition". Thus, the general as well as specific considerations and statements (including the disclosure as to Length of peptide addition, Stability, Nature of amino acid residues of the peptide addition, Test of suitability of peptide addition, and the general formula of peptide additions of said section) is intended to apply for the peptide addition to be used according to this aspect of the invention. With respect to stability the peptide addition should preferably be chosen so as to provide a modified lipolytic enzyme with a stable peptide addition and an acceptable structural stability of the parent enzyme.

Thus, the peptide addition to be applied in accordance with this aspect of the invention may be any of the peptide additions specified in the above section entitled "Peptide addition". In addition, it has been found that a suitable peptide addition to provide a first wash lipolytic enzyme may simply be constituted by or comprise a part of or the entire propeptide sequence normally associated with the parent lipolytic enzyme in question. Thus, for instance in relation to first wash *H. lanuginosa* lipolytic enzyme variants a suitable peptide addition may comprise or be constituted of SPIRR (SEQ ID NO:29)—i.e. part of the normal propeptide sequence of the *H. lanuginosa* lipolytic enzyme sequence.

The peptide addition of the first wash lipolytic enzyme may be added to the parent lipolytic enzyme as described in the below section entitled "Methods of applying a peptide addition to a parent lipolytic enzyme".

Methods of Applying a Peptide Addition to a Parent Lipolytic Enzyme

Although a modified enzyme of the invention (including a first wash lipolytic enzyme comprising a peptide addition) may be obtained by adding (fusing or inserting) a synthetically produced peptide addition into the parent lipolytic enzyme in question, it is presently preferred that the modified (including first wash) enzyme of the invention is prepared by i) modifying the nucleotide, preferably DNA, sequence encoding the parent enzyme so as to encode the desired peptide addition applied to the N- and/or the C-terminal end(s) of the parent enzyme (e.g. by inserting a nucleic acid (preferably DNA) sequence encoding the peptide addition at the relevant location in the nucleic acid (preferably DNA) sequence encoding the parent enzyme), ii) expressing the resulting modified nucleic acid (preferably DNA) sequence in a suitable expression system, and iii) recovering the resulting modified enzyme.

In the present context, the term "applied to" is intended to indicate that the addition is fused to the N- and/or C-terminal end (e.g. to the first or last amino acid residue) of the mature enzyme or inserted into a non-structural part of the N-terminal and/or C-terminal end of the mature enzyme.

Many enzymes are expressed as "prepro-enzymes", i.e. as enzymes consisting of the mature enzyme, a secretory signal peptide (i.e. prepeptide) and a pro-peptide. The preproenzyme is processed intracellularly to be secreted into the fermentation medium, from which the mature enzyme can be isolated and/or purified. The peptide addition to the parent enzyme can be carried out by applying nucleic acid sequences encoding the desirable peptide additions upstream (for N-terminal peptide additions) and/or downstream (for C-terminal peptide additions) to the DNA sequence encoding the parent enzyme.

The insertion should be performed in such a way that the desired modified enzyme (i.e. having the desired peptide addition(s)) is expressed and secreted by the host cell after transcription, translation, and processing of the enzyme. The term "processing" means in this context removal of pre- and pro-peptides (except, of course, when the pro-peptide is identical to the desired peptide addition. This will be dealt with further below).

Downstream sequences (encoding a C-terminal addition) can be inserted between the DNA sequence encoding the parent enzyme and the terminating codon. However, if the unprocessed DNA sequence comprises a pro-peptide encoding DNA sequence at the C-terminal end the insertion/addition of the DNA sequence encoding the peptide addition can also take place between the DNA sequences encoding the pro-peptide and the mature enzyme, respectively.

In most cases it is possible to extend the parent enzyme upstream by inserting a DNA sequence encoding the peptide addition between the DNA sequence encoding the propeptide or the prepeptide (if no prosequence is present) and the DNA sequence encoding the mature enzyme.

The insertion/addition of a DNA sequence encoding the peptide addition can be carried out by any standard techniques known by any skilled person in the field of molecular biology, cf., e.g. Sambrook et al., 1989). This include, e.g., the polymerase chain reaction (PCR) using specific primers, for instance described in U.S. Pat. No. 4,683,202 or R. K. Saiki et al., (1988), Science, 239, 487–491, How to provide for the expression and secretion of adjacent DNA sequence (s) will be described below.

The DNA sequence encoding the peptide addition in question shall, of course, be chosen so as to match the codon preferences of the expression system intended for the production of the modified or first wash lipolytic enzyme of the invention.

In connection with the present invention it has been found that some host cells may be less suited for the production of a desired modified or first wash lipolytic enzyme, in that part or all of the peptide addition(s) may be cut off during the posttranslational or other processesing performed by the host cell. Accordingly, the term "suitable expression system" is intended to indicate an expression system (host cell and optionally expression vector) which allows for at least a portion of an intact desired modified or first wash lipolytic enzyme to be produced, i.e. an expression system which does not, e.g. as part of the posttranslational or other processing by the host cell of choice, remove part or all of the peptide addition (and thereby produce the enzyme without the desired peptide addition). Expressed differently, the expression system (including the host cell, cultivation conditions and/or recovery conditions) are preferably selected so that at the most a partial processing of the pre, pro or prepro-form of the lipolytic enzyme occur resulting in that at least 5%, such as at least 10%, such as at least 15%, such as at least 20%, such as at least 25%, such as at least 50%, such as at least 75% of the produced enzyme molecules comprise the desired peptide addition, e.g. the entire prosequence or a substantial part thereof. Typically, the expression system to be used is devoid of or reduced in one or more proteolytic activities exerting the undesired posttranslational processing, e.g. by abolishing the production of one or more proteolytic enzymes by the host cell.

The choice of expression system and thus host cell will depend on the lipolytic enzyme to be produced as will be discussed in detail further below.

While care must be exerted to select a proper expression system for producing a modified or first wash lipolytic enzyme of the invention (in particular when a modified DNA sequence is used for the production), it has been found that when the peptide addition constitutes a part of or the entire propeptide sequence it may be applied by—and thus a modified lipolytic enzyme according to the invention (having an improved or first wash performance) may be obtained by—expressing a DNA sequence encoding the parent lipolytic enzyme in question in an expression system which is incapable of processing the translated polypeptide in the normal manner, and thereby results in the production of an enzyme which comprises a part of or the entire propeptide or a similar peptide sequence associated with the mature protein prior to its processing. In this case, the propeptide or similar peptide sequence constitutes the peptide addition. The pro-peptide or similar peptide sequence may be heterologous or homologous to the parent enzyme and can be present in both the N- and C-terminal of the parent enzyme. The production of a modified or first wash lipolytic enzyme according to the invention using this latter technique is described further below.

Accordingly, if a suitable stretch of amino acids is already encoded in the prepro form of the parent enzyme and this stretch of amino acids is cut off in the processing of the enzyme by a given expression system, the peptide addition can be applied by changing the expression host system to a system in which said processing of said stretch of amino acids does not occur or modify the gene sequence to eliminate the post-translation processing, e.g. by saturating the processing enzyme(s) with one or more copies of a pro-like peptide (such as one of the peptide additions shown herein) or by changing the pro-peptide sequence, e.g. to remove a post-translational processing site. In such a case the secretory signal pre-peptide will be cut off during or after the secretion, resulting in a modified enzyme consisting of the parent enzyme comprising the pro-peptide or part thereof or a similar peptide sequence encoded by the corresponding DNA sequence, i.e. a lipolytic enzyme being extended at either its N-terminal or C-terminal end.

In other words, in a further aspect the invention relates to a method for increasing the wash performance or other activity of a parent enzyme (by designing or producing a modified or first wash lipolytic enzyme), which method comprises (a) cultivating a host cell transformed with a DNA sequence encoding the parent lipolytic enzyme including its (pre)pro (i.e. pre, pro or prepro) sequence under conditions suitable for production of the enzyme comprising at least a part of the entire pre(pro)-sequence, the host cell being one which is incapable or inefficient in the processing of the pro-enzyme to be expressed into the mature enzyme, and recovering and optionally purifying the resulting modified enzyme.

The DNA sequence encoding the parent lipolytic enzyme may be the gene or cDNA sequenceencoding the parent enzyme in its pro or prepro-form and may be present on an expression vector, when transformed into the host cell.

The host cell may be of a different origin than the parent enzyme, e.g. of another genus than the one from which the parent enzyme is derived, or may have another posttranslational processing machinery than the source of the parent enzyme. Yeast cells have been found of particular use for applying peptide additions (in the form of the propeptide or a part thereof) to parent fungal lipolytic enzymes, in particular the *H. lanuginosa* lipase enzyme or *H. lanuginosa* lipolytic enzyme variants, due to the different processesing system of the yeast cells as compared to the filamentous fungal cells. Examples of suitable yeast cells for said purpose are cells derived from a strain of Saccharomyces sp., in particular *Saccharomyces cerevisiae*, or a strain of Hansenula sp.

Preferably, the host cell, cultivation conditions and/or recovery conditions are selected so that at the most a partical processing of the pre, pro or prepro-form of the parent enzyme as occurred resulting in that at least 5%, such as at least 10%, such as at least 15%, such as at least 20%, such as at least 25%, such as at least 50%, or at least 75% of the produced modified enzyme molecules comprise the desired, e.g. the entire pre-sequence, or a substantial part thereof.

In an alternative and highly preferred embodiment the peptide addition is designed and applied by means of random mutagenesis according to the following principle:

(a) subjecting a DNA sequence encoding the parent lipolytic enzyme with a peptide addition to localized random mutagenesis in the part of the DNA sequence encoding the peptide addition or a non-structural part of the C-terminal or N-terminal end of the parent enzyme, (b) expressing the mutated DNA sequence obtained in step a) in a host cell, and (c) screening for host cells expressing a mutated lipolytic enzyme which has an improved performance as compared to the parent lipolytic enzyme.

When a first wash lipolytic enzyme is prepared the method involves the further step of d) selecting a mutated lipolytic enzyme among those resulting from step c) which, when present in detergent composition A and/or B with 12500 LU/l detergent, is capable of removing at least 15% more lard from a lard stained swatch, than the same detergent composition without the enzyme, in a one cycle wash assay as disclosed herein.

By this approach a number of highly advantageous peptide additions have been created. The peptide addition present on the DNA sequence to be mutagenized may be constituted by or comprise the prosequence or a part thereof normally associated with the parent lipolytic enzyme or may be any other peptide addition, e.g. one of the peptide additions exemplified above. The localized random mutagenesis may be performed essentially as described in WO 95/22615 (i.e. the mutagenesis is performed under conditions in which only one or more of the above areas are subjected to mutagenesis).

Subsequent to the mutagenesis the mutated DNA is expressed by culturing a suitable host cell carrying the DNA sequence under conditions allowing expression to take place. The host cell used for this purpose may be one which has been transformed with the mutated DNA sequence, optionally present on a vector, or one which carried the DNA sequence encoding the parent enzyme during the mutagenesis treatment. Examples of suitable host cells are given below, and is preferably a host cell which is capable of secreting the mutated enzyme (enabling an easy screening). Yeast cells, such as cells of S. cereviciae, have been found to be suitable host cells.

The screening criteria of step c) will have to be chosen in dependence of the desired properties of the modified lipolytic enzyme. If it is desirable to construct a modified lipolytic enzyme with an improved wash performance the screening is conveniently conducted for a reduced dependency to calcium and/or an improved tolerance towards a detergent or a detergent component. The detergent or detergent component may be any of the specific components mentioned further below in the Detergent Composition section. A preferred detergent component is a non-ionic or an anionic surfactant such as an alcohol ethoxylate or LAS, a preferred detergent is the detergent PCS described in the Materials and Methods section below. Non-ionic surfactants are of particular interest for screening of H. lanuginosa type of lipases (e.g. fungal lipases) whereas anionic surfactants are of interest for screening of Pseudomonas type lipases.

The screening of step c) is conveniently performed by use of a filter assay based on the principle described below in the section entitled "Random Mutagenesis". Also, the type of filter and the detection of enzymatic activity is as described in that section.

It will be understood that the screening criteria used in the filter assay of the invention may be chosen so as to comply with the desired properties or uses of the enzymes to be screened. For instance, in a screening for lipolytic enzymes of particular use in the paper and pulp industry, it may be relevant to screen for an acid enzyme having an increased temperature stability. This may be performed by using a buffer with acidic pH (e.g. pH 4) and/or incubate under higher temperature before or under the assay. For detergent enzymes screening is normally conducted at alkaline pH.

Alternatively, the screening may be performed by isolating the mutated lipolytic enzyme resulting from step b) and testing the wash performance (or any other relevant property) thereof. Also, the latter "in vivo" test may be used in addition to the screening assay so as to identify the best of the mutated lipolytic enzymes selected in the screening assay. Finally, amino acid sequencing of the resulting modified lipolytic enzyme may be used to confirm the amino acid sequence of the peptide addition.

Each of steps a)–d) may be carried out as described in the sections further below entitled "Random mutagenesis" and "Localized Random Mutagenesis".

It is also contemplated, according to the invention, to introduce a mutation in the non-structural part of the C-terminus or N-terminus of the parent enzyme in its mature form, e.g. by deleting or replacing a negatively charged amino acid residue of the non-structural part with a neutral or positively charged amino acid residue or with a hydrophobic amino acid residue, or replacing a neutral amino acid residue with a positively charged amino acid residue.

Parent Lipolytic Enzyme

According to the invention the enzyme of the invention may be any lipolytic enzyme including lipases, phospholipases, esterases and cutinases (according to conventional terminology).

It is to be understood that lipolytic enzymes normally comprising pro- and/or pre-peptides in their unprocessed state as well as enzymes which do not are contemplated to serve as parent enzymes for the modification according to the invention.

The parent lipolytic enzyme to be modified in accordance with the invention may be of any origin. Thus, the enzyme may be of mammalian, plant, vertebrate or any other origin. However, it is presently preferred that the enzyme is of microbial origin in that a number of microbial strains have been found to produce enzymes of particular use for detergent purposes.

More specifically, the parent lipolytic enzyme may be derived from a fungus, i.e. a yeast or a filamentous fungus. For instance, the enzyme may be derived from a filamentous fungus of the class of Plectomycetes, preferably the order of Eurotiales and more preferably the family like Eremascaceae, Monoascaceae, Pseudoeurotiaceae and Trichocomaceae, the latter containing genera like Emericella, Aspergillus, Penicillium, Eupenicillium, Paecilomyces, Talaromyces, Thermoascus and Sclerocleista. More specifically, the parent enzyme may be one which is derivable from a strain of a Humicola sp., e.g. H. brevispora, H. lanuginosa, H. brevis var. thermoidea and H. insolens (U.S. Pat. No. 4,810,414) or WO 96/13580, a strain of a Rhizomucorsp., e.g. Rh. miehei (EP 238023), a strain of a Rhizopus sp., e.g. R. delemar (Hass et al., (1991), Gene 109, 107–113), R. niveus (Kugimiya et al., (1992) Biosci.Biotech. Biochem 56, 716–719) or R. oryzae, a strain of a Candida sp., e.g. C. cylindracea (also called C. rugosa) or C. antarctica (WO 88/02775) or C. antarctica lipase A or B (EP 214 761), a strain of a Fusarium sp., e.g. F. oxysporum (EP 130,064) or F. solani pisi (WO 90/09446) or variants thereof (WO 94/14964), F. solani pisi (GB 2 296 011) a strain of a Venturia spp., e.g. V. inaequalis, a strain of a Colletotrichum spp., e.g. C. gloeosporioides, or C. lagenarium, a strain of Geotricum, e.g., G. candidum (Schimada et al., (1989), J.Biochem., 106, 383–388), a strain of Aspergillus, e.g. A. niger, or an Aspergillus sp. lipolytic enzyme variant (EP 167,309), or a strain of a Penicillium spp., e.g. P. spinulosum or P. camembertii (Yamaguchi et al.,(1991), Gene 103, 61–67).

In the present context, "derivable from" is intended not only to indicate an enzyme produced by a strain of the organism in question, but also an enzyme encoded by a DNA sequence isolated from such strain and produced in a host organism transformed with said DNA sequence. Furthermore, the term is intended to indicate an enzyme which is encoded by a DNA sequence of synthetic and/or cDNA origin and which has the identifying characteristics of the enzyme in question. Finally, the term is intended to embrace variants of the enzyme, e.g. carrying one or more mutations as compared to the naturally occurring enzyme, or homologous enzymes which may be naturally-occurring enzymes produced by other strains or organisms, which, e.g. may be isolated by hybridization to oligonucleotide probes prepared on the basis of the amino acid or DNA sequence of any of the above enzymes (the hybridization conditions involving presoaking in 5×SSC and prehybridizing for 1 h at ~40° C. in a solution of 20% formamide, 5×Denhardt's solution, 50 mM sodium phosphate, pH 6.8, and 50 g of denatured sonicated calf thymus DNA, followed by hybridization in the same solution supplemented with 100 M ATP for 18h at ~40° C., or other methods described by Sambrook et al., 1989) or which is immunologically cross-reactive with said enzymes (e.g. as determined by the method of Hudson et al., 1989).

Of particular interest as a parent lipolytic enzyme is one derivable from a strain of *H. lanuginosa*, e.g., the *H. lanuginosa* strain DSM 4109, e.g. the mature form of the enzyme described in EP 305 216 or a variant thereof as described in WO 92/05249, WO 94/01541, WO 94/14951, WO 94/25577, PCT/DK94/00079 (all from Novo Nordisk A/S), which are hereby incorporated by reference.

Throughout the present application the name *Humicola lanuginosa* has been used to identify one preferred parent enzyme, i.e., the one mentioned immediately above. However, in recent years *H. lanuginosa* has also been termed *Thermomyces lanuginosus* (a species introduced the first time by Tsiklinsky in 1989) since the fungus show morphological and physiological similarity to *Thermomyces lanuginosus*. Accordingly, it will be understood that whenever reference is made to *H. lanuginosa* this term could be replaced by *Thermomyces lanuginosus*. The DNA encoding part of the 18S ribosomal gene from *Thermomyces lanuginosus* (or *H. lanuginosa*) have been sequenced. The resulting 18S sequence was compared to other 18S sequences in the GenBank database and a phylogenetic analysis using parsimony (PAUP, Version3.1.1, Smithsonian Institution, 1993) have also been made. This clearly assigns *Thermomyces lanuginosus* to the class of Plectomycetes, probably to the order of Eurotiales. According to the Entrez Browser at the NCBI (National Center for Biotechnology Information), this relates *Thermomyces lanuginosus* to families like Eremascaceae, Monoascaceae, Pseudoeurotiaceae and Trichocomaceae, the latter containing genera like Emericella, Aspergillus, Penicillium, Eupenicillium, Paecilomyces, Talaromyces. Thermoascus and Sclerocleista.

The parent lipolytic enzyme to be modified in accordance with the present invention may be derivable from a bacterium. For instance, the DNA sequence encoding the parent lipolytic enzyme may be derivable from a strain of Pseudomonas spp., such as *Ps. cepacia, Ps. alcaligenes, Ps. pseudoalcaligens, Ps. mendocina* (also termed *Ps. putida*), *Ps. syringae, Ps. aeroginosa, Ps. wisconsinensis* (WO 96/12012) or *Ps. fragi*, a strain of Bacillus spp., e.g. *B. subtilis* or *B. pumilus* or a strain of Streptomyces sp., e.g. *S. scabies*.

In connection with the Pseudomonas sp. lipases it has been found that lipases from the following organisms have a high degree of homology, such as at least 60% homology, at least 80% homology or at least 90% homology, and thus are contemplated to belong to the same family of lipases: Ps. ATCC 21808, Pseudomonas sp. lipase commercially available as Liposam®, *Ps. aeruginosa* EF2, *Ps. aeruginosa* PAC1R, *Ps. aeruginosa* PAO1, *Ps. aeruginosa* TE3285, Ps. sp. 109, *Ps. pseudoalcaligenes* M1, *Ps. glumae, Ps. cepacia* DSM3959, *Ps. cepacia* M-12–33, Ps. sp.

KWI-56, *Ps. putida* IFO3458, *Ps. putida* IFO12049 (Gilbert, E. J., (1993), Pseudomonas lipases: Biochemical properties and molecular cloning. Enzyme Microb. Technol., 15, 634–645). The species *Pseudomonas cepacia* has recently been reclassified as *Burkholderia cepacia*, but is termed *Ps. cepacia* in the present application.

Specific examples hereof include a Pseudomonas lipolytic enzyme, e.g. *Ps. fragi, Ps. stutzeri, Ps. cepacia* and *Ps. fluorescens* (WO 89/04361), or *Ps. plantarii* or *Ps. gladioli* (U.S. Pat. No. 4,950,417) or *Ps. alcaligenes* and *Ps. pseudoalcaligenes* (EP 218 272, EP 331 376, or WO 94/25578 (disclosing variants of the *Ps. pseudoalcaligenes* lipolytic enzyme with the mutation M21S, M21L or M21A), the Pseudomonas sp. variants disclosed in EP 407 225, or a Pseudomonas sp. lipolytic enzyme, such as the *Ps. mendocina* lipolytic enzyme described in WO 88/09367 and U.S. Pat. No. 5,389,536 or variants thereof as described in U.S. Pat. No. 5,352,594, Other specific examples include a Bacillus lipolytic enzyme, such as the lipolytic enzyme from *B. subtilis* (Dartois et al., (1993) Biochemica et Biophysica acta 1131, 253–260) or *B. stearothermophilus* (JP 64/7744992) or*B. pumilus* (WO 91/16422) and a Chromobactenum lipolytic enzyme (especially one derivable from *C. viscosum*).

Specific examples of readily available commercial lipolytic enzyme which may serve as parent lipolytic enzymes according to the invention include Lipolase®, Lipolase® Ultra (available from Novo Nordisk A/S).

Examples of other lipolytic enzymes specifically contemplated to be modifiable according to the invention are Lumafast®, i.e. a *Ps. mendocina* lipolytic enzyme and Lipomax®, i.e. a *Ps. alcaligenes* lipolytic enzyme, a *Fusarium solani* lipase (cutinase) from Unilever, a Bacillus sp. lipase from Solvay enzymes (U.S. Pat. No. 5427936, EP 528828); and Liposam®, (a *Ps. mendocina* lipase from Showa Denko) and further the Pseudomonas sp. lipase described in WO 95/06720 which have been sequenced and found to have the amino acid sequence shown in SEQ ID NO:91.

It is to be emphasized that the parent lipolytic enzyme to be modified according to the invention may be any of the above mentioned lipolytic enzymes and any variant, modification, or truncation thereof. Examples of such parent enzymes which are specifically contemplated include the enzymes described in WO92/05249, WO 94/01541, WO 94/14951, WO 94/25577, WO 95/22615 and a protein engineered lipase variants as described in EP 407 225; a protein engineered *Ps. mendocina* lipase as described in U.S. Pat. No. 5,352,594; a cutinase variant as described in WO 94/14964; a variant of an Aspergillus lipolytic enzyme as described in EP patent 167,309; and Pseudomonas sp. lipase described in WO 95/06720.

In the most preferred embodiment the parent enzyme is derived from a strain of a Humicola sp. or or from a strain of a Pseudomonas sp. or a genus considered to belong to the Pseudomonas family.

In a specific embodiment of the invention the DNA sequence encoding the parent enzyme with lipolytic activity (to be processed into a modified or first wash lipolytic enzyme of the invention) is the DNA sequence encoding the enzyme with lipolytic activity derived from the filamentous fungi *Humicola lanuginosa* described in EP 305 216. The amino acid sequence of the parent enzyme is in this case that of the secreted mature enzyme.

It is presently contemplated that the washing performance and/or thermostability of the modified enzyme of the invention may be further improved if the enzyme is glycosylated. Accordingly, in an embodiment of the invention the modified enzyme may be glycosylated. The amino acid sequence may have any degree of glycosylation.

Specific First Wash *H. lanuginosa* Lipolytic Enzyme Variants

For ease of reference specific variants of the invention are described by use of the following nomenclature: Original amino acid(s):position(s):substituted amino acid(s)

According to this nomenclature, for instance the replacement of aspartic acid by valine in position 96 is shown as:

Asp 96 Val or D96V a deletion of aspartic acid in the same position is shown as:

Asp 96* or D96* and insertion of an additional amino acid residue such as lysine is shown as:

Asp 96 ValLys or D96VK

Multiple mutations are separated by pluses, i.e.:

Asp 96 Val+Glu 87 Lys or D96V+E87K representing mutations in positions 96 and 87 replacing aspartic acid and glutamic acid by valine and lysine, respectively.

When one or more alternative amino acid residues may be inserted in a given position it is indicated as D96V,N or D96V or D96N.

Furthermore, when a position suitable for modification is identified herein without any specific modification being suggested, it is to be understood that any amino acid residue may be substituted for the amino acid residue present in the position. Thus, for instance, when a modification of an aspartic acid in position 96 is mentioned, but not specified, it is to be understood that the aspartic acid may be deleted or replaced by any other amino acid, i.e. any one of R,N,A,C,Q,E,G,H,I,L,K,M,F,P,S,T,W,Y,V, or a further amino acid residue inserted at that position.

Finally, when a mutation of the parent *H. lanuginosa* lipolytic enzyme is identified herein, it is intended to be understood to include a mutation of an amino acid residue occupying a homologous position in a lipolytic enzyme which has substantially the same structure as or a structure or amino acid sequence which can be aligned with that of the *H. lanuginosa* enzyme (e.g. *Rhizopus oryzae*, *Rhizomucor miehei*, *Absidia* sp. and *Penicillium camembertii* lipolytic enzymes mentioned herein). The homologous position can easily be identified by comparison between the structures.

The first wash *H. lanuginosa* lipolytic enzyme variants may be characterized by being a combination of at least two different parent variants which indvidually have been found or indicated to have a good wash performance or otherwise interesting properties as described above. The good wash performance may e.g. be determined as described in Example 13. The combination between the parent variants may be random or specific. In connection with the present invention it has been found that particularly interesting results are obtained when the parent variants to be combined contains a mutation in at least one, but preferably more of the following positions: 1, 2, 3, 4, 5, 19, 49, 53, 56, 57, 59, 62, 83, 85, 90, 94, 96, 97, 99, 101, 102, 111, 116, 126, 127, 137, 167, 170, 181, 187, 210, 221, 225, 234, 239, 249, 252 256, 263, 264, 267, such as at least one or preferably more of the following mutations:

E1K, E1S, V2G, S3T, Q4P, D5E, A19T, A49P, Y53C, E56K, D57G, G59V, D62R, S83T, S85F, I90F, N94K, F95L, D96A, D96H, D96L, L97M, E99K, N101S, D102Y, D111N, S116P, Q126R, K127C, D137G, D167G, S170P, F181L, V187A, E210K, E210V, W221L, W221A, G225P, D234R, D234Y, E239C, Q249R, I252L, P256T, G263A, L264Q, T267R. It will be understood that the above mutations or mutated positions may be present on the same parent lipolytic enzyme, but preferably on various of the different parent lipolytic enzymes to be combined.

In particular, it has been found that a first wash *H. lanuginosa* lipolytic enzyme of the invention may be a combination of at least two of the following parent *H. lanuginosa* lipolytic enzyme variants or parts of these variants:

(a) E56R+D57L+I90F+D96L+E99K
(b) E56R+D57L+V60M+D62N+S83T+D96P+D102E
(c) D57G+N94K+D96L+L97M
(d) E87K+G91A+D96R+I100V+E129K+K237M+I252L+P256T+G263A+L264Q
(e) E56R+D57G+S58F+D62C+T64R+E87G+G91A+F95L+D96P+K98I
(f) E210K
(g) S83T+N94K+D96N
(h) E87K+D96V
(i) N94K+D96A
(j) E87K+G91A+D96A
(k) D167G+E210V
(l) S83T+G91A+Q249R
(m) E87K+G91A
(n) S83T+E87K+G91A+N94K+D96N+D111N
(o) N73D+E87K+G91A+N94I+D96G
(p) L67P+I76V+S83T+E87N+I90N+G91 A+D96A+K98R
(q) S83T+E87K+G91A+N92H+N94K+D96M
(s) S85P+E87K+G91A+D96L+L97V
(t) E87K+I90N+G91A+N94S+D96N+I100T
(u) I34V+S54P+F80L+S85T+D96G+R108W+G109V+D111G+S116P+L124S+V132M+V140Q+V141A+F142S+H145R+N162T+I166V+F181P+F183S+R205G+A243T+D254G+F262L,
(v) N94K, D96A, Q249R,
(w) E87K, G91A, D96W, D102N.

Methods suitable for combining different parent variants are described below in the section in entitled "Combination of DNA sequences encoding lipolytic enzymes". A particular suitable method is the one described in Materials and Methods section herein.

In another embodiment the first wash lipolytic enzyme of the invention is a variant of the *H. lanuginosa* lipolytic enzyme (the amino acid sequence of which is shown in SEQ ID No. 15) which comprises a mutation in at least one, but preferably more of the following positions: 1, 2, 3, 4, 5, 19, 49, 53, 56, 57, 59, 62, 83, 85, 90, 94, 96, 97, 99, 101, 102, 111, 116, 126, 127, 137, 167, 170, 181, 187, 210, 221, 225, 234, 239, 249, 252 256, 263, 264, 267, such as at least one or preferably more of the following mutations, E1K, E1S, V2G, S3T, Q4P, D5E, A19T, A49P, Y53C, E56K, D57G, G59V, D62R, S83T, S85F, I90F, N94K, F95L, D96A, D96H, D96L, L97M, E99K, N101S, D102Y, D111N, S116P, Q126R, K127C, D137G, D167G, S170P, F181L, V187A, E210K, E210V, W221L, W221A, G225P, D234R, D234Y, E239C, Q249R, I252L, P256T, G263A, L264Q, T267R.

In a more specific embodiment the first wash lipolytic enzyme of the invention is a variant of the *H. lanuginosa* lipolytic enzyme (the amino acid sequence of which is shown in SEQ ID No. 15), in which at least one of the following amino acid residues has been replaced with another amino acid residue:

A49, G59, S85, I90, S116, Q126, D137, S170 or W221.

Although the above identified amino acid residues may be replaced by any other of the 19 possible amino acid residues it is preferred that the amino acid residue is replaced as follows:

A49P, G59V, S85F, I90F, S116P, Q126R, D137G, S170P or W221L or by an amino acid residue belonging to the same charge group (cf the definition below) as that of the inserted amino acid residue, e.g. A49T instead of A49P. If a negatively charged amino acid residue is replaced, e.g. D137, it is preferred that it is replaced by an amino acid residue belonging to the positive charge group or the neutral group, e.g. D137G,N,K, as defined below:

Negative charge group: D,E
Positive charge group: K,R,H
Neutral group: I,C,S,T,P,W,M,G,A,P,N,Y,Q,L,V.

It is contemplated that a variant comprising a mutation in the following positions is capable of exhibiting first wash activity or improved wash performance:

D57X+N94(K or R)+D96X+L97X+Q249(K or R)
N94(K or R)+D96X+L97X+Q249(K or R)
N94(K or R)+D96X+Q249(K or R)
D137X+D167X+E210X+W221X
D137X+D167X+E210X
I90X+D96X+E99X+V187X
I90X+D96X+E99X
I90(F or W or Y)+D96X+E99X
E56X+D57X+D62X+S85X+D96X+D102X+E210X
N94(K or R)+F95L+D96X+D234X, in which X, may be any amino acid residue and may be identical, pairwise identical or different.

In one embodiment, a first wash H. lanuginosa lipolytic enzyme variant of the invention may comprise one of the following sets of mutations:

D57G+N94K+D96L+Q249R
D57G+N94K+D96L+S116P+Q249R
D57G+G59V+N94K+D96L+Q249R
D57G+N94K+D96L+S116P+S170P+Q249R
D57G+G59V+N94K+D96L+S170P+Q249R
D57G+N94K+D96L+S170P+Q249R
D167G+E210V+Q249R
E56K+D167G+E210V
D137G+D167G+E210V+Q249R
D167G+E210V+W221L+Q249R
D57G+N94K+F95L+D96H,L+Q249R
D57G+N94K+D96L+E210K
D57G+G59V+N94K+D96L+S116P+S170P+Q249R
S3R+D137G+D167G+E210V+W221L
D137G+D167G+E210V+W221L+N233R
S3R+I90F+D96L+E99K+V187A+Q249R
I90F+D96L+E99K+V187A+D233R
I90F+D96L+E99K+V187A+D234Y
I90F+D96L+E99K+V187A+T231R
I90F+D96L+E99K+V187A
D62R+I90F+D96L+E99K+V187A
I90F+D96L+E99K+V187A+N200R+R209A
I90F+D96L+E99K+V187A+T199R+N200R+R209A
D57G+D62R+N94K+D96L+Q249R
D57G+N94K+D96L+N200R+R209A+Q249R
D57G+N94K+D96L+T199R+N200R+Q249R
I90F+D96L+E99K+V187A+T199R
D57G+N94K+D96L+T199R+R209A+Q249R
I90F+D96L+E99K+V187A+Q249R
I90F+D96L+E99K+V187A+P253R
I90F+D96L+E99k+D137G+D167G+V187A+Q249R
I90F+D96L+E99K+D137G+V187A+Q249R
D96L+E99K+V187A+Q249R
V2P+N94K+D96L+Q249R
V2W+S3R+N94K+D96L+Q249R
V2R+S3R+N94K+D96L+Q249R
V2R+S3R+N94K+D96L+Q249R
V2R+S3W+N94K+D96L+Q249R
V2W+S3R+N94K+D96L+Q249R
N94K+D96L+Q249R
V2G+S3T+D57G+N94K+D96L+L97M+Q249R
V2G+S3T+Q4P+D5E+D57G+N94K+D96L+L97M+Q249R
V2G+D5Q+L6M+D57G+N94K+D96L+L97M+Q249R

The following variants are of particular interest:

D57G+G59V+N94K+D96L+L97M+S116P+S170P+Q249R
A49P+D167G+E210V
E56K+D57G+D62R+S83T+S85F+D96L+D102Y+E210K
D57G+N94K+D96L+L97M+Q249R
D137G+D167G+E210V+W221L
N94K+F95L+D96H+N101S+F181L+D234Y+I252L+P256T+G263A+L264Q
I90F+D96L+E99K+V187A
N94K+D96A+Q249R
A19P+D167G+E210V+W221L
N94K+D96L+L97M+Q249R
D57G+N94K+D96L+Q249R
I90F+D96L+E99K+D137G+V187A
N94K+D96L+E99K+Q249R
N94K+D96L+E99K+T231R+N233R+D234R+Q249R
N94K+D96L+E99K+D111N+F211A+G225P+Q249R+T267R
N94K+D96L+E99K+D111N+F211A+G225P+T231R+N233R+D234R+Q249R+T267R
E1K+N94K+D96L+E99K+Q249R
N94K+D96L+K223R+Q249R
N94K+D96L+E99K+N233R
N94K+D96L+E99K+T231R+N233R+Q249R
N94K+D96L+E99K+N233R+Q249R
N94K+D96L+E99K+D234R+Q249R

The variant of the invention may advantageously comprise an additional mutation in position E1, the mutation being a deletion of E1 or a replacement of E by any other amino acid residue, in particular P or S.

In addition the above specific variants may comprise any of the N-terminal or C-terminal peptide extensions discussed herein (in particular in the section entitled "Peptide Additions"), specific examples of which are SPIRR (SEQ ID NO:29), TAIRPRK (SEQ ID NO:46), SPIRPRP(SEQ ID NO:31), SPPRRP (SEQ ID NO:35), RP, GPIRPRP (SEQ ID NO:48), SRSRHNA (SEQ ID NO:50), SALRPRK (SEQ ID NO:87), STRRPRP (SEQ ID NO:47), SPRRPRT (SEQ ID NO:33), APPPRPRPLLPIS (SEQ ID NO:89), SPIRK (SEQ ID NO: 22), SPPRPRP (SEQ ID NO:152), WP, SPPPRPRP (SEQ ID NO:64), SPIRRP (SEQ ID NO:24), APPPRPRPRPR (SEQ ID NO:60) or SPIRPR (SEQ ID NO:31). An N-terminal extension is e.g. applied to the amino acid residue E1 of the mature parent lipase or is applied to amino acid residue 2–20, such as 2, 3,4 or 5 of the mature parent enzyme, the residue E1 (and optionally more amino acid residues of the non-structural part of the parent enzyme, e.g. amino acid residues within the 2–20 N-terminal part of the mature parent enzyme) being deleted. In addition, the peptide addition may be applied so that the one or more of the last amino acid residues of the peptide extensions mentioned herein replaces the amino acid residue(s) of the mature parent enzyme occupying position 1, and optionally 2 and further positions. For instance, the peptide extension "SPPRRP" (SEQ ID NO:35) may be applied by substituting E1 of the mature parent *H. lanuginosa* lipase with the last "P" of the peptide addition and substituting the wildtype propeptide "SPIRR" (SEQ ID NO:29) with "SPPRR" (SEQ ID NO:25).

When no replacements are to be performed in the N-terminal part of the mature parent enzyme, the N-terminal addition may be applied either as a result of the variants having been expressed in S. cerevisiae (if the N-terminal extension is identical to (a part of) the propeptide of the parent enzyme, or more preferably by the relevant modification of the part of the DNA sequence encoding the parent enzyme, which encodes the (pre)pro sequence or another sequence downstream of the codon encoding amino acid residue 1 of the mature parent enzyme.

The presently most preferred variants of the inventions include:

SPIRPRP(SEQ ID NO:31)+D57G+N94K+D96L+Q249R

SPPRRP(SEQ ID NO:35)+I90F+D96L+E99K+D137G+V187A

SPIRPRP(SEQ ID NO:31)+N94K+D96L+L97M+Q249R

SPPPRPRP(SEQ ID NO:64)+N94K+D96L+L97M+Q249R

SPIRPRP(SEQ ID NO:31)+D57G+N94K+D96L+L97M+Q249R

SPPRRP(SEQ ID NO:35)+I90F+D96L+E99K+V187A

SPIRPRP(SEQ ID NO:31)+D137G+D167G+E21V+W221L

E1SPIRPRP(SEQ ID NO:31)+I90F+D96L+E99K+V187A

E1SRKRKRK(SEQ ID NO:146)+I90F+D96L+E99K+V187A

E1SPRIKPRIK (SEQ ID NO:147)+I90F+D96L+E99K+V187A

E1SPPRRP(SEQ ID NO:35)+D62R+I90F+D96L+E99K+V187A

E1SPPRRP(SEQ ID NO:35)+I90F+D96L+E99K+V187A+N200R+R209A

E1SPPRRP(SEQ ID NO:35)+I90F+D96L+E99K+V187A+T199R+N200R+R209A

E1SPIRPRP(SEQ ID NO:31)+D57G+D62R+N94K+D96L+Q249R

E1SPIRPRP(SEQ ID NO:31)+D57G+N94K+D96L+N200R+R209A+Q249R

E1 SPIRPRP(SEQ ID NO:31)+D57G+N94K+D96L+T199R+N200R+Q249R

E1SPPRRP(SEQ ID NO:35)+I90F+D96L+E99K+V187A+T199R

E1SPIRPRP(SEQ ID NO:31)+D57G+N94K+D96L+T199R+R209A+Q249R

E1SPIRPRP(SEQ ID NO:31)+I90F+D96L+E99K+V187A+Q249R

E1SPPRRP(SEQ ID NO:35)+I90F+D96L+E99K+V187A+P253R

E1SPPRRP(SEQ ID NO:35)+I90F+D96L+E99K+D137G+D167G+V187A+Q249R

E1SPPRRP(SEQ ID NO:35)+I90F+D96L+E99K+D137G+V187A+Q249R

E1SPPRRP(SEQ ID NO:35)+D96L+E99K+V187A+Q249R

E1SPPRPR(SEQ ID NO:38)+V2P+N94K+D96L+Q249R

E1SPPWWP(SEQ ID NO:39)+V2W+S3R+N94K+D96L+Q249R

E1SPPWRP(SEQ ID NO:40)+V2R+S3R+N94K+D96L+Q249R

E1SPPRWP(SEQ ID NO:41)+V2R+S3R+N94K+D96L+Q249R

E1SPPWWP(SEQ ID NO:39)+V2R+S3W+N94K+D96L+Q249R

E1SPPRWP(SEQ ID NO:41)+V2W+S3R+N94K+D96L+Q249R

E1SPPRWP(SEQ ID NO:41)+V2R+S3W+N94K+D96L+Q249R

E1SPPRWP(SEQ ID NO:41)+N94K+D96L+Q249R

E1SPPRRP(SEQ ID NO:35)+N94K+D96L+Q249R

E1APPPRPRPRPRP(SEQ ID NO:60)+V2G+S3T+D57G+N94K+D96L+L97M+Q249R

E1APPPRTRPRPRS(SEQ ID NO:61)+V2G+S3T+Q4P+D5E+D57G+N94K+D96L+L97M+Q249R

E1 APPPKASPRQRP(SEQ ID NO:67)+V2G+D5Q+L6M+D57G+N94K+D96L+L97M+Q249R

SCIRR(SEQ ID NO:30)+N94K+D96L+E239C+Q249R

E1SPPRRP(SEQ ID NO:35)+D57G+N94K+D96L+Y53C+K127C+Q249R

E1SPPRRPR(SEQ ID NO:148)+V2R+S3P+N94K+D96L+Q249R

E1SPPWPRP(SEQ ID NO:76)+V2R+S3P+N94K+D96L+Q249R

E1SPPRRP(SEQ ID NO:35)+N94K+D96L+E99K

E1SPPRRP(SEQ ID NO:35)+N94K+D96L+E99K+Q249R

E1SPPCGRRP(SEQ ID NO:149)+N94K+D96L+E239C+Q249R

E1SPCRPRP(SEQ ID NO: 150)+N94K+D96L+E239C+Q249R

SPPCRRRP(SEQ ID NO:151)+N94K+D96L+E239C+Q249R or is one of the variants disclosed in the Examples hereinafter. When an N-terminal extension is present in the above specified variants the nomenclature "E1 . . . " is intended to indicate that the E in position 1 has been replaced by the last amino acid residue of the peptide addition listed after "E1", the remaining residues having been fused to the amino acid residue occupying position 1, For instance, "E1SPPEQP" is intended to indicate that amino acid residue E1 has been replaced by "P" and that the remaining residues "SPPEQ" have been fused to E1P. In practice, such variants are conveniently constructed by replacing amino acid residues (−5)–(−1) of the unprocessed parent enzyme with the relevant amino acid residues of the peptide extension and replacing E1 with the relevant amino acid residue, the replacements being performed by introducing the relevant mutations in the corresponding DNA sequence, and subsequently produce the resulting variant in an expression system allowing at least a portion of the expressed variants to maintain their N-terminal extension (as is further disclosed herein). Where no replacements of E1 are indicated the N-terminal peptide addition is simply fused to the amino acid residue occupying position 1 of the mature parent enzyme.

The above variants have initially been constructed using the random mutagenesis and/or gene shuffling methods of the invention and subsequently characterized with respect to the thereby introduced mutations. It will be apparent that an alternative method of constructing these variants would be based on site-directed mutagenesis using suitable oligonucleotide probes in accordance with methods known in the art.

It is contemplated that the good washing performance/first wash activity will be maintained when one of the above specific individual mutations is replaced by a mutation to an amino acid residue belonging to the same charge group as the above suggested mutation. For instance, the mutation N94K may be replaced by N94R, H, the "G" in mutation D137G or D167G maybe replaced by one of the other amino acid residues belonging to the neutral group, etc. Furthermore, it may be advantageous to replace an amino acid residue of the neutral group with one belonging to the positive charge group, e.g. the "G" in D137G and D167G, respectively, may be replaced with a K, R or H resulting in the mutations D137K,R,H and D167K, R,H, respectively.

As already mentioned the *H. lanuginosa* lipolytic enzyme is structurally closely related to other lipolytic enzymes such as those derivable from *Rhizomucor miehei, Penicillium camembertii*, Absidia sp. and the various Rhizopus sp. disclosed herein. Accordingly, it is believed that modifications corresponding to those mentioned above in *H. lanuginosa* lipase and introduced into homologous positions in other structurally related lipolytic enzyme will also be functional with respect to the first wash performance. Accordingly, in a further aspect the invention relates to a first wash variant of a parent lipolytic enzyme which has an amino acid sequence or a three-dimensional structure which can be aligned with the *H. lanuginosa* lipase amino acid sequence or structure (with e.g. at least 20% sequence identity allowing gaps or an overall protein similarity of at least 50%, such as at leas 60% or 70% using the UWGGG GAP programme or a "structural" similarity), the amino acid sequence of which has been modified so as to introduce mutations corresponding to those of the *H. lanuginosa* lipase mentioned above and/or to introduce amino acid residues found in the wildtype *H. lanuginsa* lipase into the parent lipolytic enzyme in question. The amino acid residues or positions to be modified in the structurally or sequence homologous lipases may be identified from an alignment of the relevant structure/sequence with that of the *H. lanuginosa* lipase. Such variants may be constructed by a method of constructing a first wash lipolytic enzyme variant prepared from a parent lipolytic enzyme exhibiting structural and/or sequence homology to the *H. lanuginosa* lipase (such lipolytic enzymes being identified above), which method comprises aligning the sequence of the parent enzyme in question with that of the *H. lanuginosa* lipase or a first wash variant thereof or superimposing the structure of the parent enzyme in question with that of the *H. lanuginosa* lipase or variant, identifying the position(s) in the parent enzyme which are homologous to position(s) of the *H. lanuginosa* lipase or variant believed to be essential for achieving first wash activity (cf the mutations disclosed above), and replacing the amino acid residue occupying the relevant position (s) according to t, and producing the resulting variant enzyme.

Cloning a DNA Sequence Encoding a Parent Lipolytic Enzyme

The DNA sequence encoding a parent lipolytic enzyme from which a modified or a first wash lipolytic enzyme is created in accordance with the present invention may be isolated from any cell or microorganism producing the parent enzyme in question by use of methods known in the art.

For instance, the DNA sequence may be isolated by establishing a cDNA or genomic library from an organism expected to harbour the sequence, and screening for positive clones by conventional procedures. Examples of such procedures are hybridization to oligonucleotide probes prepared on the basis of the amino acid or DNA sequence of the parent enzyme (if sequence information is available) or of a related lipolytic enzyme (if sequence information as to the parent enzyme is not available) in accordance with standard techniques (cf. Sambrook et al., 1989), and/or selection for clones expressing lipolytic activity, and/or selection for clones producing a protein which is reactive with an antibody raised against a parent lipolytic enzyme. For instance, the DNA sequence may be isolated from a genomic or DNA library prepared from the relevant organism or may be obtained by expression cloning, e.g. as described in WO 93/11249.

A preferred method of isolating a DNA sequence encoding a parent lipolytic enzyme to be modified in accordance with the invention from a cDNA or genomic library is by use of polymerase chain reaction (PCR) using degenerate oligonucleotide probes prepared on the basis of DNA or amino acid sequence of the parent enzyme. For instance, the PCR may be carried out using the techniques described in U.S. Pat. No. 4,683,202 or by R. K. Saiki et al. (1988).

Alternatively, the DNA sequence encoding the parent enzyme may be prepared synthetically by established standard methods, e.g. the phosphoamidite method described by Beaucage and Caruthers (1981), or the method described by Matthes et al. (1984). According to the phosphoamidite method, oligonucleotides are synthesized, e.g. in an automatic DNA synthesizer, purified, annealed, ligated and cloned in appropriate vectors.

Finally, the DNA sequence encoding the parent enzyme may be prepared from DNA of mixed genomic and synthetic, mixed synthetic and cDNA or mixed genomic and cDNA origin prepared by ligating fragments of synthetic, genomic or cDNA origin (as appropriate), the fragments corresponding to various parts of the entire DNA sequence encoding the parent enzyme, in accordance with standard techniques.

Methods of Constructing of First Wash Lipolytic Enzyme Variants

As will be apparent from the brief description of the invention the present inventors have developed a very efficient method for creating lipolytic enzymes capable of removing a substantial amount of fatty matter during a one wash cycle assay as described herein.

Thus, in one highly preferred embodiment the first wash lipolytic enzyme of the invention is a variant of a naturally-occurring parent lipolytic enzyme which is the result of a process comprising at least the following steps:

(a) expressing a variety of mutated DNA sequences originating from a parent lipolytic enzyme in suitable host cells;

(b) screening for host cells expressing a mutated lipolytic enzyme which has a decreased dependence on calcium and/or an improved tolerance towards a detergent or a detergent component as compared to the parent lipolytic enzyme; and (c) selecting a mutated lipolytic enzyme among those resulting from step (b) which, when present in detergent composition A or B in a concentration of 12500 LU/l, is capable of removing at least 15% more lard from a lard stained swatch, than the same detergent composition without the enzyme, in a one cycle wash assay as described herein.

The variety of mutated DNA sequences referred to in step (a) may conveniently be obtained by subjecting a DNA sequence encoding the parent lipolytic enzyme to mutagenesis to form mutated DNA sequences. Although the mutagenesis may be performed by any suitable method, such as by site-directed mutagenesis, it is presently preferred that the mutagenesis is carried out as a random mutagenesis. Thus, by use of random mutagenesis it is possible to create a much higher number of mutated DNA sequences than would be possible by use of site-directed mutagenesis. The random mutagenesis is explained in further detail below in the section entitled "Random mutagenesis". In that section it is also described how one or more of the steps (a)–(c) of the method may be repeated one or more times in order to make successive improvements. For instance, the mutated lipolytic enzyme selected from the first round of steps (a)–(c) is subjected to a second round of the method in which the screening step (b) involves selection at more stringent conditions than those used in the screening step (b) of the first round thereby selecting for mutated lipolytic enzymes which has a decreased calcium dependence and/or an improved tolerance towards a detergent or a detergent component as compared to the mutated lipolytic enzyme resulting from the first round.

Random Mutagenesis

The random mutagenesis of the DNA sequence encoding the parent lipolytic enzyme (or the peptide addition) to be performed in accordance with step a) of the above methods (cf the sections "Methods of applying a peptide addition to a parent lipolytic enzyme" and "Methods of constructing of first wash lipolytic enzymes") may conveniently be performed by use of any method known in the art.

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents.

The mutagenizing agent may, e.g., be one which induces transitions, transversions, inversions, scrambling, deletions, and/or insertions.

Examples of a physical or chemical mutagenizing agent suitable for the present purpose includes ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, gamma irradiation, 1-methyl-3-nitro-1-nitrosoguanidine (NTG), and nucleotide analogues.

When such agents are used the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions wanted to be changed. The doping or spiking may be done so that codons for unwanted amino acids are avoided by lowering the amount of or completely avoiding the nucleotides resulting in these codons. State of the art knowledge and computer programs can be used for calculating the most optimal nucleotide mixture for a given amino acid preference. The doped or spiked oligonucleotide can be incorporated into the DNA encoding the lipolytic enzyme by any published technique using e.g. PCR, LCR or any DNA polymerase and ligase.

When PCR generated mutagenesis is used either a chemically treated or non-treated gene encoding a parent lipolytic enzyme is subjected to PCR under conditions that increases the misincorporation of nucleotides (Deshler 1992, Leung et al. 1989).

A mutator strain of *E. coli* (Fowler et al. 1974), *S. cerevisiae* or any other microbial organism may be used for the random mutagenesis of the DNA encoding the lipolytic enzyme by e.g. transforming a plasmid containing the parent enzyme into the mutator strain, growing the mutator strain with the plasmid and isolating the mutated plasmid from the mutator strain. The mutated plasmid may subsequently be transformed into the expression organism.

The DNA sequence to be mutagenized may conveniently be present in a genomic or cDNA library prepared from an organism expressing the parent lipolytic enzyme. Alternatively, the DNA sequence may be present on a suitable vector such as a plasmid or a bacteriophage, which as such may be incubated with or otherwise exposed to the mutagenizing agent. The DNA to be mutagenized may also be present in a host cell either by being integrated in the genome of said cell or by being present on a vector harboured in the cell. Finally, the DNA to be mutagenized may be in isolated form. The DNA sequence to be subjected to random mutagenesis is preferably a cDNA or a genomic DNA sequence.

In some cases it may be convenient to amplify the mutated DNA sequence prior to the expression or screening being performed. Such amplification may be performed in accordance with methods known in the art, the presently preferred method being PCR generated amplification using oligonucleotide primers prepared on the basis of the DNA or amino acid sequence of the parent enzyme.

Subsequent to the incubation with or exposure to the mutagenizing agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which carried the DNA sequence encoding the parent enzyme during the mutagenesis treatment. Examples of suitable host cells are given below. It is particularly preferred to use a yeast cell as a host cell, in particular when the parent lipolytic enzyme is derived from a fungus such as a filamentous fungus or yeast. The mutated DNA sequence may further comprise a DNA sequence encoding functions permitting expression of the mutated DNA sequence.

It will be understood that the screening criteria mentioned in step (c) ("Methods of applying a peptide addition to a parent lipolytic enzyme") and (b) ("Methods of constructing first wash lipolytic enzymes") of the method of the invention have been carefully selected. Thus, without being limited to any theory the screening for a decreased dependency on calcium at alkaline pH (pH above 7) is believed to result in variants having an over-all improved performance in that the requirement for calcium may be considered a limiting factor for optimal activity, in particular under most wash conditions which are caracterized by the fact that the concentration of free calcium ions is deliberately lowered by chelating agents in the detergent matrix (builders).

The detergent or detergent component towards which the variant has improved tolerance may be of any type, e.g. as further described below. Preferably, the detergent component is a non-ionic, anionic, cationic, zwitterionic or amphoteric surfactant. Examples of non-ionic surfactants include an alcohol ethoxylate, examples of anionic surfactants include LAS, alkyl sulphate, alcohol ethoxy sulphate and the like. The choice of detergent will, e.g., depend on the inherent weakness (in relation to detergent tolerances) of the parent lipolytic enzyme.

In relation *Humicola lanuginosa* lipolytic enzymes and homologous enzymes (such as the Penicillium, Rhizomucor, Rhizopus and Absidia sp. lipolytic enzymes), it is contemplated that an improved tolerance towards a non-ionic surfactant alcohol ethoxylate, a commercially available example of which is Dobanol® 25-7, may be indicative of improved wash performance. In relation to Pseudomonas type lipolytic enzymes such as *P. pseudoalcaligenes, P. cepacia*, it is contemplated that an improved tolerance towards an anionic surfactant such as an alkyl sulphate (a commerically available example of which is NEODOL 45) or LAS (a commercially available example of which is Nansa 1169/P) may be indicative of improved wash performance.

The screening of step (c) ("Methods of applying a peptide addition to a parent lipolytic enzyme") or (b) ("Methods of constructing first wash lipolytic enzymes") is conveniently performed by use of a filter assay based on the following principle:

A microorganism capable of expressing the mutated lipolytic enzyme of interest is incubated on a suitable medium and under suitable conditions for the enzyme to be secreted, the medium being provided with a double filter comprising a first protein-binding filter and on top of that a second filter exhibiting a low protein binding capability. The microorganism is located on the second filter. Subsequent to the incubation, the first filter comprising enzymes secreted from the microorganisms is separated from the second filter comprising the microorganisms. The first filter is subjected to screening for the desired enzymatic activity and the corresponding microbial colonies present on the second filter are identified.

Alternatively, the second filter carrying the colonies may be used directly on the screening plate. This makes it easier to pick the right colonies and in some cases gives a stronger signal. And using only one filter, either protein binding or none-protein binding is sufficient in many cases.

The filter used for binding the enzymatic activity may be any protein binding filter e.g. nylon or nitrocellulose. The topfilter carrying the colonies of the expression organism may be any filter that has no or low affinity for binding proteins e.g. cellulose acetate or Durapore™. The filter may be pretreated with any of the conditions to be used for screening or may be treated during the detection of enzymatic activity.

The enzymatic activity may be detected by a dye, fluorescence, precipitation, pH indicator, IR-absorbance or any other known technique for detection of enzymatic activity.

The detecting compound may be immobilized by any immobilizing agent e.g. agarose, agar, gelatine, polyacrylamide, starch, filter paper, cloth; or any combination of immobilizing agents.

Lipolytic activity may be detected by Brilliant green, Rhodamine B or Sudan Black in combination with a lipid e.g. olive oil or lard. The screening criteria for identifying variants of parent lipolytic enzymes having improved washing performance may be e.g. EGTA, EDTA, non-ionic and/or anionic tensides, alkaline pH, or any detergent composition in combination with one of the above detectors of enzymatic activity.

Subsequent to the screening in step (c) ("Methods of applying a peptide addition to a parent lipolytic enzyme") or (b) ("Methods of constructing first wash lipolytic enzymes") lipolytic enzymes having desired properties (i.e. as defined by the screening criteria) are isolated and their first wash capability tested in the one cycle wash assay described in the Materials and Methods section herein.

If the first wash activity of the enzyme is not sufficiently good after one round of the above treatment, the enzyme may be modified, e.g. by site-directed or random mutagenesis in order to improve the first wash activity of the enzyme, e.g. in accordance with any of the principles given further above for modifacation of lipases to achieve a first wash performance.

Most conveniently, the host cells produced in step (c) ("Methods of applying a peptide addition to a parent lipolytic enzyme") or (b) ("Methods of constructing first wash lipolytic enzymes") are subjected to further rounds of mutagenesis as defined in steps (a)–(b) and optionally (c) (for the method outlined in "Methods of applying a peptide addition to a parent lipolytic enzyme") above, conveniently by using more stringent selection criteria than employed in a previous mutagenesis treatment. The further round(s) of mutagenesis may be random, localized random or site-directed so as to introduce previously identified advantageous mutations, in particular D96L, Q249R, E87K, D254K, E210K or to introduce random mutations in selected regions, e.g. the lipid contact zone, in particular random mutations with doped or spiked oligonucleotides towards introduction of positive and/or hydrophobic amino acid residues, or to introduce any of the other specific mutations mentioned herein. Alternatively, genes encoding different homologous parent lipolytic enzymes may be combined in a random manner in order to obtain a novel variant carrying one or more mutations from each variant. This is discussed in further detail below in the section entitled "Combination of DNA sequences encoding lipolytic enzymes".

The host cells selected for in step (c) ("Methods of applying a peptide addition") or (b) ("Methods of constructing first wash lipolytic enzymes") may be used directly for the production of the variant of the lipolytic enzyme. Alternatively, DNA encoding the variant may be isolated from the host cell and inserted into another suitable host cell, conveniently by use of the procedure described below in the section entitled "Expression of a variant of the invention", in which suitable host cells are also listed.

Localized Random Mutagenesis

In accordance with the invention the random mutagenesis may advantageously be located to a part of the parent lipolytic enzyme in question. This may, e.g., be advantageous when a certain region of the enzyme has been identified to be of particular importance for a given property of the enzyme, and which, when modified, is expected to result in a variant having improved properties. Such region may normally be identified when the tertiary structure of the parent enzyme has been elucidated and related to the function of the enzyme.

One area of particular interest for modification amino acid residues located at the surface of the parent enzyme within or outside the lipid contact zone, i.e. the part of the lipolytic enzyme which is in contact with the lipid substrate and e.g. comprising the lid region, the hydrophobic cleft or any part of these structures. Another area of interest for lipolytic enzymes of the invention which contains a peptide addition or another modification within a non-structural part of the N-terminal or C-terminal end of the mature parent enzyme.

The localized random mutagenesis is conveniently performed by use of PCR generated mutagenesis techniques as described above or any other suitable technique known in the art. Especially for mutagenizing large peptide additions, it may be relevant to use PCR generated mutagenesis (e.g. as described by Deshler 1992 or Leung et al., 1989), in which one or more suitable oligonucleotide probes are used which flanks the area to be mutagenized. For mutagenesis of shorter peptide additions, it is more preferably perform the localized random mutagenesis by use of doped or spiked oligonucleotides. The doping or spiking is used, e.g., to avoid codons for unwanted amino acid residues or to increase the likelihood that a particular type of amino acid residue, such as a positively charged or hydrophobic amino acid residue, is introduced at a desired position.

Alternatively, the DNA sequence encoding the part of the DNA sequence to be modified may be isolated, e.g. by being inserted into a suitable vector, and said part may subsequently be subjected to mutagenesis by use of any of the mutagenesis methods discussed above.

Of particular interest is that the DNA sequence subjected to random mutagenesis comprises a part of or constitutes a part of a DNA sequence encoding the lipid contact zone or the lid region of the parent lipolytic enzyme. The localized random mutagenesis may be performed in one or more of these regions and/or one or more of the regions constituting the lipid contact zone, and is preferably performed in at least two of the regions. Parent lipolytic enzymes of particular interest for modification according to this aspect of the invention includes the H. lanuginosa lipolytic enzyme obtainable from strain DSM 4109 or a variant or analogue thereof, a parent lipolytic enzyme derived from Penicillium camembertii, a parent lipolytic enzyme derived from Rhizopus oryzae, a parent lipolytic enzyme derived from Rhizomucor miehei, a parent lipolytic enzyme derived from a Absidia sp. lipolytic enzyme, a parent lipolytic enzyme derived from a Pseudomonas sp., prefereably belonging to the Ps. aeroginosa family such as the Pseudomonas cepacia lipase, the Pseudomonas pseudoalcaligenes lipase, the Pseudomonas glumae lipase, the Pseudomonas mendocina lipase, the Pseudomonas wisconsinensis, or the Pseudomonas sp. lipase (SD705) (Liposam®) shown in SEQ ID NO:92.

The lipid contact zones and lid regions are identified in the "Definitions" section above.

The localized random mutagenesis may be done by use of doped oligonucleotides which are doped in the direction of L, I, V, F, W, A (hydrophobic amino acid residues) or K,R (positive amino acid residues), for instance under conditions ensuring about 90–93% wildtype and about 7–10% mutant. Specific examples of suitable doping regimes are given in the Examples section below.

In Vivo Recombination

According to a preferred embodiment of the invention a DNA sequence encoding a first wash lipolytic enzyme may be constructed by a method, which as an important step involves combination of selected DNA sequences encoding different parent lipolytic enzymes or parts of such DNA sequences.

Preferably, the DNA sequences to be combined are derived from genes encoding lipolytic enzymes which have a satisfactory washing and/or dishwashing performance (e.g. as identified in Example 13). The aim of combining the DNA sequences is that the best elements from each "parent enzyme" are combined into one and the same variant enzyme.

In the context of in vivo recombination the term "satisfactory washing performance" is intended to indicate that the parent enzymes are capable of removing fatty stains during one or several wash cycles when present in a suitable detergent. Preferably, the parent enzyme in question has a better washing performance than Lipolase(TM).

The combination of DNA sequences may be performed by any suitable method known in the art. For instance, when the DNA sequences to be combined comprises homologous fragments, the combination is preferably achieved by homologous cross-over, e.g. by use of conventional methods such as U.S. Pat. No. 5,093,257, or by gene shuffling (Stemmer (1994), Proc. Natl. Acad. Sci. USA, vol. 91, 10747–10751; Stemmer (1994), Nature, vol. 370, 389–391; Smith (1994), Nature vol. 370, page 324–25), WO 95/17413, Gene shuffling means recombination of nucleotide sequence(s) between two or more homologous DNA sequences resulting in output DNA sequences having a number of nucleotides exchanged.

Of particular interest is an in vivo Gene Shuffling Method which is based on the following procedure:

(a) forming at least one circular expression vector comprising a DNA sequence encoding a parent lipolytic enzyme or a substantial part thereof, (b) opening said circular expression vector within the DNA sequence encoding the lipolytic enzyme or part thereof, (c) preparing at least one DNA fragment comprising a DNA sequence homologous to at least a part of the enzyme coding region on at least one of the circular expression vector(s), (d) introducing at least one of said opened vector(s), together with at least one of said homologous DNA fragment(s) covering full-length DNA sequences encoding said lipolytic enzyme(s) or a part thereof, into a recombination host cell, (e) cultivating said yeast recombination host cell under conditions conducive for recombination between the homologous DNA fragments to take place, and (f) screening for positive lipolytic enzyme variants with an improved wash performance.

The vector used in step a) above may be a yeast expression vector which can be transformed into and expressed in a yeast recombination host cell. Examples of such expression vectors include yeast expression vectors constructed from pYES 2.0 (Invitrogene), such as pJSO37 comprising the wild type Humicola lanuginosa lipase gene.

Opening of the vector in step b) may be accomplished by any conventional techniques known in the art, and may for instance be performed by opening the vector within the lipase gene by cutting at a single site or by gapping the vector (i.e. cutting e.g. at two sites resulting in cutting out a little part of the gene).

The preparation of the homologous DNA fragment(s) in step c) may be performed by amplifying homologous DNA sequence(s) (e.g., comprising one or more mutation in the lipolytic gene and comprising in a plasmid or vector) by any suitable methods, such as by a standard PCR amplification method described in U.S. Pat. No. 4,683,202 or Saiki et al., (1988), Science 239, 487–491).

The vector(s) may be introduced into the recombination host cell (in step d) by transformation. In the case of the recombination host cell is a strain of *Saccharomyces cerevisiae*, such as *Saccharomyces cerevisiae* YNG318 (described below) the transformation may be performed as described by Sambrooks et al., (1989), Molecular Cloning: A Laboratory Manual, 2nd Ed., Cold Spring Harbor, N.Y., USA).

The screening for positive lipolytic enzyme variants may, e.g., be performed by the screening method described in connection with the random mutagenesis above.

One of more cycle of step a) to f) may be performed before a selection of a first wash lipolytic enzyme variant is made using the selection conditions defined further above.

According to the shuffling method significantly more than two DNA sequences can be shuffled. Any number of different DNA fragments and homologous lipolytic enzymes comprised in suitable plasmids may be shuffles at the same time.

The DNA sequences to be combined may be entire genes of which at least one part exhibits sufficient homology to the other genes to allow for recombination of the genes to take place.

Alternatively, the DNA sequences may be partial genes, which when combined can give rise to a functional gene capable of expressing a lipolytic enzyme.

When the DNA sequences to be combined are highly homologous or partially identical controlled combination may be performed, e.g. in the case of combination of two DNA sequences, to combine the N-terminal part of one of the sequences with the C-terminal part of the other (corresponding to the remaining part of the first sequence) or by combining other relevant parts of the respective genes in question.

Naturally occurring enzymes may be genetically modified by random, localized random or site directed mutagenesis as described above prior to being subjected to gene shuffling. Alternatively, part of one enzyme may be replaced by a part of another to obtain a chimeric enzyme. This replacement can be achieved either by conventional in vitro gene splicing techniques or by in vivo recombination or by combinations of both techniques. When using conventional in vitro gene splicing techniques, a desired portion of the lipolytic enzyme gene may be deleted using appropriate site-specific restriction enzymes; the deleted portion of the coding sequence may then be replaced by insertion of a desired portion of a different lipolytic enzyme coding sequence so that a chimeric nucleotide sequence encoding a new lipolytic enzyme is produced. Alternatively, lipolytic enzyme genes may be fused, e.g. by use of the PCR overlay addition method described by Higuchi et al. 1988.

The in vivo recombination techniques depend on the fact that different DNA segments with highly homologous regions (identity of DNA sequence) may recombine, i.e. break and exchange DNA, and establish new bonds in the homologous regions. Accordingly, when the coding sequences for two or more different but homologous lipolytic enzymes are used to transform a host cell, recombination of homologous sequences in vivo will result in the production of chimeric gene sequences. Translation of these coding sequences by the host cell will result in production of a chimeric lipolytic enzyme gene product. Specific in vivo recombination techniques are described in U.S. Pat. No. 5,093,257 and EP 252 666.

In order to allow homologous recombination to take place it is desirable that the lipolytic enzymes comprises parts which are at least 60% homologous. It is particularly preferred that the entire enzymes are at least 60% homologous. The enzymes to be combined may be different variants of the same parent enzyme, e.g. variants derived from the *H. lanuginosa* lipolytic enzyme disclosed herein, or variants derived from the *Ps. alcaligenes* or *Ps. pseudoalcaligenes* lipolytic enzymes referred to further above, or variants derived from the *F. solani* pisi lipolytic enzyme (cf above), or variants derived from the *P. mendocina* lipolytic enzyme or the Pseudomonas sp. lipase (Liposam) (cf. above). It will be understood that the random recombination may be performed between a naturally-occurring lipolytic enzymes and one or more variants of said enzyme, between differerent naturally ocurring enzymes, between variants of naturally ocurring enzymes (the variants being variants of the same parent enzyme or of different enzymes), or between any combination of naturally occurring enzymes and variants of naturally occurring enzyme as long as the corresponding DNA sequences are capable of recombining. When the DNA sequences to be combined are variants of a parent enzyme these variants may conveniently be prepared by the mutagenesis, in particular random mutagenesis method disclosed above.

In an alternative embodiment, the hybrid enzyme may be synthesized by standard chemical methods known in the art. For example, see Hunkapiller et al. (1984). Accordingly, peptides having the amino acid sequences described above may be synthesized in whole or in part and joined to form the hybrid enzymes of the invention.

In a highly preferred embodiment first wash lipolytic enzymes of the invention are constructed by a method which comprises subjecting a parent lipolytic enzyme to mutagenesis, in particular random mutagenesis, to form a variety of mutated DNA sequences, expressing the mutated DNA sequences in a suitable host and screening for host cells which produces a mutated lipolytic enzyme which has a decreased dependency on calcium and/or an improved tolerance towards a detergent or a detergent component, subjecting the DNA sequence encoding the mutated lipolytic enzyme selected in said screening to in vivo recombination, in particular gene shuffling or sexual PCR, with one or more other mutated DNA sequences prepared in a similar manner from the same parent lipolytic enzyme, expressing the mutated recombined DNA sequences in a suitable host, optionally selecting for host cells producing a mutated lipolytic enzyme which has a decreased dependency on calcium and/or an improved tolerance towards a detergent or a detergent component, optionally repeating either or both of the above mutagenesis and in vivo recombination procedures one or more times using more stringent screening criteria, and finally selecting a recombined DNA sequence endoding a lipolytic enzyme exhibiting first wash activity as defined herein.

Furthermore, it will be understood that a first wash lipolytic enzyme of the invention which comprises a peptide addition as well as mutation(s) in a structural part of the parent enzyme may be constructed by a method which involves localized mutagenesis, in particular localized random mutagenesis, in the part of the DNA sequence encoding the peptide addition and selected parts of the DNA sequence encoding the mature part of the parent lipolytic enzyme, i.e. a combination of the random mutagenesis method according to the third aspect of the invention performed in a structural part of the parent enzyme and random mutagenesis in a non-structural part of the N-terminal and/or C-terminal end and/or in a peptide addition applied to the N-terminal and/or C-terminal part.

It will be understood that the in vivo recombination and mutagenesis methods disclosed herein may be applied to any of the parent lipolytic enzymes mentioned in the "Parent Lipolytic Enzymes" section herein. Particularly preferred parent lipolytic enzymes are derived from *Humicola lanuginosa* and from Pseudomonas sp. such as *Ps. alcaligenes* and *Ps. pseudoalcaligenes*.

Expression of a Lipolytic Enzyme of the Invention

An isolated nucleic acid sequence encoding a modified or a first wash lipolytic enzyme of the invention may be manipulated in a variety of ways to provide for expression of the enzyme. Manipulation of the nucleic acid sequence encoding a modified or a first wash lipolytic enzyme prior to its insertion into a vector may be desirable or necessary depending on the expression vector. The techniques for modifying nucleic acid sequences utilizing cloning methods are well known in the art.

The term "control sequences" is defined herein to include all components which are necessary or advantageous for expression of the coding sequence of the nucleic acid sequence. Each control sequence may be native or foreign to the nucleic acid sequence encoding the lipolytic enzyme. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding the lipolytic enzyme.

The control sequence may be an appropriate promoter sequence, a nucleic acid sequence which is recognized by a host cell for expression of the nucleic acid sequence. The promoter sequence contains transcription and translation control sequences which mediate the expression of the modified or first wash lipolytic enzyme. The promoter may be any nucleic acid sequence which shows transcriptional activity in the host cell of choice and may be obtained from genes encoding extracellular or intracellular polypeptides either homologous or heterologous to the host cell. Examples of suitable promoters for directing the transcription of the nucleic acid constructs of the present invention, especially in a bacterial host cell, are the promoters obtained from the *E. coli* lac operon, the Streptomyces coelicolor agarase gene (dagA), the *B. subtilis* levansucrase gene (sacB) or the alkaline protease gene, the *B. licheniformis* alpha-amylase gene (amyL), the *B. stearothermophilus* maltogenic amylase gene (amyM), the *B. amyloliquefaciens* alpha-amylase gene (amyQ), the *B.licheniformis* penicillinase gene (penP), the *B. subtilis* xylA and xylB genes, the *B. pumilus* xylosidase gene, and the prokaryotic beta-lactamase or tryptophan gene (Villa-Kamaroff et al., 1978, *Proceedings of the National Academy of Sciences USA* 75:3727–3731), as well as the tac gene (DeBoer et al., 1983, *Proceedings of the National Academy of Sciences USA* 80:21–25). Further promoters are described in "Useful proteins from recombinant bacteria" in *Scientific American*, 1980, 242:74–94; and in Sambrook et al, 1989, supra. Examples of suitable promoters for directing the transcription of the nucleic acid constructs of the present invention in a filamentous fungal host cell are promoters obtained from the genes encoding A. oryzae TAKA amylase, *A. oryzae* triose phosphate isomerase, *Rhizomucor miehei* aspartic proteinase, *A. niger* neutral alpha-amylase, *A. niger* acid stable alpha-amylase, *A. niger* or *A.awamori* glucoamylase (glaA), *Rhizomucor miehei* lipase, *A. oryzae* alkaline protease, *A. oryzae* triose phosphate isomerase, *A. nidulans* acetamidase, *Fusarium oxysporum* trypsin-like protease (as described in U.S. Patent No. 4,288,627, which is incorporated herein by reference), or the ADH-3 promoter (McKnight et al., (1985). The EMBO J. 4, 2093–3099) and hybrids thereof. Particularly preferred promoters for use in filamentous fungal host cells is the TAKA amylase and the glaA promoters. In a yeast host, promoters from yeast glycolytic genes (Hitzeman et al.,(1980), J. Biol. Chem. 255, 12073–12080;

Alber and Kawasaki, (1982), J. Mol. Appl. Gen. 1, 419–434) or alcohol dehydrogenase genes (Young et al., in Genetic Engineering of Microorganisms for Chemicals (Hollaender et al, eds.), Plenum Press, New York, 1982), or the TPI1 (U.S. Pat. No. 4,599,311) or ADH2-4c (Russell et al., (1983), Nature 304, 652–654) promoters. useful promoters are obtained from the *S. cerevisiae* enolase (ENO-1) gene, the *S. cerevisiae* galactokinase gene (GAL1), the *S. cerevisiae* alcohol dehydrogenase/glyceraldehyde-3-phosphate dehydrogenase genes (ADH2/GAP), and the *S. cerevisiae* 3-phosphoglycerate kinase gene. Other useful promoters for yeast host cells are described by Romanos et al., 1992, *Yeast* 8:423–488.

The control sequence may also be a suitable transcription terminator sequence, a sequence recognized by a host cell to terminate transcription. The terminator sequence is operably linked to the 3' terminus of the nucleic acid sequence encoding the modified or first wash lipolytic enzyme. The terminator sequence may be native to the nucleic acid sequence encoding the lipolytic enzyme or may be obtained from foreign sources. Any terminator which is functional in the host cell of choice may be used in the present invention. Preferred terminators for filamentous fungal host cells are obtained from the genes encoding *A. oryzae* TAKA amylase, *A. niger* glucoamylase, *A. nidulans* anthranilate synthase, *A. niger* alpha-glucosidase, and *Fusarium oxysporum* trypsin-like protease. Preferred terminators for yeast host cells are obtained from the genes encoding *S. cerevisiae* enolase, *S. cerevisiae* cytochrome C (CYC1), or *S. cerevisiae* glyceraldehyde-3-phosphate dehydrogenase. Other useful terminators for yeast host cells are described by Romanos et al., 1992, supra.

The control sequence may also be a suitable leader sequence, a nontranslated region of a mRNA which is important for translation by the host cell. The leader sequence is operably linked to the 5' terminus of the nucleic acid sequence encoding the lipolytic enzyme. The leader sequence may be native to the nucleic acid sequence encoding the lipolytic enzyme or may be obtained from foreign sources. Any leader sequence which is functional in the host cell of choice may be used in the present invention. Preferred leaders for filamentous fungal host cells are obtained from the genes encoding *A. oryzae* TAKA amylase and *A. oryzae* triose phosphate isomerase. Suitable leaders for yeast host cells are obtained from the *S. cerevisiae* enolase (ENO-1) gene, the *S. cerevisiae* 3-phosphoglycerate kinase gene, the *S. cerevisiae* alpha-factor, and the *S. cerevisiae* alcohol dehydrogenase/glyceraldehyde-3-phosphate dehydrogenase genes (ADH2/GAP).

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. The polyadenylation sequence may be native to the nucleic acid sequence encoding the lipolytic enzyme or may be obtained from foreign sources. Any polyadenylation sequence which is functional in the host cell of choice may be used in the present invention. Preferred polyadenylation sequences for filamentous fungal host cells are obtained from the genes encoding *A. oryzae* TAKA amylase, *A. niger* glucoamylase, *A. nidulans* anthranilate synthase, and *A. niger* alpha-glucosidase. Useful polyadenylation sequences for yeast host cells are described by Guo and Sherman, 1995, *Molecular Cellular Biology* 15:5983–5990, Polyadenylation sequences are well known in the art for mammalian host cells.

The control sequence may also be a signal peptide coding region, which codes for an amino acid sequence linked to the amino terminus of the modified or first wash lipolytic enzyme which can direct the expressed lipolytic enzyme into the cell's secretory pathway. The signal peptide coding region may be native to the lipolytic enzyme of the invention or may be obtained from foreign sources. The 5' end of the coding sequence of the nucleic acid sequence may inherently contain a signal peptide coding region naturally linked in translation reading frame with the segment of the coding region which encodes the secreted lipolytic enzyme. Alternatively, the 5' end of the coding sequence may contain a signal peptide coding region which is foreign to that portion of the coding sequence which encodes the secreted lipolytic enzyme. The foreign signal peptide coding region may be required where the coding sequence does not normally contain a signal peptide coding region. Alternatively, the foreign signal peptide coding region may simply replace the natural signal peptide coding region in order to obtain enhanced secretion of the lipolytic enzyme relative to the natural signal peptide coding region normally associated with the coding sequence. The signal peptide coding region may be obtained from a glucoamylase or an amylase gene from an Aspergillus species, a lipase or proteinase gene from a Rhizomucor species, the gene for the a-factor from *Saccharomyces cerevisiae*, an amylase or a protease gene from a Bacillus species, or the calf preprochymosin gene. An effective signal peptide coding region for bacterial host cells is the signal peptide coding region obtained from the maltogenic amylase gene from Bacillus NCIB 11837, the *B. stearothermophilus* alpha-amylase gene, the *B. licheniformis* subtilisin gene, the *B. licheniformis* beta-lactamase gene, the *B. stearothermophilus* neutral proteases genes (nprT, nprS, nprM), and the *B. subtilis* PrsA gene. Further signal peptides are described by Simonen and Palva, 1993, *Microbiological Reviews* 57:109–137. An effective signal peptide coding region for filamentous fungal host cells is the signal peptide coding region obtained from *A. oryzae* TAKA amylase gene, *A. niger* neutral amylase gene, the *Rhizomucor miehei* aspartic proteinase gene, the *H. lanuginosa* cellulase gene, or the *Rhizomucor miehei* lipase gene. Useful signal peptides for yeast host cells are obtained from the genes for *S. cerevisiae* a-factor and *S. cerevisiae* invertase. Other useful signal peptide coding regions are described by Romanos et al, 1992, supra. However, any signal peptide coding region capable of directing the expressed enzyme into the secretory pathway of a host cell of choice may be used in the present invention.

The nucleic acid constructs of the present invention may also comprise one or more nucleic acid sequences which encode one or more factors that are advantageous in the expression of the modified or first wash lipolytic enzyme, e.g., an activator (e.g., a trans-acting factor), a chaperone, and a processing protease. The nucleic acids encoding one or more of these factors are not necessarily in tandem with the nucleic acid sequence encoding the modified or first wash lipolytic enzyme. An activator is a protein which activates transcription of a nucleic acid sequence encoding a first wash lipolytic enzyme (Kudla et al., 1990, *EMBO Journal* 9:1355–1364; Jarai and Buxton, 1994, *Current Genetics* 26:2238–244; Verdier, 1990, Yeast 6:271–297). The nucleic acid sequence encoding an activator may be obtained from the genes encoding *B. stearothermophilus* NprA (nprA), *S. cerevisiae* heme activator protein 1 (hap1), *S. cerevisiae* galactose metabolizing protein 4 (gal4), and *A. nidulans* ammonia regulation protein (areA). For further examples, see Verdier,1990, supra and MacKenzie et al., 1993, *Journal of General Microbiology* 139:2295–2307. A chaperone is a protein which assists another polypeptide in folding properly (Hartl et al., 1994, TIBS 19:20–25; Bergeron et al., 1994, *TIBS* 19:124–128; Demolder et al., 1994, *Journal of Biotechnology* 32:179–189; Craig, 1993, *Science* 260:1902–1903; Gething and Sambrook, 1992, *Nature* 355:33–45; Puig and Gilbert, 1994, *Journal of Biological Chemistry* 269:7764–7771; Wang and Tsou, 1993, *The FASEB Journal* 7:1515–11157; Robinson et al., 1994, *Bio/Technology* 1:381–384). The nucleic acid sequence encoding a chaperone may be obtained from the genes encoding *B. subtilis* GroE proteins, *A. oryzae* protein disulphide isomerase, *S. cerevisiae* calnexin, *S. cerevisiae* BiP/GRP78, and *S. cerevisiae* Hsp70. For further examples, see Gething and Sambrook,1992, supra, and Hartl et al., 1994, supra. Any factor that is functional in the host cell of choice may be used in the present invention.

It may also be desirable to add regulatory sequences which allow the regulation of the expression of the modified or first wash lipolytic enzyme relative to the growth of the host cell.

Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *A. niger* glucoamylase promoter, and the *A. oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the modified or first wash lipolytic enzyme would be placed in tandem with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the modified or first wash lipolytic enzyme at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from B. subtilis or B. licheniformis, or markers which confer antibiotic resistance such as ampicillin, kanamycin, chloramphenicol or tetracycline resistance. A frequently used mammalian marker is the dihydrofolate reductase gene. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), and glufosinate resistance markers, as well as equivalents from other species. Preferred for use in an Aspergillus cell are the amdS and pyrG markers of A. nidulans or A. oryzae and the bar marker of Streptomyces hygroscopicus. Furthermore, selection may be accomplished by co-transformation, e.g., as described in WO 91/17243, where the selectable marker is on a separate vector.

The vectors of the present invention preferably contain an element(s) that permits stable integration of the vector into the host cell genome or autonomous replication of the vector in the cell independent of the genome of the cell.

The vectors of the present invention may be integrated into the host cell genome when introduced into a host cell. For integration, the vector may rely on the nucleic acid sequence encoding the modified or first wash lipolytic enzyme or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination. These nucleic acid sequences may be any sequence that is homologous with a target sequence in the genome of the host cell, and, furthermore, may be non-encoding or encoding sequences.

For autonomous replication, the vector may further comprise an origin of replication enabling the vector to replicate autonomously in the host cell in question. Examples of bacterial origins of replication are the origins of replication of plasmids pBR322, pUC19, pACYC177, pACYC184, pUB110, pE194, pTA1060, and pAMβ1. Examples of origin of replications for use in a yeast host cell are the 2 micron origin of replication, the combination of CEN6 and ARS4, and the combination of CEN3 and ARS1. The origin of replication may be one having a mutation which makes its functioning temperature-sensitive in the host cell (see, e.g., Ehrlich, 1978, *Proceedings of the National Academy of Sciences USA* 75:1433).

More than one copy of a nucleic acid sequence encoding a modified or first wash lipolytic enzyme of the present invention may be inserted into the host cell to amplify expression of the nucleic acid sequence. Stable amplification of the nucleic acid sequence can be obtained by integrating at least one additional copy of the sequence into the host cell genome using methods well known in the art and selecting for transformants.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the modified or first wash lipolytic enzymes. The cell is preferably transformed with a vector comprising a nucleic acid sequence of the invention followed by integration of the vector into the host chromosome. "Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome may occur by homologous or non-homologous recombination as described above.

The choice of a host cell will to a large extent depend upon the gene encoding the modified or first wash lipolytic enzyme and its source. In addition, the choice of host cell will often depend on the proteolytic enzyme system of the host cell and its impact on the production of a modified or first wash lipolytic enzyme of the invention. Accordingly, it may be desirable to use a host cell which is deficient in one or more proteolytic enzymes or other enzyme processing means. Protease deficient host cells of bacteria as well as fungal (filamentous fungal and yeast) cells are well-known in the art.

When the first wash lipolytic enzyme of the invention comprises a peptide addition, and in case of a modified lipolytic enzyme of the invention, it may be advantageous that the host is a strain reduced or deficient in one or more exo-proteases capable of cleaving the modified lipolytic enzyme at a site close to the peptide addition or a protease capable of cleaving within the peptide addition. For instance, the host cell may be reduced or deficient in a tripeptidyl-aminopeptidase (TPAP) (see e.g. WO 96/14404 from Novo Nordisk A/S), a dipeptidyl-aminopeptidase (DPAP), and/or a Kex2 protease or Kex2-like protease and therefore not capable of cleaving at di-basic sites such as Arg—Arg (RR).

Other examples of host cells include alkaline protease deficient or reduced host cells, aspartic proteinase deficient host cells (EP 429 490), and host cells deficient of proteolytic enzymes such as the host cells described in WO 93/00925, WO 92/17595, EP 341 215, EP 574 347, and PCT/DK96/00111.

The host cell may be a unicellular microorganism or a non-unicellular microorganism. Useful unicellular cells are bacterial cells such as gram positive bacteria including, but not limited to, a Bacillus cell, e.g., *B. subtilis, B. licheniformis, B. lentus, B. brevis, B. stearothermophilus, B. alkalophilus, B. amyloliquefaciens, B. coagulans, B.circulans, B. lautus, B. megaterium*, and *B. thuringiensis*; or a Streptomyces cell, e.g., *S. lividans* or *S. murinus*, or gram negative bacteria such as *E. coli* and Pseudomonas sp. (especially when a bacterial lipolytic enzyme, such as a Pseudomonas sp. enzyme is to be produced). The transformation of a bacterial host cell may, for instance, be effected by protoplast transformation (see, e.g., Chang and Cohen, 1979, *Molecular General Genetics* 168:111–115), by using competent cells (see, e.g., Young and Spizizin, 1961, *Journal of Bacteriology* 81:823–829, or Dubnar and Davidoff-Abelson, 1971, *Journal of Molecular Biology* 56:209–221), by electroporation (see, e.g., Shigekawa and Dower, 1988, *Biotechniques* 6:742–751), or by conjugation (see, e.g., Koehler and Thorne, 1987, *Journal of Bacteriology* 169:5771–5278).

The host cell may be a eukaryote, and is preferably a fungal, i.e. a yeast cell or a filamentous fungal cell, especially for the production of a modified or a first wash lipolytic enzyme of eukaryotic origin.

"Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae (e.g., genus Schizosaccharomyces), Nadsonioideae, Lipomycoideae, and Saccharomycoideae (e.g., genera Pichia, Kluyveromyces and Saccharomyces). The basidiosporogenous yeasts include the genera Leucosporidim, Rhodosporidium, Sporidiobolus, Filobasidium, and Filobasidiella. Yeast belonging to the Fungi Imperfecti are divided into two families, Sporobolomycetaceae (e.g., genera Sorobolomyces and Bullera) and Cryptococcaceae (e.g., genus Candida). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9,1980. The biology of yeast and manipulation of yeast genetics are well known in the art (see, e.g., *Biochemistry and Genetics of Yeast*, Bacil, M., Horecker, B. J., and Stopani, A. O. M., editors, 2nd edition, 1987; The Yeasts, Rose, A. H., and Harrison, J. S., editors, 2nd edition, 1987; and *The Molecular Biology of the Yeast Saccharomyces*, Strathern et al., editors, 1981). In connection with the present invention the use of yeast cells which typically have another proteolytic enzyme processing system that, e.g., bacteria and filamentous fungi, may be of particular use for preparing modified or first wash lipolytic enzymes which, as the peptide addition, comprise a part or all of the natural prosequences of the parent lipolytic enzyme in question. When the fungal host cell is a yeast cell (e.g. to be used in applying a peptide addition (in the form of part of or the entire prosequence of the parent enzyme, the yeast host cell may be a cell of a species of Candida, Kluyveromyces, Saccharomyces, Schizosaccharomyces, Pichia, or Yarrowia, such as a *S. cerevisiae* cell, a *S.s carlsbergensis*, a *S. diastaticus* cell, a *S. douglasii* cell, a *S. kluyveri* cell, a *S. norbensis* cell, or a *S. oviformis* cell.

"Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171)and all mitosporicfungi (Hawksworth et al, 1995, supra). Representative groups of Ascomycota include, e.g., Neurospora, Eupenicillium (=Penicillium), Emericella (=Aspergillus), Eurotium (=Aspergillus), and the true yeasts listed above. Examples of Basidiomycota include mushrooms, rusts, and smuts. Representative groups of Chytridiomycota include, e.g., Allomyces, Blastocladiella, Coelomomyces, and aquatic fungi. Representative groups of Oomycota include, e.g., Saprolegniomycetous aquatic fungi (water molds) such as Achlya. Examples of mitosporic fungi include Aspergillus, Penicillium, Candida, and Altemaria. Representative groups of Zygomycota include, e.g., Rhizopus and Mucor.

"Filamentous fungi" include all filamentous forms of the subdivision Eumycota and Oomycota (as defined by Hawksworth et al., 1995, supra). The filamentous fungi are characterized by a vegetative mycelium composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a preferred embodiment, the fungal host cell is a filamentous fungal cell. In a more preferred embodiment, the filamentous fungal host cell is a cell of a species of, but not limited to, Acremonium. Aspergillus, Fusarium, Humicola, Myceliophthora, Mucor, Neurospora, Penicillium, Thielavia, Tolypocladium, and Trichoderma. In an even more preferred embodiment, the filamentous fungal host cell is an Aspergillus cell. In another even more preferred embodiment, the filamentous fungal host cell is a Fusarium cell. In a most preferred embodiment, the filamentous fungal host cell is an *A. oryzae* cell, an *A. niger* cell, an *A. foetidus* cell, or an *A. japonicus* cell. In another most preferred embodiment, the filamentous fungal host cell is a *Fusarium oxysporum* cell or a *F. graminearum* cell.

Fungal cells may be transformed by a process involving protoplast formation, transformation of the protoplasts, and regeneration of the cell wall in a manner known perse. Suitable procedures for transformation of Aspergillus host cells are described in EP 238 023 and Yelton et al., 1984, *Proceedings of the National Academy of Sciences USA* 81:1470–1474. A suitable method of transforming Fusarium species is described by Malardier et al., 1989, *Gene* 78:147–156 or in WO 96/00787, Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182–187. Academic Press, Inc., New York; Ito et al., 1983, *Journal of Bacteriology* 153:163; and Hinnen et al., 1978, *Proceedings of the National academy of Sciences USA* 75:1920, Mammalian cells may be transformed by direct uptake using the calcium phosphate precipitation method of Graham and Van der Eb (1978, *Virology* 52:546).

Methods of Production

The present invention also relates to methods for producing a modified or a first wash lipolytic enzyme of the invention comprising (a) cultivating a host cell transformed with a DNA sequence encoding the enzyme under conditions conducive to expression of lipolytic enzyme; and (b) recovering the lipolytic enzyme.

The host cells may be cultivated in a nutrient medium suitable for production of the modified or first wash lipolytic enzyme using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the lipolytic enzyme to be expressed and/or isolated. The cultivation takes place in a suitable nutrient medium comprising carbon and nitrogen sources and inorganic salts, using procedures known in the art (see, e.g., references for bacteria and yeast; Bennett, J. W. and LaSure, L., editors, *More Gene Manipulations in Fungi*, Academic Press, CA, 1991). Suitable media are available from commercial suppliers or may be prepared according to published compositions (e.g., in catalogues of the American Type Culture Collection). If the modified or first wash lipolytic enzyme is secreted into the nutrient medium, the modified lipolytic enzyme can be recovered directly from the medium. If the lipolytic enzyme is not secreted, it is recovered from cell lysates.

The resulting modified or first wash lipolytic enzyme may be recovered by methods known in the art. For example, the lipolytic enzyme may be recovered from the nutrient medium by conventional procedures including, but not limited to, centrifugation, filtration, extraction, spray-drying, evaporation, or precipitation. The recovered lipolytic enzyme may then be further purified by a variety of chromatographic procedures, e.g., ion exchange chromatography, gel filtration chromatography, affinity chromatography, or the like.

The modified or first wash lipolytic enzymes of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification*, J. -C. Janson and Lars Ryden, editors, VCH Publishers, New York, 1989).

In accordance with the invention, it is also contemplated to apply, to the first wash lipolytic lipolytic enzyme, one or more charged amino acids which permit effective purification of the modified enzyme. Techniques for doing this is well known by a person skilled in the art of molecular biology.

Enzyme Composition of the Invention

In a further aspect the invention relates to an enzyme composition comprising an enzyme with lipolytic activity of the invention.

As defined herein, a "substantially pure" enzyme is an enzyme which is essentially free of other homologous contaminants (originating from the same source as the modified lipolytic enzyme), e.g., at least about 20% pure, preferably at least about 40% pure, more preferably about 60% pure, even more preferably about 80% pure, most preferably about 90% pure, and even most preferably about 95% pure, as determined by SDS-PAGE.

In certain cases, when the enzyme of the invention comprises a peptide addition, the host cell does not process all of the modified lipolytic enzyme molecules expressed by that host at the same cleavage site. This has the consequence that the modified or first wash lipolytic enzyme product recovered from the fermentation by such host cells comprise a portion having the full length peptide addition and one or more other portions with only a part of the peptide addition. The inventors found that this does not influence the wash performance significantly. Consequently, even though not all of the lipolytic enzyme of the enzyme composition of the invention may have retained the full length peptide addition the enzyme composition is still capable of exerting the desired effect, such as an improved wash performance. Actually, it has been found that as long as at least about 5% of the total amount of modified lipolytic enzyme of the invention to be used for a given purpose has the intact peptide addition as disclosed above, this may be found to be sufficient for providing the desired effect. The remaining part of the modified lipolytic enzyme molecules may then have a peptide addition which is shorter than the one intended (e.g. as a consequence of one or more amino acid residues have been cut off during processing of the enzyme by the host organism) or no peptide addition at all. Therefore, the enzyme composition of the invention need only to comprise at least about 5%, preferably at least about 10%, such as at least about 25%, better at least about 50%, especially at least about 75% of the modified lipolytic enzyme with its full length addition.

Said enzyme composition may further comprise an enzyme selected from the group of proteases, cellulases, peroxidases, cutinases, amylases and/or lipases, and when intended for washing also ingredients normally used in detergent compositions.

Modified lipolytic enzymes of the invention have been found to be of particular interest as components in detergent compositions such as washing powder or dishwashing compositions which will be described in details in the following section. In addition, due to their improved properties the modified lipolytic enzymes of the invention are contemplated to be useful in, for example, the baking industry, as a catalyst in organic syntheses (e.g. esterification, transesterification orester hydrolysis reactions), in the papermaking industry (e.g. for pitch removal), and in the leather, wool and related industries (e.g. for degreasing of animal hides, sheepskin or wool), and for other applications involving degreasing/defatting.

MATERIALS AND METHODS

Figure 7:
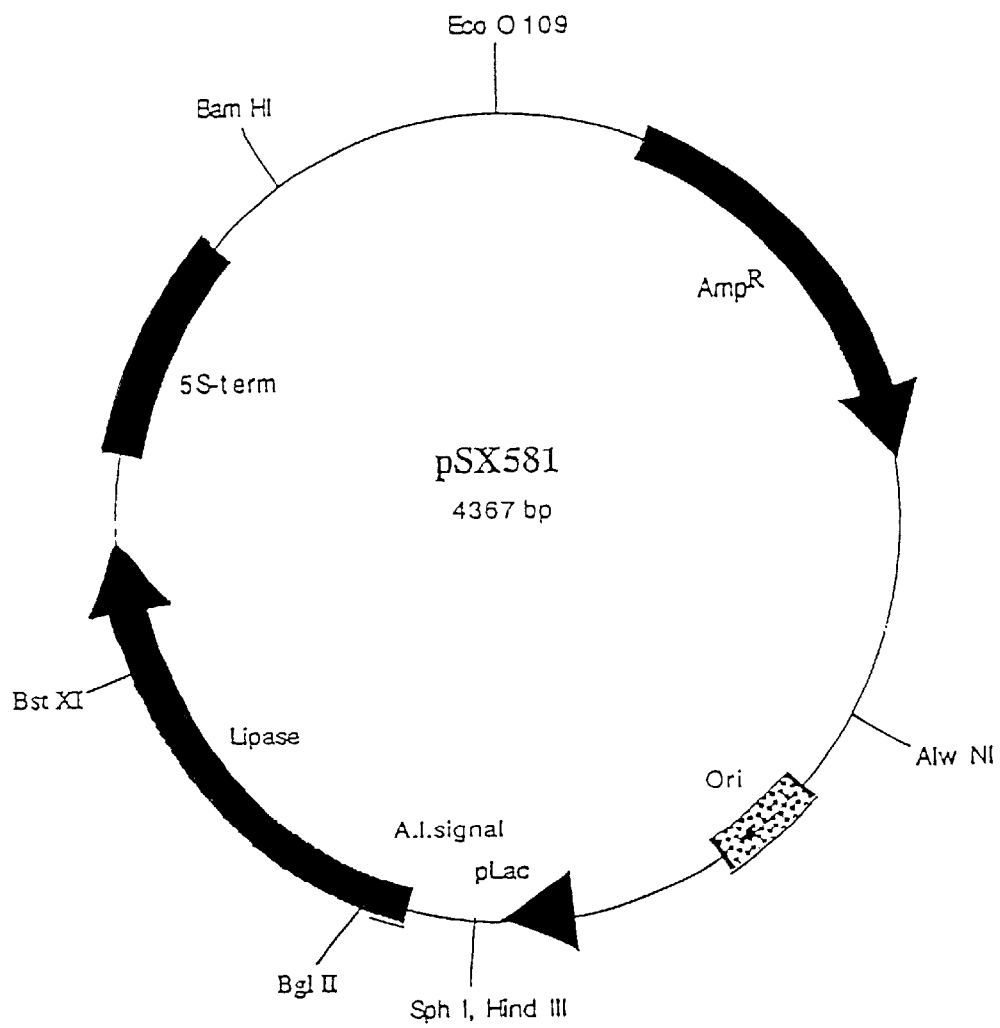
FIG. 7 shows the plasmid pSX581.
Figure 8:
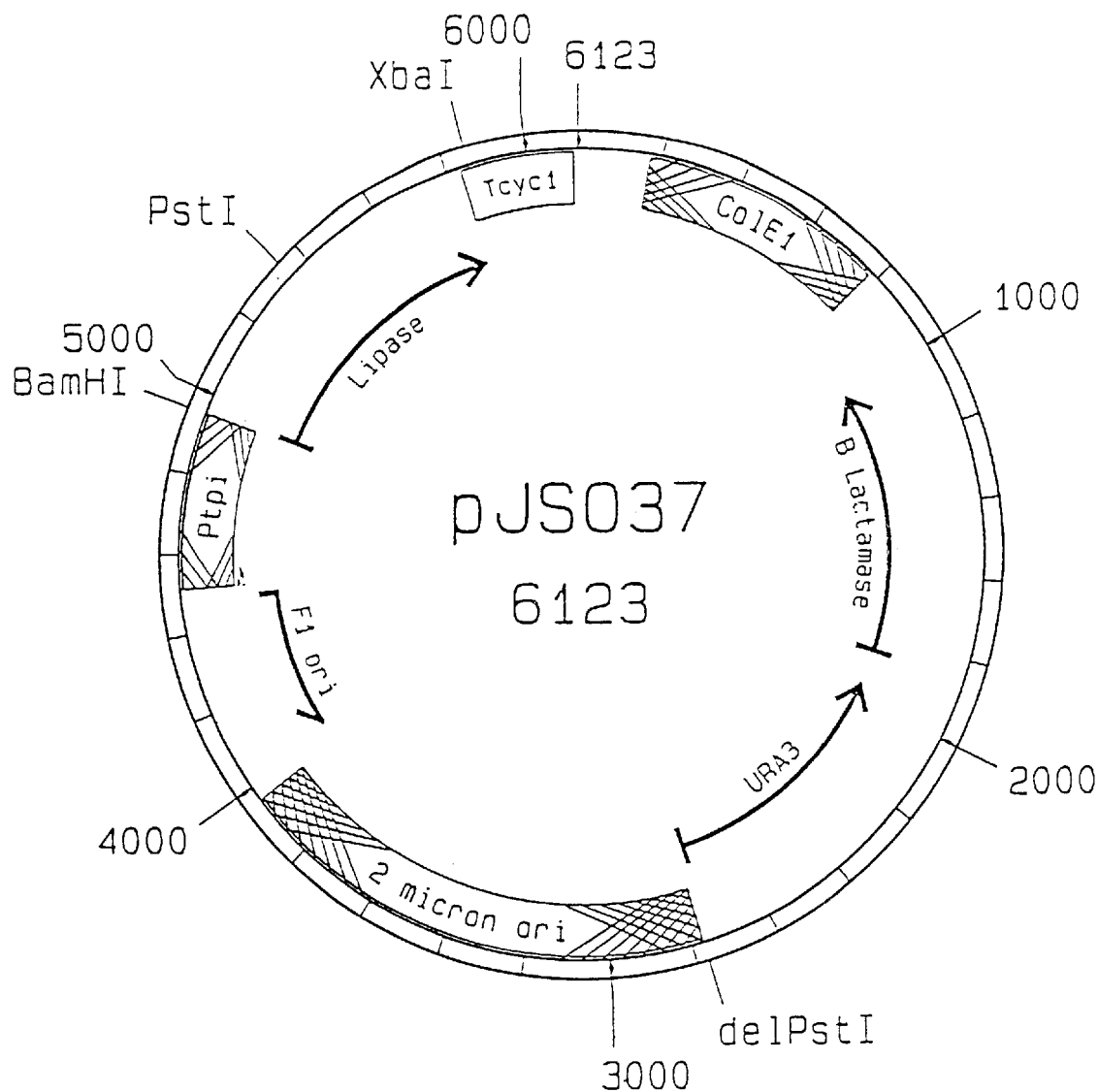
FIG. 8 shows the plasmid pJSO37.
Figure 9:
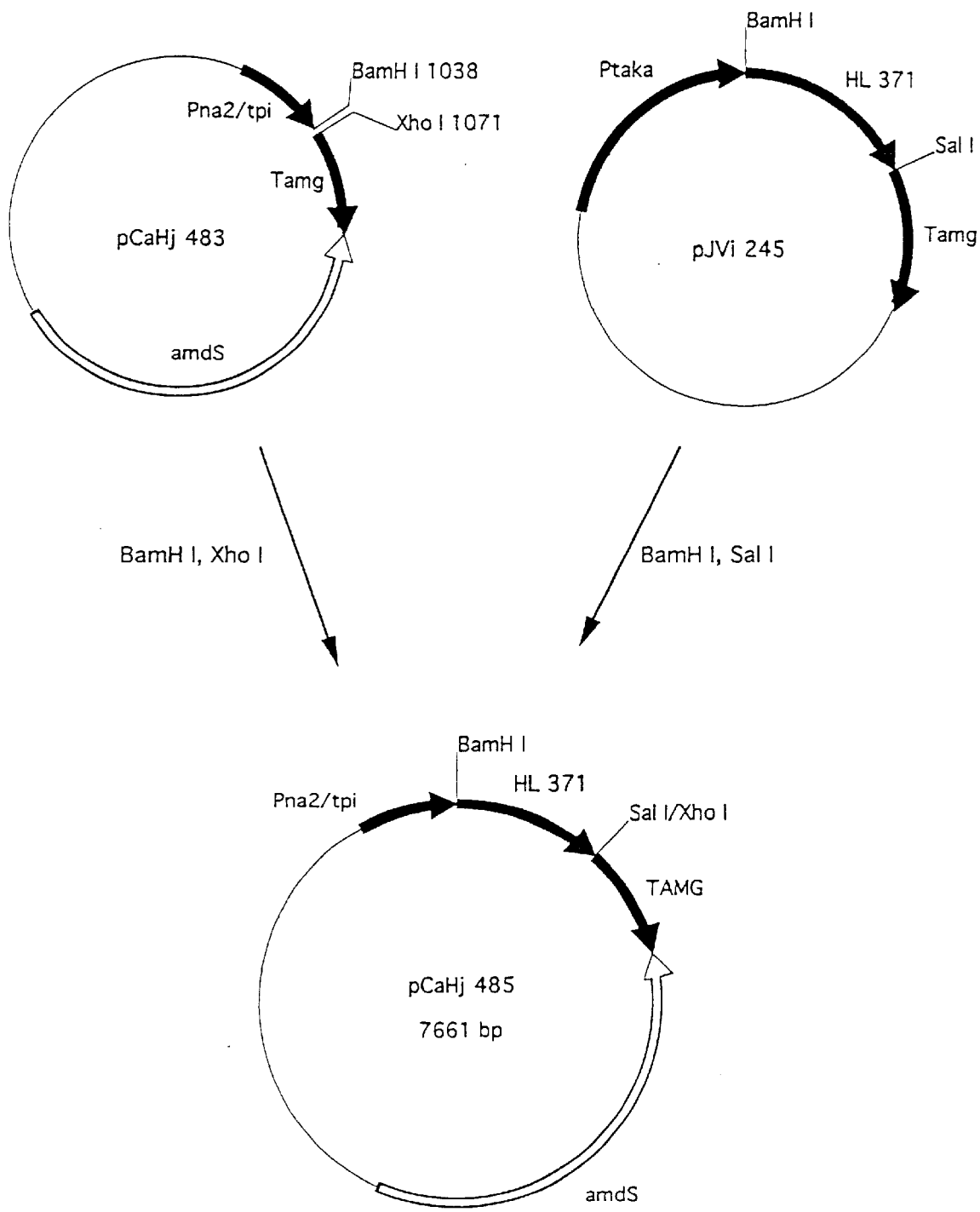
FIG. 9 shows the construction of Aspergillus vector pCaHj485.
Figure 10:
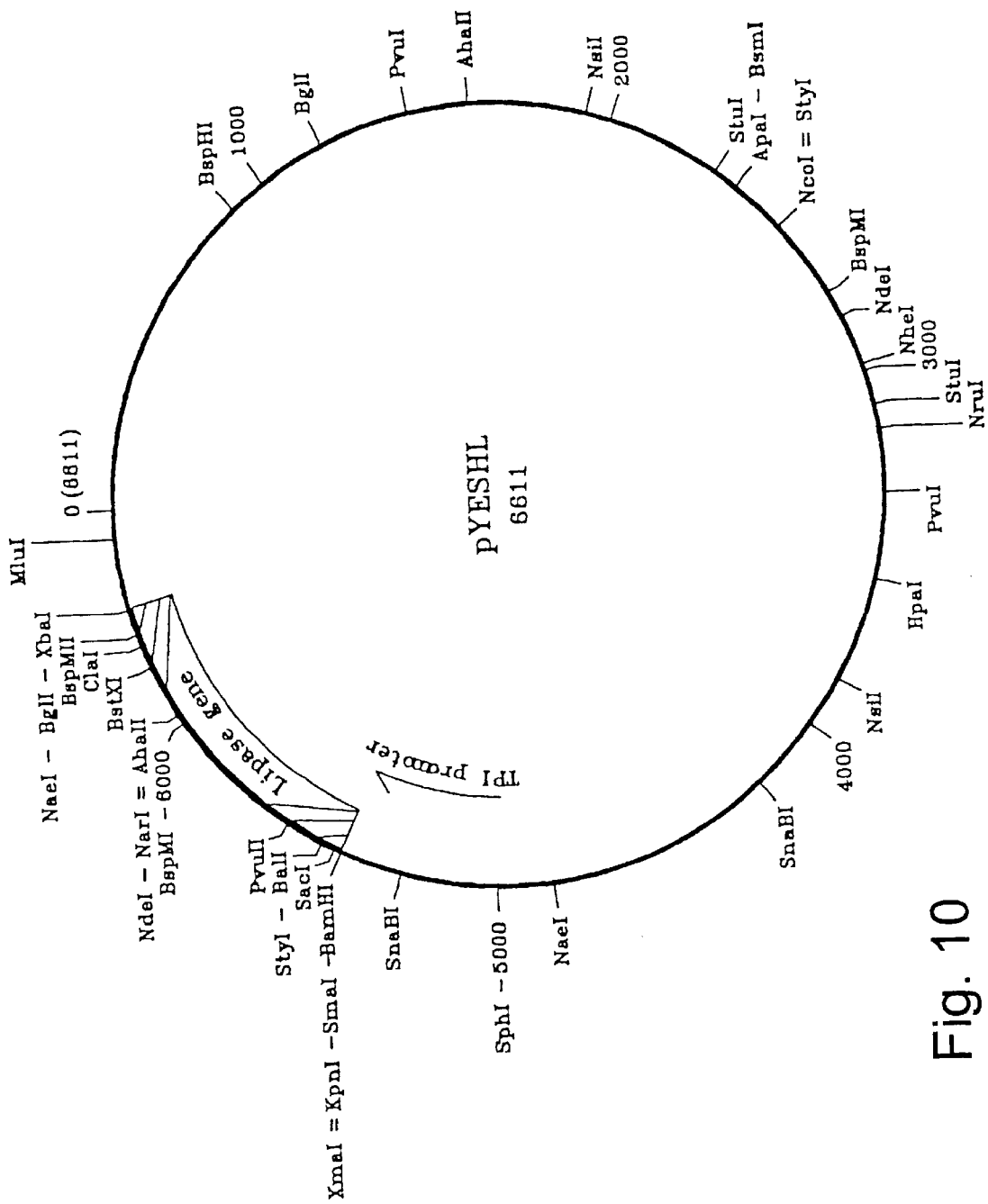
FIG. 10 shows the plasmid pYESHL.

Plasmids:
pYES 2.0 (Invitrogen Corp., UK)
p960 *A. oryzae* expression plasmid (described in EP 305 216 from Novo Nordisk A/S)
pSX581 (*E. coli* expression plasmid) (see FIG. 7)
PJSO37 (*S. cerevisiae* expression plasmid)(J. S. Okkels, (1996)"A URA3-promoter deletion in a pYES vector increases the expression level of a fungal lipase in *Saccharomyces cerevisiae*. Recombinant DNA Biotechnology III: The Integration of Biological and Engineering Sciences, vol.782 of the Annals of the New York Academy of Sciences) More specifically, the expression plasmid pJSO37, is derived from pYES 2.0 by replacing the inducible GAL1-promoter of pYES 2.0 with the constitutively expressed TPI (triose phosphate isomerase)-promoter from *Saccharomyces cerevisiae* (Albert and Karwasaki, (1982), J. Mol. Appl Genet., 1, 419–434), and deleting the URA3 promoter. A restriction map of pJSO37 is shown in FIG. 8.

pSX167 (see FIG. 4)
pSX92 (WO 89/06279)
pUC19 (Yanish-Perron et al. (1985) Gene 33, 103–119)
pHD414 (Aspergillus expression vector being a derivative of the plasmid p775 described in EP 238 023). The construction of pHD414 is further described in WO 93/11249).
PJVi245 (See FIG. 9)
pCaHj383 (see FIG. 9)
pCaHj385 (see FIG. 9)
pAHE2: Hobson, A. H., Buckley, C. M., Aamand, J. L., Jørgensen, S. T., Diderichsen, B., and McConnell, D. J. (1993). Activation of a bacterial lipase by its chaperone. Proc. Natl. Acad. Sci. USA, 90, p. 5682–5686.
pTiK04: constructed from pJSO37 including the mature Ab reflexa NL 127 lipase gene with a SPIRR encoding extension upstream of the start of the lipase gene.
pTiK05: As pTiK04 without the SPIRR (SEQ ID NO:29) extension
pTiK06: pTik04 with the MFα1 signal sequence
pTiK07: pTik05 with the MFα1 signal sequence
pYESHL is a yeast/*E coli* shuttle vector that expresses and secretes a low level of the *H. lanuginosa* lipolytic enzyme in yeast. More specifically pYESHL is a derivative of pYES2 in which the GAL1 promoter was excised and the *H. lanuginosa* lipolytic enzyme gene and the TPI (triose phosphate isomerase) promoter from *S. cerevisiae* (Alber, T. and Kawasaki, G., J.Mol.Appl. Genet 1, 419–434 (1982) were cloned between the Sphl and Xbal sites. A restriction map of pYESHL is shown in FIG. 10.

Microorganisms:
*Saccharomyces cerevisiae* YNG318: MATa Dpep4[cir$^+$] ura3-52, leu2-D2, his 4-539
*Aspergillus oryzae* IFO 4177
*A. oryzae* A1560-T40, a protease deficient derivative of *A. oryzae* IFO 4177 (WO 91/17243).
*A. oryzae* JaL 125: *Aspergillus oryzae* IFO 4177 available from Institute for Fermention, Osaka; 17–25 Juso Hammachi 2-Chome Yodogawa-ku, Osaka, Japan, having the alkaline protease gene named "alp" (described by Murakami K et al., (1991), Agric. Biol. Chem. 55, p.2807–2811) deleted by a one step gene replacement method (described by G. May in "Applied Molecular Genetics of Filamentous Fungi" (1992), p. 1–25, Eds. J. R. Kinghorn and G. Turner; Blackie Academic and Professional), using the *A. oryzae* pyrG gene as marker.
*E coli*W3110 lacl$^q$ (*E. coli*W3110 is an early isolate used as ancestral stock for the K-12 strain (Bachman, (1972), Bacteriol. Rev. 36). The W3110 stain has been made lacl$^q$ in order to overproduce the Lac repressor, turning off expression from plac more completely.
*E. coli* SJ6: Diderichsen, B., Wedsted, U., Hedegaard, L., Jensen, B. R., Sjøholm, C., (1990), Cloning of aldB, which encodes alpha-acetolactate decarboxylase, an exoenzyme from *Bacillus brevis*. J. Bacteriol., 172, p. 4315–4321).
Strain SJ1503 is *E. coli* JA221 containing plasmid pAHE2: Hobson, A. H., Buckley, C. M., Aamand, J. L., Jørgensen, S. T., Diderichsen, B., and McConnell, D. J. (1993). Activation of a bacterial lipase by its chaperone. Proc. Natl. Acad. Sci. USA, 90, p. 5682–5686.

Yeast cell YPH499 (Stratagene)
*E. coli* DH 10 B (Gibco)

Donor Organisms:
*Humicola lanuginosa* DSM 4109 available from the Deutsche Sammlung von Mikroorganismen und Zellkulturen GmbH, Mascheroderweg 1b, D-3300 Braunschweig, Federal Republic of Germany (EP 305,216)
*Humicola insolens* DSM 1800 (WO 96/13580)
*Pseudomonas cepacia* SB10, DSM 3959, is described in WO 89/01032.
*Absidia reflexa* ATTC 44896 is available from ATCC (American Type Culture Collection, 12301, Parklawn Drive, Rockville, Md. 20852, USA) as *Absidia reflexa* ATTC 44896 and from IFO (Institute for Fermentation, 17–85 Juso-horrmachi 2-chomee, Yodogawa-ku, Osaka 532, Japan) as *Absidia reflexa* IFO 5874 as described in WO 96/113578 (Novo Nordisk A/S).

Enzymes:
Bovine trypsin (Boehringer Mannheim)
The following lipases are variants of the *Humicola lanuginosa* DSM 4109 lipase (EP 305 216) which are either used as parent enzymes in the context of the present invention or which constitute modified enzymes according to the invention.

TABLE M1

| Lipase variants | Peptide addition | Mutations |
|---|---|---|
| HLv1s | SPIRR (SEQ ID NO:29) | D57G, N94K, D96L, L97M, D57G, N94K, |
| HLv1 | — | D96L, L97M |
| HLv2s | SPIRR (SEQ ID NO:29) | D137G, D167G, E210V, W221L |
| HLv2 | — | D137G, D167G, E210V, W221L |
| HLv3s | SPIRR (SEQ ID NO:29) | N94K, F95L, D96H, N101S, F181L, D234Y, I252L, P256T, G263A, L264Q |
| HLv3 | — | N94K, F95L, D96H, N101S, F181L, D234Y, I252L, P256T, G263A, L264Q |
| HLv4s | SPIRR (SEQ ID NO:29) | I90F, D96L, E99K, V187A |
| HLv4 | — | I90F, D96L, E99K, V187A |
| HLv5s | SPIRR (SEQ ID NO:29) | N94K, D96A, Q249R |
| HLv5 | — | N94K, D96A, Q249R |
| HLv7s | SPIRR (SEQ ID NO:29) | D57G, G59V, N94K, D96L, L97M, S116P, S170P, Q249R |
| HLv7 | — | D57G, G59V, N94K, D96L, L97M, S116P, S170P, Q249R |
| HLv8s | SPIRR (SEQ ID NO:29) | A49P, D167G, E210V |
| HLv8 | — | A49P, D167G, E210V |
| HLv9s | SPIRRPRP (SEQ ID NO:31) | D57G, N94K, D96L, Q249R |
| HLv9 | — | DS7G, N94K, D96L, Q249R |
| HLv10s1 | GPIRPRP (SEQ ID NO:48) | DS7G, N94K, D96L, L97M, Q249R |
| HLv10s2 | SHSRHNA (SEQ ID NO:153) | D57G, N94K, D96L, L97M, Q249R |
| HLv10s3 | TAIRPRK (SEQ ID NO:46) | D57G, N94K, D96L, L97M, Q249R |
| HLv10s4 | SALRRRP (SEQ ID NO:154) | D57G, N94K, D96L, L97M, Q249R |
| HLv10s5 | STRRPRP (SEQ ID NO:47) | D57G, N94K, D96L, L97M, Q249R |

TABLE M1-continued

| Lipase variants | Peptide addition | Mutations |
| --- | --- | --- |
| HLv10s6 | SPRRPRT (SEQ ID NO:33) | D57G, N94K, D96L, L97M, Q249R |
| HLv10s7 | SPIPPGP (SEQ ID NO:155) | D57G, N94K, D96L, L97M, Q249R |
| HLv10s8 | LPFRQRP (SEQ ID NO:49) | D57G, N94K, D96L, L97M, Q249R |
| HLv10s9 | SPFRPKL (SEQ ID NO:34) | D57G, N94K, D96L, L97M, Q249R |
| HLv10s10 | SALRRP (SEQ ID NO157) | D57G, N94K, D96L, L97M, Q249R |
| HLv10s11 | SPIRK (SEQ ID NO:22) | D57G, N94K, D96L, L97M, Q249R |
| HLv10s12 | SPIR (SEQ ID NO:28) | D57G, N94K, D96L, L97M, Q249R |
| HLv10 | — | D57G, N94K, D96L, L97M, Q249R |
| HLv11s | SPIRP (SEQ ID NO:31) | E1P, D57G, N94K, D96L, L97M, Q249R |

The following lipases are variants of the *B. cepacia* (formerly *Pseudomonas cepacia*) lipase to which an N-terminal addition has been applied in accordance with the present invention.

TABLE M2

| Lipase variants | Peptide addition |
| --- | --- |
| SJ3708 | SPIRR (SEQ ID NO:29) |
| SJ3717 | SPIRPRP (SEQ ID NO:31) |
| SJ3718 | SPIRPRP (SEQ ID NO:31) |
| SJ3719 | TAIRPRK (SEQ ID NO:53) |
| 5J3720 | STRRPRP (SEQ ID NO:52) |
| SJ3720 | STRRPRP (SEQ ID NO:52) |
| SJ3721 | GPIRPRP (SEQ ID NO:48) |

The following lipases are variants of the Humicola insolens DSM 1800 lipolytic enzyme.

TABLE M3

| Lipase variants | Peptide addition |
| --- | --- |
| HILv1s | SPPRRP (SEQ ID NO:35) |
| HILV2s | SPPRP (SEQ ID NO:37) |
| HILv3s | SPIRK (SEQ ID NO:22) |
| HILv4s | PPPRRPR SEQ ID NO:60) |

Enzyme Inhibitor:
Soy bean trypsin inhibitor (Boehringer Mannheim)
Media:
YPD: 10 g yeast extract, 20 g peptone, $H_2O$ to 810 ml. Autoclaved, 90 ml 20% glucose (sterile filtered) added.
LB-medium: 10 g Bacto-tryptone, 5 g Bacto yeast extract, 10 g NaCl in 1 liter water.
SC Ura-plates: 10% 10×Basal salts with out amino acids, 0.5% Casamino acids, 0.02% Threonine, 0.01% Tryptophane, 2% Glucose, 1.5% Agar. 10×Basal salts with out amino acids: 60g NaOH, 66.8g Yeast nitrogen base with out amino acids (Difco), and 100 g Succinic acid in 1 liter water.
FG4 medium: 3% soy meal, 3% maltodextrin, 1% peptone, pH adjusted to 7.0 with 4 M NaOH Litex Agarose HSB 2000 (CAT NO: F90472)
BG-reagent: 4 mg/ml Brilliant Green (BG) dissolved in water Substrate 1:
10 ml Olive oil (Sigma CAT NO. 0-1500)
20 ml 2% polyvinyl alcohol (PVA)
The Substrate is homogenized for 15–20 minutes.
PCS Detergent
10 g/l:

| SDS | 0.52 g |
| --- | --- |
| Dobanol 25-3 | 0.60 g |
| Dobanol 25-7 | 0.58 g |
| $NaBO_3H_2O$ | 1.50 g |

Add 1 liter 0.1 M Tris buffer (pH 9), and dilute further with the Tris buffer to the double concentration of the desired concentration on the PCS plates.
PCS-plates
Solution for making PCS plates

| Brilliant Green (BG-reagent) | 10 ml |
| --- | --- |
| Substrate 1 | 24 ml |
| PCS detergent | 500 ml |
| 2% agarose (in TRIS buffer (pH 9) | 500 ml |

Lipase Substrate (Sigma catalogue no. 800-1)
Brilliant Green (Merck, art. No. 1.01310)
Swatches:
3.5×3.5 cm and 9×9 cm cotton swatches (style #400 from TestFabrics, Inc. (New Jersey) stained with lard/sudan red
Lard:
Lard coloured with 0.75 mg sudan red/gram lard.
Detergent I:

| 1.17 g/l | LAS (Nansa 1169/P, 30% a.m.) |
| --- | --- |
| 0.15 g/l | AEO (Dobanol 25-7) |
| 1.25 g/l | Sodium triphosphate |
| 1.00 g/l | Sodium sulphate |
| 0.45 g/l | Sodium carbonate |
| 0.15 g/l | Sodium silicate |

The pH adjusted to 10
Detergent Composition A:
0.300 g/l of alkyl sulphate (AS; $C_{4-16}$)
0.650 g/l of alcohol ethoxylate (AEO; $C_{12-14}$, 6EO)
1.750 g/l of Zeolite P
0.145 g/l of $Na_2CO_3$
0.020 g/l of Sokalan CP5
0.050 g/l of CMC (carboxy- methyl-cellulose)
Mixed in 3.2 mM $Ca^{2+}/Mg^{2+}$ (5:1) in Milli-Q water, pH 10.2
Detergent Composition B
as Detergent Composition A but additional containing the following bleaching agents:
0.900 g/l Sodium carbonate peroxyhydrate
0.300 g/l TAED (tetra-acetyl-ethylene-diamine)
Inactivated Ariel Futur (Procter and Gamble) (commercially available batch No.4279 B 23:35): The enzymes in the detergent were inactivated by heat (4 minutes at 85° C. in microoven).
Chameleon double-stranded, site directed mutagenesis kit (cat. no.200509) (Stratagene, Lajolle, Calif.)

Equipment:
473A Protein Sequencer (Applied Biosystems)
Toyopearl Butyl column (XK 16/10) (Pharmacia, Sweden)
Q-Sepharose column (HPQ XK 26/10) (Pharmacia, Sweden)
MonoQ column (1 ml) (Pharmacia, Sweden)
Highperformance Q SeparoseÔ (Pharmacia, Sweden)
Spin100 column (Clontech Lab. Inc., CA, USA)

DNA sequencing was performed by using Applied Biosystems ABI DNA sequence model 373A according to the protocol in the ABI Dye Terminator Cycle Sequencing kit.

Hybridization Conditions
Medium to high stringency
Presoaking in 5×SSC and prehydbridizing for 1 hour at about 40° C. in a solution of 20% formamide, 5×Denhardt's solution, 50 mM sodium phosphate, pH 6.8, and 50 mg denatured sonicated calf thymus DNA, followed by hybridization in the same solution supplemented with 100 mM ATP for 18 hours at about 40° C., followed by a wash in 0.4× SSC at a temperature of about 45° C.

Construction of Yeast Expression Vector

The expression plasmid pJSO37, is derived from pYES 2.0. The inducible GAL1-promoter of pYES 2.0 was replaced with the constitutively expressed TPI (triose phosphate isomerase)-promoter from *Saccharomyces cerevisiae* (Albert and Karwasaki, (1982), J. Mol. Appl Genet., 1,419–434), and the URA3 promoter has been deleted. A restriction map of pJSO37 is shown in FIG. 8.

Method for Constructing Lipolytic Variants

The peptide addition and/or mutations in the non-structural N-terminal and/or C-terminal end of the parent lipolytic enzyme to construct modified lipolytic enzymes of the invention were performed either by site-directed mutagenesis or by random mutagenesis.

Site-directed in Vitro Mutagenesis of Lipolytic Enzymes

Figure 13:
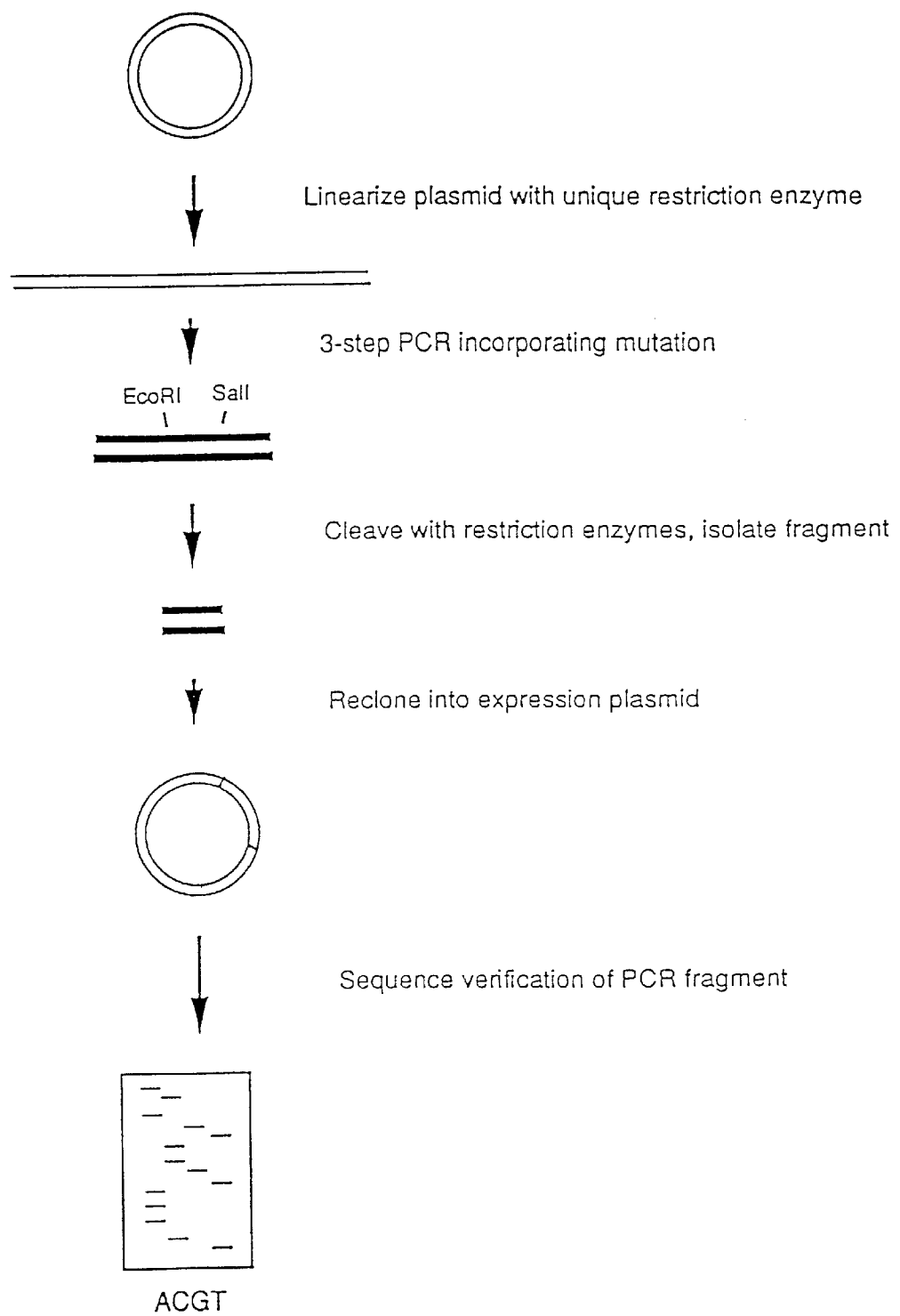
FIGS. 13 and 14 are a graphical illustration of a PCR mutagenesis method.
Figure 14:
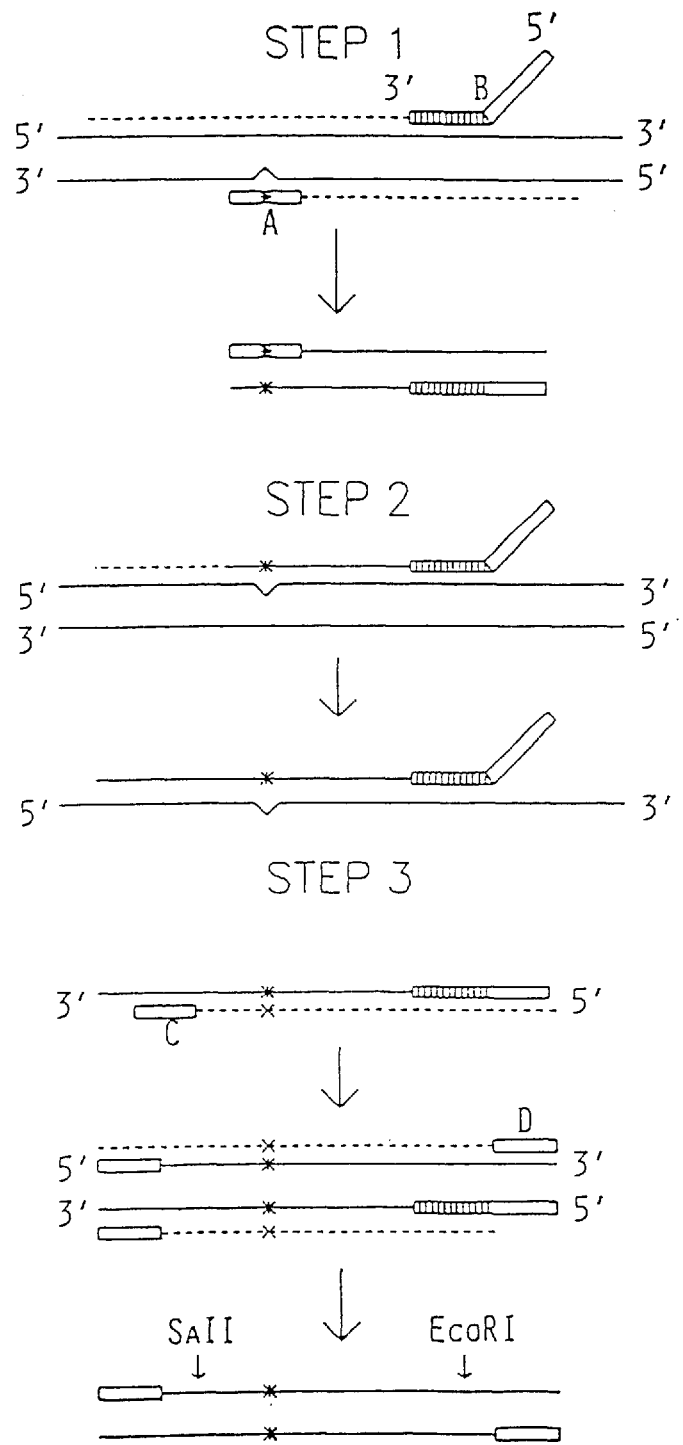
Figure 15:
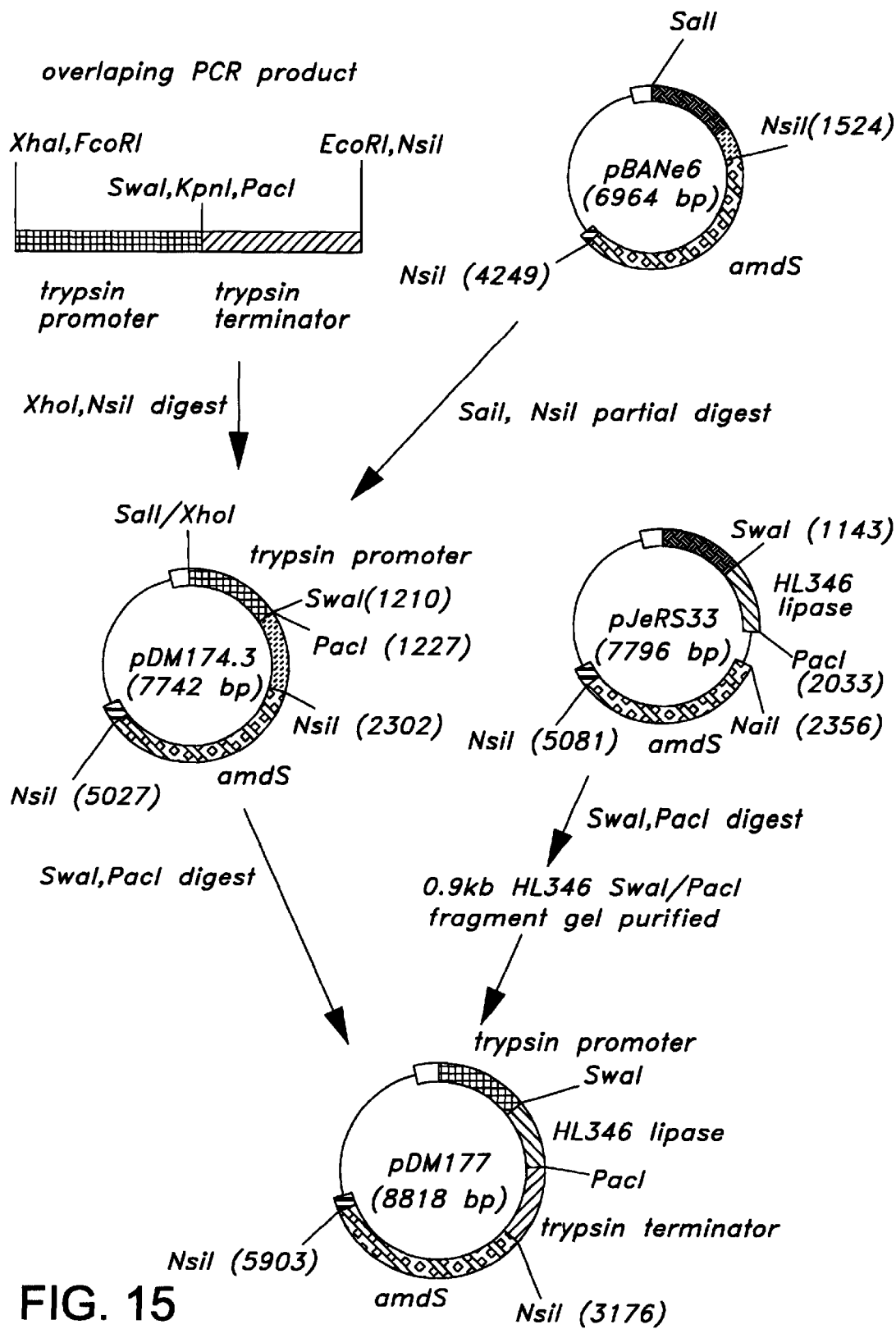
FIG. 15 shows the construction of the plasmid pDM177.

One approach which may be used for introducing mutations into the lipolytic enzyme gene is described in Nelson & Long. Analytical Biochemistry, 180, 147–151 (1989). It involves the 3-step generation of a PCR (polymerase chain reaction) fragment containing the desired mutation introduced by using a chemically synthesized DNA-strand as one of the primers in the PCR-reactions. The construction of a PCR fragment may be performed in accordance with methods known in the art. From the PCR generated fragment, a DNA fragment carrying the mutation can be isolated by cleavage with restriction enzymes and re-inserted into the expression plasmid. In FIGS. 13 and 14 the method is further outlined.

An alternative method for the construction of variants of a *H. lanuginosa* lipolytic enzyme involves the use of the commercial kit, Chameleon double-stranded, site-directed mutagenesis kit according to the manufacturer's instructions.

The gene encoding the lipolytic enzyme in question is inserted into the plasmid pHD414. In accordance with the manufacturer's instructions the Scal site of the Ampicillin gene of pHD414 is changed to a Mlul site by use of the following primer:

Primer 3: AGAAATCGGGTATCCTTTCAG (SEQ ID NO:6)

The pHD414 vector comprising the lipolytic gene in question is then used as a template for DNA polymerase and oligos 7258 and 7770 the sequences of which are disclosed in the Examples hereinafter. The desired mutation (e.g. in the N-terminal of the lipolytic gene) is introduced into the lipolytic gene in question by addition of an appropriate oligos comprising the desired mutation. When an N-terminal peptide addition is applied this may be accomplished by mutating codons of the DNA sequence encoding the pro- or prepro part of the parent lipolytic enzyme.

PCR reactions are performed according to the manufacturer's recomendations.

Random Mutagenesis

May be performed essentially as described in WO 95/22615, More specifically, for performing random mutagenesis in short DNA stretches such as in the peptide addition, the random mutagenesis is performed by use of doped or spiked oligonucleotide probes. For larger DNA stretches PCR generated mutagenesis may be used.

Construction of Random Mutagenized Libraries a) Rationale and Mathematics Behind the Desing of Random Mutagenized Libraries The overall rationale for the random mutagenesis is to mimic the evolution in nature where a low continuous mutagenesis is coupled to a continuous selection for a better mutant which is then further mutagenized. Similarly, the recent in vitro evolution studies described in the litterature have been performed with consecutive rounds of mutagenesis with increasing selection pressure (for a review see Joyce 1992). We have adapted this by using the wt gene in the first rounds of mutagenesis. Improved variants are then used in the next rounds of mutagenesis (to improve by small steps). We have screened under wash correlated conditions that are only just enough to knock out the wt enzyme activity or improved variants activity. This means that we increase the stringency of screening when better and better variants are isolated.

To increase the number of exchanges and to increase the likelyhood of finding improved variants, localized random mutagenesis have also been performed. Important regions deduced from the structure of Lipolase and from results from site-directed mutagenesis were selected. E.g. the whole lipid contact zone was considered as important for improvement, especially the lid region and the lid-contact regions. The lipid contact zone corresponds to 7 regions on the gene which have been mutated. Combinations of the regions have also been done.

b) Random Mutagenesis of an Entire Lipolytic Enzyme Coding Gene

The plasmid pYESHL is treated with 12 M formic acid for 20 min. at room temperature. The resulting lipolytic enzyme encoding gene is amplified from the formic acid treated plasmid using PCR under mutagenic conditions (0.5 mM $MnCl_2$ and ⅕ the normal amount of ATP, see e.g. Leung et al., 1989, This treatment is expected to give a broad range of mutations since formic acid gives mainly transversions and PCR generated mutations mainly transitions.

The resulting PCR fragments are cloned either by double recombination (Muhirad et al., 1992) in vivo into the shuttle vector or digestion and ligation into the shuttle vector and transformation of *E. coli*.

Eight randomly picked clones have been sequenced and were found to contain 2–3 mutations in average—both transversion and transitions.

By use of this method seven libraries were made containing from 10,000 to 140,000 clones.

c) Localized Random Mutagenesis

A mutagenic primer (oligonucleotide) is synthesized which corresponds to the part of the DNA sequence to be mutagenized except for the nucleotide(s) corresponding to amino acid codon(s) to be mutagenized. Subsequently, the resulting mutagenic primer is used in a PCR reaction with a suitable opposite primer. The resulting PCR fragment is purified and digested and cloned into the shuttle vector. Alternatively and if necessary, the resulting PCR fragment is used in a second PCR reaction as a primer with a second suitable opposite primer so as to allow digestion and cloning of the mutagenized region into the shuttle vector. The PCR reactions are performed under normal conditions.

When synthesizing the oligonucleotides used for the localized random mutagenesis, calculation of the doping level is important to estimate the mutagenesis frequency. The frequency of nucleotide exchanges can be calculated using the Binomial distribution formula:

$$P(i)=N!/(i!(N-i)!) \times p^i \times (1-p)^{N-i}$$

where N=the number of doped oligo nucleotides; p=the fraction of none wt nucleotides; i=number of nucleotide exchanges; P(i)=the probability for the i number of exchanges. It is difficult to calculate the exact number of aa exchanges from the number of nucleotide exchanges, because the third position in a codon for most of the aa can be two or all four nucleotides with out changing the aa. The same is the case for the first or second position for the three aa with 6 codons. For estimating the number of aa exchanges a Monte-Carlo simulation is more appropriate. For example the program called RAMHA performs such a simulation (described in Siderovski and Mak 1993). This program simulates the synthesis of e.g. 10,000 oligonucleotides with the desired doping and calculates the frequency of 0 to n aa exchanges.

A Doping Example

The relationship between doping and aa exchanges in a region of 13 codons is (calculated using a Monte Carlo simulation):

| doping mutations level | Percent | | | | | | | |
|---|---|---|---|---|---|---|---|---|
|  | 0 | 1 | 2 | 3 | 4 | 5 | 6 | 7 |
| 5% | 0.2 | 0.35 | 0.27 | 0.13 | 0.05 | 0 | 0 | 0 |
| 10% | 0.04 | 0.13 | 0.24 | 0.25 | 0.19 | 0.11 | 0.05 | 0 |
| 15% | 0.005 | 0.03 | 0.10 | 0.20 | 0.24 | 0.23 | 0.13 | 0.07 |

The possible number of combinations of aa exchanges for 13 aa can be calculated using the formula:

$$N=y!20^x/(x!(y-x)!)$$

y=number of aa mutagenized
x=number of aa exchanges 1 aa exchange in 13 aa = 260 possible combination
2 aa exchange in 13 aa = 31200 possible combinations
3 aa exchange in 13 aa = 2.3 × $10^6$ possible combinations From this follows that when screening e.g 100,000 colonies of a library doped with 10% in 13 codons giving the distribution shown in the above table will mean screening of about 13,000 with one aa exchange (13%). There are, however, only 260 possible one aa exchanges, so a large number of the same one aa exchanges are being screened. A higher doping of e.g. 15% (in the above table) will give fewer one aa exchanges (about 3%), however, the two aa exchanges will also be lowered to a degree (10%) that will not enable screening of the 31200 possible combinations with a screenings capacity around 100.000.

Finally, the aa exchanges are biased by the origin of the wt amino acid. E.g. it takes only one nucleotide exchange to change Glu to Ala, but three from Glu to Phe. This means that the probability is lower for the aa exchanges that requires 2 or 3 nucleotide exchanges than for those that requires one nucleotide exchange. Therefore we have in some cases allowed more than one aa at positions where we know it is possible. We have always chosen G/C at the third position of the codons with four or six codons. This lowers the bias of the wt codon and also lowers the likelyhood of stop codon (from 4.7% to 3.1% if completely scrambled). For a calculation of the probability of whether a given pool size contain the most probable and least probable replacement mutants, see Palzkill et al. 1994.

Calculation of Population Distribution in Screening of Amplified Libraries

Another consideration may be taken into account. Most of the libraries presented herein are amplified in *E. coli* before they are transformed into yeast. This means that there is a probability for screening the same amplified clone more than once—see box 1.

Box I

Screening of an Amplified Random Mutagenized Library of e.g. 100,000 Different Clones 64% of the library is screened when 100,000 colonies have been screened.
90% of the library is screened when 230,000 colonies have been screened.
95% of the library is screened when 300,000 colonies have been screened.

This is assuming that all 100,000 clones are amplified evenly.

The following formula can be used to calculate this:

$$N=\ln(1-P)/\ln(1-1/D)$$

N is the number of screened clones, P is the fraction of different clones screened and D is the total number of different clones.

Anti-termination Strategies

In order to avoid premature truncated proteins nonsense mutations should be avoided in the codons with a potential to form stop codons. For codons that can be substituted with alternative codons with out the potential to form stop codons, the following strategies can be used:

| | |
|---|---|
| Gly: GGA | GG (G,C,T) |
| Leu: TT (A,G) | CTN |
| Arg: (A,C) GA | (A,C) GG or CG (C,T) |
| Ser: TC (A,G) | TC (C,T) or AG (C,T) |

The following aa can, however, only be specified with codons exhibiting stop-codon potential: Cys, Glu, Lys, Gln, Trp, and Tyr. Therefore only the doping can be designed to circumvent the random placement of nucleotides producing stop codons. For example:

Glu (similar for Lys and Gln): (90% G/5%C,A) (90% A/3.3%C,G,T) (90% A/3.3%C,G,T). No TAA or TAG= STOP.

Tyr (similar for Cys): (90% T/3.3% A,C,G) (90% A/3.3%C,G,T) (90%C/10% T). No TAG or TAA=STOP.

Trp: (90% T/3.3% A,C,G) (90% G/5%C,T) (90% G/5%C,T). No TGA or TAG=STOP.

Such a strategy will of course abolish certain a.a. exchanges. Using these strategies the number of premature truncated proteins will be lowered dramatically.

Low Calcium Filter Assay

Procedure

1) Provide SC Ura replica plates (useful for selecting strains carrying an expression vector) with a first protein binding filter (Nylon membrane) and a second low protein binding filter (Cellulose acetate) on the top.
2) Spread yeast cells containing a parent lipase gene or a mutated lipase gene on the double filter and incubate for 2 or 3 days at 30° C.
3) Keep the colonies on the top filter by transferring the topfilter to a new plate.
4) Remove the protein binding filter to an empty petri dish.
5) Pour an agarose solution comprising an olive oil emulsion (2% P.V.A.:Olive oil=3:1), Brilliant green (indicator, 0.004%), 100 mM tris buffer pH9 and EGTA (final concentration 5 mM) on the bottom filter so as to identify colonies expressing lipase activity in the form of blue-green spots.
6) Identify colonies found in step 5) having a reduced dependency for calcium as compared to the parent lipase.

Dobanol®25-7 Filter Assay:

The screening for an improved tolerance towards a detergent component is performed by use of a filter assay corresponding to that described above except for the fact that the solution defined in 5) further comprises 0.02% Dobanol®25-7 and optionally without any EGTA.

An alternative screening assay is the following:

Procedure

1) Provide SC Ura-plates (useful for selecting strains carrying an expression vector) with a protein binding filter (Cellulose acetate) on the top.
2) Spread yeast cells containing a parent lipase gene or a mutated lipase gene on the filter and incubate for 3 or 4 days at 30° C.
3) Keep the colonies on the top filter by transferring the topfilter to a new plate.
4) Remove the protein binding filter to a petri dish containing:
An agarose solution comprising an olive oil emulsion (2% P.V.A. Olive oil=2:1), Brilliant green (indicator,0.004%), 100 mM tris buffer pH10 and the detergent or detergent component, e.g. PCS-plates. The protein binding filter should have the colony side facing the screening plate.
5) Identify colonies expressing lipase activity in the form of blue-green spots found in step 4).

Alternatively, the non-protein binding filter (or a protein binding filter) carrying the yeast colonies may be used directly on the screening plate.

In Vivo Recombination of *Humicola lanuginosa* Lipase Variants (Gene Shuffling)

The DNA sequences of a number of *Humicola lanuginosa* lipase variants can be in vivo recombined in the same mixture.

Vectors are prepared from the lipase variants by ligation into the yeast expression vector pJSO37. All vectors are cut open with NruI.

DNA fragment of all homologous DNA sequences are prepared by PCR amplification using standard methods.

The DNA fragments and the opened vectors are mixed and transformed into the yeast *Saccharomyces cerevisiae* YNG318 by standard methods. The recombination host cell is cultivated and screened as described above. Apearing transformants are isolated and tested for improved wash performance using one of the filter assay methods described above.

Positive transformants are variants with improved wash performance resulting from gene shuffling of homologous DNA sequences.

Fermentation in Yeast 10 ml of SC-ura$^-$ medium are inoculated with a *S. cerevisiae* colony and grown at 30° C. for 2 days. The resulting 10 ml culture is used for inoculating a shake flask containing 300 ml SC-ura$^-$ medium which is grown at 30° C. for 3 days. The 300 ml is used for inoculation 5 liter of the following G-substrate:

400 g Amicase
6.7 g yeast extract (Difco)
12.5 g L-Leucin (Fluka)
6.7 g $(NH_4)_2SO_4$
10 g $MgSO_4 7H_2O$
17g $K_2SO_4$
10 ml Tracecompounds
5 ml Vitamin solution
6.7 ml $H_3PO_4$
25 ml 20% Pluronic (antifoam)
In a total volume of 5000 ml:

The yeast cells are fermented for 5 days at 30° C. They are given a start dosage of 100 ml 70% glucose and added 400 ml 70% glucose/day. A pH=5.0 is kept by addition of a 10% $NH_3$ solution. Agitation is 300 rpm for the first 22 hours followed by 900 rpm for the rest of the fermentation. Air is given with 1 l air/l/min for the first 22 hours followed by 1.5 l air/l/min for the rest of the fermentation.

Trace compounds: 6.8 g of $ZnCl_2$, 54.0 g of $FeCl_2 6H_2O$, 19.1 g of $MnCl_2 4H_2O$, 2.2 $CuSO_4 5H_2O$, 2.58 g of $CaCl_2$, 0.62 g of $H_3BO_3$, 0.024 g of $(NH_4)_6Mo_7O_{24} 4H_2O$, 0.2 g of Kl, 100 ml of HCl (concentrated), in a total volume of 1 l.

Vitamin solution: 250 mg of Biotin, 3 g of Thiamin, 10 g of D-Calciumpanthetonate, 100 g of Myo-Inositol. 50 g of Cholinchlorid, 1.6 g of Pyridoxin, 1.2 g of Niacinamid, 0.4 g of Folicacid, 0.4 g Riboflavin. In a total volume of 1 liter.

Expression of Wild Type *Humicola lanuginosa* Lipolytic Enzyme in *Aspergillus oryzae*

Cloning of *H. lanuginosa* lipolytic enzyme is described in EP 305 216, It also describes expression and characterization of the enzyme in *A. oryzae*. The expression plasmid used is named p960.

Figure 11:
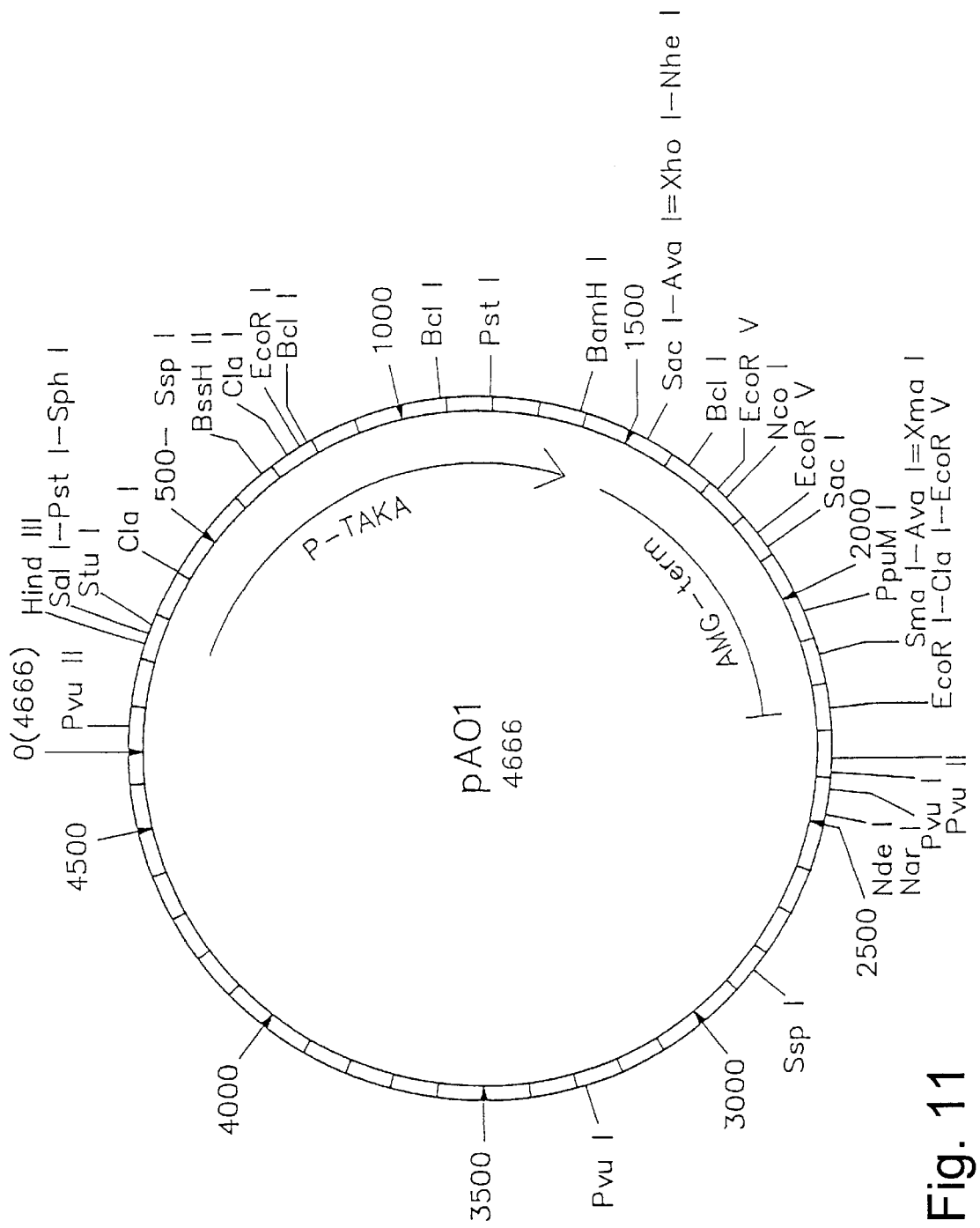
FIG. 11 shows the plasmid pAO1.
Figure 12:
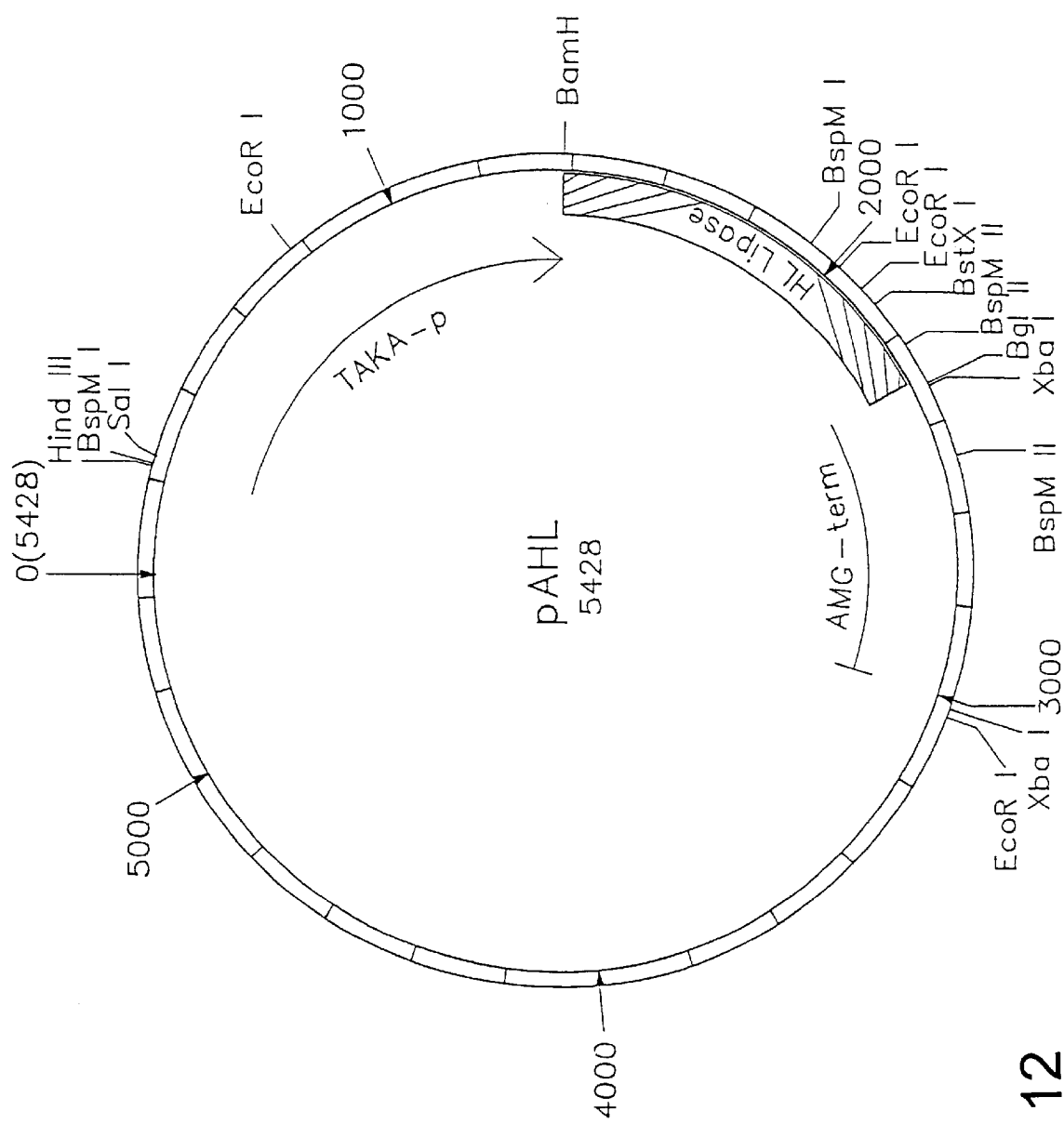
FIG. 12 shows the plasmid pAHL.

The expression plasmid used in this application is identical to p960, except for minor modifications just 3' to the lipase coding region. The modifications are described in WO 95/22615 and were made the following way: p960 was digested with NruI and BamHI restriction enzymes. Between these two sites the BamHI/NheI fragment from plasmid pBR322, in which the NheI fragment was filled in with Klenow polymerase, was cloned, thereby creating plasmid pAO1 (FIG. 11), which ontains unique BamHI and NheI sites. Between these unique sites BamHI/XbaI fragments from p960 was cloned to give pAHL (FIG. 12).

Transformation of *Aspergillus oryzae* (General Procedure)

100 ml of YPD (Sherman et al., (1981), Methods in Yeast Genetics, Cold Spring Harbor Laboratory) are inoculated with spores of *A. oryzae* and incubated with shaking for about 24 hours. The mycelium is harvested by filtration through miracloth and washed with 200 ml of 0.6 M $MgSO_4$. The mycelium is suspended in 15 ml of 1.2 M $MgSO_4$, 10 mM NaH$_2$PO$_4$, pH 5.8. The suspension is cooled on ice and 1 ml of buffer containing 120 mg of Novozym® 234, batch 1687 is added. After 5 min., 1 ml of 12 mg/ml BSA (Sigma type H25) is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayed with 5 ml of 0.6 M sorbitol, 100 mM Tris-HCl, pH 7.0, Centrifugation is performed for 15 min. at 1000 g and the protoplasts are collected from the top of the MgSO$_4$ cushion. 2 volumes of STC (1.2 M sorbitol, 10 mM Tris-HCl, pH 7.5, 10 mM CaCl$_2$) are added to the protoplast suspension and the mixture is centrifuged for 5 min. at 1000 g. The protoplast pellet is resuspended in 3 ml of STC and repelleted. This is repeated. Finally, the protoplasts are resuspended in 0.2–1 ml of STC.

100 µl of protoplast suspension are mixed with 5–25 pg of p3SR2 (an *A. nidulans* amdS gene carrying plasmid described in Hynes et al., Mol. and Cel. Biol., Vol.3, No.8,1430–1439. August 1983) in 10 µl of STC. The mixture is left at room temperature for 25 min. 0.2 ml of 60% PEG 4000 (BDH 29576), 10 mM CaCl$_2$ and 10 mM Tris-HCl, pH 7.5 is added and carefully mixed (twice) and finally 0.85 ml of the same solution are added and carefully mixed. The mixture is left at room temperature for 25 min., spun at 2.500 g for 15 min. and the pellet is resuspended in 2 ml of 1.2M sorbitol. After one more sedimentation the protoplasts are spread on minimal plates (Cove, (1966), Biochem. Biophys. Acta 113, 51–56) containing 1.0 M sucrose, pH 7.0, 10 mM acetamide as nitrogen source and 20 mM CsCl to inhibit background growth. After incubation for 4–7 days at 37° C. spores are picked, suspended in sterile water and spread for single colonies. This procedure is repeated and spores of a single colony after the second re-isolation are stored as a defined transformant.

Transformation of *A. oryzae* A1560-T40

The plasmid carrying a DNA sequence encoding a variant of the invention is transformed into *Aspergillus oryzae* A1560-T40, a protease deficient derivative of A. oryzae IFO 4177, using selection on acetamide by cotransformation with pToC 90 harboring the amdS gene from *A. nidulans* as a 2.7 kb Xba I fragment (Corrick et al. (1987), GENE 53, 63–71) on a pUC 19 vector (Yannisch-Perron et al. (1985), GENE 33, 103–119). Transformation is performed as described in EP 238 023.

Fed Batch Fermentation

Fed batch fermentation is performed in a medium comprising maltodextrin as a carbon source, urea as a nitrogen source and yeast extract. The fed batch fermentation was performed by inoculating a shake flask culture of A. oryzae host cells in question into a medium comprising 3.5% of the carbon source and 0.5% of the nitrogen source. After 24 hours of cultivation at pH 5.0 and 34° C. the continuous supply of additional carbon and nitrogen sources are initiated. The carbon source is kept as the limiting factor and it is secured that oxygen is present in excess. The fed batch cultivation is continued for 4 days, after which the enzymes can be recovered by centrifugation, ultrafiltration, clear filtration and germ filtration. Further purification may be done by anionexchange chromatographic methods known in the art.

Purification of *H. lanuginosa* Lipolytic Enzyme Variants Expressed in *S. cerevisiae*

The fermentation broth is sterile filtered and ammonium acetate (92 g) is added to the filtrate (1400 ml) to give a 0.8 M solution of ammonium acetate. The solution is added onto a Toyopearl Butyl column (XK 16/10). The column is washed with 0.8 M ammonium acetate and the lipolytic enzyme eluted in H$_2$O at a flow rate of 5 ml/min. 10 ml fractions are collected and lipolytic enzyme containing fractions are pooled according to activity in the standard lipase titration assay. The lipase containing pool are filtered and the pH is adjusted to pH 8.5 and added onto a Q-Sepharose column (HPQ XK 26/10). The column is washed with 200 ml 0.1 M Tris-HCl, pH 8.5 and the lipolytic enzyme eluted in a linear gradient of 0 to 0.3 M NaCl in 400 ml of 0.1 M Tris-HCl, pH 8.5 at a flow rate of 5 ml/min. 10 fractions are collected and the lipase containing fractions pooled according to activity in the standard lipase titration assay. Fractions containing lipase activity and absorption A280/A260 nm is greater than 1.7 are pooled.

Purification of *H. lanuginosa* Lipolytic Enzyme Variants Without Peptide Addition and Expressed *A. oryzae*

Fermentation supernatant from the *A. oryzae* culture is centrifuged and cell debris discarded. The supernatant is filtered though a 0.45µmillipore filter. Then the is precipitated with 60% saturated ammonium sulphate. The precipitate is dissolved in water and solid ammonium acetate added to a final concentration of 0.8 M. The solution is applied onto a Butyl Toyopearl column pre-equilibrated with 0.8 M ammonium acetate. The bound enzyme is eluted with gradient using water and 50% ethanol as eluent.

Fractions containing enzyme activity are then pooled and conductance is adjusted to lower than 5 mSi and pH is adjusted to 8.5.

The pools containing activity are then applied onto an anion exchange column (e.g. High performance Q Separose®) pre-equilibrated with 25 mM Tris-acetate buffer, pH 8.5. The bound activity is eluted with linear salt gradient using same buffer and 0.5 M sodium chloride. Fractions containing high lipolytic enzyme activity are pooled. Fractions containing lipase activity and absorption A280/A260 nm is greater than 1.7 are pooled.

Purification of wild type *H. lanuginosa* lipolytic enzyme expressed *A. oryzae* were performed as described above with the exception that the pH of the lipase containing fractions were adjusted to 7.5, Lipase Activity (LU—Lipase Units)

Lipase activity is assayed using glycerine tributyrate (Merck) as a substrate and gum-arabic as an emulsifier. 1 LU (Lipase Unit) is the amount of enzyme which liberates 1 µmol titratable butyric acid per minute at 30° C., pH 7.0. The lipase activity is assayed by pH-stat using Radiometer titrator VIT90, Radiometer, Copenhagen.

Application of Lard on the Swatches

50 µl of stained lard heated to 70° C. are applied to the canter of each swatch. After application of the stain the swatches are heated in an oven for 25 minutes at 75° C. and stored overnight at room temperature prior to the first wash.

3-cycle Wash Performance

The 3-cycle wash performance of a modified lipolytic enzyme of the invention can be evaluated on the basis of the enzyme dosage in mg of protein (or LU) per liter compared to the parent lipolytic enzyme. Wash trials are carried out in 150 ml beakers placed in a thermostated water bath. The beakers are stirred with triangular magnetic rods.

The experimental conditions are as follows:
Method: 3 cycles with overnight drying between each cycle
Wash liquor: 100 ml per beaker
Swatches: 6 swatches (3.5×3.5 cm, stained with lard coloured with 0.75 µg sudan red/gram of lard) per beaker
Detergent: Detergent I, pH adjusted to 10.2
Enzyme conc.: 0.075, 0.188, 0.375, 0.75 and 2.5 mg of lipase protein per liter
Time: 20 minutes
Temperature: 30° C.
Rinse: 15 minutes in running tap water
Drying: overnight at room temperature (~20° C., 30–50% RH)
Evaluation: after the 3rd wash, the reflectance at 460 nm was measured.

Evaluations of Wash Results

Dose-response curves are compared for the modified lipolytic enzyme and the parent lipolytic enzyme. The dose-response curves is calculated by fitting the measured data to the following equation:

$$DR = DR_{max} \times (C^{0.5}/(K+C^{0.5})) \quad (I)$$

where DR is the effect expressed in reflectance units
C is the enzyme concentration (mg/l)
$DR_{max}$ is a constant expressing the maximum effect
K is a constant; $K^2$ expresses the enzyme concentration at which half of the maximum effect is obtained.

Based on the characteristic constants $DR_{max}$ and K found for each modified lipolytic enzyme as well as the parent lipolytic enzyme, improvement factors are calculated. The improvement factor, defined as $$f_{improve} = C_{parent}/C \quad (II)$$

expresses the amount of modified lipase protein needed to obtain the same effect as that obtained with 0.25 mg/l of the reference parent protein ($C_{parent}$).

Thus, the procedure for calculating the improvement factor is as follows:

1) The effect of the parent protein at 0.25 mg/l ($DR_{parent}$) was calculated by means of equation (I);
2) the concentration of the modified lipolytic enzyme resulting in the same effect as the parent enzyme at 0.25 mg/l was calculated by means of the following equation:

$$c = (k_{(modify)} \times (DR_{(parent)}/(DR_{max(modify)} - DR_{(parent)}))^2 \quad (III)$$

3) the improvement factor was calculated by means of equation (II).

1 Cycle Wash Performance=Assay for Test of First Wash Effect 1 cycle wash trials are carried out in a termostated Terg-O-to-Meter (TOM).
Method: 1 cycle wash followed by linedrying.
Wash liquor: 1000 ml per beaker
Swatches: 7 cotton swatches (9×9 cm, stained with lard coloured with 0.75 µg sudan red/gram of lard)
Water: 3.2 mM $Ca^{2+}/Mg^{2+}$ (5:1)
Detergent: 5 g/l inactivated Ariel Futur™. Natural pH around 10.3, (commercially available batch No.4279 B 23:35) or 5 g/l of Detergent Composition A or Detergent B. pH adjusted artificially to 10 by NaOH.
Lipase concentrations: 0, 1250, 12500 LU/l
Time: 20 minutes
Temperature: 30° C.
Rinse: 15 minutes in running tap water.
Drying: Overnight at room temperature (~20° C., 30–40% RH).
Evaluation: The fatty matter is extracted using the soxhlet method and the amount of fatty matter is gravimetrically determined (examples 11 and 23), and for examples 12–15, 26, 27) as follows:
Evaluation: The reflectance was measured at 460 nm. Afterwards, the fatty matter was extracted from the swatches with chloroform in a Soxhlet extraction apparatus, distilling off the solvent and determining the amount of fatty matter left on the swatches gravimetrically.

The amout of fatty material may alternatively be determined using thin layer chromatography(TLC)/Flame Ionization Detector (FID)].

The percentage of lard removed is determined as:
1) % removal defined as:
   [(remaining fat on swatches washed with detergent without lipolytic enzyme) minus (remaining fat on swatches washed with detergent with lipolytic enzyme)] divided by (remaining fat on swatches washed with detergent without lipolytic enzyme) and multiplied by 100%, or
2) delta reflectance (dR) defined as:
   (R(swatches washed in detergent with lipase)-R(swatches washed in detergent without lipase). The reflectance (which may also be termed remission) is measured on an Elrepho 2000 apparatus from Datacolor which illuminates the sample with 2 xenon blitzlambs and measures the amount of reflected light so that entirely white correspond to a 100% reflection and entirely black a 0% reflection.

EXAMPLES

Example 1

Production of Wildtype *Humicola lanuginosa* Lipase in Yeast

For expression *Humicola lanuginosa* lipase in the yeast *Saccharomyces cerevisiae* YNG318 the yeast expression vector pJSO37 (see FIG. 8) was constructed as described in the Material and Methods section above. pJSO37 comprises the DNA sequence encoding the parent lipase and includes the DNA sequences encoding the signal peptide and propeptide (see FIG. 1). The plasmid was transformed into the yeast by standard methods (cf. Sambrooks et al., (1989), Molecular Cloning: A Laboratory Manual, 2nd Ed., Cold Spring Harbor). The yeast was cultivated as described in the Material and Methods section above.

Purification of *H. lanuginosa* lipase expressed in *S. cerevisiae* was performed as described in the Materials and Methods section above with the exception that the pH of the lipase containing pool was adjusted to pH 7.6 (instead of pH 8.5) and the elution of lipolytic enzyme was conducted at pH 7.25. The lipase containing pool was diluted with $H_2O$ and added onto a I ml MonoQ column at a flow rate of 1 ml/min. The column was washed with 30 ml of $H_2O$ and the lipase was eluted in linear gradient of 0 to 0.25 M NaCl in 40 ml. The lipase was manually collected according to absorption at 280 nm.

N-terminal Amino Acid Sequencing of *H. lanuginosa* Lipase Expressed in Yeast The N-terminal amino acid sequencing was conducted on the *S. cerevisiae* expressed lipase using the 473A Protein Sequencer according to the manufacturer's instructions.

When the N-terminal amino acid sequence of *S. cerevisiae* expressed lipase is compared to the N-terminal amino acid sequence of the same lipase expressed in *A. oryzae* (as described in EP 305 216) a difference was observed, as the major part of the *S. cerevisiae* expressed enzyme contains 5 amino acid residues extra (SPIRR-) (SEQ ID NO:29) at the N-terminus (see Table E1) which includes the corresponding information for the A. oryzae expressed lipase.

TABLE E1

| Expression system | Fraction containing SPIRR-EVSQ . . . | Fraction containing EVSQ . . . |
|---|---|---|
| S. cerevisiae | 75% | 25% |
| A. oryzae | 0% | 100% |

As can be seen from the table a major portion of the secreted lipase expressed in *S. cerevisiae* has been extended by the five amino acid SPIRR (SEQ ID NO:29) (from the pro-peptide). The relative amount of enzyme containing the extra amino acid residues can be established from the yields of PTH-amino acids in amino acid sequencing.

Example 2

Removal of the SPIRR-peptide from the N-terminus of the *H. lanuginosa* Lipase Expressed in *S. cerevisiae*

To 4.5 mg of the above purified modified ("SPIRR"-containing) lipase expressed in *S. cerevisiae* (in 1.8 ml 0.05 M $NH_4HCO_3$) was added 50 μg bovine trypsin (sequencing grade) and the mixture was incubated for 1 hour at 37° C. Upon incubation the tryptic digest was stopped by adding more than 50 mg soy bean trypsin inhibitor.

The removal of the N-terminal SPIRR-peptide addition was observed by N-terminal amino acid sequencing where the fraction containing SPIRR was reduced from 75% to 13% (See Table E2).

TABLE E2

| Treatment | Fraction containing SPIRR-EVSQ . . . | Fraction containing EVSQ . . . |
|---|---|---|
| Untreated (i.e. modified lipase) | 75% | 25% |
| Trypsin treatment | 13% | 87% |

The mild trypsin treatment did not result in internal cleavages in the modified lipase as no internal amino acid sequences were observed by amino acid sequencing. Also the specific activity of the trypsin treated lipase was comparable to specific activity of the untreated lipase showing that the trypsin treatment did not affect enzyme activity in the standard assay (See Table E3).

TABLE E3

| Sample | $A_{280}$ | $A_{280}/A_{260}$ | Activity (LU/ml) | Specific Activity (LU/$A_{280}$) |
|---|---|---|---|---|
| Untreated (i.e. modified lipase) | 2.5 | 1.8 | 9725 | 3890 |
| Trypsin treated | 2.2 | 1.8 | 9163 | 4127 |

Example 3

Construction of Parent *Humicola lanuginosa* Lipase Expression Vector and Expression in *E. coli* pSX92 (see FIG. 4) was cut with Hind III, blunt ended with Klenow polymerase and then cut with ClaI. The large fragment was isolated (A). pHLL (see EP 305,216 FIGS. 3 and 4) (comprising the DNA sequence encoding the parent lipase) was cut with BamH1, blunt ended, and cut with XhoII. The fragment containing the mature part of the modified lipase gene was isolated (B).

A and B were ligated together with a synthetic linker (KFN 575/576) which codes for the last 5 amino acids in the subtilisin 309 signal fused to the first four amino acids of the mature lipase. The last nucleotide "A" in the upper strand changed the XhoII site in the mature lipase gene to a Bgl II site.

Synthetic linker:
KFN 575/576: 5'-CGATCGCATCGGCTGCTGAGGT CTCGCAA-3' (SEQ ID NO:124)
3-TAGCGTAGCCGACGACTCCAGAGGCTTCTAG-5' (SEQ ID NO:125)

The resulting plasmid (pSX167) comprised the DNA sequence encoding the mature lipase. pSX167 was cut with Pme I and Bam H1 and the fragment containing the subtilisin 309 signal sequence-lipase fusion and the 5S terminator was isolated (1769 bp). This fragment was ligated into Hinc II-Bam H1 cut pUC19 creating pSX578.

DNA coding for mature lipase down to Bst XI (from pSX167, 654 bp) was fused to the *Achromobacter lyticus* protease I signal sequence (see FIG. 3) from Sph I using the PCR technique "Splicing by Overlap Extension", Horton et al., (1989), Gene).

Figure 5:
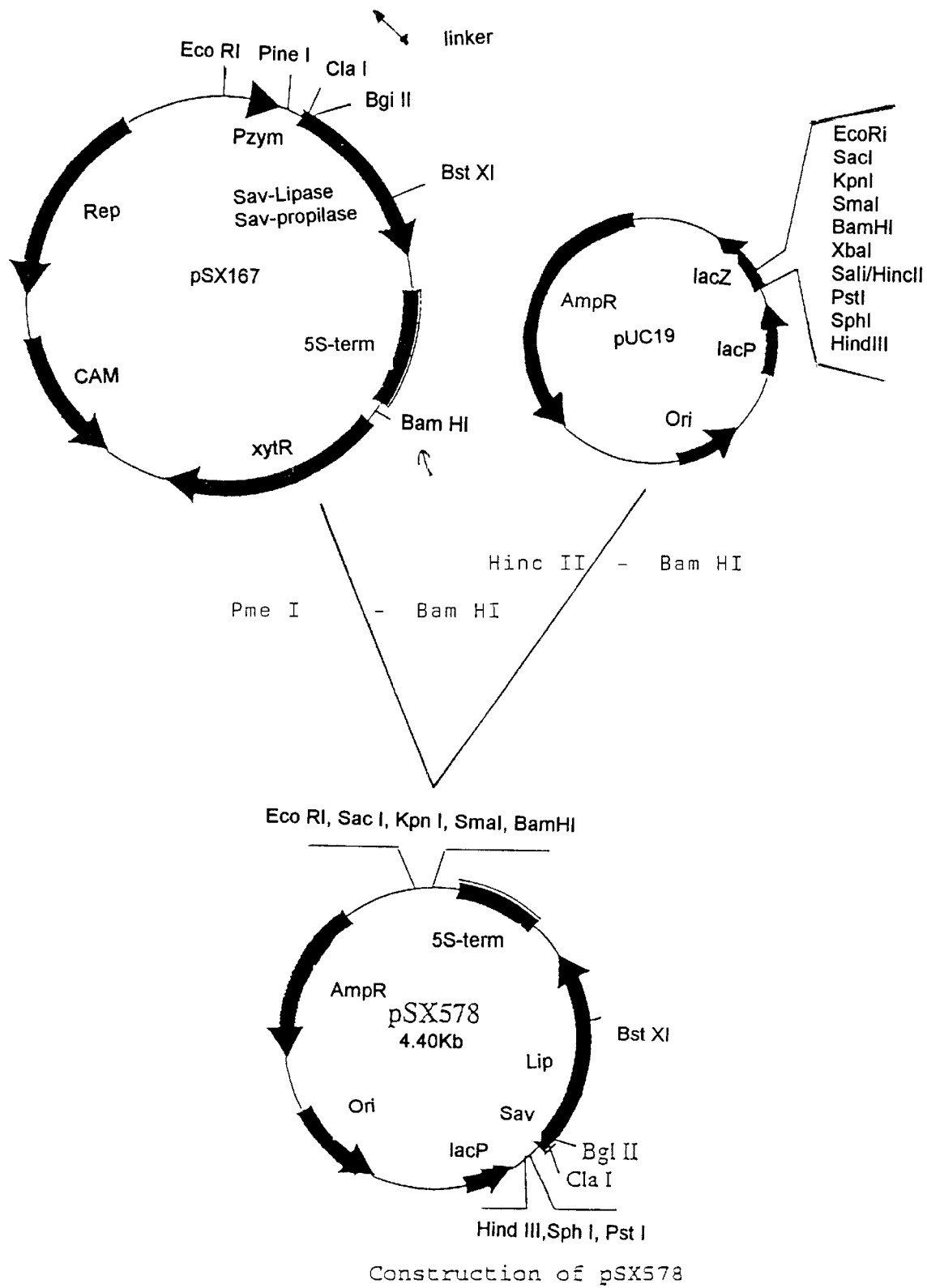
FIG. 5 shows the construction of pSX578.
Figure 6:
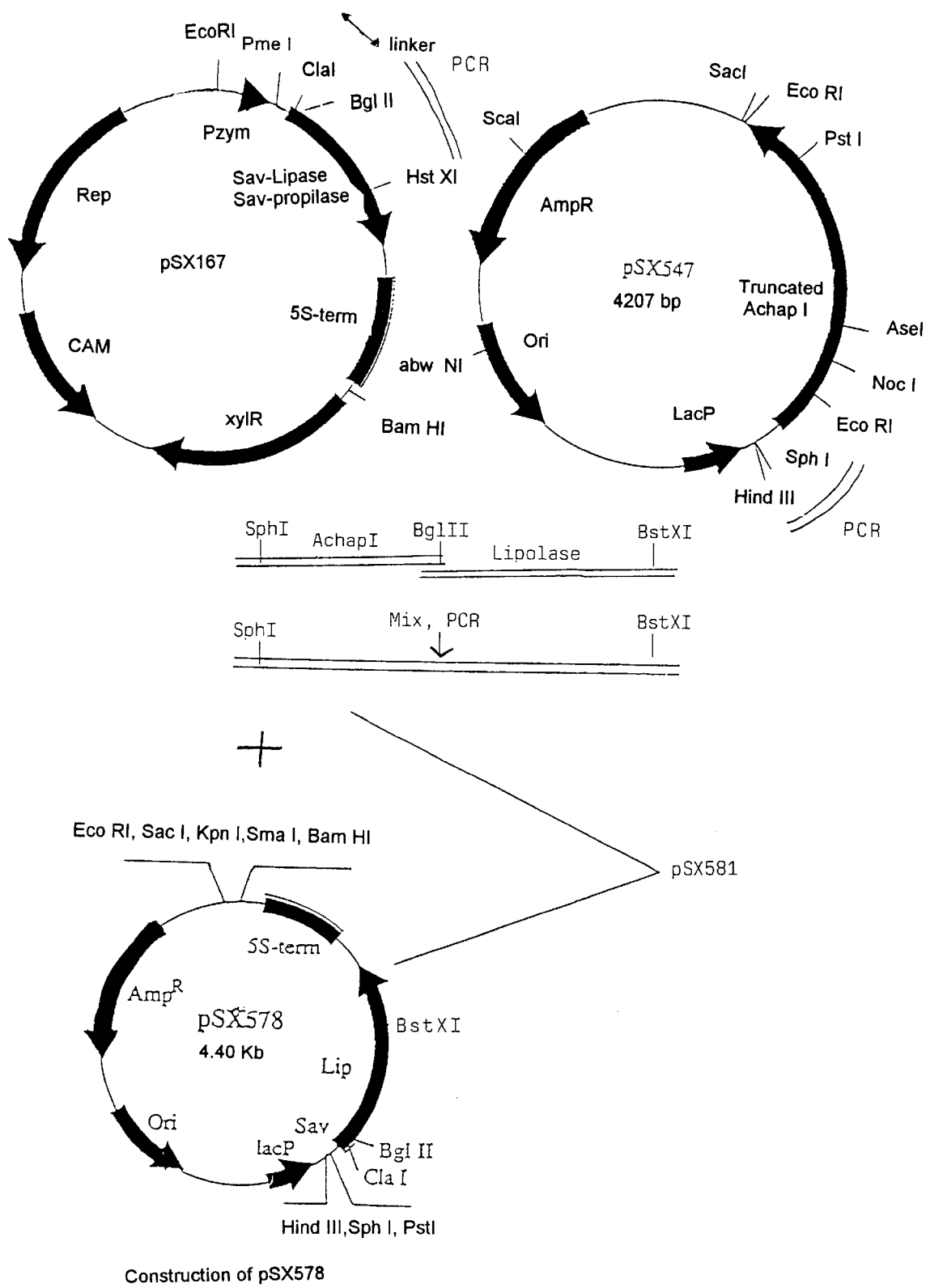
FIG. 6 shows the construction of pSX581.

Plasmid (pSX578) (see FIG. 5) was cut with Sph I and Bst XI and the above mentioned PCR DNA was inserted (FIG. 6). The resulting plasmid pSX581 (see FIG. 7) was transformed into *E. coli* W3110 lacl$^q$. When grown in shake flasks for 72 hours in LB-medium containing 0.4% lactose at 30° C. the resulting strain produces non-glycosylated lipase with the same specific activity as the normal glycosylated parent lipase enzyme.

Example 4

Construction of *H. lanuginosa* Lipase with Peptide Addition in *E. coli*

The pSX581 plasmid (see FIG. 7) was digested with BglII/HindIII and the vector fragment was purified from an agarose gel using standard methods.

A PCR reaction was performed with the following primers using pSX581 as template:
SPIRR Primer: Primer 1 (SEQ ID NO:3):
5'-AA CAG ATC TTG CGA GAC CTC TCT ACG TAT AGG GCT AGC GAG CGC GGC GCT GAT CG-3' (55-mer)
PCR primer: Primer 2 (SEQ ID NO:4):
GTTGTGTGGMTTGTGAGCGG (21-mer)

The resulting 300 bp fragment was purified on Spin 100 columns and digested with BglII/HindIII and again spin 1000 purified. This fragment was ligated to the above vector fragment. The resulting plasmid was named pJSO215 and used to transform *E.coli* W3110 lacl$^q$. A plasmid preparation was made from a transformant and DNA sequenced to verify the introduction of the SPIRR (SEQ ID NO:29) peptide addition.

Example 5

Construction of Random Lipolytic Enzyme Variants

Random mutagenized libraries of the entire *H. lanuginosa* lipolytic enzyme gene and of amino acids (aa) 91–97 and 206–211 thereof were prepared as described in Materials and Methods above.

The amino acid regions 91–97 and 206–211 were chosen for the first round of localized mutagenesis since these regions have been found to be important for wash performance. Region 91-97 is a part of the lid region of the enzyme and region 206–211 constitutes part of the hydrophobic cleft of the enzyme.

One oligonucleotide was synthesized for each of these regions comprising 93% of the wild type nucleotides and 2.33% of each of the other three nucleotides at amino acid codons wanted to be mutagenized. Where possible without changing the amino acid, the third nucleotide (the wobble base) in codons were synthesized with 50% G/50% C to give a larger likelihood for changes to amino acids with one or two codons. The composition of the mutagenic oligonucleotide of region 91–97 is shown in Table E5-1.

By use of this oligonucleotide a calculated mutation frequency of approximately 65–70% is obtained in the library for one amino acid change having been introduced in the parent lipolytic enzyme. The mutation frequency for two or more amino acid changes having been introduced are less than 35%. This low mutation frequency is chosen to ensure that the observed amino acid changes in positive clones are involved in improving the enzyme and not just "neutral" changes due to a high mutation frequency.

The mutagenic primers were used in a PCR reaction with a suitable opposite primer. The resulting PCR fragments were purified and in the case of region 206–211 digested and cloned into the shuttle vector. In the case of region 91–97 the resulting PCR fragment was used in a second PCR reaction as a primer with a second suitable opposite primer. This step was necessary to be able to digest and clone the mutagenized region into the shuttle vector.

Libraries of region 91–97 and of region 206–211 have been prepared containing from 10,000 to 80,000 clones/library. Most colonies were positive (more than 90%) when checked under conditions where the parent lipase is positive, i.e. exhibits lipase activity. The positive reaction was determined in a filter assay with 2.5 mM Ca (instead of 5 mM EGTA).

450,000 colonies were screened from the different libraries using the Dobanol®25-7 and low calcium assays described in Materials and Methods above. 25 low calcium positives from the aa 91–97 library (lid-region) and twelve Dobanol®25-7 positives from the whole gene libraries were isolated. Fourteen of the low calcium positives from mutagenesis of aa 91–97 were sequenced.

The three other mutations (in codon 83, 103, 145), outside the mutagenized region, can be explained by PCR misincorporation, although the mutation of S83T is a transversion which is quite unusual for PCR misincorporations.

Sequence:

| | | | |
|---|---|---|---|
| 5' | 5 | C | G |
| T | 5 | C | 3' |
| T | 7 | A | |
| A | 8 | G | Bottle 5: 93% A; 2.33% C; 2.33% G and 2.33% T |
| T | 8 | T | |
| T | A/C | T | |
| T | 5 | C | |
| C | 7 | T | |
| T | 5 | C | Bottle 6: 93% C; 2.33% A; 2.33% G and 2.33% T |
| T | 8 | T | |
| T | 8 | A | |
| 6 | C/G | T | |
| 5 | 6 | G | Bottle 7: 93% G; 2.33% A; 2.33% C and 2.33% T |
| 5 | 6 | G | |
| 7 | G | A | |
| 8 | AA | A | |
| 6 | T | C | Bottle 8: 93% T; 2.33% A; 2.33% C and 2.33% G |
| 7 | | | |

Table E5-1: Illustration of the construction of oligonucleotides (SEQ ID No.92) used for localized random mutagenesis of amino acids 91–97 of the *H. lanuginosa* lipolytic enzyme. The numbers presented in the sequence refer to the bottles the composition of which is apppearing to the right of the sequence.

TABLE E5-2

| Strain number | Variant type | | | | | |
|---|---|---|---|---|---|---|
| 59 | I | | | G91A | N94K | D96A |
| 60 | II | S83T | | | N94K | D96N |
| 61 | II | S83T | | | N94K | D96N |
| 62 | III | | E87K | | | D96V |
| 63 | IV | | E87K | G91A | | D96V |
| 64 | II | S83T | | | N94K | D96N |
| 65 | III | | E87K | | | D96V |
| 67 | V | | | | N94K F95L | D96H |
| 69 | V | | | | N94K F95L | D96H |
| 71 | III | | E87K | | | D96V |
| 72 | II | S83T | | | N94K | D96N |

Table E5-2: Strain number refers to the originally picked clones cloned into Aspergillus expression vector pAHL. Variant type refers to identical clones, which probably have arisen during amplification of the random mutagenized library. Variant types I and II are active in 0.01% Dobanol®25-7 while the rest are inactive like wild type.

TABLE E5-3

| Strain number wt | Variant type | DNA sequence (Amino acid number above the sequence) | | | | | | | | | | | | | | | | | | |
|---|---|---|---|---|---|---|---|---|---|---|---|---|---|---|---|---|---|---|---|---|
| | | 82 | 83 | 84 | 85 | 86 | 87 | 88 | 89 | 90 | 91 | 92 | 93 | 94 | 95 | 96 | 97 | 98 | 99 | 100 | -103 | -145 |
| | | GGC | TCT | CGT | TCC | ATA | GAG | AAC | TGG | ATC | GGG | AAT | CTT | AAC | TTC | GAC | TTG | AAA | GAA | ATA | -ATT | -CAT |
| 59 | I | | | | | | | | | | C | | G | G | | C | | | | | | |
| 60 | II | | A | | | | | | | | C | | G | G | | A | | | | | | |
| 61 | II | | A | | | | | | | | C | | G | G | | A | | | | | | |
| 62 | III | | | | | | A | | | | C | | | | | T | | | | | | |
| 63 | IV | | | | | | A | | | C | | | | | | C | | | | | C | C |
| 64 | II | | A | | | | | | | | C | | G | G | | A | | | | | | |
| 65 | III | | | | | | A | | | | C | | G | | | T | | | | | | |
| 67 | V | | | | | | | | | | C | | | A C A C | | | | | | | | |

TABLE E5-3-continued

| Strain number wt | Variant type | _____DNA sequence_____ (Amino acid number above the sequence) | | | | | | | | | | | | | | | | | | | | |
|---|---|---|---|---|---|---|---|---|---|---|---|---|---|---|---|---|---|---|---|---|---|
| | | 82 | 83 | 84 | 85 | 86 | 87 | 88 | 89 | 90 | 91 | 92 | 93 | 94 | 95 | 96 | 97 | 98 | 99 | 100 | -103 | -145 |
| | | GGC | TCT | CGT | TCC | ATA | GAG | AAC | TGG | ATC | GGG | AAT | CTT | AAC | TTC | GAC | TTG | AAA | GAA | ATA | -ATT | -CAT |
| 52/68 | wt | | | | | | | | | | | | | | | | | | | | | |
| 53 | wt | | | | | | | | | | | | | | | | | | | | | |
| 69 | V | | | | | | | | | | C | | | A | C | A | C | | | | | |
| 71 | III | | | | A | | | | | | C | | | G | | | T | | | | | |
| 72 | II | A | | | | | | | | | C | | | G | | A | A | | | | | |
| 73 | VI | | | | | | | | | | | | | | | | A | ? | | | | |

Table E5-3: The wild type seqence is shown at the topline. Only nucleotides differing from wt are written at the variant sequences. The base of codon 91 and 93 were doped with 1:1 of C/T and T/G, respectively. Otherwise the nucleotides at codon 91–97 were doped using 93% wt and 2.33% of the three other nucleotides.

Results from screening a random mutagenized library of aa 85–99 (the lid region) with a doping based on the results obtained from positives from random mutagenesis of aa 91–97.

Construction of the Random Mutagenized Library

Background

Five different types of strong positive mutants were found in screening of the first library of the lid region (aa 91–97, see previous example). D96 was changed to A, V, N or H and amino acid change E87K, G91A and N94K were found in two to three independent mutants in combination with a change of D96 indicating their importance for independence of calcium of Lipolase. Since these mutations were improved with respect to low calcium/Dobanol activity compared to wt in several assays, they were used as a starting point in a second random mutagenesis of the whole lid region.

Localized Random Mutagenesis

The amino acid region aa 85–99+83S/T were random mutagenized as follows. Doping scheme: S83—50% S/50% T; E87—93% K/7% X; G91—93% A/7% X; N94—50% K/50% 100% X; the rest were 93% wt/7% X (the percentages refers to the doping of the codons at the nucleotide level (see the sequence of the oligo). The theoretical percentage of the various amino acid codons resulting from these dopings may be calculated using a state of the art computer program). Where possible without changing the amino acid, the third nucleotide (the wobble base) in codons were synthesized with 50% G/50% C to give a larger likelyhood for changes to amino acids with only one or two codons. The composition of the mutagenic oligonucleotide is shown in SEQ ID NO:94. The none mutagenized nucleotide region were chosen using the Oligo program optimizing for stability and no secondary structure.

This mutagenesis gives a calculated frequency of approximately 93% changes of the starting point (not including S83, N94 and D96) in the library. This is a very high mutation frequency which should give the chance af major changes of the lid region.

The mutagenic primer were used in a PCR reaction with a suitable opposite primer. The resulting PCR fragment was used in a second PCR reaction as a primer with a second suitable opposite primer. This step was necessary to be able to digest and clone the mutagenized region into the yeast expression vector pYESHL. It is important to take the A added to the 3' end of the PCR fragment by Taq polymerase into account when designing a mutagenic primer for such a two step PCR method.

In this way random mutagenized libraries of the region aa 85–99+83S/T were prepared.

Screening

The low calcium filter assay was used with Dobanol and LAS. Screening of the lid2 library was made with 5 mM EGTA, 0.01% Dobanol and 0.006% LAS. Several positives were detected and isolated, sequenced, transformed into Aspergillus, purified and tested in wash tests.

Sequence and Wash Results of Selected Positives

Underlined shows conditions used in the filter assay. IF=improvement factor in 3-cycle wash.
5 mM EGTA. 0.01% Dobanol,0.006% LAS
E87K,G91A,L93I,N94K,D96A. IF=1.3
5 mM EGTA, 0.02% Dobanol
N73D,S85T,E87K,G91 A,N94K,D96A. IF=1.1
S83T,E87K,W89G,G91A,N94K,D96V. IF=0.8
E87K,G91 A,D96R,I100V. IF=5.2
S83T,E87K,Q249R
2 g/l PCS
E87K,G91A. IF=5.0

Sequence of Oligo-lid2 (SEQ ID NO. 94)

5'-C ATT TAT 886 888 655 (CIG)(A/C/G/T)(A/C/G/T) 755 (C/G)88 (A/C)57 588 (C/G)76 (7/8)58 665 788 688 (8/7)58 775 ACG AG(A/T) GCC ACG-3'
Flask 5: 93% A; 2,33% C; 2,33% G og 2,33% T.
Flask 6: 93% C; 2,33% A; 2,33% G og 2,33% T.
Flask 7: 93% G; 2,33% A; 2,33% C og 2,33% T.
Flask 8: 93% T; 2,33% A; 2,33% C og 2,33% G.

Local Random Mutagenesis Performed on Two Regions Simultaneously

Random mutagenized libraries of aa region 56 to 64 and 81 to 99+102 were prepared as described in the Materials and Methods using the two oligo nucleotides 004 and 005 as shown in Table 4 in a PCR reaction. Oligo 004 was synthesized for the aa region 81 to 99+102 with 93% wt nucleotides and 2.33% of each of the other 3 nucleotides in each position except for the S83 codon which was doped to give 50% S/50% T (see table 4). For aa with 4 or 6 codons a 50%/50% mixture of G/C or A/C was used for the third base (see table 4). For the third base of the Ile codon a 50%/50% mixture of bottle 7 and 8 was used. D96L was used as starting point in the random mutagenesis since it was found in previous good performing variants. Oligo 005 was synthesized for the aa region 56 to 64 with 93% wt nucleotides and 2.33% of each of the other 3 nucleotides in each position. For the positions 56, 57 and 62 a bias of positively charged aa among others were introduced (see table 4). For aa with 4 or 6 codons a 50%/50% mixture of G/C or G/T was used for the third base. In general the PCR reaction may introduce mutations outside the doped region which is an advantage since such mutations may benefit to the property of a variant.

The oligo 004 was also used in combination with oligo 006 (see table 4) cloned by a double PCR reaction resulting in library covering region 81 to 99+102 and region 248–257, 259, 263–269. The oligo 006 was synthesized for the aa region 248–257, 259, 263–269 with 93% wt nucleotides and 2.33% of each of the other 3 nucleotides in each position. For aa with 4 or 6 codons a 50%/50% mixture of G/C or A/C was used for the third base (see table 4). For the third base of the Ile codon a 50%/50% mixture of bottle 7 and 8 was used.

The oligo 005 and 006 were also used for construction of random mutagenized libraries using positives in the lid region as a template.

Table E5-4

Some of the positives obtained from screening these libraries on detergent containing plates are shown below:

E56R+D57L+I90F+D96L+E99K

E56R+D57L+V60M+D62N+S83T+D96P+D102E

D57G+N94K+D96L+L97M

E87K+G91A+D96R+I100V+E129K+K237M+I252L+ P256T+G263A+L264Q

E56R+D57G+S58F+D62C+T64R+E87G+G91A+F95L+ D96P+K98I

A47V+D62G+D96L+A121T

E56G+D57G+V60E+D62G+N94K+D96L

The following variants were obtained from random mutagenesis of the whole gene alone (by PCR or PCR+ formic acid as described in the Materials and Methods section) and screened on detergent containing plates:

I34V+S54P+F80L+S85T+D96G+R108W+G109V+ D111G+S116P+L124S+V132M+V140Q+V141A+ F142S+H145R+N162T+I166V+F181P+F183S+ R205G+A243T+D254G+F262L

A19T+D167G+E210V+W221L (random mutagenesis based on D167G+E210V)

A49P+D167G+E210V (random mutagenesis based on D167G+E210V)

Example 6

Construction of First Wash Variants of the *H. lanuginosa* Lipolytic Enzyme

1. Domain Shuffling by Recombination and Screening

20 *H. lanuginosa* lipolytic enzyme variants having a very good washing performance (as evaluated in various wash related tests) some of which were constructed according to Example 5 were allowed to recombine by an in vivo recombination method in *S. cerevisiae* YNG318 as described in the Materials and Methods section herein. The lipolytic enzyme variants used are apparent from table E6-1, Most of these variants had been constructed by random or localized random mutagenesis as described in the Materials and Methods section above and screening for a decreased dependence on calcium and an improved tolerance towards the detergent component Dobanol 25-7 (cf. the Materials and Methods section above). Some of the variants are the result of two or more consecutive rounds of mutagenesis and screening.

The restriction enzyme opened vector and the PCR fragments apparent from the table below and further discussed in the Materials and Methods section were mixed in a molar ratio of approximately 1:1 and used for transformation of competent *S. cerevisiae* cells (made by the lithium acetate method as described in Current Protocols in Molecular Biology, eds. F. M. Ausubel et al., chapter 13.7, John Wiley & Sons, Inc., USA.). The transformed cells were plated on filters and screened for a reduced calcium dependency and an increased detergent tolerance using the filter assay described in the Materials and Methods section above.

Colonies giving a positive signal were streaked out to single colonies on new plates and filters and re-screened. After2 to 4 rescreenings positive colonies were fermented according to the method given in the Materials and Methods section above.

After purification the capability of the variant in removing lard was tested in the one cycle wash assay described in the Materials and Methods section above. The results are given in Example 14 and 15 hereinbelow.

Table E6-1: Variants used for recombination

*Humicola lanuginosa* Lipase Variants Used for Preparing Vector (Opened With NruI) for Invo Recombination (Gene Shuffling):

E56R,D57L,I90F,D96L,E99K E56R,D57L,V60M,D62N, S83T,D96P,D102E

D57G,N94K,D96L,L97M

E87K,G91 A,D96R,I100V,E129K,K237M,I252L,P256T, G263A,L264Q

E56R,D57G,S58F,D62C,T64R,E87G,G91A,F95L,D96P, K98I,(K237M)

E210K

*Humicola lanuginosa* Lipase Variants Used for Preparing DNA Fragments (by Standard PCR Amplification of the Whole Gene From the Plasmids Containing the Variant) for Invo Recombination (Gene Shufflinq):

S83T,N94K,D96N

E87K,D96V

N94K,D96A

E87K,G91A,D96A

D167G,E210V

S83T,G91A,Q249R

E87K,G91A

S83T,E87K,G91A,N94K,D96N,D111N.

N73D,E87K,G91A,N94I,D96G.

L67P,I76V,S83T,E87N,I90N,G91A,D96A,K98R.

E210K

S83T,E87K,G91A,N92H,N94K,D96M

S85P,E87K,G91A,D96L,L97V.

E87K,I90N,G91A,N94S,D96N,I100T. I34V,S54P,F80L, S85T,D96G,R108W,G109V,D111G,S116P,L124S, V132M,V140Q,V141A, F142S,H145R,N162T,I166V, F181P,F183S,R205G,A243T,D254G,F262L.

E56R,D57L,I90F,D96L,E99K

E56R,D57L,V60M,D62N,S83T,D96P,D102E

D57G,N94K,D96L,L97M

E87K,G91 A,D96R,I100V,E129K,K237M,I252L,P256T, G263A,L264Q

E56R,D57G,S58F,D62C,T64R,E87G,G91A,F95L,D96P, K98I,(K237M)

2, Domaine Shuffling by Traditional Cloning of Two Positives Together

The Aspergillus expression vector pHD414 containing a DNA sequence encoding the *Humicola lanuginosa* lipase variant (D57G+N94K+D96L+L97M) were digested with the restriction enzymes NarI and XbaI resulting in two fragments. The fragments were separated by agarose gel electrophoresis and the largest fragment were isolated from the agarose gel. This fragment were ligated to the smallest fragment from digestion of the variant (S83T+G91A+Q249R) with NarI and XbaI. The ligation was transformed into *E. coli* and the resulting plasmid constructions were isolated from one of the transformants and sequenced to test for the correct assembly. The plasmid was transformed into *Aspergillus oryzae* fermented and purified as described in the Materials and Methods section. This variant contained the following mutations D57G+N94K+D96L+L97M+Q249R.

Example 7

Construction and Expression of Modified *H. lanuginosa* Lipolytic Enzyme (HLv9s) in *Aspergillus oryzae* JaL125

The variant HLv9s contains the following mutations in the mature part:
E1P+D57G+N94K+D96L+Q249R and the N-terminal peptide addition SPIRPR (SEQ ID NO:20) fused to E1P (resulting in the overall N-terminal peptide addition SPIRPRP (SEQ ID NO:31).

An N-terminal peptide addition was applied to the parent *H. lanuginosa* (DSM 4109) lipolytic enzyme having the amino acid and DNA sequence, respectively, apparent from EP 305 216, and in addition carrying the following mutations D57G, N94K, D96L, Q249R in its mature part (inserted by conventional site-directed mutagenesis) in the DNA sequence (EP 305 216). The peptide addition SPIR-PRP (SEQ ID NO:31) was applied to the N-terminus of the parent enzymes as follows:

Construction of pIVI220

The plasmid was constructed using the Chamelon double stranded, site-directed mutagenesis kit from Stratagene according to the described protocol.

pHL296 was used as the plasmid template. Said plasmid contains the gene encoding the *H. lanuginosa* lipolytic enzyme with the above mentioned mutations (D57G, N94K, D96L, L97M, Q249R) cloned into pHD464.

Primer no. 7258 was used as the selection primer.
7258: 5'p gaa tga ctt ggt tga cgc gtc acc agt cac 3' (SEQ ID NO. 77)
(Thus changing the ScaI site found in the ampicillin resistance gene and used for cutting to a MluI site).
Primer no. 7770 was used as the selection primer.
7770: 5'p tct agc cea gaa tac tgg atc aaa tc 3' (SEQ ID NO. 2) (Changes the ScaI site found in the *H. lanuginosa* lipase gene without changing the amino acid sequence).
Primer no.8479 was used as the mutagenic primer.
8479: 5'p gcg tgg acg gcc ttg gct agc cct att cgt cct cga ccg gtc tcg cag gat ctg 3 (SEQ ID NO:80) (replacing the propeptide and the N-terminal E1 of the parent *H. lanuginosa* enzyme (SPIRRE (SEQ ID NO:36) by SPIRPRP (SEQ ID. NO:31)).

Construction of pIVI245

The plasmid was constructed using the Chameleon double-stranded, site-directed mutagenesis kit from Stratagene (cat no. 200509) according to the described protocol.

pIVI220 was used as the plasmid templated and primer no.7887 as the selection primer (changing the introduced Mlu1 site found in the ampicillin resistance gene and used for cutting to a ScaI site). 7887: 5'p-gaa tga ctt ggt tga gta ctc acc agt cac 3' (SEQ ID NO. 77).

Primer no. 8932 was used as the mutagenic primer (8932: 5'p-g aac tgg ata gga aat ttg aag ttc ctg ttg aaa gaa ata aat gac 3' (SEQ ID NO. 78) (thus changing M97 back to L97 as wildtype and still preserving the two mutations N94K and D96L)).

2. Construction of the *A. oryzae* Expression Plasmid pCaHj483 pCaHj483 is depicted in FIG. 9. It is built from the following fragments:
a) The vector pToC65 (WO91/17243) cut with EcoRI and XbaI.
b) A 2.7 kb XbaI fragment from *A. nidulans* carrying the amdS gene (C. M. Conick et al., (1987), Gene 53, p. 63–71). The amdS gene is used as a selective marker in fungal transformations. The amdS gene has been modified so that the BamHI site normally present in the gene is destroyed. This has been done by introducing a silent point mutation using Primer 3: AGAAATCGGGTATC-CTTTCAG (SEQ ID No. 6)
c) A 0.6 kb EcoRI/BamHI fragment carrying the *A. niger* NA2 promoter fused to a 60 bp DNA fragment of the sequence encoding the 5' untranslated end of the mRNA of the *A. nidulans* tpi gene. The NA2 promoter was isolated from the plasmid pNA2 (EP 383 779) and fused to the 60 bp tpi sequence by PCR. The primer (Primer 4) encoding the 60 bp tpi sequence had the following sequence:
5'-GCTCCTCATGGTGGATCCCCAGTTGTGTATATA GAGGATTGAGGMGGAAGAGMGTGTGGA TAGAGGTAAATTGAGTTGGAAACTCCMGCATG GCATCCTTGC—3' (SEQ ID No. 14)
d) A 675 bp XbaI fragment carrying the *A. niger* glucoamylase transcription terminator. The fragment was isolated from the plasmid plCAMG/Term (EP 238 023).
The BamHI site of fragment c) was connected to the XbaI site in front of the transcription terminator on fragment d) via the plC19R linker (BamHI to XbaI)

Construction of the HLv9s Expression Plasmid pCaHj485

The plasmid pJVi 245 was digested with BamH I and Sal I, and the resulting 904 bp fragment encoding the HLv9s lipolytic enzyme was isolated. pCaHj 483 was digested with BamH I and Sal I, and the large vector fragment (6757) was ligated to the HLv9s fragment. The ligation mixture was used to transform *E. coli* DH5α cells, and a transformant harbouring the expected plasmid was isolated. The plasmid was termed pCaHj485.

3. Transformation of pCaHj 485 Into JaL125

*Aspergillus oryzae* JaL 125 is *Aspergillus oryzae* IFO 4177 deleted in the alkaline protease was transformed with pCaHj 485 using selection on acetamide as described in patent EP 0 531 372. Transformants were spore reisolated twice. Spores from second reisolation of each transformant were used to inoculate 200 µl YPM (1% yeast extract, 2% peptone, 2% maltose) in 96 well microtiter dishes. The YPM cultures were grown for 4 days at 34° C., and the higest producers were selected using a p-nitro phenylbutyrate assay:

Stock solution: 18 µl p nitro phenyl butyrate was dissolved in 1 ml isopropanol.
Working solution: 0.1 ml stock solution was mixed with 10 ml 50 mM Tris/HCl pH 7.5; 10 mM $CaCl_2$.

Assay: 1 μl of YPM supernatant was mixed with 200 μl of working solution in 96 well microtiterdishes, and the color development was measured at 450 nm using an ELISA reader.

One transformant was selected for tank fermentation.

4. Tank Fermentation of JaL 125/pCaHj 485

The fermentation was carried out as a fed-batch fermentation using a constant medium temperature of 34° C. and a start volume of 1.2 liter. The initial pH of the medium was set to 6.5. Once the pH had increased to 7.0 this value was maintained through addition of 10% $H_3PO_4$. The level of dissolved oxygen in the medium was controlled by varying the agitation rate and using a fixed aeration rate of 1.0 liter air per liter medium per minute. The feed addition rate was maintained at a constant level during the entire fed-batch phase.

The batch medium contained maltose syrup as carbon source, urea and yeast extract as nitrogen source and a mixture of trace metals and salts. The feed added continuosly during the fed-batch phase contained maltose syrup as carbon source whereas yeast extract and urea were added in order to assure a sufficient supply of nitrogen.

5. Purification of the Modified Lipolytic Enzyme
1) Fermentation supernatant was filtered through milipore filter Cat. No. AP2504700 Filter type AP25.
2) Fermentation supernatant was filtered once more on through the sterile filter from Millipore ammonium acetate.
4) A Hydrophobic chromatography on TSK gel Butyl-Toyopearl 650.50 ml column was packed with the Butyl-Toyopearl matrix. The column was washed and equilibrated with 0.8 M ammonium acetate. One liter fermentation supernatant adjusted with amonium acetate was then applied on the Butyl column. The column was washed with 0.8 M ammonium acetate till all unbound material was washed out. Bound material was then eluted with water and 50% ethanol sequentially. Fractions were collected and analyzed for lipase activity using Standard LU assay. Fractions containing lipase activity were pooled and diluted to adjust conductivity of the pool below 4 mSi and pH to 8.5.
5) Anion exchange chromatography on High Performance Q sepharose (Pharmacia, Code No.17-1014-01). 50 ml column was packed and washed with 50 mM Borate buffer pH 8.5, Pool containing lipase activity was then applied on The High performance Q sepharose column. Unbound material was washed with the Borate buffer pH 8.5, Bound activity was then eluted with linear gradient using Borate buffer containing 1 M Sodium Chloride pH 8.5, Fractions were collected and assayed for Lipase activity. Fractions containing Lipase activity with a ratio of UV absorbence at A280/A260 more than 1.7 are pooled.

Example 8

Site-directed Mutagenesis of N-terminal Addition of H. lanuginosa Lipase

Mutations in the *Humicola lanuginosa* lipase having a SPIRR (SEQ ID NO:29) N-terminal addition was performed using the method described above in the Materials and Methods section.

First the gene encoding the lipase was inserted into the plasmid pHD414. The Scal site of the Ampicillin gene of pHD414 was then changed to a Mlul site. The unique Scal site present in the lipase gene was then removed.

The desired mutation (i.e. SPIRPRP(SEQ ID NO:31)) was introduced in the N-terminal of the lipase gene by addition of the following oligo comprising the desired mutation:

oligo 8479 (SEQ ID NO: 5):
5'-P GCG TGG ACG GCC TTG GCT AGC CCT ATT CGT CCT CGA CCG GTC TCG CAG GAT 5 CTG-3'

This resulted in a *H. lanuginosa* lipase gene with a SPIRPRP (SEQ ID NO:31) N-terminal peptide addition.

Example 9

Construction of N-terminal Additions by Random Mutagenesis

Random mutagenesis of the part of the DNA sequence encoding the N-terminal addition SPIRPRP added to the first amino acid residue of the mature *H. lanuginosa* lipolytic enzyme (obtainable from DSM 4109) and containing the following further mutations in its mature part: D57G+N94K+D96L+L97M+Q249R was performed. The mutations in the mature part of the parent lipolytic enzyme was performed by PCR driven site-directed mutagenesis using the appropriate primer sequences using the procedures described in WO 95/26215. The peptide addition SPIRPRP (SEQ ID NO:31) was applied as described in Example 7, (i.e. the last P replacing E1).

The nucleotide doping scheme of the SPIRPRP (SEQ ID NO:31) codons was as follows:

Oligo 1: 5'-GCG TGG ACG GCC TTG GCC 86(T/A) 66(A/T) 58(T/A) 67(T/A) 66(T/A) 575 66(T/A) GAG GTC TCG CAG GAT CTG-3' (57-mer) (SEQ ID NO:81)

the numbers referring to which of the following flasks to be used.

Flask 5: 80% A; 6.66% C; 6.66% G og 6.66% T.
Flask 6: 80% C; 6.66% A; 6.66% G og 6.66% T.
Flask 7: 80% G; 6.66% A; 6.66% C og 6.66% T.
Flask 8: 80% T; 6.66% A; 6.66% C og 6.66% G.

A two step PCR reaction protocol was used: The first step with the above primer as the 5' primer and with the primer 2056 (5'gca cgt aat gtt tgt acc 3')) (SEQ ID NO:96) as the 3' primer conducted using pHL296 as the plasmid template. The product of the first PCR round was used in a new PCR with 4699 (5'cgg tac ccg ggg atc cac 3')) (SEQ ID NO:97) as the 5' primer (to introduce the BamHI site and the first part of the coding sequence) and with the PCR product as the 3' primer using the same template. The resulting product was purified on Spin 100 (from Clonetech Lab., Inc.) and cut with BamHI and PvuII. The resulting DNA fragment was purified from the agarose gel with SpinX (Costar) and ligated into the yeast expression vector pJSO37 containing the *H. lanuginosa* lipolytic enzyme gene from pHL296 cloned as a BamHI-Xbal fragment cut with BamHI and PvuII. The resulting DNA was electrotransformed into DH10/DH12 *E. coli* cells (Gibco/BRG Lifetechnologies) using the conventional technique.

After transformation into *E. coli* and amplification the plasmid was purified and transformed into *S. cerevisiae* YNG 318. The resulting *S. cerevisiae* cells were screened for good performers in the alternative lipase filter assay containing detergent (3 g/l of PCS). The positives were sequenced and found to contain the following peptide additions: GPIRPRP (SEQ ID NO:48), SHSRHNA (SEQ ID NO:153), TAIRPRK (SEQ ID NO:46), SALRRRP (SEQ ID NO:154), STRRPRP (SEQ ID NO:47), SPRRPRT (SEQ ID NO:33), SPIPPGP (SEQ ID NO:155), LPFRQRP (SEQ ID NO:49), SPFRPKL (SEQ ID NO:34), and SALRRP (SEQ ID NO:157) (termed HLv10s1–10, respectively—see Table M1 of the Materials and Methods section).

The one-cycle wash performance of each of HLv10s1–6 was tested as described in the Materials and methods section above (Assay for test of first wash effect) at a temperature 30° C. and using 5 g/l of enzyme inactivated Ariel Futur as detergent. The amount of fatty material removed by each of the modified enzymes are shown below:

| Lipase variant | Low dosage | % lard removed | High dosage | % lard removed |
|---|---|---|---|---|
| HLv10s1 | 1250 LU/I | 26 | 12500 LU/I | 54 |
| HLv10s2 | 1250 LU/I | 22 | 12500 LU/I | 53 |
| HLv10s3 | 1250 LU/I | 34 | 12500 LU/I | 55 |
| HLv10s4 | 1250 LU/I | 33 | 12500 LU/I | 55 |
| HLv10s5 | 1250 LU/I | 23 | 12500 LU/I | 47 |
| HLv10s6 | 1250 LU/I | 30 | 12500 LU/I | 53 |

The tendency was that the best performers had more positive charged amino acids in the N-terminal addition.

Analogously, random mutagenesis of the N-terminal addition RPRPRPRP (SEQ ID NO:57)added to the *H. lanuginosa* lipase variant E1*+D57G+N94K+D96L+L97M+Q249R plus other variants were performed. The nucleotide doping scheme of the RPRPRPRP (SEQ ID NO:57) codons was as follows:

Oligo 2: 5'-GTC TCT GCG TGG ACG GCC TTG GC G GCG CCA CCT CCA 67(T/A) 66(T/A) 575 66(T/A) 67(T/A) 66(T/A) 575 66(T/A) (6/7)(7/8)(C/G) 57(C/G) C57 (5/7)5(C/G) CTG TTT AAC CAG TTC AAT CTC-3' (93-mer) (SEQ ID NO:82)

Flask 5: 80% A; 6.66% C; 6.66% G og 6.66% T.
Flask 6: 80% C; 6.66% A; 6.66% G og 6.66% T.
Flask 7: 80% G; 6.66% A; 6.66% C og 6.66% T.
Flask 8: 80% T; 6.66% A; 6.66% C og 6.66% G.

APPP is added in the N-terminal of the randomly mutagenized RPRPRPRP (SEQ ID NO:57) and prior to the signal peptide in order to protect against proteolytic degradation of the N-terminal addition. This may not be required. E1 was deleted in order to remove one negatively charged amino acid. The amino acids in position 2 to 5 of the mature *H. lanuginosa* lipase sequence were also mutagenized in order to find improved mutants in this non-structural part of the lipase. Otherwise the procedure is as stated above for the random mutagenesis of SPIRPRP (SEQ ID NO:31).

The following N-terminal peptide additions were obtained:

Ala-Pro-Pro-Pro-Arg-Pro-Arg-Leu-Leu-Pro-Ile-Ser (APPPRPRLLPIS) (SEQ ID NO:88)(in addition to the deleted E1 residue this variant carries the additional mutation D5E in its non-structural N-terminal part of the mature enzyme).

Ala-Pro-Pro-Pro-Thr-Arg-Gln-Arg-Gln-Ser-Pro (APPPTRQRQSP) (SEQ ID NO:89) (in addition to the deleted E1 residue this variant carries the additional mutations V2L, S3T and D5V in its non-structural N-terminal part of the mature enzyme).

Ala-Pro-Pro-Pro-Arg-Thr-Ile-Pro-Arg-Ser-Ser-Pro (APPPRTIPRSSP) (SEQ ID NO:90) (in addition to the deleted E1 residue this variant carries the additional mutations V2L, S3R and D5E in its non-structural N-terminal part of the mature enzyme).

Ala-Pro-Pro-Pro-Arg-Pro-Arg-Pro-Arg-Pro-Arg-Pro (APPPRPRPRPRP) (SEQ ID NO:60) (in addition to the deleted E1 residue this variant carries the additional mutations V2G and D5E in its non-structural N-terminal part of the mature enzyme).

Ala-Pro-Pro-Pro-Arg-Thr-Arg-Pro-Arg-Pro-Arg-Ser (APPPRTRPRPRS) (SEQ ID NO:61) (in addition to the deleted E1 residue this variant carries the additional mutations V2GL, S3T, Q4P and D5E in its non-structural N-terminal part of the mature enzyme).

Ala-Pro-Pro-Pro-Lys-Ala-Ser-Pro-Arg-Gln-Arg-Pro (APPPKASPRQRP) (SEQ ID NO:67) (in addition to the deleted E1 residue this variant carries the additional mutations V2GL, D5Q and L6M in its non-structural N-terminal part of the mature enzyme).

Example 10

3-cycle Wash Performance of *H. lanuginosa* Lipase With a Peptide Addition

The wash performance of the *Humicola lanuginosa* lipase described in EP 305 216 and variants thereof (i.e. modified lipolytic enzymes of the invention) was tested using the 3-cycle wash performance test (described in the Materials and Methods section above) using 4.2 g/l of a European type powder detergent composition. The detergent did not contain any enzymes prior to the addition of the modified lipase of the invention. The detergent was dissolved in approximately 18° dH (German Hardness) water. The pH of the wash liquor was about 10.

After the third wash cycle the performance of a modified lipase of the invention and of the parent lipase expressed in *Aspergillus oryzae* was assessed. This was done by calculating the improvement factor (fimprove) as described above.

The results of these tests are shown in Table E10 below.

TABLE E10

| Lipase | N-terminal +/− SPIRR (SEQ ID NO:29) | 3-cycles $f_{improve}$ (Improvement factor) |
|---|---|---|
| Parent lipase (expressed in *A. oryzae*) | − | 1.0 (reference) |
| Modified lipase (expressed in yeast) | + | 2.2 |
| Modified lipase (expressed in yeast) (treated with trypsin) | − | 0.6 |
| Variant of parent lipase (HLv1s) (expressed in yeast) | + | 9.3 |
| Variant of parent lipase (HLv1) (expressed in *A. oryzae*) | − | 1.8 |
| Parent lipase (expressed in *E. coli*) | − | 1.0 |
| Modified lipase (expressed in *E. coli*) (+SPIRR) (SEQ ID NO:29) | + | 2.0 |
| Modified lipase (expressed in Hansenula) | + | 2.1 |

It can be seen from Table E10 that the peptide addition (i.e. SPIRR) (SEQ ID NO:29)applied to the N-terminal of parent *Humicola lanuginosa* lipase at least doubles the wash performance.

Example 11

One Cycle Wash Performance of Modified *H. lanuginosa* Lipases Containing an Addition The one cycle wash performance test (described above in the Materials and Methods section above) was performed of *Humicola lanuginosa* lipase variants of Table M1 with and without the SPIRR-peptide (SEQ ID NO:29) addition in 5 g/l of enzyme inactivated Ariel™ Futur (Procter and Gamble). The tests were performed at lipase concentrations of 0, 1250 12500 LU/l.

The detergent was dissolved in approximately 18° dH (German Hardness) water. The pH of the wash liquor was about 10.3.

The amount of soxhlet extracted fatty matter removed from textile are shown in the table below. Corresponding lipase variants with and without peptide addition are listed two and two.

TABLE E11

| Lipase variant | +/− SPIRR (SEQ ID NO:29) | low dosage | % lard removed | High dosage | % lard removed |
|---|---|---|---|---|---|
| HLv2s | SPIRR (SEQ ID NO:29) | 1250 LU/l | 12.5 | 12500 LU/l | nd |
| HLv2 | — | 1250 LU/l | 1.7 | 12500 LU/l | 6.0 |
| HLv3s | SPIRR (SEQ ID NO:29) | 1250 LU/l | 8.9 | 12500 LU/l | 33.9 |
| HLv3 | — | 1250 LU/l | 4.6 | 12500 LU/l | 6.9 |
| HLv4s | SPIRR (SEQ ID NO:29) | 2500 LU/l | 26.5 | 12500 LU/l | 47.6 |
| HLv4 | — | 0.25 mg/l | 1 | 12500 LU/l | 26 |
| HLv1s | SPIRR (SEQ ID NO:29) | 1250 LU/l | 12.8 | 12500 LU/l | 45 |
| HLv1 | — | 1250 LU/l | 1.8 | 12500 LU/l | 7.2 |
| HLv5s | SPIRR (SEQ ID NO:29) | 1250 LU/l | 11.4 | 12500 LU/l | 36.5 |
| HLv5 | — | 1250 LU/l | 1 | 12500 LU/l | 10.6 |
| HLv8s | SPIRR (SEQ ID NO:29) | 1250 LU/l | 4.5 | 12500 LU/l | Nd |
| HLv8 | — | 1250 LU/l | 0 | 12500 LU/l | 1 | nd: not determined

The above results clearly shows that the lipase variants with a peptide addition have a significantly improved one cycle wash performance in comparison to the corresponding lipase variant without a peptide addition.

Example 12

First Wash Activity of Lipolytic Enzymes of the Invention

The first wash activity of lipolytic enzymes was tested using the "Assay for test of First Wash effect" described in the Materials and Methods section above with Detergent Composition A or B. A few of the new first wash lipase are compared to what is considered as being the present state of art within lipolytic enzymes for detergents.
Note: ¤ are produced in *Aspergillus oryzae* as described in example 7.

| Lipolytic Enzyme | % removal at 1250 LU/l | % removal at 12500 LU/l |
|---|---|---|
| Detergent Composition A | | |
| E1SPIRPRP (SEQ ID NO:31) + D57G + N94K + D96L + L97M + Q249R | 15% | 49% |
| Lumafast ™ (*Ps. mendocina*) | 0% | 2% |
| Lipomax ™ (Ps. Pseuodoalcaligenes L21M) | 0% | 9% |
| *Fusarium solani* pisi | 0% | 0% |
| Lipolase | 0% | 0% |
| Lipolase Ultra | 0% | 0% |
| Detergent Composition | | |
| E1SPIRPRP (SEQ ID NO:31) + D57G + N94K + D96L + L97M + Q249R | 15% | 46% |
| Lumafast ™ (*Ps. mendocina*) | 6% | 6% |
| Lipomax ™ (Ps. Pseuodoalcaligenes L21M) | 0% | 0% |
| Liposam ™ | 4% | 7% |
| *Fusarium solani* pisi | 2% | 5% |
| Lipolase | 5% | 6% |
| Lipolase Ultra | 6% | 0% |

-continued

Additional examples:
Detergent Composition A

| Lipolytic Enzyme | % removal at 12500 LU/l |
|---|---|
| SPIRR (SEQ ID NO:29) + D57G + G59V + N94K + D96L + L97M + S116P + S170P + Q249R* | 42% |
| SPIRR (SEQ ID NO:29) + A49P + D167G + E210V* | 44% |
| SPIRR (SEQ ID NO:29) + E56K + D57G + D62R + S83T + S85F + D96L + D102Y + E210K* | 36% |
| SPIRR (SEQ ID NO:29) + N94K + F95L + D96H + N101S + F181L + D234Y + I252L + P256T + G263A + L264Q* | 41% |

* are produced in yeast as described in example 6.

Example 13

Activity-in-Detergent (AiD) Assay

The AiD assay is an analytical assay that is useful for selecting parent lipolytic enzymes to be used in the construction of a first wash lipolytic enzyme as described herein.

Equipment: Water bath with 150 ml beakers. Stirring is obtained by an agitator.
Lipolytic enzyme dosage: 12500 LU/l.
Substrate: 6 pieces (3.5*3.5 cm) of cotton with 6 pl olive oil for one test.
Detergent: 0.5 g/l model liquid detergent dissolved in 0.36 mM $Ca^2/Mg^2$ (5:1), adjusted to pH 10, 100 ml per beaker.
After stirring the sample for 60 min. at 30° C. the remaining detergent on the swatches is removed by addition of tap water for 15 min. The swatches are put into a flask containing 10 ml Tetrahydrofuran and 6.25 ml 4 M HCl and evaporated over night, after which the sample is redissolved in Tetrahydrofuran. The fat composition is determined by TLC/FID and the amount of % FFA (free fatty acids) is used to distinguish between the lipolytic enzymes. detergent formulation below Note ¤ are produced in *Aspergillus oryzae* ast as described in example 7

| AiD assay | |
|---|---|
| Lipolytic Enzyme | % FFA |
| SPIRR (SEQ ID NO:29) + D57G + G59V + N94K + D96L + L97M + S116P + S170P + Q249R* | 20% |
| SPIRR (SEQ ID NO:29) + A49P + D167G + E210V* | 25% |
| SPIRR (SEQ ID NO:29) + E56K + D57G + D62R + S83T + S85F + D96L + D102Y + E210K* | 25% |
| SPIRR (SEQ ID NO:29) + N94K + F95L + D96H + N101S + F181L + D234Y + I252L + P256T + G263A + L264Q* | 20% |
| E1SPIRPRP (SEQ ID NO:31) + D57G + N94K + D96L + L97M + Q249R¤ | 27% |
| Lumafast ™ (*Ps. mendocina*) | 5% |
| Lipomax ™ Cos (*Ps. pseudoalcaligenes*) | 31% |
| *Fusarium solani* pisi | 6% |
| Lipolase | 5% |
| Lipolase Ultra | 5% |

-continued

Model liquid detergent:

| Component | % w/w |
|---|---|
| LAS | 17.50 |
| AEO | 14.40 |
| DTSA | 10.00 |
| Oleic acid | 3.00 |
| Coconut oil | 5.00 |
| MEA | 14.50 |
| MPG | 10.70 |
| Ethanol | 1.40 |
| Phosphonate | 1.00 |
| Boric acid | 0.80 |
| Citric acid | 3.90 |
| Sodium chloride | 0.13 |
| Potassium chloride | 0.38 |
| Hydrochloric acid 4 M | 6.00 |
| Water | 9.7 |

* all variants are produced in yeast as described in example 6.

Example 14

The first wash activity of a large number of potential first wash lipolytic enzyme was tested using the "Assay for test of First Wash effect" described in the Materials and Methods section above with a specific commercial detergent—Ariel Futur (commercially available batch No.4279 B 23:35). The enzymes already present in the detergents were inactivated by heat (4 minutes at 85° C. in micro oven) prior to wash.

The first table can be used to compare to example 12 and 13.

Afterwards the results are divided as follows:

a) % removal when dosing after LU-units (see methods & materials for definition)
b) % removal when dosing after milligrams of pure enzyme protein
c) delta Reflectance when dosing after LU-units (see methods & materials for definition)
d) delta Reflectance when dosing after milligrams of pure enzyme protein Note: ¤ are produced in *Aspergillus oryzae* as described in example 7

The following results were obtained:

Enzyme Inactivated Commercial European Detergent

| | % removal at | |
|---|---|---|
| Lipolytic Enzyme | 1250 LU/l | 12500 LU/l |
| SPIRR (SEQ ID NO:29) + D57G + G59V + N94K + D96L + L97M + S116P + S170P + Q249R* | 12% | 37% |
| SPIRR (SEQ ID NO:29) + A49P + D167G + E210V* | 8% | 38% |
| SPIRR (SEQ ID NO:29) + E56K + D57G + D62R + S83T + S85F + D96L + D102Y + E210K* | 8% | 34% |
| SPIRR (SEQ ID NO:29) + N94K + F95L + D96H + N101S + F181L + D234Y + I252L + P256T + G263A + L264Q* | 11% | 37% |
| E1SPIRPRP (SEQ ID NO:31) + D57G + N94K + D96L + L97M + Q249R¤ | 27% | 53% |
| Lumafast ™ (*Ps. mendocina*) | 3% | 3% |
| Lipomax ™ (*Ps. pseuodoalcaligenes* L21M) | 1% | 0% |
| *Fusarium solani* pisi | 0% | 1% |
| Lipolase | 0% | 0% | a) Enzyme Inactivated Commercial European Detergent

| | % removal at | | |
|---|---|---|---|
| Lipolytic Enzyme | 1250 LU/l | 2500 LU/l | 12500 LU/l |
| SPIRR (SEQ ID NO:29) + D57G + N94K + D96L + L97M + Q249R* | 12% | n.d. | 38% |
| SPIRR (SEQ ID NO:29) + N94K + D96L + Q249R* | 13% | n.d. | 45% |
| SPIRR (SEQ ID NO:29) + I90F + D96L + E99K + V187A* | n.d. | 27% | 48% |
| SPIRR (SEQ ID NO:29) + D137G + D167G + D210V + W221L* | 13% | n.d. | 47% |
| SHSRHNA (SEQ ID NO:153) + D57G + N94K + D96L + L97M + Q249R* | n.d. | 22% | 53% |
| GPIRPRP (SEQ ID NO:48) + D57G + N94K + D96L + L97M + Q249R* | n.d. | 26% | 54% |
| TAIRPRK (SEQ ID NO:46) + D57G + N94K + D96L + L97M + Q249R* | n.d. | 34% | 55% | b) Enzyme Inactivated Commercial European Detergent

| | % removal at | |
|---|---|---|
| Lipolytic Enzyme | 0.25 mg/l | 2.50 mg/l |
| I90F + D96L + E99K + V187A¤ | 1% | 26% |
| E1PSPIRPR (SEQ ID NO:20) + D57G + N94K + D96L + L97M + Q249R¤ | 21% | 51% | c) Enzyme Inactivated Commercial European Detergent

| | delta Reflectance (dR) | | |
|---|---|---|---|
| Lipolytic Enzyme | 1250 LU/l | 5000 LU/l | 12500 LU/l |
| A47V + D92G + D96L + A121T¤ | 1 | n.d. | 2 |
| D57G + N94K + D96L + P256T¤ | 0 | n.d. | 2 |
| N94K + D96A + Q249R¤ | 0 | n.d. | 2 |
| SPIRR (SEQ ID NO:29) + Lipolase ™* | n.d. | n.d. | 3 |
| D57G + G59V + N94K + D96L + L97M + S116P¤ | 1 | n.d. | 3 |
| D57G + N94K + D96L + L97M + D167G + E210V¤ | 1 | n.d. | 3 |
| QPIRR + D57G + N94K + D96L + L97M + Q249R¤ | 1 | n.d. | 3 |
| SPIR (SEQ ID NO:28) + D57G + N94K + D96L + L97M + Q249R¤ | n.d. | n.d. | 4 |
| SHWQQ (SEQ ID NO:56) + D57G + N94K + D96L + L97M + Q249R¤ | 1 | n.d. | 4 |
| I90F + D96L + E99K + V187A + D234Y¤ | 1 | 4 | n.d. |
| E1AWWPSPIRPRP (SEQ ID NO:59) + D57G + N94K + D96L + L97M + Q249R¤ | 2 | 6 | n.d. |
| SPIRR (SEQ ID NO:29) + A19T + D167G + E210V + W221L* | 1 | n.d. | 6 |
| SPIRR (SEQ ID NO:29) + D57G + N94K + D96L + P256T* | 1 | n.d. | 6 |
| SPIRR (SEQ ID NO:29) + E56K + D57G + D62R + S83T + S85F + D96L + D102Y + E210K* | 4 | n.d. | 11 |
| SPIRR (SEQ ID NO:29) + N94K + F95L + D96H + N101S + F181L + D234Y + Y252L + P256T + G263A + L264Q* | 4 | n.d. | 11 |
| SPIRR (SEQ ID NO:29) + D57G + G59V + N94K + D96L +L97M + S116P + S170P + Q249R* | 5 | n.d. | 11 |
| SPIRR (SEQ ID NO:29) + A49P + D167G + E210V* | 3 | n.d. | 12 |
| SPIRR (SEQ ID NO:29) + N94K + D96L + Q249R* | 4 | n.d. | 13 |
| SPIRR (SEQ ID NO:29) + D137G + D167G + E210V + W221L* | 5 | n.d. | 13 |
| SPIRR (SEQ ID NO:29) + D57G + N94K + D96L + L97M + Q249R* | 6 | n.d. | 13 |

-continued

| Lipolytic Enzyme | | | |
|---|---|---|---|
| SPIRR (SEQ ID NO:29) + I90F + D96L + E99K + V187A* | 6 | n.d. | 15 | d) Enzyme Inactivated Commercial European Detergent

| Lipolytic Enzyme | Delta Reflectance (dR) | | |
|---|---|---|---|
| | 0.25 mg/l | 1.00 mg/l | 2.50 mg/l |
| D57G + N94K + D96L + L97M + D167G + E210V¤ | 1 | n.d | 3 |
| S3R,D137G + D167G + E210V + W221L¤ | 0 | 2 | 2 |
| D57G + N94K + D96L + L97M + E210K¤ | n.d. | n.d. | 3 |
| E1SPPRRP (SEQ ID NO:35) + I90F + D96L + E99K + D137G + D167G + V187A + Q249R¤ | n.d. | 4 | n.d. |
| E87K + G91A + D167G + E210V¤ | n.d. | n.d. | 4 |
| E87K + G91A + E210K¤ | 1 | n.d. | 4 |
| I90F + D96L + E99K¤ | 0 | 2 | 5 |
| APPPRTRPRPRPR (SEQ ID NO:61) + E1S + V2G + S3T + Q4P + D5E + D57G + N94K + D96L + L97M + Q249R¤ | 0 | 2 | n.d. |
| N94K + D96L + L97M + N233R + Q249R¤ | 0 | 3 | n.d. |
| SPIRKSPIRR (SEQ ID NO:157) + I90F + D96L + E99K + V187A¤ | 1 | 3 | 5 |
| D137G + D167G + E210V + W221L + N233R¤ | 1 | 3 | 5 |
| SPIRRSPIRR (SEQ ID NO:29) + I90F + D96L + E99K + V187A¤ | 1 | 3 | 6 |
| D167G + E210V + N233R + Q249R¤ | 1 | 3 | n.d. |
| E1W + V2P + N94K + D96L + Q249R¤ | 1 | 3 | n.d. |
| D96L + E99K + V187A¤ | 1 | 3 | n.d. |
| E1SPPWWPRW (SEQ ID NO:73) + N94K + D96L + Q249R¤ | 2 | 3 | n.d. |
| N94K¤ | 2 | 3 | n.d. |
| D96L + D137G + D167G + E210V¤ | 2 | 3 | n.d. |
| E1SQRIKQRIK (SEQ ID NO:63) + I90F + D96L + E99K + V187A¤ | 0 | 4 | n.d. |
| E1SPPRRP (SEQ ID NO:35) + I90F + D96L + E99K + D137G + D167G + V187A + Q249R¤ | 0 | 4 | n.d. |
| I90F + D96L + E99K + V187A + D234Y + Q249R¤ | 0 | 4 | n.d. |
| I90F,D96L + E99K + V187A + N233R¤ | 1 | 4 | n.d. |
| E1A + S3R + N94K + D96L + Q249R¤ | 1 | 4 | n.d. |
| S3R + I90F + D96L + E99K + V187A + Q249R¤ | 1 | 4 | n.d. |
| E1A + I90F + D96L + E99K + V187A¤ | 1 | 4 | 7 |
| I90F + D96L + E99K + V187A¤ | 1 | 4 | 8 |
| E1SPIRPRP (SEQ ID NO:31) + D57G + N94K + D96L¤ | 2 | 4 | n.d. |
| E1SPPWWP (SEQ ID NO:39) + N94K + D96L + Q249R¤ | 2 | 4 | n.d. |
| SPIRK (SEQ ID NO:22) + D57G + N94K + D96L + L97M + Q249R¤ | 3 | 4 | 10 |
| SPIRRP (SEQ ID NO:24) + D57G + N94K + D96L + L97M + Q249R¤ | 3 | n.d. | 11 |
| I90F + D96L + E99K + V187A + Q249R¤ | 1 | 5 | 8 |
| I90F + D96L + E99K + V187A + T231R¤ | 2 | 5 | n.d. |
| E1SPPRWP (SEQ ID NO:41) + N94K + D96L + Q249R¤ | 2 | 5 | n.d. |
| E1SPPRWPWR (SEQ ID NO:71) + N94K + D96L + Q249R¤ | 2 | 5 | n.d. |
| N94K + D96L + E99K¤ | 2 | 5 | n.d. |
| E1A + I90F + D96L + E99K + Q249R* | 1 | 6 | n.d. |
| E1K + D96L + D167G + E210V + N233R + Q249R¤ | 2 | 6 | n.d. |
| E1SPIRKPRIK (SEQ ID NO:147) + I90F + D96L + E99K + V187A¤ | 2 | 6 | n.d. |
| SHWRK (SEQ ID NO:44) + D57G + N94K + D96L + L97M + Q249R¤ | 3 | 6 | n.d. |
| SPIRKAWWP (SEQ ID NO:22) + I90F + D96L + E99K + V187A¤ | 2 | 7 | 10 |
| N94K + D96L + E99K + Q249R¤ | 2 | 7 | n + d. |
| E1SPPWRPRR (SEQ ID NO:72) + N94K + D96L + Q249R¤ | 2 | 7 | n.d. |
| EISPPRWPRR (SEQ ID NO:69) + N94K + D96L + Q249R¤ | 2 | 7 | n.d. |
| D137G + D167G + E210V + W221L + D234R¤ | 2 | 7 | n.d. |
| P-4C + N94K + D96L + E239C + Q249R¤ | 3 | 7 | n.d. |
| E1SPIRPRPSPIRPRP (SEQ ID NO:31) + D57G + N94K + D96L + L97M + Q249R¤ | 3 | 7 | n.d. |
| E1APPPRPRPRPRP (SEQ ID NO:60) + V2G + D5E + D57G + N94K + D96L + L97M + Q249R* | 4 | 7 | n.d. |
| E1SPPWPRPRP (SEQ ID NO:76) + N94K + D96L + Q249R¤ | 2 | 8 | n + d. |
| E1SPKRKPRP (SEQ ID NO:62) + D137G + D167G + E210V + W221L¤ | 3 | 8 | n.d. |
| E1SPPRRP (SEQ ID NO:35) + D96L + E99K + D137G + D167G + V187A + Q249R¤ | 4 | 8 | n.d. |
| E1SPPRRP (SEQ ID NO:35) + D57G + N94K + D96L + L97M + Q249R¤ | 4 | 9 | 11 |
| E1SPIRPRP (SEQ ID NO:31) + N94K + D96A + Q249R¤ | 4 | 9 | n.d. |
| E1SPPRRP (SEQ ID NO:35) + D57G + N94K + D96L + L97M + Q249R¤ | 5 | 9 | n.d. |
| E1SPPRRP (SEQ ID NO:35) + I90F + D96L + E99K + D137G + V187A¤ | 5 | 9 | n.d. |
| E1SPPRRP (SEQ ID NO:35)+ Y53C + D57G + N94K + D96L + K127C + Q249R¤ | 5 | 9 | n.d. |
| E1SPPRRP (SEQ ID NO:35) + I90F + D96L + E99K + D137G + V187A + Q249R¤ | 4 | 10 | n.d. |
| E1SPPRRP (SEQ ID NO:35) + N94K + D96L + Q249R¤ | 5 | 10 | n.d. |
| E1SPPRRP (SEQ ID NO:35) + N94K + D96L + E99K¤ | 5 | 10 | n.d. |
| E1SPPRRP (SEQ ID NO:35) + N94K + D96L + E99K + Q249R¤ | 5 | 10 | n.d. |
| E1SPIRPRP (SEQ ID NO:31) + D57G + N94K + D96L + Q249R¤ | 6 | 10 | 13 |
| E1SPPRRP (SEQ ID NO:35) + I90F + D96L + E99K + V187A¤ | 6 | 10 | 15 |
| E1SPIRPRP (SEQ ID NO:31) + N94K + D96L + L97M + Q249R¤ | 6 | 10 | n.d. |
| E1SPPPRPRP (SEQ ID NO:152) + N94K + D96L + Q249R¤ | 6 | 10 | n.d. |
| APPPRPRLLPIS (SEQ ID NO:88) + D5E + D57G + N94K + D96L + L97M + Q249R* | 6 | 10 | n.d. |
| E1SPIRPRP (SEQ ID NO:31) + D137G + D167G + E210V + W221L¤ | 7 | 10 | 13 |
| E1SPPPRPRP (SEQ ID NO:64) + N94K + D96L + L97M + Q249R¤ | 7 | 10 | n.d. |
| E1SPIRPRP (SEQ ID NO:31) + N94K + D96L + Q249R¤ | 7 | 11 | n.d. |
| E1SPIRPRP (SEQ ID NO:31) + D57G + N94K + D96L + L97M + Q249R¤ | 7 | 13 | 16 |

* are produced in yeast as described in example 6

Example 15

The first wash activity of one first wash lipolytic enzyme was tested using the "Assay for test of First Wash effect" described in the Materials and Methods section above with an array of commercial detergents. The enzymes already present in the detergents were inactivated by heat (4 minutes at 85° C. in microoven) prior to wash.

The Lipolase variant E1SPIRPRP(SEQ ID NO:31)+D57G+N94K+D96L+L97M+Q249R produced in *Aspergillus oryzae* as described in example 7 was used.

The following different geographic condtions were used:
European: Time: 20 min.
 Temperature: 30° C.
 Water hardness: 3.2 mM $Ca^2/Mg^2$ (5:1) ~18° dH
US: Time: 10 min.
 Temperature: 30° C.
 Water hardness: 1.07 mM $Ca^2/Mg^2$ (5:1) ~6° dH

| Detergent | dR at 0.25 mg/l | dR at 1.00 mg/l |
|---|---|---|
| E1SPIRPRP (SEQ ID NO:31) + D57G + N94K + D96L + L97M + Q249R in US detergents | | |
| Wisk HDL (2 g/l) | 3 | 5 |
| Wisk w. bleach (1 g/l) | 3 | 7 |
| Surf w. bleach (1 g/l) | 1 | 4 |
| Tide HDL (2 g/l) | 1 | 4 |
| Tide w. bleach (1 g/l) | 2 | 5 |
| E1SPIRPRP (SEQ ID NO:31) + D57G + N94K + D96L + L97M + Q249R in European detergents | | |
| Ariel Futur (5 g/l) UBA 06731122 | 6 | 12 |
| Ariel Futur color (5 g/l) UBA 06730101 | 7 | 11 |
| Tandil Ultra Plus (5 g/l) UBA 02500191 | 4 | 12 |
| Tandil Ultra Plus Color (5 g/l) UBA 05761612 | 5 | 13 |
| Sunil Aktiv (5.5 g/l) UBA 05580168 | 4 | 15 |
| Sunil Aktiv Citrus (5.5 g/l) UBA 05580168 | 3 | 13 |
| Sunil Aktiv Color (5.5 g/l) UBA 05580169 | 4 | 13 |
| Persil Megapearls (5 g/l) UBA 04163661 | 2 | 12 |
| Persil Megapearls Color (5 g/l) UBA 04163662 | 3 | 16 |

Example 16

Construction of *Ps. cepacia* Lipase Variants Comprising Peptide Additions

A lipase gene from *Pseudomonas cepacia* SB10, DSM 3959, described in WO 89/01032 (from Novo Nordisk A/S) recently reclassified as *Burkholderia cepacia* was cloned, and temperature-inducible expression of the lipase in *Escherichia coli* was obtained by use of the plasmid pAHE2. Strain SJ1503 is *E. coli* JA221 containing pAHE2.

To construct vectors expressing variant lipases with N-terminal extensions, use were made of two unique restriction sites present in pAHE2, a unique BstXI site approximately 9 codons into the lipase signal peptide coding sequence, and a unique Mlul site approximately 7 codons downstream from the processing site, i.e. in the beginning of the sequence for the mature lipase.

PCR primers were designed to allow amplification across this region, with the primers reading upstream from the Mlul site encompassing sequences encoding the N-terminal extensions. All primers had incorporated EcoRI sites in their extreme 5' ends.

The following sequences were chosen to encode N-terminal extensions:
1) S P I R P R P(SEQ ID NO:31)
   AGC CCG ATC CGC CCG CGC CCG (SEQ ID NO:126)
2) T A I R P R K(SEQ ID NO:46)
   ACG GCG ATC CGC CCG CGC AAG (SEQ ID NO:127)
3) S T R R P R P (SEQ ID NO:47)
   TCG ACG CGC CGT CCG CGC CCG (SEQ ID NO:128)
4) G P I R P R P (SEQ ID NO:48)
   GGC CCG ATC CGC COG CGC CCG (SEQ ID NO:129)
5) S P I R R(SEQ ID NO:29)
   AGC CCG ATC CGC CGG (SEQ ID NO:130)
6) R P R P R P R P (SEQ ID NO:57)
   CGC CCG CGT CCC AGG CCG CGT CCG (SEQ ID NO:131)

The following primers were used:
LWN9476 (SEQ ID No. 7) (reading downstream from the BstXI site):
   5'-CGMTTCGATGCGTTCCAGGGTGGTGGCAGG-3'

LWN9472 (SEQ ID No. 8) (reading upstream from Mlul, designed to incorporate SPIRPRP):
   5'-CGMTTCACGCGTCGCCGCGTAGCCAGCGGCC GGGCGCGGGCGGATCGGGCTGGGCGCGGTG GCCGCCATTGCC-3'
LWN9473 (SEQ ID No. 9) (reading upstream from Mlul, designed to incorporate TAIRPRK):
   5-GAATTCACGCGTCGCCGCGTAGCCAGCGGCCT TGCGCGGGCGGATCGCCGTGGGCGCGGTG GCCGCCATTGCC-3'
LWN9471 (SEQ ID No. 10) (reading upstream from Mlul, designed to incorporate STRRPRP):
   5'-CGAATTCACGCGTCGCCGCGTAGCCAGCGGCC GGGCGCGGACGGCGCGTCGAGGGCGCGGT GGCCGCCATTGCC-3'
LWN9474 (SEQ ID No. 11) (reading upstream from Mlul, designed to incorporate GPIRPRP):
   5'-CGAATTCACGCGTCGCCGCGTAGCCAGCGGCC GGGCGCGGGCGGATCGGGCCGGGCGCGGTG GCCGCCATTGCC-3'
LWN9475 (SEQ ID No. 12) (reading upstream from Mlul, designed to incorporate SPIRR):
   5'-CGMTTCACGCGTCGCCGCGTAGCCAGCGGCC CGGCGGATCGGGCT-GGGCGCGGTGGCC GCCATTGCC-3'
LWN9470 (SEQ ID No. 13) (reading upstream from Mlul, designed to incorporate RPRPRPRP):
   5'-CGMTTCACGCGTCGCCGCGTAGCCAGCGGCC GGACGCGGCCTGGGACGCGGGCGGGGCG CGGTGGCCGCCATTGCC-3'

For PCR amplifications, primer LWN9476 was used in combination with each of primers LWN9470-LWN9475, with pAHE2 as template. Annealing temperature was 70° C., and reactions were performed in the presence of 2% DMSO; otherwise using standard conditions and Taq™ polymerase.

Amplified fragments were purified from a 2% agarose gel, digested with BstXI and Mlul, ligated to the 7.1 kb BstXI-Mlul fragment obtained from pAHE2, and the ligation mixture used to transform, by electroporation, *E. coli* SJ6 to ampicillin resistance. Transformants were plated on LB plates with ampicillin (200 mg/ml) at 30° C.

By replica plating colonies were transferred to lipase screening plates (containing, pr. liter of agar, 20 ml of Sigma Lipase Substrate (catalogue no. 800-1)) and 4 ml of a 1% Brilliant Green (Merck, art. No. 1.01310) solution), which were incubated at 42° C. Eventually, green halos, indicating lipase activity, developed around several colonies from each transformation mixture.

Lipase positive colonies were re-isolated, plasmids extracted, and the BstXI-Mlul region DNA sequenced. The following strains were kept:
SJ3606 (SJ6/pSJ3606); contains the SPIRPRP (SEQ ID NO:31)encoding addition, and has also the second codon in the native, mature enzyme changed from alanine to valine.
SJ3608 (SJ6/pSJ3608); contains a SPRP (SEQ ID NO:27) encoding addition (DNA sequence of insert TCT CCG CGC CCG (SEQ ID NO:132) (Obtained as a variant in attempts to produce a STRRPRP (SEQ ID NO:47) encoding addition.
SJ3708 (SJ6/pSJ3708); contains the SPIRR (SEQ ID NO:29)encoding addition.
SJ3717 (SJ6/pSJ3717); contains the SPIRPRP (SEQ ID NO: 31)encoding addition.
SJ3718 (SJ6/pSJ3718); contains the SPIRPRP (SEQ ID NO:31) encoding addition.
SJ3719 (SJ6/pSJ3719); contains the TAIRPRK (SEQ ID NO:46)encoding addition.

SJ3720 (SJ6/pSJ3720); contains the STRRPRP (SEQ ID NO:47)encoding addition.

SJ3721 (SJ6/pSJ3721); contains the GPIRPRP (SEQ ID NO:48)encoding addition.

Example 17

Shake Flask Fermentation of Ps. cepacia Lipase Variants

Cultures provided in Example 16 were grown on TY-ampicillin plates (pH 7) and used to inoculate shake flasks containing 100 ml double concentrated TY-medium with ampicillin (100 mg/ml) pH 7. The inoculum was checked for lipase productivity (as described in the Materials and Methods section) by streaking on indicator plates: all cells were found to be lipase positive (plates were incubated at 30° C. for 2 days, then transferred to 40° C. for 1 day).

The shake flasks were incubated shaking at 275 rpm at 30° C. for 6 hours until the cultures reached optical densities (578 nm) of 2.8 to 5.3. The cultures were then transferred to 40° C. for another 17 hours.

Check of Lipase Production in a Ps. cepacia Culture

The culture was harvested, centrifuged (20 minutes at 9000 rpm), the supernatant discarded and the pellet re-suspended in NaCl (0.5 ml 0.9% NaCl) and sonicated (2 minutes non-stop, on ice). The sonicated pellet was used to measure Lipase units (LU) using the titration method with tributyrate as substrate at pH 7.0.

All 8 strains except 1 (SJ3720) showed lipase activity as indicated in the table below.

| Strain | time (hs) | OD = 578 | AmpR: cell# | OOBGAmp:cell# | LU/ml¤ |
|---|---|---|---|---|---|
| SJ1503wt | t0 = 0 h | 0.010 | | | |
| | t1 = 6 hs | 2.89 | 7 | 7 | |
| | t2 = 17 hs | 7.45 | 0 | 0 | 230.5 |
| SJ3606 | t0 = 0 h | 0.006 | | | |
| | t1 = 6 hs | 5.24 | 43 | 43 | |
| | t2 = 17 hs | 9.15 | 0 | 0 | 244.45 |
| SJ3608 | t0 = 0 h | 0.015 | | | |
| | t1 = 6 hs | 4.40 | 67 | 65 | |
| | t2 = 17 hs | 9.2 | 0 | 0 | 298.6 |
| SJ3708 | t0 = 0 h | 0.028 | | | |
| | t1 = 6 hs | 4.69 | 32 | 32 | |
| | t2 = 17 hs | 11.05 | 0 | 0 | 142.2 |
| SJ3717 | t0 = 0 h | 0.007 | | | |
| | t1 = 6 hs | 4.03 | 28 | 28 | |
| | t2 = 17 hs | 11.2 | 15 | 15 | 163.8 |
| SJ3719 | t0 = 0 h | 0.001 | | | |
| | t1 = 6 hs | 4.49 | 13 | 13 | |
| | t2 = 17 hs | 11.7 | 0 | 0 | 33.55 |
| SJ3720 | t0 = 0 h | 0.004 | | | |
| | t1 = 6 hs | 3.70 | 20 | 20 | |
| | t2 = 17 hs | 10.5 | 0 | 0 | 0 |
| SJ3721 | t0 = 0 h | 0.016 | | | |
| | t1 = 6 hs | 4.20 | 12 | 12 | |
| | t2 = 17 hs | 11.35 | 0 | 0 | 125.75 |

Example 18

Characterization of Ps. cepacia Lipase Variants

The lipases produced from the strains described In Example 16 were characterized with respect to activity in the presence of detergent, using the PCS plate screening assay. One set of samples was prepared from strains SJ1503, SJ3606 and SJ3608, which had been propagated as described above, cells harvested, and lysed by sonication to liberate the lipase. 15 ml of samples, containing around 230 LU/ml, were applied in wells in screening plates either without detergent, or containing 1.5 and 3.5 grams/liter of detergent, respectively. Plates were incubated at 37° C. overnight, and the diameter of the green zone formed around the wells measured. The following results were obtained:

| STRAIN DETERGENT | SJ1503 | SJ3606 | SJ3608 |
|---|---|---|---|
| None | 17 mm | 15 mm | 16 mm |
| 1.5 gram/l | 7 mm | 13 mm | 10 mm |
| 3.5 gram/l | 0 mm | 8 mm | 6 mm |

Green zones were not observed at higher detergent concentrations.

Another set of samples were prepared by plating of the strains SJ1503, SJ3708, and SJ3717-SJ3721 on cellulose acetate filters (each filter containing all 7 strains), which were placed on LB plates with ampicillin (200 mg/ml) at 37° C. overnight, these plates with filters then incubated at 42° C. for 5 hours, after which the filters were transferred (colony side up) to screening plates which were incubated overnight at 37° C.

Pronounced green zones developed under all colonies on the plate without detergent; SJ3720 produced a significantly smaller zone then the rest, most likely due to reduced expression of the lipase.

Green zones were also observed under all colonies on the plate containing 1.5 gram/l of detergent. However, the zone produced from SJ1503, producing the native, unmodified lipase, was significantly reduced as compared to the zones produced from the other strains.

On the plate containing 3.5 grams/liter detergent, no green coloration developed from SJ1503, whereas a greenish stain was still discernible from some strains expressing modified B. cepacia lipases, in particular SJ3717, SJ3718 and SJ3721.

Thus, modification of the B. cepacia lipase gene to encode N-terminal additions to the native, mature lipase, as those described above, allow the production of lipases which in the presence of detergent has an improved activity as compared to the native lipase.

Example 19

Fermentation of SJ1503 and SJ3717 in 10 liter Tanks

The method described for shake flask was used for the fermentation in 10 liter scale. The medium used was Bacto Tryptone 400g, Bacto Yeast extract 200 g, Glucose x 2 $H_2O$ 500 g, Ampicillin 1 g, Pluronic 1 ml. The pH was kept constant at pH 7.1; the temperature was 30° C. for 7 hours then adjusted to 40° C. Cells were harvested after 16 hours by centrifugation and the cells were opened using a high pressure homogenizer (800 bar).

Purification of cepacia Expressed in E. coli

E. coli cells from 10 liter fermentation broth from SJ1503 and SJ3717 were centrifuged and the supernatant was discarded. Cells were opened using rannie homogenizer under pressure 800 bar. Homogenized cells were centrifuged at 350×g for 60 minutes. Cell supernatant was decanted.

1. Salt Precipitation

Activity containing supernatant was precipitated with addition of solid ammonium sulphate to saturation of 35% at room temperature. Precipitation was allowed for 2 hour at room temperature and centrifuged at 350×g for 1 hour. Supernatant was decanted and discarded. Precipitate containing activity was dissolved in 30% ethanol to avoid hydrophobic biding of the lipase activity to insoluble material.

To get rid of insoluble material from the 30% ethanol dissolved material, the solution was centrifuged. The lipase activity was recovered as supernatant and insoluble material was discarded. The supernatant containing activity was concentrated and dialyzed against 25 mM Tris-acetate pH 8, by ultra-filtration using Amicon membrane with cut-off of 10 kDa. The concentrated sample was then diluted five fold in order to reduce any leftover ethanol in the supernatant containing activity.

2, Hydrophobic Chromatography

The above sample containing activity was adjusted to 0.8 M ammonium acetate by adding solid ammonium acetate. 50 ml Toyopearl Butyl column (Tosho Hass, Japan) was packed and equilibrated with 0.8 M ammonium acetate. The samples from above step containing lipase activity was then adjusted to 0.8 M ammonium acetate and applied on the Toyopearl Butyl column. All the activity binds to the matrix. Unbound material was washed with 0.8 M ammonium acetate till Uv absorbence of the effluent was under 0.05 at 280 nm. Bound activity was eluted with 25 mM Tris acetate buffer containing 50% ethanol. Fractions containing lipase activity were pooled and dialyzed against 25 mM Tris acetate buffer pH 8.5.

3. Anion Exchange Chromatography 50 ml Column was packed with anion exchanger High-performance Q-sepharose (Pharmacia). The column was washed and equilibrated with 25 mM Tris acetate buffer pH 8.5. The dialyzed sample was then applied on the column. Unbound activity was washed out by using the Tris buffer. Bound activity was eluted with a linear salt gradient from 0 to 0.5 M NaCl in the Tris buffer pH 8, Flow rate was 2 ml/min and total volume of the buffer used for elution was 10 column volumes. Fractions containing lipase activity were pooled and tested for performance in a PCS plate assay.

More specifically, 3 LU of each of the recovered modified lipases were added into holes of a PCS plate (cf. Example 21 hereinafter) and incubated overnight at 37° C. After 18 hours the following results were obtained:

| STRAIN DETERGENT | SJ1503 | SJ3717 |
|---|---|---|
| None | 17 mm | 13 mm |
| 0.5 gram/l | 6 mm | 10 mm |
| 1.0 gram/l | 4 mm | 7 mm |

Thus, it can be seen that the presence of a peptide addition results in a signifantly higher wash performance being obtained.

Example 20

Construction of Modified *H. insolens* Lipolytic Enzymes With an N-terminal Peptide Addition The gene encoding the parent lipolytic enzyme was isolated from *Humicola insolens* DSM 1800 essentially as described in WO 96/13580. Three different peptide additions were applied to the N-terminus of the mature enzyme using the plasmid pIVI1303 as the plasmid template.

Construction of pIVI303 (encoding a *H. insolens* lipolytic enzyme variant which contains a mutation in the region 304–369 base downstream from ATG without changes in amino acid sequence and removing a possible secondary DNA structure which might otherwise have hampered the use of the chameleon double stranded kit.).

The plasmid was constructed using the Chameleon double-stranded, site-directed mutagenesis kit from Stratagene (cat no. 200509) according to the described protocol.

pIVI296 was used as the plasmid template and primer no 7258 as the selection primer.

7258: 5'p gaa tga ctt ggt tga cgc gtc acc agt cac 3' (SEQ ID NO:1)

(Thus changing the Scal site found in the ampicillin resistance gene and used for cutting to a Mlul site).

Primer no 9349 was used as the mutagenic primer:

9349: 5'p gag tcc cac atc cga aac atc tgg ata caa gga gta gga gga cct tac gac gcc gcg 3' (SEQ ID NO:86)

1. Variant: HILv4s Containing the Mutation: PPRRPR (SEQ ID NO: 60)(Instead of PELVAR in the Native *H. insolens* Propeptide)

Construction of pIVI335

The plasmid was constructed by use of the Chameleon double-stranded, site-directed mutagenesis kit from Stratagene (cat no. 200509) according to the described protocol. pIVI303 was used as a plasmid template.

Primer no.7887 was used as a selection primer:

7887: :5'p-gaa tga ctt ggt tga gta ctc acc agt cac 3 (SEQ ID NO:79)

(changing the introduced Mlu1 site found in the ampicillin resistance gene and used for cutting to a Scal site).

Primer no 19473 was used as a mutagenic primer:

19473: 5'p ac cat acc ccg gcc gct cct cct agg cgt cct cgg cag ctg gga gcc 3 (SEQ ID NO:85)

2, Variant: HILv1s Containing the Mutation SPPRRP (SEQ ID NO: 35)(Instead of ELVARQ in the Native *H. insolens* Propeptide)

Construction of pIVI359

The plasmid was constructed by use of the Chameleon double-stranded, site-directed mutagenesis kit from Stratagene (cat no. 200509) according to the described protocol.

pIVI303 was used as a plasmid template. Primer no.7887 (cf. above) was used as a selection primer. Primer no 21992 was used as a mutagenic primer:

21992: 5'p ac cat acc ccg gcc gct cct agc cct ccg cgg cgg ccg ctg gga gcc atc gag aac ggc 3 (SEQ ID NO:85)

3, Variant: HILv2s Containing the Mutation SPPRP (SEQ ID NO:37) (Instead of ELVARQ in the Native *H. insolens* Propeptide)

Construction of pIVI360

The plasmid was constructed using the Chameleon double-stranded, site-directed mutagenesis kit from Stratagene (cat no. 200509) according to the described protocol.

pIVI303 was used as a plasmid template, and primer no.7887 as a selection primer.

The following primer was used as the selection primer:

5'p ac cat acc ccg gcc gct cct agc cct ccg cgg ccg ctg gga gcc atc gag aac ggc 3 (SEQ ID NO:85)

4, Variant: HILv3s Containing the Mutation: SPIRK (SEQ ID NO: 22)(Instead of ELVARQ in the Native *H. insolens* Propeptide)

Construction of pIVI361

The plasmid was constructed using the Chameleon double-stranded, site-directed mutagenesis kit from Stratagene (cat no. 200509) according to the described protocol.

pIVI303 was used as a plasmid template and primer no 7887 as a selection primer.

Primer no 21994 was used as a mutagenic primer:

21994: 5'p ac cat acc ccg gcc gct cct agc cct ata cgt aag ctg gga gcc atc gag aac ggc 3 (SEQ ID NO:85)

5, Construction of an *A. oryzae* Expression Vector pIVI296 pA2L79 is described in Example 2 of WO 96/13580. The plasmid contains the *H.insolens* lipolytic enzyme cDNA sequence inserted into the *A. oryzae* expression plasmid pD414, PA2L79 was cut with the restriction enzymes HindIII and XhoI. The fragment containing the lipolytic enzyme encoding cDNA sequence (1088 bp) was purified from agarose gel. PHD414 was cut with the restriction enzymes HindIII and XhoI and the vector purified form an agarose gel.

The purified vector fragment (pHD414) and the lipase containing fragment was ligated thus creating pIVI296.

Each of the above expression vectors were transformed into *A. oryzae* IFO 4177 by use of the general transformation method disclosed in the Materials and Methods section above. One transformant of each type was isolated as HILv1–4s, respectively. The *H. insolens* transformants were grown for 3 days in shake flaks at 30° C. in 500 ml YPM medium (10 g/L bacto yeast extract, 20 g/L bacto peptone, 20 g/L maltose).

Fermentation supernatent was filtered as described for modified *H. lanuginosa* lipolytic enzymes.

Purification Step 1: 1 liter of the Fermentation supernatent was adjusted to pH 8 and diluted so conductance of the supernatent was under 4 mSi.

Step 1: Batch treatment of the fermentation supernatent on anion exchanger DEAE A50.

DEAE-Sephadex A50 from Pharmacia was washed and equilibrated with 25 mM tris acetate buffer pH 8 using Scintered glass funnel with appropriate pore size. Fermentation supernatent was then applied on the DEAE Sephadex A50 using the scintered glass funnel. The Lipolytic activity from *H.insolence* did not bind to anion exchanger at pH 8 and collected as effluent from DEAE Sephadex A50.

Step 2: pH of the efflent from DEAE Sephadex was adjusted to 4.5 by adding dilute Acetic acid. Condctance was also adjusted under 4 mSi by adding water.

Cation Exchange chromatography on SP-Sepharose. 50 ml Column was packed with SP Sepaharose Fast Flow Code no 17-0729-01 Pharmacia. Column was then washed and equilibrated with 25 mM Sodium acetate buffer pH 4.5.

Sample containing Lipolytic activity adjusted to pH 4.5 and the conductance under4 mSi was then applied on SP-Sepharose column. Unbound material was washed using 25 mM Sodium acetate buffer pH 4.5. Lipolytic activity bound to the SP-Sepharose was then eluted with linear salt gradient with 25 mM Acetate buffer pH 4.5 containing 1 M Sodium Chloride. Fractions containing Lipolytic activity and ratio of the UV absorbence at A280/A260 was higher than 1.8 were pooled. Purity of the sample was checked on SDS-PAGE.

Verification of N-terminal Peptide Addition

The N-terminal amino acid sequence of the HILv1s lipolytic enzyme was determined (i.e. the variant in which the last 5 amino acid residues in the propeptide and the first amino acid residue in the mature enzyme (ELVARQ) have been substituted with SPPRRP (SEQ ID NO: 35)).

The N-terminal amino acid sequence found was

Arg-Arg-Pro-Leu-Gly-Ala-Ilecorresponding to the last three amino acid residues in the substituted sequence and the first four amino acid residues following the substitution.

The N-terminal amino acid sequence of the HILv2s lipolytic enzyme was also determined (i.e. in the variant in which the last 5 amino acid residues in the propeptide and the first amino acid residue in the mature enzyme (ELVARQ) have been substituted with SPPRP(SEQ ID NO:37)).

The N-terminal amino acid sequence found was

Arg-Pro-Leu-Gly-Ala-Ile-Glu-Asn corresponding to the last two amino acid residues in the substituted sequence and the first six amino acid residues following the substitution.

Example 21

Characterization of Modified *Humicola insolens* Lipolytic Enzymes

The modified lipolytic enzymes comprising peptide additions, produced by the strains HILv1s, HILv2s, HILv3s, respectively, (described in Example 20), and the wild-type strain HIL, were characterized with respect to lipase activity on PCS-plates containing 0.5 g/l, 1.0 g/l and 1.5 g/l PCS-detergent.

25 μl (corresponding to 5 LU) purified modified HILvs1, HILvs2 and HILvs3 lipase, and wild-type HIL lipase were entered into holes made in the PCS-plates by a pipette (4 mm) and incubated for 3 and 6 hours, respectively.

The result of the test in displayed in the tables below:

| Variant | 0.5 g/l PCS-detergent | 1.0 g/l PCS-detergent | 1.5 g/l PCS-detergent |
|---|---|---|---|
| HIL (wild-type) | 4 mm | 4 mm (weak) | 0 mm |
| HILv1s | 6 mm | 5 mm | 4 mm (weak) |
| HILv2s | 5 mm | 4 mm | 0 mm |
| HILv3s | 6 mm | 6 mm | 5 mm |

Incubation of 3 hours on PCS-plates containing FY-detergent.

| Variant | 0.5 g/l PCS-detergent | 1.0 g/l PCS-detergent | 1.5 g/l PCS-detergent |
|---|---|---|---|
| HIL (wild-type) | 4 mm | 4 mm (weak) | 0 mm |
| HILv1s | 7 mm | 5 mm | 4 mm (weak) |
| HILv2s | 5 mm | 5 mm (weak) | 4 mm (weak) |
| HILv3s | 6 mm | 6 mm | 4 mm (weak) |

Incubation for 6 hours on PCS-plates containing PCS-detergent.

As can be seen from the tables the modified lipase variants (i.e. produced by HILv1s, HILv2s and HILvs3) generally have a higher lipase activity in the presence of the PCS-detergent than the wild-type lipase.

Example 22

Construction of Modified *H. lanuiqnosa* Lipolytic Enzymes With a C-terminal Extension C-terminal peptide additions were applied to the *H. lanuginosa* lipolytic enzyme variant HLv12s containing the N-terminal peptide addition SPIRPRP (SEQ ID NO::31) and the internal mutations D57G,N94K,D96L,Q249R.

1. Variant HLv13s (HLv12s With the C-terminal Peptide Addition: 270R,271 R,272P,Stop)

Construction of Plasmid pS14–1

The plasmid was constructed using the Chameleon double-stranded,site directed mutagenesis kit from Stratagene (cat no. 200509) according to the described protocol.

pIVI245 was used as the plasmid template (The construction of pIVI245 is described in Example 6) and primer no.7258 as the selection primer.

7258: 5'p gaa tga cft ggt tga cgc gtc acc agt cac 3' (SEQ ID NO: 95) (Thus changing the ScaI site found in the ampicillin resistance gene and used for cutting to a MluI site).

Primer no.20694 was used as the mutagenic primer.

20694: 5'p-gg gac atg tct tcg acg acc gta gcg gct ggg tcg act c 3, (SEQ ID NO:134)

2. Variant HLv14s (HLv12s With the Mutation: 270R,271R, Stop)

Construction of Plasmid pS20–2

The plasmid was constructed using the Chameleon double-stranded, site-directed mutagenesis kit from Stratagene (cat no. 200509) according to the described protocol. pIVI245 was used as the plasmid template and primer no. 7258 as the selection primer.

7258: 5'p gaa tga cft ggt tga cgc gtc acc agt cac 3' (SEQ ID NO:95) (Thus changing the ScaI site found in the ampicillin resistance gene used for cutting to a MluI site).

Primer no. 20695 was used as the mutagenic primer:

20695: 5'p-gg gac atg tct tcg gcg gta ggc gcg gct ggg tcg ac 3' (SEQ ID NO:135)

Production of Enzyme Variants

The enzymes were produced in an analogous manner to that described in Example 7 using the plasmid pToC 202 for the cotransformation step and *A. oryzae* JAL 125 as a host cell.

Verification of the Presence of the C-terminal Extension in HLv12s

A 1 mg sample of HLv12s Containing the C-terminal Extension Arg-Arg-Pro (RRP) was S-carboxamidomethylated using standard procedures before degradation with a lysyl-specific protease. The resulting peptides were separated using reversed phase HPLC and the collected fractions subjected to matrix assisted laser desorption ionization time-of-flight mass spectrometry. A fraction containing a peptide with the experimental mass of 3906.7 Da was found. This mass is within experimental error identical to the theoretical mass of the C-terminal peptide of HLv12s containing the RRP extension which is 3906.4 Da.

The amino acid sequence of the peptide in this fraction was determined to be

Ile-Glu-Gly-Ile-Asp-Ala-Thr-Gly-Gly-Asn-Asn-Arg-Pro-Asn-Ile-Pro-Asp-Ile-Pro-Ala-His-Leu-Trp-Tyr-Phe-Gly-Leu-Ile-Gly-Thr-Cys-Leu-Arg-Arg-Pro (SEQ ID NO:136)

which is the correct amino acid sequence of the C-terminal peptide of HLv12s and it contains the C-terminal extension Arg-Arg-Pro.

Example 23

A part of the N-terminal extension of HLv15s (HLv15s containing the N-terminal peptide addition SPIRPR (SEQ ID NO:20) and the following mutations in the mature part of the *H. lanuginosa* lipolytic enzyme EP, D57G, N94K, D96L, L97M, Q249R) was cleaved off by prolonged incubation with Clostripain (EC 3.4.22.8; Sigma No. C-0888).

The incubation mixture contained: HLv15s (1 mg/ml) and Clostripain (20 µg/ml) in 25 mM sodium phosphate, pH 7.4 containing 2.5 mM DTT and 1 mM calcium chloride.

Before incubation with Clostripain 60% of the lipase carried an intact propeptide (N-terminal amino acid sequence SPIRPRP(SEQ ID NO:31)), while 10% had lost the first Ser-residue (N-terminal amino acid sequence PIRPRPV) (SEQ ID NO:31) and 30% the first 5 amino acid residues of the propeptide (N-terminal amino acid sequence (RPVSQDL) (SEQ ID NO:162).

Following incubation for 62 h at ambient temperature (resulting in HLv15s-C) 60% of the lipase had lost the first 4 amino acid residues of the propeptide (resulting in the following peptide extension PRPVSQ) (SEQ ID NO:158), 20% were without 5 amino acid residues (thus having the peptide extension RPVSQD) (SEQ ID NO:159) while the remaining 20% had lost 6 amino acid residues (thus having the peptide extension PVSQDL) (SEQ ID NO:160).

The propeptide processing was determined using N-terminal amino acid sequence determination and it should be noted that the percentages given are approximate values.

| Variant | Peptide addition | Mutations |
|---------|------------------|-----------|
| HLv15s | 60% SPIRPRPVSQD (SEQ ID NO: 161) 10% PIRPRPVSQD (SEQ ID NO: 161) 30% RPVSQD (SEQ ID NO: 159) | D57G, N94K, D96L, L97M, Q249R |
| Hlv15s-C | 60% PRPVSQ (SEQ ID NO: 158) 20% RPVSQ (SEQ ID NO: 159) 20% PVSQDL (SEQ ID NO: 160) | D57G, N94K, D96L, L97M, Q249R |

One Cycle Wash Performance With a Modified Lipolytic Enzyme Treated With Clostripain The one cycle wash performance test (described above in Materials and Methods section above) was performed with *H. lanuginosa* lipase variant HLv15s treated with clostripain. Wash test was made both with the clostripain treated sample and the non clostripain treated variant. The wash test was carried out in 5 g/l enzyme inactivated Ariel Futur (Procter and Gamble). Lard stained swatches were washed for 20 minutes at 30° C. The tests were performed at lipase concentrations of 0, 5000 LU/l and 12500 LU/l.

The detergent was dissolved in approx. 18° dH (German Hardness) water. The pH of the wash liquor was about 10.3. Seven swatches were washed in 1000 ml wash liquor. Subsequent to the washing, the swatches were flushed in running tap water for 15 minutes and then air-dried overnight at room temperature.

Evaluation: The reflectance of the swatches was measured at 460 nm, and the lipase performance (_R) calculated as:

$$\Delta R = \text{delta Reflectance} = (R_{\text{swatches washed in detergent with lipase}} - R_{\text{swatches washed in detergent without lipase}})$$

The mutations of the lipases and the additions are described above.

The ΔR, are shown in the table below.

| Variant | +/− treatment w. clostripain | low dosage | ΔR | high dosage | ΔR |
|---|---|---|---|---|---|
| HLv15s | no clostripain treatment | 5000 LU/l | 10 | 12500 LU/l | 13 |
| HLv15s-C | + clostripain treatment | 5000 LU/l | 6 | 12500 LU/l | 7 |

The results show that the presence of an intact peptide addition leads to the best wash performance. A reduced (but not entirely removed) peptide addition provides an improved wash performance, especially when positively charged amino acid residues are present in the addition.

Example 24

Modified *H. lanuginosa* Lipolytic Enzyme Containing an Cysteine Bridge (HLv16s)

The modified *H. lanuginosa* lipolytic enzyme HLv16s contains the following mutations: N94K, D96L, E239C and Q249R and the peptide addition SCIRR (SEQ ID NO:30).

The parent enzyme HLv16 contains the following mutations: N94K, D96L, Q249R.

HLv16s was constructed as follows:
1. Construction of N94K, D96L Mutations in the Wildtype *H. lanuginosa* Lipolytic Enzyme Construction of pIVI290

The plasmid was constructed using the Chamelon double stranded, site-directed mutagenesis kit from Stratagene according to the described protocol using the pAHL (cf FIG. 6 of WO 92/05249) as the plasmid template and primers no 7258 and 7770 as the selection primers.

7258: 5'p gaa tga ctt ggt tga cgc gtc acc agt cac 3' (SEQ ID NO:1) (Thus changing the ScaI site found in the ampicillin resistans gene to a MluI site)(ScaI has been used for cutting).

7770: Sequence: 5'p tct agc cca gaa tac tgg atc aaa tc 3' (SEQ ID NO:2) (Changes the ScaI site found in the wild type *H. lanuginosa* lipase gene).

Primer no. 8932 was used as the mutagenic primer.

8932: 5'pgaac tgg ata gga aat ttg aag ttc ctg ttg aaa gaa ata aat gac 3' (SEQ ID NO:78) (Introducing N94K,D96L)

2. Construction of HLv16s (SCIRR (SEQ ID NO:30), N94K,D96L, E239C, Q249R)

Construction of pIVI319

The plasmid was constructed using the Chamelon double-stranded,site directed mutagenesis kit from Stratagene (cat no. 200509) according to the described protocol using pIVI290 as the plasmid template and primer no 7887 as the selection primer.

7887: 5'p-gaa tga ctt ggt tga gta ctc acc agt cac 3' (SEQ ID NO:1) (changing the introduced Mlu1 site found in the ampicillin resistans gene to a ScaI site)(MluI has been used for cutting)

Primers no 8829, 9639 and 9646 were used as mutagenic primers

8829: 5'p-ggc ggc aat aac cgg ccg aac att ccg gat atc cc (SEQ ID NO:1 38) 3' (Introducing Q249R)

9639: 5'p-at atc gtg aag ata tgc ggc att gat gcc acc 3' (SEQ ID NO:139) (Introducing E239C)

9646: 5'p-cg gcc ttg gct agc tgt att cgt cga gag gtc 3' (SEQ ID NO:140) (Modifying the propeptide from SPIRR (SEQ ID NO:29) to SCIRR(SEQ ID NO:30))

Production of Enzymes HLv16s and HLv16

The enzymes were produced in an analogous manner to that described in Example 7 using *A. oryzae* JAL 125 as a host cell. Subsequently, the one cycle wash performance of the enzymes were tested (using 5 g/l of inactivated Ariel Future as detergent and an enzymew dosage of 0.25 mg enzyme protein/l and 1.0 mg enzyme protein/l, respectively.

The following results were obtained:

|  | dR | (0.25 mg EP/l) | dR | (1.0 mg EP/l) |
|---|---|---|---|---|
| HLv16s |  | 3 |  | 7 |
| HLv16 | 1 |  | 2 |  |

It is seen that a significantly improved washing performance is obtained for HLv16s containing a cystein bridge between the peptide addition and the mature part of the enzyme.

Example 25

Production of a First Wash Lipase in *F. Graminarum*

Strains and Media

The starting strain is *Fusarium graminearum* A3/5 (ATCC 20334).

COVE plates are comprised of 343.3 g of sucrose, 20 ml of COVE salts solution, 10 ml of 1 M acetamide, 10 ml of 3 M CsCl, and 25 g of Noble agar per liter. The COVE salts (50×) solution is comprised of 26 g of KCl, 26 g of $MgSO_4$—$7H_2O$, 76 g of $KH_2PO_4$, and 50 ml of COVE trace metals solution. COVE trace metals solution is comprised of 0.04 g of $NaB_4O_7$—$10H_2O$, 0.040 g of $CuSO_4$—$5H_2O$, 0.70 g of $FeSO_4$—$H_2O$, 0.80 g of $Na_2MoO_2$—$2H_2O$, and 10 g of $ZnSO_4$ per liter.

M400Da medium is comprised of 50 g of maltodextrin, 2.0 g of $MgSO_4$—$7H_2O$, 2.0 g of $KH_2PO_4$, 4.0 g of citric acid, 8.0 g of yeast extract, 2.0 g of urea, and 0.5 ml of trace metals solution per liter. The medium is adjusted to pH 6.0 with 5 N NaOH. The trace metals solution is comprised of 14.3 g of $ZnSO_4$—$7H_2O$, 2.5 g of $CuSO_4$—$5H_2O$, 0.5 g of $NiCl_2$—$6H_2O$, 13.8 g of $FeSO_4$—$7H_2O$, 8.5 g of $MnSO_4$—$H_2O$, and 3.0 g of citric acid per liter.

Construction of the *H. lanuginosa* Lipolytic Enzyme Variant HL A (E1SPIRPRP (SEQ ID NO:31) +D57G+N94K+D96L+L97M+Q249R) Expression Plasmid for *Fusarium graminearum*

The construction an expression plasmid for *Fusarium graminearum* is outlined in FIG. 15. Specifically, a Fusarium expression cassette is made using the technique of overlapping PCR (Higuchi. R., In Innis, M. A. Gelfond, D. H., Snisky. J. J., and White. T. J., editors. PCR Protocols: *A Guide to Methods and Applications*, pages 177–183,. Academic Press, Inc., New York) to fuse the 1.24 kb *Fusarium oxysporum* trypsin promoter to the 1.1 kb *Fusarium oxysporum* trypsin terminator (Royer et al., 1995 Bio/Technology 13: 1479–1483). A polylinker region containing Swal, Kpnl and Pacl restriction sites is inserted between the promoter and terminator as part of the overlapping PCR reaction. At the 5' end of the promoter an Xhol site is added and the native EcoRI site is preserved. At the 3' end of the terminator, EcoRI, HindIII and Nsil sites are incorporated by the PCR reaction.

A PCR fragment containing −1208 to −1 of the Fusarium oxysporum trypsin promoter plus a 25 bp polylinker is generated from plasmid pJRoy20 (Royer et al., 1995, supra) using the following primers:

Xhol EcoRI 5' end of promoter Forward primer 1: 5'-gagctcgagGA TTC TTACAAACCTTCAC-3' (SEQ ID NO:98)

PacI KpnI SwaI 3' end of promoter
Reverse primer 2: 5'-ttaattaaggtacctgaatttaaatGGTGAAG AGATAGATATCCAAG-3' (SEQ ID NO:99)

Upper case letters are the native sequence of the *Fusarium oxysporum* trypsin promoter.

The PCR conditions used are 95° C. for 3 minutes followed by 25 cycles each at 95° C. for 30 seconds, 50° C. for 1 minute, and 72° C. for 1 minute. The final extension cycle is at 72° C. for minutes. Pwo DNA polymerase (Boehringer Mannheim, Indianapolis, Ind.) is used with the manufacturer's supplied buffer.

A PCR fragment containing −5 to −1 of the *Fusarium oxysporum* trypsin promoter, the 25 bp polylinker and 1060 bp of the 3' untranslated region of the *Fusarium oxysporum* trypsin gene (terminator region) is generated from plasmid pJRoy20 using the following primers:

promoter SwaI KpnI PacI 5' end of terminator
Forward primer 3: 5'-TCACCatttaaattcaggtaccttaattaaATT CCTTGTTGGAAGCGTCGA-3' (SEQ ID NO:100)

NsiI HindIII EcoRI 3' end of terminator
Reverse primer 4: 5'-tggtatgcataagcttgaattcAGGTAAAC AAGATATAATTT-3' (SEQ ID NO:101)

Upper case letters are the native sequence of the *Fusarium oxysporum* trypsin promoter and terminator. The PCR conditions used are as described above.

The final 2.3 kb overlapping PCR fragment which contains −1208 to −1 of the *Fusarium oxysporum* trypsin promoter, the 25 bp polylinker and 1060 bp of the *Fusarium oxysporum* trypsin terminator is made using 0.2 μl of the first PCR (promoter) reaction and 3 μl of the second (terminator) reaction as template and primers number 1 and 4. The PCR conditions used are 95° C. for 3 minutes followed by 30 cycles each at 95° C. for 30 seconds, 62° C. for 1 minute, and minutes. The final extension cycle is 5 minutes at 72° C. Pwo DNA polymerase is also used for this reaction.

The resulting 2.3 kb band is digested with Xhol and NsiI and cloned into plasmid pBaNe6 that is digested partially with NsiI and to completion with SaiI. In effect, the Aspergillus promoter and terminator sequences of pBaNe6 are replaced with the *Fusarium oxysporum* trypsin promoter and terminator sequences. The resulting construct (pDM174.3) is digested with SwaI and PacI.

DNA primers HLIP-A and HLIP-B shown below are used in a PCR reaction to amplify the HLA lipase gene from plasmid pJVi220:

HLIP-A (Primer 5): 5'-cccafttaaatATGAGGAGC TCCCTTGTGCTG-3' (SEQ ID NO:102)

HLIP-B (Primer 6): 5'-cccttaattaaCTAAAGACATG TCCCMTTAA-3' (SEQ ID NO:103)

Uppercase letters represent sequences in the lipase gene

The PCR is performed in a 50 μl reaction containing ca. 50 ng of pHLA, 0.05 mM each of dATP, dTTP, dGTP, dCTP, 100 pmol each of HLIP-A and HLIP-B. 1×Pwol Buffer (Boehringer Mannheim, Indianapolis, Ind.), and 2.5 units Pwol (Boehringer Mannheim, Indianapolis, Ind.). The PCR conditions are 95° C. for 3 minutes, 30 cycles each at 95° C. for 1 minute, 60° C. for 1 minute; and 72° C. for 1.5 minutes, and then 72° C. for 5 minutes. The PCR reaction mixture is run on a agarose gel and the ca. 0.9 kb HLA DNA band is excised. The DNA is purified by solubilization of the agarose with 3 volumes Qia-ex solubilization buffer (Qiagen, Los Angeles, Calif.) followed by a Qiaquick PCR spin column according to the manufacturer's directions (Qiagen, Los Angeles, Calif.). The DNA is recovered in 50 μl of 1 mM EDTA-10 mM Tris pH 8. A 20 μl aliquot of the DNA is cut in a final volume of 25 μl containing 1×restriction enzyme buffers and restriction enzymes PacI and SwaI as suggested by the manufacturers. The reaction mixture is then heated at 80° C. for 10 minutes. One μl of the PacI/SwaI cut HLA lipase gene is ligated into PacI/SwaI cut plasmid pBANe6. The ligation mixture is used to transform *E. coli* strain DH5α. The plasmid containing pBANe6 and the HLA sequences is designated pJeRS33.

The 0.9 kb SwaI/PacI HLA fragment from pJeRS33 is cloned into the SwaI/PacI digested pDM174.3 vector to create plasmid pDM177.

Transformation of *Fusarium graminearum*

*F. graminearum* strain A3/5 (ATCC 20334) is grown on 10×15 mm petri plates of Vogels medium (Vogel, 1964, Am. Nature 98: 435–446) plus 1.5% glucose and agar for 3 weeks at 25° C.

Conidia (approximately $10^8$ per plate) are dislodged in 10 ml of sterile water using a transfer loop and purified by filtration through 4 layers of cheesecloth and finally through one layer of Miracloth. Conidial suspensions are concentrated by centrifugation. Fifty ml of YPG medium comprised of 1% yeast extract, 2% bactopeptone, and 2% glucose are inoculated with approximately 100 conidia, and incubated for 14 hours at 24° C., 150 rpm. Resulting hyphae are trapped on a sterile 0.4 mm filter and washed successively with sterile distilled water and 1.0 M $MgSO_4$. The hyphae are 10 resuspended in 10 ml of NOVOZYM 234™ (Novo Nordisk A/S, Bagsvaerd, Denmark) solution (2–10 mg/ml in 1.0 M $MgSO_4$) and digested for 15–30 minutes at 34° C. with agitation at 80 rpm. Undigested hyphal material is removed from the resulting protoplast suspension by successive filtration through 4 layers of cheesecloth and through Miracloth. Twenty ml of 1 M sorbitol are passed through the cheesecloth and Miracloth and combined with the protoplast solution. After mixing, protoplasts (approximately $5 \times 10^8$) are pelleted by centrifugation and washed successively by resuspension and centrifugation in 20 ml of 1 M sorbitol and in 20 ml of STC (0.8 M sorbitol, 0.05 M Tris pH 8.0, 0.05 M $CaCl_2$). The washed protoplasts are resuspended in 4 parts STC and 1 part SPTC (0.8 M sorbitol, 40% PEG 4000, 0.05 M Tris pH 8.0, 0.05 M $CaCl_2$) at a concentration of $1-2 \times 10^8$/ml. One hundred μl of protoplast suspension are added to 3 μg pDM177 DNA and 5 μl heparin (5 mg/ml in STC) in polypropylene tubes (17×100 mm) and incubated on ice for 30 minutes. One ml of SPTC is mixed gently into the protoplast suspension and incubation is continued at room temperature for 20 minutes. Fifteen ml of molten solution (cooled to 40° C.) consisting of COVE salts, 0.8 M sucrose and 1% low melting agarose (Sigma Chemical Company, St. Louis, Mo.) are mixed with the protoplasts and then plated onto a 150 mm petri plate containing COVE agar. Incubation is continued at room temperature for 10 to 14 days.

Expression of Lipase Activity

Five pDM177 transformants of *Fusarium graminearum* A3/5 are cultured on M400Da medium in shake flasks for 7 days at 30° C. As a control culture, an A3/5 transformant of plasmid 30 pDM 155 (Royer et al., 1995 Bio/Technology 13:1479–1483), which contains the wild-type *Humicola lanuginosa* lipase inserted between the *Fusarium oxysporum* trypsin promoter and terminator, is grown at the same time under the same conditions.

First Wash Activity of HL A

The above produced lipase as well as the analogous lipase (carrying the same mutations, but produced in *A. oryzae*) was tested in the "Assay for test of First Wash effect" described herein using enzyme inactivated Ariel Futur. The following results were obtained:

E1SPIRPRP (SEQ ID NO:31)+D57G+N94K+D96L+L97M+Q249R in dR at

|  | 1250 LU/l | 12500 LU/l |
|---|---|---|
| A. oryzae | 8 | 15 |
| F. graminearum | 9 | 14 |

Example 26

Construction of *Absidia reflexa* Mutants

Material and Methods

Strains and plasmids are listed in the Materials and Methods section.

Primers: primer TiK57, primer TiK58, primer TiK59, Primer TiK60, Primer TiK61, primer TiK62, primer TiK64, primer Tik66, primer TiK72, primer TiK74, primer Tik75, primers TiK76, Kits, Solutions, Media and the Like:

Taq-DNA polymerase (Promega)

LB medium supplemented with 100 pg/ml ampicillin

DNA Maxi-Prep kit (QIAGEN).

Polyethyleneglycol/LiOAc yeast transformation kit (Yeastmaker, Clontech).

Yeast nitrogen base w/o amino acids (Difco 0919-15-3)

Casamino acids (Difco 0230-01-1)

Bacto-agar (Difco)

YPG-medium (20 g casein-peptone and 10 g yeast extract (Difco))

LB medium supplemented with 100 pg/ml ampicillin

Equipment

Applied Biosystems 373 DNA Sequencer

Cellulose acetate filters (Schleicher-Schüll)

SYC-plates 13.6 g NaOH and 22.6 g succinic acid are completely dissolved in 500 ml $H_2O$, 15 g yeast nitrogen base w/o amino acids (Difco 0919-15-3),10 g casamino acids (Difco 0230-01-1). 20 ml of 2% threonine solution, and 20 ml of a 1% tryptophan solution are added. The solution is filled up to 1 liter $H_2O$, sterile-filtered, and stored at 4° C. For liquid media preparation 1 liter of SYC is diluted by adding 200 ml of a 20% glucose solution and 800 ml of $H_2O$. For preparation of agar plates 1 liter of SYC is diluted at 60° C. with 800 ml of bacto-agar (37.5 g bacto-agar (Difco) dissolved in 1 liter $H_2O$) and 200 ml of a 20% glucose solution.

Brilliant Green Assay

For preparation of BG-agar plates 10 g of agarose are dissolved by heating in 500 ml of a 100 mM Tris-Cl buffer pH 9.0. This agarose solution is mixed at 60° C. with 24 ml of an olive oil emulsion (8 ml olive oil (Sigma) and 16 ml of a 2% polyvinylalcohol (Sigma) solution in $H_2O$ are mixed and thoroughly homogenized on ice with an Ultra-Turrax T25), 10 ml of a Brilliant Green stock (4 mg/ml $H_2O$), 465 ml of 100 mM Tris-Cl buffer pH 9.0 containing 6.45 g of the detergent, and 1.4 ml of a 250 mM $CaCl_2$ solution.

Transformed yeast colonies are grown for 3 days at 30° C. on sterile cellulose acetate filters (Schleicher-Schüll) on SYC-agar plates. The filters are then transferred to the BG-agar plates and incubated for 2–8 hours at 37° C. Colonies which generate a green spot in the agar are judged positive.

Restriction Enzyme Analysis and Sequencing of Mutant Libraries

The recovered plasmid DNA was subjected to Ncol-digestion. Correct clones yielded two fragments of 2.9 and 3.1 kb. The plasmid DNA was subsequently either dye-terminator PCR cycle sequenced or sequenced on an Applied Biosystems 373 DNA Sequencer. In the case of clones isolated from libraries 3 and 4 (Table E26-1) the oligonucleotides TiK61 and TiK66 were used for double-strand sequencing whereas for libraries 7 and 8 TiK62 and TiK72 were applied.

Example 26A

Construction of *Absidia reflexa* ATTC 44896 Lipase Expression Vectors

Two vectors were constructed for expression of the wild-type *Absidia reflexa* ATTC 44896 lipase (with/without SPIRR (SEQ ID NO:29) peptide extension) in *Saccharomyces cerevisiae*.

The cDNA clone encoding the mature *Absidia reflexa* ATTC 44896 lipase (SEQ ID No. 13 and FIG. 16) was PCR amplified ($T_a$=50° C., 25 cycles, 5 units Taq-DNA polymerase) using either the primer pair TiK57/59 (providing a N-terminal SPIRR (SEQ ID NO:29)extension) or the primer pair TiK58/59 (without SPIRR extension(SEQ ID NO:29)). The PCR fragments were ligated via Nhel/Xbal-sites into the yeast expression vector pJSO37 (with a Nhel site introduced downstream of the signal peptide) which harbours region encoding an active *H. lanuginosa* lipase in the original BamHI/Xbal cloning site.

The gene encoding the active *H. lanuginosa* lipase was slightly modified by the introduction of a Nhel-site downstream of the BamHI site (see FIG. 12). Since Nhel- and Xbal-sites are compatible, the vector was treated with alkaline phosphatase prior to ligation. Finally, two vector constructs were obtained, namely pTiK04 which includes the SPIRR (SEQ ID NO:29) extension just upstream of the start of the mature lipase gene, and pTiK05 which did not contain a SPIRR (SEQ ID NO:29) extension encoding part. In both cases the original signal sequence from the *Humicola lanuginosa* lipase was kept constant between the BamHI and Nhel sites.

MFα1 Signal Sequence Constructs

The *H. lanuginosa* lipase signal sequence was replaced by the mating factor α1 signal.

Genomic DNA of the yeast strain YPH499 (Stratagene) was prepared cording to standard protocols (Ausubel et al., (1995). Current Protocols in Molecular Biology, John Wiley and Sons). One μg of genomic DNA was subjected to PCR ($T_a$=50° C., 25 cycles, 5 units Taq-DNA polymerase) with the primer pair TiK74/75. The amplified MFα1 signal sequence fragment (FIG. 18) was inserted into pTiK04 and pTiK05 via the BamHI and Nhel sites to yield pTiK06 and pTiK07, respectively.

Example 26B

Construction of *Absidia reflexa* ATTC 44896 Lipase Variants by Mutagenesis With Doped Oligonucleotides Four libraries were constructed with doped oligonucleotides.

In libraries A and B (see Table E26-1 below)) random mutations were introduced in the putative lid region of *Absidia reflexa* ATTC 44896 lipase. In library A the SPIRR (SEQ ID NO:29)sequence was kept constant, in library B it was omitted.

Libraries C and D were constructed with mutations in two putative lipid contact zones in the N-terminus of *Absidia reflexa* ATTC 44896. In library C the SPIRR (SEQ ID NO:29) sequence was again kept constant.

The mutagenesis of the putative lid region of *Absidia reflexa* ATTC 44896 lipase gene (amino acid positions 82–99) was performed by standard PCR (Sambrook et al., (1989), Molecular cloning—A laboratory manual, Cold Spring Harbor Laboratory Press, Cold Spring Harbor. N.Y.) with 5 units Taq-DNA polymerase with the primer pair TiK60/TiK64 at $T_a=50°$ C. and 25 cycles using pTiK05 as template. In a second standard PCR, using primer TiK62 and the agarose gel-purified DNA fragment generated in the first PCR, the whole *Absidia reflexa* ATTC 44896 lipase gene was restored using the same amplification conditions as for the first PCR. In contrast to the first PCR, pTiK04 or pTiK05 were chosen as templates so that libraries (with/without SPIRR (SEQ ID NO:29)N-terminal extension) were obtained.

For mutagenesis of the amino acid positions 30–45 the primers TiK76 and TiK64 were used for the first PCR. The second PCR was in principle identical to the above described one.

The obtained PCR fragments were ligated into pJSO37 via the BamHI/XbaI-sites. The transformation of *E. coli* and subsequently of competent YNG318 yeast cells was performed as described above.

Example 26C

Screening of the *Absidia reflexa* ATTC 44896 Lipase Mutant Libraries and Recovery of Plasmids From Positive Colonies Transformed yeast cells obtained as described in Example 26B were spread on a cellulose acetate filter on a 14 cm SYC-agar plate. After selective growth of transformants and transfer of the filter to BG-agar plates, positive colonies were picked, resuspended in $H_2O$, and re-spread on cellulose acetate filters on SYC-agar plates to allow a second confirmatory round of the BG-assay (see Matarials and Methods section).

Positive clones from the second round were transferred to 20 ml SYC-medium and shaken for 2 days at 30° C. Plasmid DNA was prepared from 1.5 ml of this saturated yeast culture according to the standard phenol/glassbead method (Ausubel et al., (1995), Current Protocols in Molecular Biology, John Wiley and Sons).

An aliquot of the plasmid preparation was electroporated into *E.coli* DH 10B cells which were then plated on LB-agar plates supplemented with 100 μg/ml ampicillin. The DNA of the colonies was isolated and applied to restriction enzyme analysis and sequencing as described in the Material and Methods section above.

Sequencing

Sequencing of 15 randomly picked clones in library A and B showed that the chosen doping of 10% finally resulted in:

20% being wild type,
13% with 1 amino acid exchange,
20% with 2 exchanges,
13% with 3,
20% with 4,
0% with 5, and
13% with 6 amino acid exchanges per molecule.

From library A six clones out of $1.8 \times 10^5$ screened colonies at 3 g/l detergent were isolated in the BG-assay (1 per each $3 \times 10^4$ screened), and from library B two positive clones were isolated out of $2.0 \times 10^5$ screened colonies (1 per each $1.0 \times 10^5$ screened, Table E26-1). The noticed sequence differences of these 8 clones are depicted in Table E26-2 below.

TABLE E26-1

Summary of the constructed and screened Absidia reflexa ATTC 44896 mutant libraries.

| No | Comments and mutagenized regions | Library size in E. coli | Screened S. cerevisiae colonies | Positives in the BG-assay at X g/l detergent | Positives in the BG-assay at X g/l. 2.round | Restriction enzyme analysis |
|---|---|---|---|---|---|---|
| A | Lid (pos. 82–99) (.SPIRR) (SEQ ID NO: 29) | $8 \times 10^6$ | 180000 | 21 at 3 g/l | 9 at 3 g/l | 6 |
| B | Lid (pos. 82–99) | $7 \times 10^6$ | 200000 | 1 at 6 g/l  5 at 3 g/l | 0 at 6 g/l  2 at 3 g/l | —  2 |
| C | Pos. 30–45 (.SPIRR) (SEQ ID NO: 29) | $1 \times 10^6$ | 160000 | 38 at 3 g/l | 4 at 3 g/l | 3 |
| D | Pos. 30–45 | $6 \times 10^5$ | 170000 | 27 at 3 g/l | 2 at 3 g/l | 1 |

As mentioned above libraries C and D were constructed with mutations in two putative lipid contact zones in the N-terminus of *Absidia reflexa* ATTC 44896 lipase.

Sequencing of 13 randomly picked clones showed that the chosen doping level of 10% resulted in:

8% being wild type,
15% with 1 amino acid exchange,
46% with 2 exchanges,
15% with 3, and
15% with 4 exchanges per molecule.

Library C yielded 3 clones out of $1.6 \times 10^5$ screened colonies at 3 g/l of detergent in the BG assay (1 positive per each 53333 screened), and from library D one positive clone could be isolated out of $1.7 \times 10^5$ (Table E26-1). The sequences of these 4 clones are also depicted in Table E26-2.

Table E26-2 Sequences of the improved Absidia reflexa ATTC 44896 variants.

LU/ml are significant enzyme activities as confirmed by repeated measurements.

Table E26-3 Summary of the obtained lipase unit secreted to the medium or measured from the cytosol fraction of ATTC 44896 variants from library A.

The standard deviation is 10%.

| Sample | Lipase units in the supernatant (LU/ml) | Lipase units in the cytosol (LU/ml) |
|---|---|---|
| YNG318 (negative control) | 0.0 | 0.0 |
| 303 | 0.0 | 1.0 |
| 309 | 0.0 | 0.5 |
| 312 | 1.7 | 0.6 |
| 321 | 0.6 | 1.0 |

Target sequence:

```
                     82                99
Library Clone number T  S  S  I  R  N  A  I        A        D  I
                     V     F  V  P  V  N  Y
A      303           W  T
       309           H  T
       312           S                    S
       315           V        T  W  L  -N L           ..H133R
       318           C  W  K  L  S  I..V102F
       321           S  E
B      401           S  S           A
       402           ..Y136H.K137H
                     30             45
                     R  T  V  I  P  G  G  R  W  S     C     P  H
                     C     G  V
C      701           W  N
       702           W  N
       703           C
                     ...Q4R
D      801
                                                         ...V95E
```

Example 26D

Expression of *Absidia reflexa* ATTC 44896 Variants and Lipase Unit Measurement

Four of the improved mutants identified from library A were subjected to measurement of LU secreted to the culture medium as well as LU measurement of the crude cytosol/membrane fraction.

10 ml of YPG-medium were dissolved in 900 ml $H_2O$, autoclaved and 100 ml of a 20% glucose solution added) were inoculated with 1 ml of a saturated yeast culture in SYC-medium. The culture was shaken at 30° C. for 2 days. The cells were harvested by centrifugation (5 minutes×4000 g) and the supernatant stored on ice for LU measurement. The cell pellet was treated with Novozym™ 234 for spheroplast preparation and lysed using the glass bead procedure (Ausubel et al., (1995). Current Protocols in Molecular Biology, John Wiley and Sons). The obtained crude cytosol fraction which also included the membrane fraction was immediately applied to LU measurement (see Materials and Methods section) in order to minimize proteolytic degradation.

The result is shown in Table E26-3. The four clones showed weak but significant LU in the cytosol/membrane fraction. Moreover, from two out of these four clones weak LU signals could be recorded. All data differing from 0.0

Example 27

Substrate Affinity of Lipolytic Enzymes

A procedure has been developed for a simple comparison of the ability of lipolytic enzymes to accumulate on/in a substrate phase (olive oil, incl. FFA) at alkaline pH (pH 9.0) and presence of the non-ionic surfactant Dobanol 25-7 (100 ppm) (i.e. a measure for substrate affinity).

Procedure:
1. Two identical buffer solutions (5 ml) are prepared in 20 ml sealable vials, ("Sample" (s) and "Reference" (r)).
2. Enzyme is added into "Sample" and "Reference" and the lipase concentration is determined (X LU/ml).
3. Olive oil is added onto the "Sample" and both lipase solutions are shaken vigorously. Incubation at 4° C. over night.
4. Remaining lipase concentration in the aqueous phases is determined after incubation, (Yi LU/ml; i=r,s).

Summary of Incubation Conditions:
Buffer: 100 mM Glycine (5 ml).
pH: 9.0.
Substrate: Olive oil (5 ml).
Dobanol 25-7: 100 ppm.
T: 4° C.
Lipase: 5–10 LU/ml.
Incubation: Over night (24–26 hours).

Evaluation of Data:

The result after an experiment is calculated by comparing the activity-loss upon incubation in the aqueous phase in contact with olive oil to the activity-loss in the aqueous phase in absence of olive oil:

α=Ys/Yr (see above)

Results:

TABLE 11

| Lipase | α (%) |
| --- | --- |
| Lipolase ™ | 95% |
| D57G + N94K + D96L + L97M + Q249R | 65% |
| SPIRPR (SEQ ID NO: 20) + E1P + D57G + N94K + D96L + L97M + Q249R | 45% |
| SALRPRK (SEQ ID NO: 87) + D57G + N94K + D96L + L97M + Q249R | 25% |
| SPIRPR (SEQ ID NO: 20) + E1P + D137G + D167G + E210V + W221L | 50% |

Comparing results presented above to wash data disclosed in examples 11–15, clearly indicate that Lipolase variants with increased first wash performance generally have increased substrate affinity as compared to Lipolase.

Example 28

Localized Random Mutagenesis of the Pseudomonas sp. Lipase (Liposam)

A suitable doping scheme to use for introducing mutations contemplated to lead to a first wash activity of the above lipase may comprise localized random mutagenesis in the whole or parts of one or more of the following regions. 93% wt/7% random means that the respective codons are synthesized with 93% wt nucleotides and 7% of the other 3 nucleotides in the oligonucleotide used for constructing the random mutagenized library. Similarly for 90% wt/10% random.

In the amino acid region 17–37:
Amino acid position 17–18+20–24+26–29+32–37: 93% wt/7% random M19: doped to give preferentially L,I,F In the amino acid region 109–161:
Amino acid position 109–118: 93% wt/7% random
Amino acid position 120+123–137+139–161: 90% wt/10% random In the amino acid region 208–239:
Amino acid position 208–212+214–215+217–231+233–239: 90% wt/10% random In the amino acid region 253–271:
Amino acid position 253+255+259–268+270–271: 90% wt/10% random
V258: 90% wt/10% random but doped not to be a positive charged amino acid.

The localized random mutagenesis may be performed as described in the Materials and Methods section and in Example 5 herein, and the resulting mutants screened for a reduced dependence to calcium and/or an increased tolerance towards a detergent or detergent component and afterwards first wash activity. Subsequently, and if necessary, localized random mutagenesis of the resulting mutants may be repeated and/or the genes may be subjected to gene shuffling as disclosed herein.

What is claimed is:

1. An isolated modified lipase from Humicola or an enzymatically active mutant thereof having improved wash performance compared to an unmodified lipase, comprising an addition of amino acid residues at its N-tarminus and/or its C-terminus selected from the following amino acid residue additions:

A. Arg-Pro-Val-Ser-Gln-Asp (SEQ ID NO:17), or
B. Ser-Pro-Ile-Arg-Met (SEQ ID NO:18), or
C. Ser-Pro-Ile-Arg-Ala-Arg (SEQ ID NO:19), or
D. Ser-Pro-Ile-Arg-Pro-Arg (SEQ ID NO:20), or
E. Ser-Pro-Ile-Arg-Glu-Arg (SEQ ID NO:21), or
F. Ser-Pro-Ile-Arg-Lys (SEQ ID NO:22), or
G. Ser-Pro-Ile-Lys-Lys (SEQ ID NO:23), or
H. Ser-Pro-Ile-Arg-Arg-Pro (SEQ ID NO:24), or
I. Ser-Pro-Pro-Arg-Arg (SEQ ID NO:25), or
J. Ser-Pro-Iso-Pro-Arg (SEQ ID NO:26), or
K. Ser-Pro-Arg-Pro-Arg (SEQ ID NO:27), or
L. Ser-Pro-Ile-Arg (SPIR)(SEQ ID NO:28), or
M. Ser-Pro-Ile-Arg-Arg (SEQ ID NO:29), or
N. Ser-Cys-Ile-Arg-Arg (SEQ ID NO:30), or
O. Ser-Pro-Ile-Arg-Pro-Arg-Pro (SEQ ID NO:31), or
P. Ser-Cys-Ile-Arg-Pro-Arg-Pro (SEQ ID NO:32), or
Q. Ser-Pro-Arg-Arg-Pro-Arg-Thr (SEQ ID NO:33), or
R. Ser-Pro-Phe-Arg-Pro-Lys-Leu (SEQ ID NO:34), or
S. Ser-Pro-Pro-Arg-Arg-Pro (SEQ ID NO:35), or
T. Ser-Pro-Ile-Arg-Arg-Glu (SEQ ID NO:36), or
U. Ser-Pro-Pro-Arg-Pro-Pro (SEQ ID NO:37), or
V. Ser-Pro-Pro-Arg-Pro-Arg (SEQ ID NO:38), or
W. Ser-Pro-Pro-Trp-Trp-Pro (SEQ ID NO:39), or
X. Ser-Pro-Pro-Trp-Arg-Pro (SEQ ID NO:40), or
Y. Ser-Pro-Pro-Arg-Trp-Pro (SEQ ID NO:41), or
Z. Ser-His-Trp-Arg-Arg-Trp (SEQ ID NO:43), or
AA. Ser-His-Trp-Arg-Lys (SEQ ID NO:44), or
BB. Ser-His-Trp-Arg-Arg (SEQ ID NO:45), or
CC. Thr-Ala-Ile-Arg-Pro-Arg-Lys (SEQ ID NO:46), or
DD. Ser-Thr-Arg-Arg-Pro-Arg-Pro (SEQ ID NO:47), or
EE. Gly-Pro-Ile-Arg-Pro-Arg-Pro (SEQ ID NO:48), or
FF. Leu-Pro-Phe-Arg-Glu-Arg-Pro (SEQ ID NO:49), or
GG. Ser-Arg-Ser-Arg-His-Asp-Ala (SEQ ID NO:50), or
HH. Ile-Pro-Ile-Arg-Pro-Arg-Arg (SEQ ID NO:51), or
II. Ser-Thr-Arg-Arg-Pro-Arg-Pro) (SEQ ID NO:52), or
JJ. Thr-Ala-Ile-Arg-Pro-Arg-Lys (SEQ ID NO:53), or
KK Trp-Arg-Trp-Arg-Trp-Arg (SEQ ID NO:54), or
LL. Glu-Pro-Ile-Arg-Arg (SEQ ID NO:55), or
MM. Ser-His-Trp-Glu-Glu (SEQ ID NO:56), or
NN. Arg-Pro-Arg-Pro-Arg-Pro-Arg-Pro (SEQ ID NO:57), or
OO. Ser-Ser-Thr-Arg-Arg-Ala-Ser-Pro-Ile-Lys-Lys (SEQ ID NO:58), or
PP. Ala-Trp-Trp-Pro-Ser-Pro-Ile-Arg-Pro-Arg-Pro (SEQ ID NO:59), or
QQ. Ala-Pro-Pro-Pro-Arg-Pro-Arg-Pro-Arg-Pro-Arg-Pro (SEQ ID NO:60), or
RR. Ala-Pro-Pro-Pro-Arg-Thr-Arg-Pro-Arg-Pro-Arg-Ser (SEQ ID NO:61), or
SS. Ser-Pro-Lys-Arg-Lys-Pro-Arg-Pro (SEQ ID NO:62), or
TT. Ser-Gln-Arg-Ile-Lys-Gln-Arg-Ile-Lys (SEQ ID NO:63), or
UU. Ser-Pro-Pro-Pro-Arg-Pro-Arg-Pro (SEQ ID NO:64), or
VV. Ser-Pro-Ile-Arg-Pro-Arg-Pro-Arg (SEQ ID NO:65), or

WW. Ser-Pro-Ile-Arg-Lys-Ala-Trp-Trp-Pro (SEQ ID NO:66), or

XX. Ala-Pro-Pro-Pro-Lys-Ala-Ser-Pro-Arg-Gln-Arg-Pro (SEQ ID NO: 67), or

YY. Ser-Pro-Ile-Agr-Pro-Arg-Pro-Ser-Pro-Ile-Arg-Pro-Arg-Pro-Arg (SEQ ID NO:68), or

ZZ. Ser-Pro-Pro-Arg-Trp-Pro-Arg-Arg (SEQ ID NO:69), or

AAA. Ser-Pro-Pro-Arg-Trp-Pro-Arg-Trp (SEQ ID NO:70), or

BBB. Ser-Pro-Pro-Arg-Trp-Pro-Trp-Arg (SEQ ID NO:71), or

CCC. Ser-Pro-Pro-Trp-Arg-Pro-Arg-Arg (SEQ ID NO:72), or

DDD. Ser-Pro-Pro-Trp-Trp-Pro-Arg-Trp (SEQ ID NO:73), or

EEE. Ser-Pro-Pro-Trp-Trp-Pro-Trp-Arg (SEQ ID NO:74), or

FFF. Ser-Pro-Pro-Trp-Trp-Pro-Trp-Trp (SEQ ID NO:75), or

GGG. Ser-Pro-Pro-Trp-Pro-Arg-Pro-Arg-Pro (SEQ ID NO:76).

2. The isolated modified lipase of claim 1, wherein said lipase further comprises an amino acid mutation selected from one of the following groups of amino acid mutations, wherein each number corresponds to a position in the amino acid sequence shown in SEQ ID NO:16:

a. E56R+D57L+I90F+D96L+E99K;
b. E56R+D57L+V60M+D62N+S83T+D96P+D102E;
c. D57G+N94K+D96L+L97M;
d. E87K+G91A+D96R+I100V+E129K+K237M+I252L+P256T+G263A+L264Q;
e. E56R+D57G+S58F+D62C+T64R+E87G+G91A+F95L+D96P+K98I+K237M;
f. E210K;
g. S83T+N94K+D96N;
h. E87K+D96V;
i. N94K+D96A;
j. E87K+G91A+D96A;
k. D167G+E210V;
l. S83T+G91A+Q249R;
m. E87K+G91A;
n. S83T+E87K+G91A+N94K+D96N+D111N;
o. N73D+E87K+G91A+N94I+D96G;
p. L67P+I76V+S83T+E87N+I90N+G91A+D96A+K98R;
q. S83T+E87K+G91A+N92H+N94K+D96M;
r. S85P+E87K+G91A+D96L+L97V;
s. E87K+I90N+G91A+N94S+D96N+I100T; or
t. I34V+S54P+F80L+S85T+D96G+R108W+G109V+D111G+S116P+L124S+V132M+V140Q+V141A+F142S+H145R+N162T+I166V+F181P+F183S+R205G+A243T+D254G+F162L.

3. The isolated modified lipase of claim 1, wherein said lipase further comprises an amino acid mutation selected from one of the following groups of amino acid mutations, wherein each number corresponds to a position in the amino acid sequence shown in SEQ ID NO:16:

A. D57G+N94K+D96L+Q249R;
B. D57G+N94K+D96L+S116P+Q249R;
C. D57G+G59V+N94K+D96L+Q249R;
D. D57G+N94K+D96L+S116P+S170P+Q249R;
E. D57G+G59V+N94K+D96L+S170P+Q249R:
F. D57G+N94K+D96L+S170P+Q249R;
G. D167G+E210V+Q249R;
H. E56K+D167G+E210V;
I. D137G+D167G+E210V+Q249R;
J. D167G+E210V+W221L+Q249R:
K. D57G+N94K+F95L+D96H,L+Q249R;
L. D57G+N94K+D96L+E210K;
M. D57G+G59V+N94K+D96L+S116P+S170P+Q249R;
N. S3R+D137G+D167G+E210V+W221L;
O. D137G+D167G+E210V+W221L+N233R;
P. S3R+I90F+D96L+E99K+V187A+Q249R;
Q. I90F+D96L+E99K+V187A+D233R;
R. I90F+D96L+E99K+V187A+D234Y;
S. I90F+D96L+E99K+V187A+T231R;
T. I90F+D96L+E99K+V187A;
U. D62R+I90F+D96L+E99K+V187A;
V. I90F+D96L+E99K+V187A+N200R+R209A;
W. I90F+D96L+E99K+V187A+T199R+N200R+R209A;
X. D57G+D62R+N94K+D96L+Q249R;
Y. D57G+N94K+D96L+N200R+R209A+Q249R;
Z. D67G+N94K+D96L+T199R+N200R+Q249R;
AA. I90F+D96L+E99K+V187A+T199R;
BB. D57G+N94K+D96L+T199R+R209A+Q249R;
CC. I90F+D96L+E99K+V187A+Q249R;
DD. I90F+D96L+E99K+V187A+P253R;
EE. I90F+D96L+E99K+D137G+D167G+V187A+Q249R;
FF. I90F+D96L+E99K+D137G+V187A+Q249R;
GG. D96L+E99K+V187A+249R;
HH. V2P+N94K+D96L+Q249R;
II. V2W+S3R+N94K+D96L+Q249R;
JJ. V2R+S3R+N94K+D96L+Q249R;
KK. V2R+S3W+N94K+D96L+Q249R;
LL. V2W+S3R+N94K+D96L+Q249R;
MM. N94K+D96L+Q249R;
NN. V2G+S3T+D57G+N94K+D96L+L97M+Q249R;
OO. V2G+S3T+Q4P+D5E+D57G+N94K+D96L+L97M+Q249R;
PP. V2G+D5Q+L6M +D57G+N94K+D96L+L97M+Q249R;
QQ. D57G+G59V+N94K+D96L+L97M+S116P+S170P+Q249R;
RR. A49P+D167G+E210V;
SS. E56K+D57G+D62R+S83T+S85F+D96L+D102Y+E210K;
TT. D57G+N94K+D96L+L97M+Q249R;
UU. D137G+D167G+E210V+W221L;
VV. N94K+F95L+D96H+N101S+F181L+D234Y+I252L+P256T+G263A+L264Q;
WW. 90F+D96L+E99K+V187A;
XX. N94K+D96A+Q249R;
YY. A19P+D167G+E210V+W221L;
ZZ. N94K+D96L+L97M+Q249R;
AAA. D57G+N94K+D96L+Q249R;
BBB. I90F+D96L+E99K+D137G+V187A;

CCC. N94K+D96L+E99K+Q249R;
DDD. N94K+D96L+E99K+T231R+N233R+D234R+Q249R;
EEE. N94K+D96L+E99K+D111N+F211A+G225P+Q249R+T267R;
FFF. N94K+D96L+E99K+D111N+F211A+G225P+T231R+N233R+D234R+Q249R+T267R;
GGG. E1K+N94K+D96L+E99K+Q249R;
HHH. N94K+D96L+K223R+Q249R;
III. N14K+D96L+E99K+N233R;
JJJ. N94K+D96L+E99K+T231R+N233R+Q249R;
KKK. N94K+D96L+E99K+N233R+Q249R; or
LLL. N94K+D96L+E99K+D234R+Q249R.

4. An isolated modified lipase which is derived from Humicola or an enzymatically active mutant thereof and has improved wash performance compared to an unmodified lipase, comprising an addition of amino acid residues at its N-terminus and/or its C-terminus and at least one mutation, selected from the following groups of amino acid residue additions and mutations, wherein each number corresponds to a position in the amino acid sequence shown in SEQ ID NO:16:

a. SPIRPRP (SEQ ID NO:31)+D57G+N94K+D96L+Q249R;
b. SPPRRP (SEQ ID NO:35)+I90F+D96L+E99K+D137G+V187A;
c. SPIRPRP (SEQ ID NO:31)+N94K+D96L+L97M+Q249R;
d. SPPPRPRP (SEQ ID NO:64)+N94K+D96L+L97M+Q249R;
e. SPIRPRP (SEQ ID NO:31)+D57G+N94K+D96L+L97M+Q249R;
f. SPPRRP (SEQ ID NO:35)+I90F+D96L+E99K+V187A;
g. SPIRPRP (SEQ ID NO:31)+D137G+D167G+E21V+W221L;
h. E1SPIRPRP (SEQ ID NO:31)+I90F+D96L+E99K+V187A;
i. E1SRKRKRK (SEQ ID NO:146)+I90F+D96L+E99K+V187A;
j. E1SPRIKPRIK (SEQ ID NO:147)+I90F+D96L+E99K+V187A;
k. E1SPPRRP (SEQ ID NO:35)+D62R+I90F+D96L+E99K+V187A;
l. E1SPPRRP (SEQ ID NO:35)+I90F+D96L+E99K+V187A+N200R+R209A;
m. E1SPPRRP (SEQ ID NO:35)+I90F+D96L+E99K+V187A+T199R+N200R+R209A;
n. E1SPIRPRP (SEQ ID NO:31)+D57G+D62R+N94K+D96L+Q249R;
o. E1SPIRPRP (SEQ ID NO:31)+D57G+N94K+D96L+N200R+R209A+Q249R;
p. E1SPIRPRP (SEQ ID NO:31)+D57G+N94K+D96L+T199R+N200R+Q249R;
q. E1SPPRRP (SEQ ID NO:35)+I90F+D96L+E99K+V187A+T199R;
r. E1SPIRPRP (SEQ ID NO:31)+D57G+N94K+D96L+T199R+R209A+Q249R;
s. E1 SPIRPRP (SEQ ID NO:31)+I90F+D96L+E99K+V187A+Q249R;
t. E1SPPRRP (SEQ ID NO:35)+I90F+D96L+E99K+V187A+P253R;
u. E1SPPRRP (SEQ ID NO:35)+I90F+D96L+E99K+D137G+D167G+V187A+Q249R;
v. E1SPPRRP (SEQ ID NO:35)+I90F+D96L+E99K+DI37G+VI 87A+Q249R;
w. E1SPPRRP (SEQ ID NO:35)+D96L+E99K+V187A+Q249R;
x. E1SPPRPR (SEQ ID NO:38)+V2P+N94K+D96L+Q249R;
y. E1SPPWWP (SEQ ID NO:39)+V2W+S3R+N94K+D96L+Q249R;
z. E1SPPWRP (SEQ ID NO:40)+V2R+S3R+N94K+D96L+Q249R;
aa. E1SPPRWP (SEQ ID NO:41)+V2R+S3R+N94K+D96L+Q249R;
bb. E1SPPWWP (SEQ ID NO:39)+V2R+S3W+N94K+D96L+Q249R;
cc. E1SPPRWP (SEQ ID NO:41)+V2W+S3R+N94K+D96L+Q249R;
dd. E1SPPRWP (SEQ ID NO:41)+V2R+S3W+N94K+D96L+Q249R;
ee. E1SPPRWP (SEQ ID NO:41)+N94K+D96L+Q249R;
ff. E1SPPRRP (SEQ ID NO:35)+N94K+D96L+Q249R;
gg. E1APPPRPRPRPRP (SEQ ID NO:60)+V2G+S3T+D57G+N94K+D96L+97M+Q249R;
hh. E1APPPRTRPRPRS (SEQ ID NO:61)+V2G+S3T+Q4P+D5E+D57G+N94K+D96L+L97M+Q249R;
ii. E1APPPKASPRQRP (SEQ ID NO:67)+V2G+D5Q+L6M+D57G+N94K+D96L+L97M+Q249R;
jj. SCI RR (SEQ ID, NO:30)+N94K+D96L+E239C+Q249R;
kk. E1SPPRRP (SEQ ID NO:35)+D57G+N94K+D96L+Y53C+Kl 27C+Q249R;
ll. E1SPPRRPR (SEQ ID NO: 148)+V2R+S3P+N94K+D96L+Q249R;
mm. E1SPPWPRP (SEQ ID NO:76)+V2R+S3P+N94K+D96L+Q249R;
nn. EISPPRRP (SEQ ID NO:35)+N94K+D96L+E99K;
oo. EISPPRRP (SEQ ID NO:35)+N94K+D96L+E99K+Q249R;
pp. E1SPPCGRRP (SEQ ID NO:149)+N94K+D96L+E239C+Q249R;
qq. E1SPCRPRP (SEQ ID NO: 150)+N94K+D96L+E239C+Q249R;
rr. SPPCRRRP (SEQ ID NO:151)+N94K+D96L+E239C+Q249R; or
ss. E1SPPRRP (SEQ ID NO:35)+D57G+N94K+D96L+Q249R.

5. The isolated modified lipase of claim 1, wherein said addition at its N-terminus and/or its C-terminus comprises Arg-Pro-Val-Ser-Gln-Asp (SEQ ID NO:17).

6. The isolated modified lipase of claim 1, wherein said addition at its N-terminus and/or its C-terminus comprises Ser-Pro-Ile-Arg-Met (SEQ ID NO:18).

7. The isolated modified lipase of claim 1, wherein said addition at its N-teminus and/or its C-terminus comprises Ser-Pro-Ile-Arg-Ala-Arg (SEQ ID NO:19).

8. The isolated modified lipase of claim 1, wherein said addition at its N-terminus and/or its C-terminus comprises Ser-Pro-Ile-Arg-Pro-Arg (SEQ ID NO:20).

9. The isolated modified lipase of claim 1, wherein said addition at its N-terminus and/or its C-terminus comprises Ser-Pro-Ile-Arg-Glu-Arg (SEQ ID NO:21).

10. The isolated modified lipase of claim 1, wherein said addition at its N-terminus and/or its C-terminus comprises Ser-Pro-Ile-Arg-Lys (SEQ ID NO:22).

11. The isolated modified lipase of claim 1, wherein said addition at its N-terminus and/or its C-terminus comprises Ser-Pro-Ile-Lys-Lys (SEQ ID NO:23).

12. The isolated modified lipase of claim 1, wherein said addition at its N-terminus and/or its C-terminus comprises Ser-Pro-Ile-Arg-Arg-Pro (SEQ ID NO:24).

13. The isolated modified lipase of claim 1, wherein said addition at its N-terminus and/or its C-terminus comprises Ser-Po-Pro-Arg-Arg (SEQ ID NO:25).

14. The isolated modified lipase of claim 1, wherein said addition at its N-terminus and/or its C-terminus comprises Ser-Pro-Iso-Pro-Arg (SEQ ID NO:26).

15. The isolated modified lipase of claim 1, wherein said at its N-terminus and/or its C-terminus comprises Ser-Pro-Arg-Pro-Arg (SEQ ID NO:27).

16. The isolated modified lipase of claim 1, wherein said addition at its N-terminus and/or its C-terminus comprises Ser-Pro-Ile-Arg (SEQ ID NO:28).

17. The isolated modified lipase of claim 1, wherein said addition at its N-terminus and/or its C-terminus comprises Ser-Pro-Ile-Arg-Arg (SEQ ID NO:29).

18. The isolated modified lipase of claim 1, wherein said addition at its N-terminus and/or its C-terminus comprises Ser-Cys-Ile-Arg-Arg, (SEQ ID NO:30).

19. The isolated modified lipase of claim 1, wherein said addition at its N-terminus and/or its C-terminus comprises Ser-Pro-Ile-Arg-Pro-Arg-Pro (SEQ ID NO:31).

20. The isolated modified lipase of claim 1, wherein said addition at its N-terminus and/or its C-terminus comprises Ser-Cys-Ile-Arg-Pro-Arg-Pro (SEQ ID NO:32).

21. The isolated modified lipase of claim 1, wherein said addition at its N-terminus and/or its C-terminus comprises Ser-Pro-Arg-Pro-Arg-Thr (SEQ ID NO:33).

22. The isolated modified lipase of claim 1, wherein said addition at its N-terminus and/or its C-terminus comprises Ser-Pro-Phe-Arg-Pro-Lys-Leu (SEQ ID NO:34).

23. The isolated modified lipase of claim 1, wherein said addition at its N-terminus and/or its C-terminus comprises Ser-Pro-Pro-Arg-Pro (SEQ ID NO:35).

24. The isolated modified lipase of claim 1, wherein said addition at its N-terminus and/or its C-terminus comprises Ser-Pro-Ile-Arg-Arg-Pro (SEQ ID NO:36).

25. The isolated modified lipase of claim 1, wherein said addition at its N-terminus and/or its C-terminus comprises Ser-Pro-Pro-Arg-Pro-Pro (SEQ ID NO:37).

26. The isolated modified lipase of claim 1, wherein said addition at its N-terminus and/or its C-terminus comprises Ser-Pro-Pro-Arg-Pro-Arg (SEQ ID NO:38).

27. The isolated modified lipase of claim 1, wherein said addition at its N-terminus and/or its C-terminus comprises Ser-Pro-Pro-Trp-Trp-Pro (SEQ ID NO:39).

28. The isolated modified lipase of claim 1, wherein said addition at its N-terminus and/or its C-terminus comprises Ser-Pro-Pro-Trp-Arg-Pro (SEQ ID NO:40).

29. The isolated modified lipase of claim 1, wherein said addition at its N-terminus and/or its C-terminus comprises Ser-Pro-Pro-Arg-Trp-Pro (SEQ ID NO:41).

30. The isolated modified lipase of claim 1, wherein said addition at its N-terminus and/or its C-terminus comprises Ser-His-Trp-Arg-Arg-Trp (SEQ ID NO:43).

31. The isolated modified lipase of claim 1, wherein said addition at its N-terminus and/or its C-terminus comprises Ser-His-Trp-Arg-Lys (SEQ ID NO:44).

32. The isolated modified lipase of claim 1, wherein said addition at its N-terminus and/or its C-terminus comprises Ser-His-Trp-Arg (SEQ ID NO:45).

33. The isolated modified lipase of claim 1, wherein said addition at its N-terminus and/or its C-terminus comprises Thr-Ala-Ile-Arg-Pro-Arg-Lys (SEQ ID NO:46).

34. The isolated modified lipase of claim 1, wherein said addition at its N-terminus and/or its C-terminus comprises Ser-Thr-Arg-Arg-Pro-Arg-Pro (SEQ ID NO:47).

35. The isolated modified lipase of claim 1, wherein said addition at its N-terminus and/or its C-terminus comprises Gly-Pro-Ile-Arg-Pro-Arg-Pro (SEQ ID NO:48).

36. The isolated modified lipase of claim 1, wherein said addition at its N-terminus and/or its terminus comprises Leu-Pro-Phe-Arg-Glu-Arg-Pro (SEQ ID NO:49).

37. The isolated modified lipase of claim 1, wherein said addition at its N-terminus and/or its C-terminus comprises Ser-Arg-Ser-Arg-His-Asp-Ala (SEQ ID NO:50).

38. The isolated modified lipase of claim 1, wherein said addition at its N-terminus and/or its tarminus comprises Ile-Pro-Ile-Arg-Pro-Arg-Arg (SEQ ID NO:51).

39. The isolated modified lipase of claim 1, wherein said addition at its N-terminus and/or its C-terminus comprises Ser-Thr-Arg-Pm-Arg-Pro (SEQ ID NO:52).

40. The isolated modified lipase of claim 1, wherein said addition at its N-terminus and/or its C-terminus comprises Thr-Ala-Ile-Arg-Pro-Arg-Lys (SEQ ID NO:53).

41. The isolated modified lipase of claim 1, wherein said addition at its N-terminus and/or its C-terminus comprises Trp-Arg-Trp-Arg-Trp-Arg (SEQ ID NO:54).

42. The isolated modified lipase of claim 1, wherein said addition at its N-terminus and/or its C-terminus comprises Glu-Pro-Ile-Arg-Arg (SEQ ID NO:55).

43. The isolated modified lipase of claim 1, wherein said addition at its N-terminus and/or its C-terminus comprises Ser-His-Trp-Glu-Glu (SEQ ID NO:56).

44. The isolated modified lipase of claim 1, wherein said addition at its N-terminus and/or its C-terminus comprises Arg-Pro-Arg-Pro-Arg-Pro-Arg-Pro (SEQ ID NO:57).

45. The isolated modified lipase of claim 1, wherein said addition at its N-terminus and/or its C-terminus comprises Ser-Ser-Thr-Arg-Arg-Ala-Ser-Pro-Ile-Lys-Lys (SEQ ID NO:58).

46. The isolated modified lipase of claim 1, wherein said addition at its N-terminus and/or its C-terminus comprises Ala-Trp-Trp-Pro-Ser-Pro-Ile-Arg-Pro-Arg-Pro (SEQ ID NO:59).

47. The isolated modified lipase of claim 1, wherein said addition at its N-terminus and/or its C-terminus comprises Ala-Pro-Pro-Pro-Arg-Thr-Arg-Pro-Arg-Pro-Arg-Ser (SEQ ID NO:60).

48. The isolated modified lipase of claim 1, wherein said addition at its N-terminus and/or its C-terminus comprises Ala-Pro-Pro-Arg-Thr-Arg-Pro-Arg-Pro-Arg-Ser (SEQ ID NO:61).

49. The isolated modified lipase of claim 1, wherein said addition at its N-terminus and/or its C-terminus comprises Ser-Pro-Lys-Arg-Lys-Pro-Arg-Pro (SEQ ID NO:62).

50. The isolated modified lipase of claim 1, wherein said addition at its N-terminus and/or its C-terminus comprises Ser-Gln-Arg-Ile-Lys-Gln-Arg-Ile-Lys (SEQ ID NO:63).

51. The isolated modified lipase of claim 1, wherein said addition at its N-terminus and/or its C-terminus comprises Ser-Pr-Pro-Pro-Arg-Pro-Arg-Pro (SEQ ID NO:64).

52. The isolated modified lipase of claim 1, wherein said addition at its N-terminus and/or its C-terminus comprises Ser-Pro-Ile-Arg-Pro-Arg-Pro-Arg-Pro-Arg (SEQ ID NO:65).

53. The isolated modified lipase of claim 1, wherein said addition at its N-terminus and/or its C-terminus comprises Ser-Pro-Ile-Lys-Ala-Trp-Trp-Pro (SEQ ID NO:66).

54. The isolated modified lipase of claim 1, wherein said addition at its N-terminus and/or its C-terminus comprises Ala-Pro-Pro-Pro-Lys-Ala-Ser-Pro-Arg-Gln-Pro) (SEQ ID NO: 67).

55. The isolated modified lipase of claim 1, wherein said addition at its N-terminus and/or its C-terminus comprises Ser-Pro-Ile-Arg-Pro-Arg-Pro-Ser-Pro-Ile-Arg-Pro-Arg-Pro-Arg (SEQ ID NO:68).

56. The isolated modified lipase of claim 1, wherein said addition at its N-terminus and/or its C-terminus comprises Ser-Pro-Pro-Arg-Trp-Pro-Arg-Arg (SEQ ID NO:69).

57. The isolated modified lipase of claim 1, wherein said addition at its N-terminus and/or its C-terminus comprises Ser-Pro-Pro-Ile-Arg-Trp-Pro-Arg-Trp (SEQ ID NO:70).

58. The isolated modified lipase of claim 1, wherein said addition at its N-terminus and/or its C-terminus comprises Ser-Pro-Pro-Arg-Trp-Pro-Trp-Arg (SEQ ID NO:71).

59. The isolated modified lipase of claim 1, wherein said addition at its N-terminus and/or its C-terminus comprises Ser-Pro-Pro-Trp-Arg-Pro-Arg-Arg (SEQ ID NO:72).

60. The isolated modified lipase of claim 1, wherein said addition at its N-terminus and/or its C-terminus comprises Ser-Pro-Pro-Trp-Trp-Pro-Arg-Trp (SEQ ID NO:73).

61. The isolated modified lipase of claim 1, wherein said addition at its N-terminus and/or its C-terminus comprises Ser-Pro-Pro-Trp-Trp-Pro-Trp-Arg (SEQ ID NO:74).

62. The isolated modified lipase of claim 1, wherein said addition at its N-terminus and/or its C-terminus comprises Ser-Pro-Pro-Trp-Trp-Pro-Trp-Trp (SEQ ID NO:75).

63. The isolated modified lipase of claim 1, wherein said addition at its N-terminus and/or its C-terminus comprises Ser-Pro-Pro-Trp-Pro-Arg-Pro-Arg-Pro (SEQ ID NO:76).

* * * * *

SEQUENCE LISTING

<160> NUMBER OF SEQ ID NOS: 162

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
gaatgacttg gttgacgcgt caccagtcac                              30

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
tctagcccag aatactggat caaatc                                  26

<210> SEQ ID NO 3
<211> LENGTH: 55
<212> TYPE: DNA
<213> ORGANISM: Artificial Sequence
<220> FEATURE:
<223> OTHER INFORMATION: primer

<400> SEQUENCE: 3
aacagatctt gcgagacctc tctacgtata gggctagcga gcgcggcgct gatcg      55

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
gttgtgtgga attgtgagcg g                                        21

<210> SEQ ID NO 5
<211> LENGTH: 54
<212> TYPE: DNA
<213> ORGANISM: Artificial Sequence
<220> FEATURE:
<223> OTHER INFORMATION: primer

<400> SEQUENCE: 5
gcgtggacgg ccttggctag ccctattcgt cctcgaccgg tctcgcagga tctg    54

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
agaaatcggg tatcctttca g                                        21

<210> SEQ ID NO 7
<211> LENGTH: 31
<212> TYPE: DNA
<213> ORGANISM: Artificial Sequence
<220> FEATURE:
<223> OTHER INFORMATION: primer

<400> SEQUENCE: 7
cgaattcgat gcgttccagg gtggtggcag g                             31

<210> SEQ ID NO 8
<211> LENGTH: 74
<212> TYPE: DNA
<213> ORGANISM: Artificial Sequence
<220> FEATURE:
<223> OTHER INFORMATION: primer

<400> SEQUENCE: 8
cgaattcacg cgtcgccgcg tagccagcgg ccgggcgcgg gcggatcggg ctgggcgcgg    60
tggccgccat tgcc                                                     74

<210> SEQ ID NO 9
<211> LENGTH: 74
<212> TYPE: DNA
<213> ORGANISM: Artificial Sequence
<220> FEATURE:
<223> OTHER INFORMATION: primer

<400> SEQUENCE: 9
cgaattcacg cgtcgccgcg tagccagcgg ccttgcgcgg gcggatcgcc gtgggcgcgg    60
tggccgccat tgcc                                                     74

<210> SEQ ID NO 10

```
<211> LENGTH: 74
<212> TYPE: DNA
<213> ORGANISM: Artificial Sequence
<220> FEATURE:
<223> OTHER INFORMATION: Primer

<400> SEQUENCE: 10
cgaattcacg cgtcgccgcg tagccagcgg ccgggcgcgg acggcgcgtc gagggcgcgg    60
tggccgccat tgcc                                                      74

<210> SEQ ID NO 11
<211> LENGTH: 74
<212> TYPE: DNA
<213> ORGANISM: Artificial Sequence
<220> FEATURE:
<223> OTHER INFORMATION: Primer

<400> SEQUENCE: 11
cgaattcacg cgtcgccgcg tagccagcgg ccgggcgcgg gcggatcggg ccgggcgcgg    60
tggccgccat tgcc                                                      74

<210> SEQ ID NO 12
<211> LENGTH: 68
<212> TYPE: DNA
<213> ORGANISM: Artificial Sequence
<220> FEATURE:
<223> OTHER INFORMATION: Primer

<400> SEQUENCE: 12
cgaattcacg cgtcgccgcg tagccagcgg cccggcggat cgggctgggc gcggtggccg    60
ccattgcc                                                             68

<210> SEQ ID NO 13
<211> LENGTH: 77
<212> TYPE: DNA
<213> ORGANISM: Artificial Sequence
<220> FEATURE:
<223> OTHER INFORMATION: Primer

<400> SEQUENCE: 13
cgaattcacg cgtcgccgcg tagccagcgg ccggacgcgg cctgggacgc gggcggggcg    60
cggtggccgc cattgcc                                                   77

<210> SEQ ID NO 14
<211> LENGTH: 105
<212> TYPE: DNA
<213> ORGANISM: Artificial Sequence
<220> FEATURE:
<223> OTHER INFORMATION: Primer

<400> SEQUENCE: 14
gctcctcatg gtggatcccc agttgtgtat atagaggatt gaggaaggaa gagaagtgtg    60
gatagaggta aattgagttg gaaactccaa gcatggcatc cttgc                   105

<210> SEQ ID NO 15
<211> LENGTH: 876
<212> TYPE: DNA
<213> ORGANISM: Humicola lanuginosa DSM 4109
<220> FEATURE:
<221> NAME/KEY: CDS
<222> LOCATION: (1)..(876)
<223> OTHER INFORMATION:
<220> FEATURE:
<221> NAME/KEY: sig_peptide
```

<222> LOCATION: (1)..(66)
<223> OTHER INFORMATION:

<400> SEQUENCE: 15

| | | | | | | | | | | | | | | | | |
|---|---|---|---|---|---|---|---|---|---|---|---|---|---|---|---|---|
| atg | agg | agc | tcc | ctt | gtg | ctg | ttc | ttt | gtc | tct | gcg | tgg | acg | gcc | ttg | 48 |
| Met | Arg | Ser | Ser | Leu | Val | Leu | Phe | Phe | Val | Ser | Ala | Trp | Thr | Ala | Leu | |
| 1 | | | | 5 | | | | | 10 | | | | | 15 | | |
| gcc | agt | cct | att | cgt | cga | gag | gtc | tcg | cag | gat | ctg | ttt | aac | cag | ttc | 96 |
| Ala | Ser | Pro | Ile | Arg | Arg | Glu | Val | Ser | Gln | Asp | Leu | Phe | Asn | Gln | Phe | |
| | | | 20 | | | | | 25 | | | | | 30 | | | |
| aat | ctc | ttt | gca | cag | tat | tct | gca | gcc | gca | tac | tgc | gga | aaa | aac | aat | 144 |
| Asn | Leu | Phe | Ala | Gln | Tyr | Ser | Ala | Ala | Ala | Tyr | Cys | Gly | Lys | Asn | Asn | |
| | | 35 | | | | | 40 | | | | | 45 | | | | |
| gat | gcc | cca | gct | ggt | aca | aac | att | acg | tgc | acg | gga | aat | gcc | tgc | ccc | 192 |
| Asp | Ala | Pro | Ala | Gly | Thr | Asn | Ile | Thr | Cys | Thr | Gly | Asn | Ala | Cys | Pro | |
| | 50 | | | | | 55 | | | | | 60 | | | | | |
| gag | gta | gag | aag | gcg | gat | gca | acg | ttt | ctc | tac | tcg | ttt | gaa | gac | tct | 240 |
| Glu | Val | Glu | Lys | Ala | Asp | Ala | Thr | Phe | Leu | Tyr | Ser | Phe | Glu | Asp | Ser | |
| 65 | | | | | 70 | | | | | 75 | | | | | 80 | |
| gga | gtg | ggc | gat | gtc | acc | ggc | ttc | ctt | gct | ctc | gac | aac | acg | aac | aaa | 288 |
| Gly | Val | Gly | Asp | Val | Thr | Gly | Phe | Leu | Ala | Leu | Asp | Asn | Thr | Asn | Lys | |
| | | | | 85 | | | | | 90 | | | | | 95 | | |
| ttg | atc | gtc | ctc | tct | ttc | cgt | ggc | tct | cgt | tcc | ata | gag | aac | tgg | atc | 336 |
| Leu | Ile | Val | Leu | Ser | Phe | Arg | Gly | Ser | Arg | Ser | Ile | Glu | Asn | Trp | Ile | |
| | | | 100 | | | | | 105 | | | | | 110 | | | |
| ggg | aat | ctt | aac | ttc | gac | ttg | aaa | gaa | ata | aat | gac | att | tgc | tcc | ggc | 384 |
| Gly | Asn | Leu | Asn | Phe | Asp | Leu | Lys | Glu | Ile | Asn | Asp | Ile | Cys | Ser | Gly | |
| | | 115 | | | | | 120 | | | | | 125 | | | | |
| tgc | agg | gga | cat | gac | ggc | ttc | act | tcg | tcc | tgg | agg | tct | gta | gcc | gat | 432 |
| Cys | Arg | Gly | His | Asp | Gly | Phe | Thr | Ser | Ser | Trp | Arg | Ser | Val | Ala | Asp | |
| | 130 | | | | | 135 | | | | | 140 | | | | | |
| acg | tta | agg | cag | aag | gtg | gag | gat | gct | gtg | agg | gag | cat | ccc | gac | tat | 480 |
| Thr | Leu | Arg | Gln | Lys | Val | Glu | Asp | Ala | Val | Arg | Glu | His | Pro | Asp | Tyr | |
| 145 | | | | | 150 | | | | | 155 | | | | | 160 | |
| cgc | gtg | gtg | ttt | acc | gga | cat | agc | ttg | ggt | ggt | gca | ttg | gca | act | gtt | 528 |
| Arg | Val | Val | Phe | Thr | Gly | His | Ser | Leu | Gly | Gly | Ala | Leu | Ala | Thr | Val | |
| | | | | 165 | | | | | 170 | | | | | 175 | | |
| gcc | gga | gca | gac | ctg | cgt | gga | aat | ggg | tat | gat | atc | gac | gtg | ttt | tca | 576 |
| Ala | Gly | Ala | Asp | Leu | Arg | Gly | Asn | Gly | Tyr | Asp | Ile | Asp | Val | Phe | Ser | |
| | | | 180 | | | | | 185 | | | | | 190 | | | |
| tat | ggc | gcc | ccc | cga | gtc | gga | aac | agg | gct | ttt | gca | gaa | ttc | ctg | acc | 624 |
| Tyr | Gly | Ala | Pro | Arg | Val | Gly | Asn | Arg | Ala | Phe | Ala | Glu | Phe | Leu | Thr | |
| | | 195 | | | | | 200 | | | | | 205 | | | | |
| gta | cag | acc | ggc | gga | aca | ctc | tac | cgc | att | acc | cac | acc | aat | gat | att | 672 |
| Val | Gln | Thr | Gly | Gly | Thr | Leu | Tyr | Arg | Ile | Thr | His | Thr | Asn | Asp | Ile | |
| | 210 | | | | | 215 | | | | | 220 | | | | | |
| gtc | cct | aga | ctc | ccg | ccg | cgc | gaa | ttc | ggt | tac | agc | cat | tct | agc | cca | 720 |
| Val | Pro | Arg | Leu | Pro | Pro | Arg | Glu | Phe | Gly | Tyr | Ser | His | Ser | Ser | Pro | |
| 225 | | | | | 230 | | | | | 235 | | | | | 240 | |
| gag | tac | tgg | atc | aaa | tct | gga | acc | ctt | gtc | ccc | gtc | acc | cga | aac | gat | 768 |
| Glu | Tyr | Trp | Ile | Lys | Ser | Gly | Thr | Leu | Val | Pro | Val | Thr | Arg | Asn | Asp | |
| | | | | 245 | | | | | 250 | | | | | 255 | | |
| atc | gtg | aag | ata | gaa | ggc | atc | gat | gcc | acc | ggc | ggc | aat | aac | cag | cct | 816 |
| Ile | Val | Lys | Ile | Glu | Gly | Ile | Asp | Ala | Thr | Gly | Gly | Asn | Asn | Gln | Pro | |
| | | | 260 | | | | | 265 | | | | | 270 | | | |
| aac | att | ccg | gat | atc | cct | gcg | cac | cta | tgg | tac | ttc | ggg | tta | att | ggg | 864 |
| Asn | Ile | Pro | Asp | Ile | Pro | Ala | His | Leu | Trp | Tyr | Phe | Gly | Leu | Ile | Gly | |
| | | 275 | | | | | 280 | | | | | 285 | | | | |
| aca | tgt | ctt | tag | | | | | | | | | | | | | 876 |
| Thr | Cys | Leu | | | | | | | | | | | | | | |

```
                290

<210> SEQ ID NO 16
<211> LENGTH: 291
<212> TYPE: PRT
<213> ORGANISM: Humicola lanuginosa DSM 4109

<400> SEQUENCE: 16

Met Arg Ser Ser Leu Val Leu Phe Phe Val Ser Ala Trp Thr Ala Leu
1               5                   10                  15

Ala Ser Pro Ile Arg Arg Glu Val Ser Gln Asp Leu Phe Asn Gln Phe
            20                  25                  30

Asn Leu Phe Ala Gln Tyr Ser Ala Ala Tyr Cys Gly Lys Asn Asn
        35                  40                  45

Asp Ala Pro Ala Gly Thr Asn Ile Thr Cys Thr Gly Asn Ala Cys Pro
    50                  55                  60

Glu Val Glu Lys Ala Asp Ala Thr Phe Leu Tyr Ser Phe Glu Asp Ser
65                  70                  75                  80

Gly Val Gly Asp Val Thr Gly Phe Leu Ala Leu Asp Asn Thr Asn Lys
                85                  90                  95

Leu Ile Val Leu Ser Phe Arg Gly Ser Arg Ser Ile Glu Asn Trp Ile
            100                 105                 110

Gly Asn Leu Asn Phe Asp Leu Lys Glu Ile Asn Asp Ile Cys Ser Gly
        115                 120                 125

Cys Arg Gly His Asp Gly Phe Thr Ser Ser Trp Arg Ser Val Ala Asp
    130                 135                 140

Thr Leu Arg Gln Lys Val Glu Asp Ala Val Arg Glu His Pro Asp Tyr
145                 150                 155                 160

Arg Val Val Phe Thr Gly His Ser Leu Gly Gly Ala Leu Ala Thr Val
                165                 170                 175

Ala Gly Ala Asp Leu Arg Gly Asn Gly Tyr Asp Ile Asp Val Phe Ser
            180                 185                 190

Tyr Gly Ala Pro Arg Val Gly Asn Arg Ala Phe Ala Glu Phe Leu Thr
        195                 200                 205

Val Gln Thr Gly Gly Thr Leu Tyr Arg Ile Thr His Thr Asn Asp Ile
    210                 215                 220

Val Pro Arg Leu Pro Pro Arg Glu Phe Gly Tyr Ser His Ser Ser Pro
225                 230                 235                 240

Glu Tyr Trp Ile Lys Ser Gly Thr Leu Val Pro Val Thr Arg Asn Asp
                245                 250                 255

Ile Val Lys Ile Glu Gly Ile Asp Ala Thr Gly Gly Asn Asn Gln Pro
            260                 265                 270

Asn Ile Pro Asp Ile Pro Ala His Leu Trp Tyr Phe Gly Leu Ile Gly
        275                 280                 285

Thr Cys Leu
    290

<210> SEQ ID NO 17
<211> LENGTH: 6
<212> TYPE: PRT
<213> ORGANISM: Artificial Sequence
<220> FEATURE:
<223> OTHER INFORMATION: Peptide addition

<400> SEQUENCE: 17

Arg Pro Val Ser Gln Asp
1               5
```

<210> SEQ ID NO 18
<211> LENGTH: 5
<212> TYPE: PRT
<213> ORGANISM: Artificial Sequence
<220> FEATURE:
<223> OTHER INFORMATION: Peptide addition

<400> SEQUENCE: 18

Ser Pro Ile Arg Met
1               5

<210> SEQ ID NO 19
<211> LENGTH: 6
<212> TYPE: PRT
<213> ORGANISM: Artificial sequence
<220> FEATURE:
<223> OTHER INFORMATION: Peptide addition

<400> SEQUENCE: 19

Ser Pro Ile Arg Ala Arg
1               5

<210> SEQ ID NO 20
<211> LENGTH: 6
<212> TYPE: PRT
<213> ORGANISM: Artificial sequence
<220> FEATURE:
<223> OTHER INFORMATION: Peptide addition

<400> SEQUENCE: 20

Ser Pro Ile Arg Pro Arg
1               5

<210> SEQ ID NO 21
<211> LENGTH: 6
<212> TYPE: PRT
<213> ORGANISM: Artificial sequence
<220> FEATURE:
<223> OTHER INFORMATION: Peptide addition

<400> SEQUENCE: 21

Ser Pro Ile Arg Glu Arg
1               5

<210> SEQ ID NO 22
<211> LENGTH: 5
<212> TYPE: PRT
<213> ORGANISM: Artificial sequence
<220> FEATURE:
<223> OTHER INFORMATION: Peptide addition

<400> SEQUENCE: 22

Ser Pro Ile Arg Lys
1               5

<210> SEQ ID NO 23
<211> LENGTH: 5
<212> TYPE: PRT
<213> ORGANISM: Artificial sequence
<220> FEATURE:
<223> OTHER INFORMATION: Peptide addition

<400> SEQUENCE: 23

Ser Pro Ile Lys Lys
1               5

```
<210> SEQ ID NO 24
<211> LENGTH: 6
<212> TYPE: PRT
<213> ORGANISM: Artificial sequence
<220> FEATURE:
<223> OTHER INFORMATION: Peptide addition

<400> SEQUENCE: 24

Ser Pro Ile Arg Arg Pro
1               5

<210> SEQ ID NO 25
<211> LENGTH: 5
<212> TYPE: PRT
<213> ORGANISM: Artificial sequence
<220> FEATURE:
<223> OTHER INFORMATION: Peptide addition

<400> SEQUENCE: 25

Ser Pro Pro Arg Arg
1               5

<210> SEQ ID NO 26
<211> LENGTH: 5
<212> TYPE: PRT
<213> ORGANISM: Artificial sequence
<220> FEATURE:
<223> OTHER INFORMATION: Peptide addition
<220> FEATURE:
<221> NAME/KEY: Misc_feature
<222> LOCATION: (3)..(3)
<223> OTHER INFORMATION: Xaa in position 3 denotes Iso

<400> SEQUENCE: 26

Ser Pro Xaa Pro Arg
1               5

<210> SEQ ID NO 27
<211> LENGTH: 5
<212> TYPE: PRT
<213> ORGANISM: Artificial sequence
<220> FEATURE:
<223> OTHER INFORMATION: Peptide addition

<400> SEQUENCE: 27

Ser Pro Arg Pro Arg
1               5

<210> SEQ ID NO 28
<211> LENGTH: 4
<212> TYPE: PRT
<213> ORGANISM: Artificial sequence
<220> FEATURE:
<223> OTHER INFORMATION: Peptide addition

<400> SEQUENCE: 28

Ser Pro Ile Arg
1

<210> SEQ ID NO 29
<211> LENGTH: 5
<212> TYPE: PRT
<213> ORGANISM: Artificial sequence
<220> FEATURE:
<223> OTHER INFORMATION: Peptide addition

<400> SEQUENCE: 29
```

```
Ser Pro Ile Arg Arg
1               5

<210> SEQ ID NO 30
<211> LENGTH: 5
<212> TYPE: PRT
<213> ORGANISM: Artificial sequence
<220> FEATURE:
<223> OTHER INFORMATION: Peptide addition

<400> SEQUENCE: 30

Ser Cys Ile Arg Arg
1               5

<210> SEQ ID NO 31
<211> LENGTH: 7
<212> TYPE: PRT
<213> ORGANISM: Artificial sequence
<220> FEATURE:
<223> OTHER INFORMATION: Peptide addition

<400> SEQUENCE: 31

Ser Pro Ile Arg Pro Arg Pro
1               5

<210> SEQ ID NO 32
<211> LENGTH: 7
<212> TYPE: PRT
<213> ORGANISM: Artificial sequence
<220> FEATURE:
<223> OTHER INFORMATION: Peptide addition

<400> SEQUENCE: 32

Ser Cys Ile Arg Pro Arg Pro
1               5

<210> SEQ ID NO 33
<211> LENGTH: 7
<212> TYPE: PRT
<213> ORGANISM: Artificial sequence
<220> FEATURE:
<223> OTHER INFORMATION: Peptide addition

<400> SEQUENCE: 33

Ser Pro Arg Arg Pro Arg Thr
1               5

<210> SEQ ID NO 34
<211> LENGTH: 7
<212> TYPE: PRT
<213> ORGANISM: Artificial sequence
<220> FEATURE:
<223> OTHER INFORMATION: Peptide addition

<400> SEQUENCE: 34

Ser Pro Phe Arg Pro Lys Leu
1               5

<210> SEQ ID NO 35
<211> LENGTH: 6
<212> TYPE: PRT
<213> ORGANISM: Artificial sequence
<220> FEATURE:
<223> OTHER INFORMATION: Peptide addition

<400> SEQUENCE: 35

Ser Pro Pro Arg Arg Pro
```

-continued

<210> SEQ ID NO 36
<211> LENGTH: 6
<212> TYPE: PRT
<213> ORGANISM: Artificial sequence
<220> FEATURE:
<223> OTHER INFORMATION: Peptide addition

<400> SEQUENCE: 36

Ser Pro Ile Arg Arg Glu
1               5

<210> SEQ ID NO 37
<211> LENGTH: 6
<212> TYPE: PRT
<213> ORGANISM: Artificial sequence
<220> FEATURE:
<223> OTHER INFORMATION: Peptide addition

<400> SEQUENCE: 37

Ser Pro Pro Arg Pro Pro
1               5

<210> SEQ ID NO 38
<211> LENGTH: 6
<212> TYPE: PRT
<213> ORGANISM: Artificial Sequence
<220> FEATURE:
<223> OTHER INFORMATION: Peptide addition

<400> SEQUENCE: 38

Ser Pro Pro Arg Pro Arg
1               5

<210> SEQ ID NO 39
<211> LENGTH: 6
<212> TYPE: PRT
<213> ORGANISM: Artificial sequence
<220> FEATURE:
<223> OTHER INFORMATION: Peptide addition

<400> SEQUENCE: 39

Ser Pro Pro Trp Trp Pro
1               5

<210> SEQ ID NO 40
<211> LENGTH: 6
<212> TYPE: PRT
<213> ORGANISM: Artificial sequence
<220> FEATURE:
<223> OTHER INFORMATION: Peptide addition

<400> SEQUENCE: 40

Ser Pro Pro Trp Arg Pro
1               5

<210> SEQ ID NO 41
<211> LENGTH: 6
<212> TYPE: PRT
<213> ORGANISM: Artificial sequence
<220> FEATURE:
<223> OTHER INFORMATION: Peptide addition

<400> SEQUENCE: 41

Ser Pro Pro Arg Trp Pro
1               5

```
<210> SEQ ID NO 42
<211> LENGTH: 6
<212> TYPE: PRT
<213> ORGANISM: Artificial sequence
<220> FEATURE:
<223> OTHER INFORMATION: Peptide addition

<400> SEQUENCE: 42

Ser Pro Pro Arg Trp Pro
1               5

<210> SEQ ID NO 43
<211> LENGTH: 6
<212> TYPE: PRT
<213> ORGANISM: Artificial sequence
<220> FEATURE:
<223> OTHER INFORMATION: Peptide addition

<400> SEQUENCE: 43

Ser His Trp Arg Arg Trp
1               5

<210> SEQ ID NO 44
<211> LENGTH: 5
<212> TYPE: PRT
<213> ORGANISM: Artificial sequence
<220> FEATURE:
<223> OTHER INFORMATION: Peptide addition

<400> SEQUENCE: 44

Ser His Trp Arg Lys
1               5

<210> SEQ ID NO 45
<211> LENGTH: 5
<212> TYPE: PRT
<213> ORGANISM: Artificial sequence
<220> FEATURE:
<223> OTHER INFORMATION: Peptide addition

<400> SEQUENCE: 45

Ser His Trp Arg Arg
1               5

<210> SEQ ID NO 46
<211> LENGTH: 7
<212> TYPE: PRT
<213> ORGANISM: Artificial sequence
<220> FEATURE:
<223> OTHER INFORMATION: Peptide addition

<400> SEQUENCE: 46

Thr Ala Ile Arg Pro Arg Lys
1               5

<210> SEQ ID NO 47
<211> LENGTH: 7
<212> TYPE: PRT
<213> ORGANISM: Artificial sequence
<220> FEATURE:
<223> OTHER INFORMATION: Peptide addition

<400> SEQUENCE: 47

Ser Thr Arg Arg Pro Arg Pro
1               5
```

```
<210> SEQ ID NO 48
<211> LENGTH: 7
<212> TYPE: PRT
<213> ORGANISM: Artificial sequence
<220> FEATURE:
<223> OTHER INFORMATION: Peptide addition

<400> SEQUENCE: 48

Gly Pro Ile Arg Pro Arg Pro
1               5

<210> SEQ ID NO 49
<211> LENGTH: 7
<212> TYPE: PRT
<213> ORGANISM: Artificial sequence
<220> FEATURE:
<223> OTHER INFORMATION: Peptide addition

<400> SEQUENCE: 49

Leu Pro Phe Arg Glu Arg Pro
1               5

<210> SEQ ID NO 50
<211> LENGTH: 7
<212> TYPE: PRT
<213> ORGANISM: Artificial sequence
<220> FEATURE:
<223> OTHER INFORMATION: Peptide addition

<400> SEQUENCE: 50

Ser Arg Ser Arg His Asp Ala
1               5

<210> SEQ ID NO 51
<211> LENGTH: 7
<212> TYPE: PRT
<213> ORGANISM: Artificial sequence
<220> FEATURE:
<223> OTHER INFORMATION: Peptide addition

<400> SEQUENCE: 51

Ile Pro Ile Arg Pro Arg Arg
1               5

<210> SEQ ID NO 52
<211> LENGTH: 7
<212> TYPE: PRT
<213> ORGANISM: Artificial sequence
<220> FEATURE:
<223> OTHER INFORMATION: Peptide addition

<400> SEQUENCE: 52

Ser Thr Arg Arg Pro Arg Pro
1               5

<210> SEQ ID NO 53
<211> LENGTH: 7
<212> TYPE: PRT
<213> ORGANISM: Artificial sequence
<220> FEATURE:
<223> OTHER INFORMATION: Peptide addition

<400> SEQUENCE: 53

Thr Ala Ile Arg Pro Arg Lys
1               5
```

```
<210> SEQ ID NO 54
<211> LENGTH: 6
<212> TYPE: PRT
<213> ORGANISM: Artificial sequence
<220> FEATURE:
<223> OTHER INFORMATION: Peptide addition

<400> SEQUENCE: 54

Trp Arg Trp Arg Trp Arg
1               5

<210> SEQ ID NO 55
<211> LENGTH: 5
<212> TYPE: PRT
<213> ORGANISM: Artificial sequence
<220> FEATURE:
<223> OTHER INFORMATION: Peptide addition

<400> SEQUENCE: 55

Glu Pro Ile Arg Arg
1               5

<210> SEQ ID NO 56
<211> LENGTH: 5
<212> TYPE: PRT
<213> ORGANISM: Artificial sequence
<220> FEATURE:
<223> OTHER INFORMATION: Peptide addition

<400> SEQUENCE: 56

Ser His Trp Glu Glu
1               5

<210> SEQ ID NO 57
<211> LENGTH: 8
<212> TYPE: PRT
<213> ORGANISM: Artificial sequence
<220> FEATURE:
<223> OTHER INFORMATION: Peptide addition

<400> SEQUENCE: 57

Arg Pro Arg Pro Arg Pro Arg Pro
1               5

<210> SEQ ID NO 58
<211> LENGTH: 11
<212> TYPE: PRT
<213> ORGANISM: Artificial sequence
<220> FEATURE:
<223> OTHER INFORMATION: Peptide addition

<400> SEQUENCE: 58

Ser Ser Thr Arg Arg Ala Ser Pro Ile Lys Lys
1               5                   10

<210> SEQ ID NO 59
<211> LENGTH: 11
<212> TYPE: PRT
<213> ORGANISM: Artificial sequence
<220> FEATURE:
<223> OTHER INFORMATION: Peptide addition

<400> SEQUENCE: 59

Ala Trp Trp Pro Ser Pro Ile Arg Pro Arg Pro
1               5                   10

<210> SEQ ID NO 60
```

```
<211> LENGTH: 12
<212> TYPE: PRT
<213> ORGANISM: Artificial sequence
<220> FEATURE:
<223> OTHER INFORMATION: Peptide addition

<400> SEQUENCE: 60

Ala Pro Pro Pro Arg Pro Arg Pro Arg Pro Arg Pro
1               5                   10

<210> SEQ ID NO 61
<211> LENGTH: 12
<212> TYPE: PRT
<213> ORGANISM: Artificial sequence
<220> FEATURE:
<223> OTHER INFORMATION: Peptide addition

<400> SEQUENCE: 61

Ala Pro Pro Pro Arg Thr Arg Pro Arg Pro Arg Ser
1               5                   10

<210> SEQ ID NO 62
<211> LENGTH: 8
<212> TYPE: PRT
<213> ORGANISM: Artificial sequence
<220> FEATURE:
<223> OTHER INFORMATION: Peptide addition

<400> SEQUENCE: 62

Ser Pro Lys Arg Lys Pro Arg Pro
1               5

<210> SEQ ID NO 63
<211> LENGTH: 9
<212> TYPE: PRT
<213> ORGANISM: Artificial sequence
<220> FEATURE:
<223> OTHER INFORMATION: Peptide addition

<400> SEQUENCE: 63

Ser Gln Arg Ile Lys Gln Arg Ile Lys
1               5

<210> SEQ ID NO 64
<211> LENGTH: 8
<212> TYPE: PRT
<213> ORGANISM: Artificial sequence
<220> FEATURE:
<223> OTHER INFORMATION: Peptide addition

<400> SEQUENCE: 64

Ser Pro Pro Pro Arg Pro Arg Pro
1               5

<210> SEQ ID NO 65
<211> LENGTH: 10
<212> TYPE: PRT
<213> ORGANISM: Artificial sequence
<220> FEATURE:
<223> OTHER INFORMATION: Peptide addition

<400> SEQUENCE: 65

Ser Pro Ile Arg Pro Arg Pro Arg Pro Arg
1               5                   10

<210> SEQ ID NO 66
<211> LENGTH: 9
```

```
<212> TYPE: PRT
<213> ORGANISM: Artificial sequence
<220> FEATURE:
<223> OTHER INFORMATION: Peptide addition

<400> SEQUENCE: 66

Ser Pro Ile Arg Lys Ala Trp Trp Pro
1               5

<210> SEQ ID NO 67
<211> LENGTH: 12
<212> TYPE: PRT
<213> ORGANISM: Artificial sequence
<220> FEATURE:
<223> OTHER INFORMATION: Peptide addition

<400> SEQUENCE: 67

Ala Pro Pro Pro Lys Ala Ser Pro Arg Gln Arg Pro
1               5                   10

<210> SEQ ID NO 68
<211> LENGTH: 15
<212> TYPE: PRT
<213> ORGANISM: Artificial sequence
<220> FEATURE:
<223> OTHER INFORMATION: Peptide addition

<400> SEQUENCE: 68

Ser Pro Ile Arg Pro Arg Pro Ser Pro Ile Arg Pro Arg Pro Arg
1               5                   10                  15

<210> SEQ ID NO 69
<211> LENGTH: 8
<212> TYPE: PRT
<213> ORGANISM: Artificial sequence
<220> FEATURE:
<223> OTHER INFORMATION: Peptide addition

<400> SEQUENCE: 69

Ser Pro Pro Arg Trp Pro Arg Arg
1               5

<210> SEQ ID NO 70
<211> LENGTH: 8
<212> TYPE: PRT
<213> ORGANISM: Artificial sequence
<220> FEATURE:
<223> OTHER INFORMATION: Peptide addition

<400> SEQUENCE: 70

Ser Pro Pro Arg Trp Pro Arg Trp
1               5

<210> SEQ ID NO 71
<211> LENGTH: 8
<212> TYPE: PRT
<213> ORGANISM: Artificial sequence
<220> FEATURE:
<223> OTHER INFORMATION: Peptide addition

<400> SEQUENCE: 71

Ser Pro Pro Arg Trp Pro Trp Arg
1               5

<210> SEQ ID NO 72
<211> LENGTH: 8
<212> TYPE: PRT
```

```
<213> ORGANISM: Artificial sequence
<220> FEATURE:
<223> OTHER INFORMATION: Peptide addition

<400> SEQUENCE: 72

Ser Pro Pro Trp Arg Pro Arg Arg
1               5

<210> SEQ ID NO 73
<211> LENGTH: 8
<212> TYPE: PRT
<213> ORGANISM: Artificial sequence
<220> FEATURE:
<223> OTHER INFORMATION: Peptide addition

<400> SEQUENCE: 73

Ser Pro Pro Trp Trp Pro Arg Trp
1               5

<210> SEQ ID NO 74
<211> LENGTH: 8
<212> TYPE: PRT
<213> ORGANISM: Artificial sequence
<220> FEATURE:
<223> OTHER INFORMATION: Peptide addition

<400> SEQUENCE: 74

Ser Pro Pro Trp Trp Pro Trp Arg
1               5

<210> SEQ ID NO 75
<211> LENGTH: 8
<212> TYPE: PRT
<213> ORGANISM: Artificial sequence
<220> FEATURE:
<223> OTHER INFORMATION: Peptide addition

<400> SEQUENCE: 75

Ser Pro Pro Trp Trp Pro Trp Trp
1               5

<210> SEQ ID NO 76
<211> LENGTH: 9
<212> TYPE: PRT
<213> ORGANISM: Artificial sequence
<220> FEATURE:
<223> OTHER INFORMATION: Peptide addition

<400> SEQUENCE: 76

Ser Pro Pro Trp Pro Arg Pro Arg Pro
1               5

<210> SEQ ID NO 77
<211> LENGTH: 30
<212> TYPE: DNA
<213> ORGANISM: Artificial sequence
<220> FEATURE:
<223> OTHER INFORMATION: Primer

<400> SEQUENCE: 77
gaatgacttg gttgagtact caccagtcac                                      30

<210> SEQ ID NO 78
<211> LENGTH: 46
<212> TYPE: DNA
<213> ORGANISM: Artificial sequence
<220> FEATURE:
```

<223> OTHER INFORMATION: Primer

<400> SEQUENCE: 78
gaactggata ggaaatttga agttcctgtt gaaagaaata aatgac        46

<210> SEQ ID NO 79
<211> LENGTH: 30
<212> TYPE: DNA
<213> ORGANISM: Artificial sequence
<220> FEATURE:
<223> OTHER INFORMATION: Primer

<400> SEQUENCE: 79
gaatgacttg gttgacgcgt caccagtcac        30

<210> SEQ ID NO 80
<211> LENGTH: 54
<212> TYPE: DNA
<213> ORGANISM: Artificial sequence
<220> FEATURE:
<223> OTHER INFORMATION: Primer

<400> SEQUENCE: 80
gcgtggacgg ccttggctag ccctattcgt cctcgaccgg tctcgcagga tctg        54

<210> SEQ ID NO 81
<211> LENGTH: 57
<212> TYPE: DNA
<213> ORGANISM: Artificial sequence
<220> FEATURE:
<223> OTHER INFORMATION: Primer

<400> SEQUENCE: 81
gcgtggacgg ccttggcctc wccwatwcgw ccwagaccwg aggtctcgca ggatctg        57

<210> SEQ ID NO 82
<211> LENGTH: 93
<212> TYPE: DNA
<213> ORGANISM: Artificial sequence
<220> FEATURE:
<223> OTHER INFORMATION: Primer
<220> FEATURE:
<221> NAME/KEY: Misc_feature
<222> LOCATION: (61)..(61)
<223> OTHER INFORMATION: n in position 61 denotes a, g,c, or t
<220> FEATURE:
<221> NAME/KEY: Misc_feature
<222> LOCATION: (62)..(62)
<223> OTHER INFORMATION: n in position 62 denotes a, g,c, or t
<220> FEATURE:
<221> NAME/KEY: Misc_feature
<222> LOCATION: (70)..(70)
<223> OTHER INFORMATION: n in position 70 denotes a, g,c, or t

<400> SEQUENCE: 82
gtctctgcgt ggacggcctt ggcggcgcca cctccacgwc cwagaccwcg wccwagaccw        60
nnsagscagn asctgtttaa ccagttcaat ctc        93

<210> SEQ ID NO 83
<211> LENGTH: 47
<212> TYPE: DNA
<213> ORGANISM: Artificial sequence
<220> FEATURE:
<223> OTHER INFORMATION: Primer

<400> SEQUENCE: 83
accatacccc ggccgctcct cctaggcgtc ctcggcagct gggagcc        47

<210> SEQ ID NO 84
<211> LENGTH: 59
<212> TYPE: DNA
<213> ORGANISM: Artificial sequence
<220> FEATURE:
<223> OTHER INFORMATION: Primer

<400> SEQUENCE: 84
accatacccc ggccgctcct agccctccgc ggcggccgct gggagccatc gagaacggc    59

<210> SEQ ID NO 85
<211> LENGTH: 56
<212> TYPE: DNA
<213> ORGANISM: Artificial sequence
<220> FEATURE:
<223> OTHER INFORMATION: Primer

<400> SEQUENCE: 85
accatacccc ggccgctcct agccctatac gtaagctggg agccatcgag aacggc    56

<210> SEQ ID NO 86
<211> LENGTH: 57
<212> TYPE: DNA
<213> ORGANISM: Artificial sequence
<220> FEATURE:
<223> OTHER INFORMATION: Primer

<400> SEQUENCE: 86
gagtcccaca tccgaaacat ctggatacaa ggagtaggag gaccttacga cgccgcg    57

<210> SEQ ID NO 87
<211> LENGTH: 7
<212> TYPE: PRT
<213> ORGANISM: Artificial sequence
<220> FEATURE:
<223> OTHER INFORMATION: Peptide addition

<400> SEQUENCE: 87

Ser Ala Leu Arg Pro Arg Lys
1               5

<210> SEQ ID NO 88
<211> LENGTH: 12
<212> TYPE: PRT
<213> ORGANISM: Artificial sequence
<220> FEATURE:
<223> OTHER INFORMATION: Peptide addition

<400> SEQUENCE: 88

Ala Pro Pro Pro Arg Pro Arg Leu Leu Pro Ile Ser
1               5                   10

<210> SEQ ID NO 89
<211> LENGTH: 11
<212> TYPE: PRT
<213> ORGANISM: Artificial sequence
<220> FEATURE:
<223> OTHER INFORMATION: Peptide addition

<400> SEQUENCE: 89

Ala Pro Pro Pro Thr Arg Gln Arg Gln Ser Pro
1               5                   10

<210> SEQ ID NO 90
<211> LENGTH: 12

-continued

```
<212> TYPE: PRT
<213> ORGANISM: Artificial sequence
<220> FEATURE:
<223> OTHER INFORMATION: Peptide addition

<400> SEQUENCE: 90

Ala Pro Pro Pro Arg Thr Ile Pro Arg Ser Ser Pro
1               5                   10

<210> SEQ ID NO 91
<211> LENGTH: 864
<212> TYPE: DNA
<213> ORGANISM: Pseudomonas sp.
<220> FEATURE:
<221> NAME/KEY: CDS
<222> LOCATION: (1)..(864)
<223> OTHER INFORMATION:
<220> FEATURE:
<221> NAME/KEY: mat_peptide
<222> LOCATION: (1)..()
<223> OTHER INFORMATION:

<400> SEQUENCE: 91 ttc ggc tcc tcg aac tac acc aag acc cag tac ccg atc gtc ctg acc       48
Phe Gly Ser Ser Asn Tyr Thr Lys Thr Gln Tyr Pro Ile Val Leu Thr
1               5                   10                  15 cac ggc atg ctc ggt ttc gac agc ctg ctt gga gtc gac tac tgg tac       96
His Gly Met Leu Gly Phe Asp Ser Leu Leu Gly Val Asp Tyr Trp Tyr
                20                  25                  30 ggc att ccc tca gcc ctg cgt aaa gac ggc gcc acc gtc tac gtc acc      144
Gly Ile Pro Ser Ala Leu Arg Lys Asp Gly Ala Thr Val Tyr Val Thr
            35                  40                  45 gaa gtc agc cag ctc gac acc tcc gaa gcc cga ggt gag caa ctg ctg      192
Glu Val Ser Gln Leu Asp Thr Ser Glu Ala Arg Gly Glu Gln Leu Leu
        50                  55                  60 acc caa gtc gag gaa atc gtg gcc atc agc ggc aag ccc aag gtc aac      240
Thr Gln Val Glu Glu Ile Val Ala Ile Ser Gly Lys Pro Lys Val Asn
65                  70                  75                  80 ctg ttc ggc cac agc cat ggc ggg cct acc atc cgc tac gtt gcc gcc      288
Leu Phe Gly His Ser His Gly Gly Pro Thr Ile Arg Tyr Val Ala Ala
                85                  90                  95 gtg cgc ccg gat ctg gtc gcc tcg gtc acc agc att ggc gcg ccg cac      336
Val Arg Pro Asp Leu Val Ala Ser Val Thr Ser Ile Gly Ala Pro His
                100                 105                 110 aag ggt tcg gcc acc gcc gac ttc atc cgc cag gtg ccg gaa gga tcg      384
Lys Gly Ser Ala Thr Ala Asp Phe Ile Arg Gln Val Pro Glu Gly Ser
            115                 120                 125 gcc agc gaa gcg att ctg gcc ggg atc gtc aat ggt ctg ggt gcg ctg      432
Ala Ser Glu Ala Ile Leu Ala Gly Ile Val Asn Gly Leu Gly Ala Leu
        130                 135                 140 atc aac ttc ctt tcc ggc agc agt tcg gac acc cca cag aac tcg ctg      480
Ile Asn Phe Leu Ser Gly Ser Ser Ser Asp Thr Pro Gln Asn Ser Leu
145                 150                 155                 160 ggc acg ctg gag tca ctg aac tcc gaa ggc gcc gca cgg ttt aac gcc      528
Gly Thr Leu Glu Ser Leu Asn Ser Glu Gly Ala Ala Arg Phe Asn Ala
                165                 170                 175 cgc ttc ccc cag ggg gta cca acc agc gcc tgc ggc gag ggc gat tac      576
Arg Phe Pro Gln Gly Val Pro Thr Ser Ala Cys Gly Glu Gly Asp Tyr
            180                 185                 190 gtg gtc aat ggc gtg cgc tat tac tcc tgg agg ggc acc agc ccg ctg      624
Val Val Asn Gly Val Arg Tyr Tyr Ser Trp Arg Gly Thr Ser Pro Leu
        195                 200                 205 acc aac gta ctc gac ccc tcc gac ctg ctg ctc ggc gcc acc tcc ctg      672
```

```
Thr Asn Val Leu Asp Pro Ser Asp Leu Leu Gly Ala Thr Ser Leu
    210                 215                 220 acc ttc ggt ttc gag gcc aac gat ggt ctg gtc gga cgc tgc agc tcc        720
Thr Phe Gly Phe Glu Ala Asn Asp Gly Leu Val Gly Arg Cys Ser Ser
225                 230                 235                 240 cgg ctg ggt atg gtg atc cgc gac aac tac cgg atg aac cac ctg gac        768
Arg Leu Gly Met Val Ile Arg Asp Asn Tyr Arg Met Asn His Leu Asp
                245                 250                 255 gag gtg aac cag acc ttc ggg ctg acc agc atc ttc gag acc agc ccg        816
Glu Val Asn Gln Thr Phe Gly Leu Thr Ser Ile Phe Glu Thr Ser Pro
            260                 265                 270 gta tcg gtc tat cgc cag caa gcc aat cgc ctg aag aac gcc ggg ctc        864
Val Ser Val Tyr Arg Gln Gln Ala Asn Arg Leu Lys Asn Ala Gly Leu
        275                 280                 285
```

<210> SEQ ID NO 92
<211> LENGTH: 288
<212> TYPE: PRT
<213> ORGANISM: Pseudomonas sp.

<400> SEQUENCE: 92

```
Phe Gly Ser Ser Asn Tyr Thr Lys Thr Gln Tyr Pro Ile Val Leu Thr
1               5                   10                  15

His Gly Met Leu Gly Phe Asp Ser Leu Leu Gly Val Asp Tyr Trp Tyr
            20                  25                  30

Gly Ile Pro Ser Ala Leu Arg Lys Asp Gly Ala Thr Val Tyr Val Thr
        35                  40                  45

Glu Val Ser Gln Leu Asp Thr Ser Glu Ala Arg Gly Glu Gln Leu Leu
    50                  55                  60

Thr Gln Val Glu Glu Ile Val Ala Ile Ser Gly Lys Pro Lys Val Asn
65                  70                  75                  80

Leu Phe Gly His Ser His Gly Gly Pro Thr Ile Arg Tyr Val Ala Ala
                85                  90                  95

Val Arg Pro Asp Leu Val Ala Ser Val Thr Ser Ile Gly Ala Pro His
            100                 105                 110

Lys Gly Ser Ala Thr Ala Asp Phe Ile Arg Gln Val Pro Glu Gly Ser
        115                 120                 125

Ala Ser Glu Ala Ile Leu Ala Gly Ile Val Asn Gly Leu Gly Ala Leu
    130                 135                 140

Ile Asn Phe Leu Ser Gly Ser Ser Asp Thr Pro Gln Asn Ser Leu
145                 150                 155                 160

Gly Thr Leu Glu Ser Leu Asn Ser Glu Gly Ala Ala Arg Phe Asn Ala
                165                 170                 175

Arg Phe Pro Gln Gly Val Pro Thr Ser Ala Cys Gly Glu Gly Asp Tyr
            180                 185                 190

Val Val Asn Gly Val Arg Tyr Tyr Ser Trp Arg Gly Thr Ser Pro Leu
        195                 200                 205

Thr Asn Val Leu Asp Pro Ser Asp Leu Leu Gly Ala Thr Ser Leu
    210                 215                 220

Thr Phe Gly Phe Glu Ala Asn Asp Gly Leu Val Gly Arg Cys Ser Ser
225                 230                 235                 240

Arg Leu Gly Met Val Ile Arg Asp Asn Tyr Arg Met Asn His Leu Asp
                245                 250                 255

Glu Val Asn Gln Thr Phe Gly Leu Thr Ser Ile Phe Glu Thr Ser Pro
            260                 265                 270

Val Ser Val Tyr Arg Gln Gln Ala Asn Arg Leu Lys Asn Ala Gly Leu
```

-continued

```
           275                 280                 285
```

<210> SEQ ID NO 93
<211> LENGTH: 54
<212> TYPE: DNA
<213> ORGANISM: Artificial sequence
<220> FEATURE:
<223> OTHER INFORMATION: Primer

<400> SEQUENCE: 93
ttatttcttt tcaagtcgaa gttmagatts ccgaatccag ttctctatgg aacg          54

<210> SEQ ID NO 94
<211> LENGTH: 64
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (18)..(18)
<223> OTHER INFORMATION: n in position 18 denotes a,g,c,or t
<220> FEATURE:
<221> NAME/KEY: misc_feature
<222> LOCATION: (19)..(19)
<223> OTHER INFORMATION: n in position 19 denotes a,g,c,or t

<400> SEQUENCE: 94
catttatttc tttcaasnng aasttmagat tsgctatcca gttctttatg gaacgagwgc    60
cacg                                                                64

<210> SEQ ID NO 95
<211> LENGTH: 30
<212> TYPE: DNA
<213> ORGANISM: Artificial sequence
<220> FEATURE:
<223> OTHER INFORMATION: Primer

<400> SEQUENCE: 95
gaatgacttg gttgagtact caccagtcac                                    30

<210> SEQ ID NO 96
<211> LENGTH: 18
<212> TYPE: DNA
<213> ORGANISM: Artificial sequence
<220> FEATURE:
<223> OTHER INFORMATION: Primer

<400> SEQUENCE: 96
gcacgtaatg tttgtacc                                                 18

<210> SEQ ID NO 97
<211> LENGTH: 18
<212> TYPE: DNA
<213> ORGANISM: Artificial sequence
<220> FEATURE:
<223> OTHER INFORMATION: Primer

<400> SEQUENCE: 97
cggtacccgg ggatccac                                                 18

<210> SEQ ID NO 98
<211> LENGTH: 30
<212> TYPE: DNA
<213> ORGANISM: Artificial sequence
<220> FEATURE:
<223> OTHER INFORMATION: Primer

```
<400> SEQUENCE: 98
gagctcgagg aattcttaca aaccttcaac                              30

<210> SEQ ID NO 99
<211> LENGTH: 47
<212> TYPE: DNA
<213> ORGANISM: Artificial sequence
<220> FEATURE:
<223> OTHER INFORMATION: Primer

<400> SEQUENCE: 99
ttaattaagg tacctgaatt taaatggtga agagatagat atccaag            47

<210> SEQ ID NO 100
<211> LENGTH: 51
<212> TYPE: DNA
<213> ORGANISM: Artificial sequence
<220> FEATURE:
<223> OTHER INFORMATION: Primer

<400> SEQUENCE: 100
tcaccattta aattcaggta ccttaattaa attccttgtt ggaagcgtcg a       51

<210> SEQ ID NO 101
<211> LENGTH: 42
<212> TYPE: DNA
<213> ORGANISM: Artificial sequence
<220> FEATURE:
<223> OTHER INFORMATION: Primer

<400> SEQUENCE: 101
tggtatgcat aagcttgaat tcaggtaaac aagatataat tt                 42

<210> SEQ ID NO 102
<211> LENGTH: 32
<212> TYPE: DNA
<213> ORGANISM: Artificial sequence
<220> FEATURE:
<223> OTHER INFORMATION: Primer

<400> SEQUENCE: 102
cccatttaaa tatgaggagc tcccttgtgc tg                            32

<210> SEQ ID NO 103
<211> LENGTH: 32
<212> TYPE: DNA
<213> ORGANISM: Artificial sequence
<220> FEATURE:
<223> OTHER INFORMATION: Primer

<400> SEQUENCE: 103
cccttaatta actaaagaca tgtcccaatt aa                            32

<210> SEQ ID NO 104
<211> LENGTH: 7
<212> TYPE: PRT
<213> ORGANISM: Artificial sequence
<220> FEATURE:
<223> OTHER INFORMATION: Peptide addition

<400> SEQUENCE: 104

Ser Ser Lys Gln Asp Tyr Arg
1               5
```

<210> SEQ ID NO 105
<211> LENGTH: 42
<212> TYPE: DNA
<213> ORGANISM: Artificial sequence
<220> FEATURE:
<223> OTHER INFORMATION: Primer

<400> SEQUENCE: 105
cttggctagc cctatacgta gatcatccac acaagattat cg                              42

<210> SEQ ID NO 106
<211> LENGTH: 32
<212> TYPE: DNA
<213> ORGANISM: Artificial Sequence
<220> FEATURE:
<223> OTHER INFORMATION: Primer

<400> SEQUENCE: 106
cttggctagc tccacacaag attatcgtat tg                                         32

<210> SEQ ID NO 107
<211> LENGTH: 32
<212> TYPE: DNA
<213> ORGANISM: Artificial sequence
<220> FEATURE:
<223> OTHER INFORMATION: Primer

<400> SEQUENCE: 107
gccctctaga ctataaacag agaccagtgt tc                                         32

<210> SEQ ID NO 108
<211> LENGTH: 83
<212> TYPE: DNA
<213> ORGANISM: Artificial sequence
<220> FEATURE:
<223> OTHER INFORMATION: Primer

<400> SEQUENCE: 108 gtagttttc gtggtacaag stcaatwcgs aackssatwg ckgacatwgt ktttgtkccs            60
gtsaattatc cacctgttaa tgg                                                   83

<210> SEQ ID NO 109
<211> LENGTH: 17
<212> TYPE: DNA
<213> ORGANISM: Artificial sequence
<220> FEATURE:
<223> OTHER INFORMATION: Primer

<400> SEQUENCE: 109
agaacagctg ttgcacc                                                          17

<210> SEQ ID NO 110
<211> LENGTH: 16
<212> TYPE: DNA
<213> ORGANISM: Artificial sequence
<220> FEATURE:
<223> OTHER INFORMATION: Primer

<400> SEQUENCE: 110
ccggggatcc accatg                                                           16

<210> SEQ ID NO 111
<211> LENGTH: 20
<212> TYPE: DNA
<213> ORGANISM: Artificial sequence
<220> FEATURE:

-continued

<223> OTHER INFORMATION: Primer

<400> SEQUENCE: 111
gccctctaga ctataaacag                                         20

<210> SEQ ID NO 112
<211> LENGTH: 17
<212> TYPE: DNA
<213> ORGANISM: Artificial sequence
<220> FEATURE:
<223> OTHER INFORMATION: Primer

<400> SEQUENCE: 112
ctgcagaact gtcattc                                            17

<210> SEQ ID NO 113
<211> LENGTH: 16
<212> TYPE: DNA
<213> ORGANISM: Artificial sequence
<220> FEATURE:
<223> OTHER INFORMATION: Primer

<400> SEQUENCE: 113
ttgagcttgt accacg                                             16

<210> SEQ ID NO 114
<211> LENGTH: 36
<212> TYPE: DNA
<213> ORGANISM: Artificial sequence
<220> FEATURE:
<223> OTHER INFORMATION: Primer

<400> SEQUENCE: 114
ccggggatcc accatgagat tccttctat ttttac                        36

<210> SEQ ID NO 115
<211> LENGTH: 31
<212> TYPE: DNA
<213> ORGANISM: Artificial sequence
<220> FEATURE:
<223> OTHER INFORMATION: Primer

<400> SEQUENCE: 115
tggagctagc tcttttatcc aaagaaacac c                            31

<210> SEQ ID NO 116
<211> LENGTH: 85
<212> TYPE: DNA
<213> ORGANISM: Artificial sequence
<220> FEATURE:
<223> OTHER INFORMATION: Primer

<400> SEQUENCE: 116
cagccaatgc atactgccaa cttaggcggt tgaagaagca agaacatgat ttgtcggata   60
agagggcatc caatttgcaa attac                                   85

<210> SEQ ID NO 117
<211> LENGTH: 1115
<212> TYPE: DNA
<213> ORGANISM: Artificial sequence
<220> FEATURE:
<223> OTHER INFORMATION: Primer

<400> SEQUENCE: 117
aaaggcattc tcattttgta gtcttattgc tagcagtatt catctgcatg tgctctgtat   60

```
cgggtgtgcc actgcaaatt gatccacgcg atgacaagag ctatgttcct gaacaatatc    120
ctttgaaggt gaatggtcct ttgccagaag gtgtaagcgt gatccaaggc tattgtgaaa    180
actgtaccat gtatcctgaa aaaatagtg tatcggcatt ctcgtcatca tccacacaag    240
attatcgtat tgcaagcgag gcagagatta aggcacacac atttacaca gcattgtcag    300 ccaatgcata ctgcagaact gtcattcctg gtggtcgatg gagctgtccc cactgtggtg    360
ttgcatccaa tttgcaaatt accaagactt tcagcacctt aatcactgat actaatgtct    420
tggtggctgt tggcgaaaag gagaagacca tctatgtagt ttttcgtggt acaagctcaa    480
ttcgcaacgc cattgctgac attgtttttg taccagtgaa ttatccacct gttaatggag    540
ccaaagtaca caaaggattt cttgatagct ataacgaagt ccaggataaa cttgttgctg    600
aagtcaaggc acaacttgat cgtcatccag gatacaagat cgtcgtcact ggacattcct    660
tgggaggtgc aacagctgtt ctcagtgcac ttgaccttta tcaccatggc catgccaata    720
tcgaaatcta tactcaaggt cagccacgta taggtactcc agcatttgca aactatgtga    780
taggcaccaa gattccatac caacgtcttg tccatgagcg tgacattgtt cctcaccttc    840
cacctggtgc atttggtttc ttgcatgctg gtgaagagtt ttggatcatg aaagatagct    900
cgttgcgcgt atgtccaaat ggcattgaaa ctgacaactg cagcaactcc attgttccct    960
tcactagtgt cattgaccat ttaagctatc ttgacatgaa cactggtctc tgtttataat   1020
ctttagtatc atccactcct cctctttaat gcaatacttt ttaagataaa tcacaagtat   1080
actttgtaca aaccaaaaa aaaaaaaaaa aaaaa                                1115
```

<210> SEQ ID NO 118
<211> LENGTH: 1020
<212> TYPE: DNA
<213> ORGANISM: Absidia reflexa
<220> FEATURE:
<221> NAME/KEY: CDS
<222> LOCATION: (3)..(878)
<223> OTHER INFORMATION:

<400> SEQUENCE: 118

```
ca cat aca gga att cat tca aga ata gtt caa aca aga aga tta caa      47
   His Thr Gly Ile His Ser Arg Ile Val Gln Thr Arg Arg Leu Gln
   1               5                   10                  15 act atc aat ttc ata cac aat ata aac gac ggt acc cgg gga tcc acc     95
Thr Ile Asn Phe Ile His Asn Ile Asn Asp Gly Thr Arg Gly Ser Thr
             20                  25                  30 atg agg agc tcc ctt gtg ctg ttc ttt gtc tct gcg tgg acg gcc ttg    143
Met Arg Ser Ser Leu Val Leu Phe Phe Val Ser Ala Trp Thr Ala Leu
         35                  40                  45 gct agc tcc aca caa gat tat cgt att gca agc gag gca gag att aag    191
Ala Ser Ser Thr Gln Asp Tyr Arg Ile Ala Ser Glu Ala Glu Ile Lys
     50                  55                  60 gca cac aca ttt tac aca gca ttg tca gcc aat gca tac tgc aga act    239
Ala His Thr Phe Tyr Thr Ala Leu Ser Ala Asn Ala Tyr Cys Arg Thr
 65                  70                  75 gtc att cct ggt ggt cga tgg agc tgt ccc cac tgt ggt gtt gca tcc    287
Val Ile Pro Gly Gly Arg Trp Ser Cys Pro His Cys Gly Val Ala Ser
 80                  85                  90                  95 aat ttg caa att acc aag act ttc agc acc tta atc act gat act aat    335
Asn Leu Gln Ile Thr Lys Thr Phe Ser Thr Leu Ile Thr Asp Thr Asn
             100                 105                 110 gtc ttg gtg gct gtt ggc gaa aag gtt gtt ttt gta cca gtg aat tat    383
Val Leu Val Ala Val Gly Glu Lys Val Val Phe Val Pro Val Asn Tyr
```

```
                  115                 120                 125
cca cct gtt aat gga gcc aaa gta cac aaa gga ttt ctt gat agc tat          431
Pro Pro Val Asn Gly Ala Lys Val His Lys Gly Phe Leu Asp Ser Tyr
        130                 135                 140 aac gaa gtc cag gat aaa ctt gtt gct gaa gtc aag gca caa ctt gat          479
Asn Glu Val Gln Asp Lys Leu Val Ala Glu Val Lys Ala Gln Leu Asp
145                 150                 155 cgt cat cca gga tac aag atc gtc gtc act gga cat tcc ttg gga ggt          527
Arg His Pro Gly Tyr Lys Ile Val Val Thr Gly His Ser Leu Gly Gly
160                 165                 170                 175 gca aca gct gtt ctc agt gca ctt gac ctt tat cac cat ggc cat gcc          575
Ala Thr Ala Val Leu Ser Ala Leu Asp Leu Tyr His His Gly His Ala
                180                 185                 190 aat atc gaa atc tat act caa ggt cag cca cgt ata ggt act cca gca          623
Asn Ile Glu Ile Tyr Thr Gln Gly Gln Pro Arg Ile Gly Thr Pro Ala
                195                 200                 205 ttt gca aac tat gtg att ggc acc aag att cca tac caa cgt ctt gtc          671
Phe Ala Asn Tyr Val Ile Gly Thr Lys Ile Pro Tyr Gln Arg Leu Val
        210                 215                 220 cat gag cgt gac att gtt cct cac ctt cca cct ggt gca ttt ggt ttc          719
His Glu Arg Asp Ile Val Pro His Leu Pro Pro Gly Ala Phe Gly Phe
225                 230                 235 ttg cat gct ggt gaa gag ttt tgg atc atg aaa gat agc tcg ttg cgc          767
Leu His Ala Gly Glu Glu Phe Trp Ile Met Lys Asp Ser Ser Leu Arg
240                 245                 250                 255 gta tgt cca aat ggc att gaa act gac aac tgc agc aac tcc att gtt          815
Val Cys Pro Asn Gly Ile Glu Thr Asp Asn Cys Ser Asn Ser Ile Val
                260                 265                 270 ccc ttc act agt gtc att gac cat tta agc tat ctt gac atg aac act          863
Pro Phe Thr Ser Val Ile Asp His Leu Ser Tyr Leu Asp Met Asn Thr
        275                 280                 285 ggt ctc tgt tta tag tctagagggc cgcatgatgt aattagttat gtcacgctta          918
Gly Leu Cys Leu
        290 cattcacgcc ctccccccac atccgctcta accgaaaagg aaggagttag acaacctgaa        978 gtctaggtcc ctatttattt ttttatagtt atgttagtat ta                          1020

<210> SEQ ID NO 119
<211> LENGTH: 291
<212> TYPE: PRT
<213> ORGANISM: Absidia reflexa

<400> SEQUENCE: 119

His Thr Gly Ile His Ser Arg Ile Val Gln Thr Arg Arg Leu Gln Thr
1               5                   10                  15

Ile Asn Phe Ile His Asn Ile Asn Asp Gly Thr Arg Gly Ser Thr Met
                20                  25                  30

Arg Ser Ser Leu Val Leu Phe Val Ser Ala Trp Thr Ala Leu Ala
        35                  40                  45

Ser Ser Thr Gln Asp Tyr Arg Ile Ala Ser Glu Ala Glu Ile Lys Ala
        50                  55                  60

His Thr Phe Tyr Thr Ala Leu Ser Ala Asn Ala Tyr Cys Arg Thr Val
65                  70                  75                  80

Ile Pro Gly Gly Arg Trp Ser Cys Pro His Cys Gly Val Ala Ser Asn
                85                  90                  95

Leu Gln Ile Thr Lys Thr Phe Ser Thr Leu Ile Thr Asp Thr Asn Val
        100                 105                 110
```

```
Leu Val Ala Val Gly Glu Lys Val Phe Val Pro Val Asn Tyr Pro
        115                 120                 125

Pro Val Asn Gly Ala Lys Val His Lys Gly Phe Leu Asp Ser Tyr Asn
    130                 135                 140

Glu Val Gln Asp Lys Leu Val Ala Glu Val Lys Ala Gln Leu Asp Arg
145                 150                 155                 160

His Pro Gly Tyr Lys Ile Val Val Thr Gly His Ser Leu Gly Gly Ala
                165                 170                 175

Thr Ala Val Leu Ser Ala Leu Asp Leu Tyr His His Gly His Ala Asn
                180                 185                 190

Ile Glu Ile Tyr Thr Gln Gly Gln Pro Arg Ile Gly Thr Pro Ala Phe
            195                 200                 205

Ala Asn Tyr Val Ile Gly Thr Lys Ile Pro Tyr Gln Arg Leu Val His
        210                 215                 220

Glu Arg Asp Ile Val Pro His Leu Pro Pro Gly Ala Phe Gly Phe Leu
225                 230                 235                 240

His Ala Gly Glu Glu Phe Trp Ile Met Lys Asp Ser Ser Leu Arg Val
                245                 250                 255

Cys Pro Asn Gly Ile Glu Thr Asp Asn Cys Ser Asn Ser Ile Val Pro
                260                 265                 270

Phe Thr Ser Val Ile Asp His Leu Ser Tyr Leu Asp Met Asn Thr Gly
            275                 280                 285

Leu Cys Leu
    290

<210> SEQ ID NO 120
<211> LENGTH: 255
<212> TYPE: DNA
<213> ORGANISM: Yeast
<220> FEATURE:
<221> NAME/KEY: CDS
<222> LOCATION: (1)..(255)
<223> OTHER INFORMATION:
<220> FEATURE:
<221> NAME/KEY: sig_peptide
<222> LOCATION: (1)..(255)
<223> OTHER INFORMATION:

<400> SEQUENCE: 120 atg aga ttt cct tct att ttt act gct gtt tta ttc gct gct tcc tcc      48
Met Arg Phe Pro Ser Ile Phe Thr Ala Val Leu Phe Ala Ala Ser Ser
1               5                   10                  15 gct tta gct gct cca gtc aac act acc act gaa gat gaa acg gct caa      96
Ala Leu Ala Ala Pro Val Asn Thr Thr Thr Glu Asp Glu Thr Ala Gln
                20                  25                  30 att cca gct gaa gct gtc atc ggt tac ctt gat tta gaa ggt gat ttc     144
Ile Pro Ala Glu Ala Val Ile Gly Tyr Leu Asp Leu Glu Gly Asp Phe
            35                  40                  45 gat gtt gct gtt ttg cca ttt tcc aac tcc acc aat aac ggt tta ttg     192
Asp Val Ala Val Leu Pro Phe Ser Asn Ser Thr Asn Asn Gly Leu Leu
    50                  55                  60 ttt atc aat act act att gcc tcc att gct gct aaa gaa gaa ggt gtt     240
Phe Ile Asn Thr Thr Ile Ala Ser Ile Ala Ala Lys Glu Glu Gly Val
65                  70                  75                  80 tct ttg gat aaa aga                                                 255
Ser Leu Asp Lys Arg
                85

<210> SEQ ID NO 121
<211> LENGTH: 85
```

-continued

```
<212> TYPE: PRT
<213> ORGANISM: Yeast

<400> SEQUENCE: 121

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg
                85

<210> SEQ ID NO 122
<211> LENGTH: 336
<212> TYPE: PRT
<213> ORGANISM: Absidia
<220> FEATURE:
<221> NAME/KEY: signal
<222> LOCATION: (1)..(85)
<223> OTHER INFORMATION:

<400> SEQUENCE: 122

Met Arg Phe Tyr Ser Val Val Ser Leu Leu Ala Val Ser Ile Cys Thr
1               5                   10                  15

Tyr Gly Val Ser Gly Val Pro Val Gln Ile Gly Pro Arg Asp Lys Ser
            20                  25                  30

Tyr Val Pro Glu Gln Tyr Pro Leu Lys Met Asn Gly Pro Leu Pro Glu
        35                  40                  45

Gly Val Ser Val Ile Gln Gly Tyr Cys Glu Asn Cys Thr Met Tyr Pro
    50                  55                  60

Glu Glu Asn Ser Val Thr Ala Leu Ser Ser Lys Gln Asp Tyr Arg
65                  70                  75                  80

Thr Ala Ser Glu Thr Glu Ile Gln Ala His Thr Phe Tyr Thr Ala Leu
            85                  90                  95

Ser Ala Asn Ala Tyr Cys Arg Asn Val Ile Pro Gly Gly Arg Trp Ser
            100                 105                 110

Cys Pro His Cys Asp Val Thr Ser Asn Leu Lys Ile Thr Lys Thr Phe
        115                 120                 125

Ser Thr Leu Ile Thr Asp Thr Asn Val Ala Val Ala Val Gly Glu Lys
    130                 135                 140

Glu Lys Thr Ile Tyr Ile Val Phe Arg Gly Thr Asn Ser Ile Arg Asn
145                 150                 155                 160

Ala Ile Ala Asp Ile Val Phe Val Pro Val Asp Tyr Pro Pro Val Asp
                165                 170                 175

Gly Ala Lys Val His Lys Gly Phe Leu Asp Ser Tyr Asn Glu Val Gln
            180                 185                 190

Asp Gln Leu Val Ala Glu Val Lys Lys Gln Leu Asp Asn His Pro Gly
        195                 200                 205

Tyr Lys Ile Val Val Ala Gly His Ser Leu Gly Gly Ala Thr Ala Val
    210                 215                 220

Leu Cys Ala Leu Asp Leu Tyr His Gly His His Asn Ile Glu Ile
225                 230                 235                 240
```

```
Tyr Thr Gln Gly Gln Pro Arg Val Gly Thr Pro Ala Phe Ala Lys Tyr
                245                 250                 255

Val Ile Gly Thr Lys Ile Pro Tyr Gln Arg Leu Val Asn Glu Arg Asp
            260                 265                 270

Ile Val Pro His Leu Pro Pro Gly Ala Phe Gly Phe Leu His Ala Gly
            275                 280                 285

Glu Glu Phe Trp Ile Met Lys Asp Ser Ser Leu Arg Val Cys Pro Asn
    290                 295                 300

Gly Ile Glu Thr Asp Asp Cys Ser Asn Ser Ile Val Pro Phe Thr Ser
305                 310                 315                 320

Val Ile Asp His Leu Ser Tyr Leu Asp Met Asn Thr Gly Leu Cys Leu
                325                 330                 335

<210> SEQ ID NO 123
<211> LENGTH: 14
<212> TYPE: PRT
<213> ORGANISM: Artificial sequence
<220> FEATURE:
<223> OTHER INFORMATION: Peptide addition
<220> FEATURE:
<221> NAME/KEY: misc_feature
<222> LOCATION: (1)..(1)
<223> OTHER INFORMATION: Xaa in position 1 denotes any amino acid
<220> FEATURE:
<221> NAME/KEY: misc_feature
<222> LOCATION: (2)..(2)
<223> OTHER INFORMATION: Xaa in position 2 denotes any amino acid
<220> FEATURE:
<221> NAME/KEY: misc_feature
<222> LOCATION: (3)..(3)
<223> OTHER INFORMATION: Xaa in position 3 denotes any amino acid
<220> FEATURE:
<221> NAME/KEY: misc_feature
<222> LOCATION: (4)..(4)
<223> OTHER INFORMATION: Xaa in position 4 denotes any amino acid
<220> FEATURE:
<221> NAME/KEY: misc_feature
<222> LOCATION: (5)..(5)
<223> OTHER INFORMATION: Xaa in position 5 denotes any amino acid
<220> FEATURE:
<221> NAME/KEY: misc_feature
<222> LOCATION: (6)..(6)
<223> OTHER INFORMATION: Xaa in position 6 denotes any amino acid
<220> FEATURE:
<221> NAME/KEY: misc_feature
<222> LOCATION: (7)..(7)
<223> OTHER INFORMATION: Xaa in position 7 denotes any amino acid
<220> FEATURE:
<221> NAME/KEY: misc_feature
<222> LOCATION: (8)..(8)
<223> OTHER INFORMATION: Xaa in position 8 denotes any amino acid
<220> FEATURE:
<221> NAME/KEY: misc_feature
<222> LOCATION: (9)..(9)
<223> OTHER INFORMATION: Xaa in position 9 denotes any amino acid
<220> FEATURE:
<221> NAME/KEY: misc_feature
<222> LOCATION: (10)..(10)
<223> OTHER INFORMATION: Xaa in position 10 denotes any amino acid
<220> FEATURE:
<221> NAME/KEY: misc_feature
<222> LOCATION: (11)..(11)
<223> OTHER INFORMATION: Xaa in position 11 denotes any amino acid
<220> FEATURE:
<221> NAME/KEY: misc_feature
<222> LOCATION: (12)..(12)
<223> OTHER INFORMATION: Xaa in position 12 denotes any amino acid
<220> FEATURE:
<221> NAME/KEY: misc_feature
<222> LOCATION: (13)..(13)
<223> OTHER INFORMATION: Xaa in position 13 denotes any amino acid
<220> FEATURE:
```

```
<221> NAME/KEY: misc_feature
<222> LOCATION: (14)..(14)
<223> OTHER INFORMATION: Xaa in position 14 denotes any amino acid

<400> SEQUENCE: 123

Xaa Xaa Xaa Xaa Xaa Xaa Xaa Xaa Xaa Xaa Xaa Xaa Xaa Xaa
1               5                   10

<210> SEQ ID NO 124
<211> LENGTH: 29
<212> TYPE: DNA
<213> ORGANISM: Artificial Sequence
<220> FEATURE:
<223> OTHER INFORMATION: Primer

<400> SEQUENCE: 124
cgatcgcatc ggctgctgag gtctcgcaa                                        29

<210> SEQ ID NO 125
<211> LENGTH: 31
<212> TYPE: DNA
<213> ORGANISM: Artificial sequence
<220> FEATURE:
<223> OTHER INFORMATION: Primer

<400> SEQUENCE: 125
gatcttcgga gacctcagca gccgatgcga t                                     31

<210> SEQ ID NO 126
<211> LENGTH: 21
<212> TYPE: DNA
<213> ORGANISM: Artificial sequence
<220> FEATURE:
<223> OTHER INFORMATION: Primer

<400> SEQUENCE: 126
agcccgatcc gcccgcgccc g                                                21

<210> SEQ ID NO 127
<211> LENGTH: 21
<212> TYPE: DNA
<213> ORGANISM: Artificial sequence
<220> FEATURE:
<223> OTHER INFORMATION: Primer

<400> SEQUENCE: 127
acggcgatcc gcccgcgcaa g                                                21

<210> SEQ ID NO 128
<211> LENGTH: 21
<212> TYPE: DNA
<213> ORGANISM: Artificial sequence
<220> FEATURE:
<223> OTHER INFORMATION: Primer

<400> SEQUENCE: 128
tcgacgcgcc gtccgcgccc g                                                21

<210> SEQ ID NO 129
<211> LENGTH: 21
<212> TYPE: DNA
<213> ORGANISM: Artificial sequence
<220> FEATURE:
<223> OTHER INFORMATION: Primer

<400> SEQUENCE: 129
```

-continued ggcccgatcc gcccgcgccc g                                              21

<210> SEQ ID NO 130
<211> LENGTH: 15
<212> TYPE: DNA
<213> ORGANISM: Artificial sequence
<220> FEATURE:
<223> OTHER INFORMATION: Primer

<400> SEQUENCE: 130
agcccgatcc gccgg                                                     15

<210> SEQ ID NO 131
<211> LENGTH: 24
<212> TYPE: DNA
<213> ORGANISM: Artificial sequence
<220> FEATURE:
<223> OTHER INFORMATION: Primer

<400> SEQUENCE: 131
cgcccgcgtc ccaggccgcg tccg                                           24

<210> SEQ ID NO 132
<211> LENGTH: 12
<212> TYPE: DNA
<213> ORGANISM: Artificial sequence
<220> FEATURE:
<223> OTHER INFORMATION: Primer

<400> SEQUENCE: 132
tctccgcgcc cg                                                        12

<210> SEQ ID NO 133
<211> LENGTH: 56
<212> TYPE: DNA
<213> ORGANISM: Artificial sequence
<220> FEATURE:
<223> OTHER INFORMATION: Primer

<400> SEQUENCE: 133
accatacccc ggccgctcct agccctccgc ggccgctggg agccatcgag aacggc       56

<210> SEQ ID NO 134
<211> LENGTH: 39
<212> TYPE: DNA
<213> ORGANISM: Artificial sequence
<220> FEATURE:
<223> OTHER INFORMATION: Primer

<400> SEQUENCE: 134
gggacatgtc ttcgacgacc gtagcggctg ggtcgactc                          39

<210> SEQ ID NO 135
<211> LENGTH: 37
<212> TYPE: DNA
<213> ORGANISM: Artificial sequence
<220> FEATURE:
<223> OTHER INFORMATION: Primer

<400> SEQUENCE: 135
gggacatgtc ttcggcggta ggcgcggctg ggtcgac                            37

<210> SEQ ID NO 136
<211> LENGTH: 35
<212> TYPE: PRT
<213> ORGANISM: Humicola insolens

```
<400> SEQUENCE: 136

Ile Glu Gly Ile Asp Ala Thr Gly Gly Asn Asn Arg Pro Asn Ile Pro
1               5                   10                  15

Asp Ile Pro Ala His Leu Trp Tyr Phe Gly Leu Ile Gly Thr Cys Leu
            20                  25                  30

Arg Arg Pro
        35

<210> SEQ ID NO 137
<211> LENGTH: 26
<212> TYPE: DNA
<213> ORGANISM: Artificial sequence
<220> FEATURE:
<223> OTHER INFORMATION: Primer

<400> SEQUENCE: 137
tctagcccag aatactggat caaatc                                           26

<210> SEQ ID NO 138
<211> LENGTH: 35
<212> TYPE: DNA
<213> ORGANISM: Artificial Sequence
<220> FEATURE:
<223> OTHER INFORMATION: Primer

<400> SEQUENCE: 138
ggcggcaata accggccgaa cattccggat atccc                                 35

<210> SEQ ID NO 139
<211> LENGTH: 32
<212> TYPE: DNA
<213> ORGANISM: Artificial Sequence
<220> FEATURE:
<223> OTHER INFORMATION: Primer

<400> SEQUENCE: 139
atatcgtgaa gatatgcggc attgatgcca cc                                    32

<210> SEQ ID NO 140
<211> LENGTH: 32
<212> TYPE: DNA
<213> ORGANISM: Artificial Sequence
<220> FEATURE:
<223> OTHER INFORMATION: Primer

<400> SEQUENCE: 140
cggccttggc tagctgtatt cgtcgagagg tc                                    32

<210> SEQ ID NO 141
<211> LENGTH: 885
<212> TYPE: DNA
<213> ORGANISM: Humicola lanuginosa lipase
<220> FEATURE:
<221> NAME/KEY: CDS
<222> LOCATION: (1)..(882)
<223> OTHER INFORMATION:
<220> FEATURE:
<221> NAME/KEY: mat_peptide
<222> LOCATION: (76)..()
<223> OTHER INFORMATION:
<220> FEATURE:
<221> NAME/KEY: sig_peptide
<222> LOCATION: (1)..(75)
<223> OTHER INFORMATION:

<400> SEQUENCE: 141
```

-continued

| | | |
|---|---|---|
| atg aaa cgc att tgt ggt tcc ctg ctg ttg ctc ggt ttg tcg atc agc<br>Met Lys Arg Ile Cys Gly Ser Leu Leu Leu Leu Gly Leu Ser Ile Ser<br>-25                        -20                      -15                    -10 | 48 |
| gcc gcg ctc gct agc cct ata cgt aga gag gtc tcg cag gat ctg ttt<br>Ala Ala Leu Ala Ser Pro Ile Arg Arg Glu Val Ser Gln Asp Leu Phe<br>                   -5                    -1 1                    5 | 96 |
| aac cag ttc aat ctc ttt gca cag tat tct gca gcc gca tac tgc gga<br>Asn Gln Phe Asn Leu Phe Ala Gln Tyr Ser Ala Ala Ala Tyr Cys Gly<br>             10                    15                    20 | 144 |
| aaa aac aat gat gcc cca gct ggt aca aac att acg tgc acg gga aat<br>Lys Asn Asn Asp Ala Pro Ala Gly Thr Asn Ile Thr Cys Thr Gly Asn<br>25                        30                    35 | 192 |
| gcc tgc ccc gag gta gag aag gcg gat gca acg ttt ctc tac tcg ttt<br>Ala Cys Pro Glu Val Glu Lys Ala Asp Ala Thr Phe Leu Tyr Ser Phe<br>40                        45                    50                    55 | 240 |
| gaa gac tct gga gtg ggc gat gtc acc ggc ttc ctt gct ctc gac aac<br>Glu Asp Ser Gly Val Gly Asp Val Thr Gly Phe Leu Ala Leu Asp Asn<br>             60                    65                    70 | 288 |
| acg aac aaa ttg atc gtc ctc tct ttc cgt ggc tct cgt tcc ata gag<br>Thr Asn Lys Leu Ile Val Leu Ser Phe Arg Gly Ser Arg Ser Ile Glu<br>        75                    80                    85 | 336 |
| aac tgg atc ggg aat ctt aac ttc gac ttg aaa gaa ata aat gac att<br>Asn Trp Ile Gly Asn Leu Asn Phe Asp Leu Lys Glu Ile Asn Asp Ile<br>             90                    95                   100 | 384 |
| tgc tcc ggc tgc agg gga cat gac ggc ttc act tcg tcc tgg agg tct<br>Cys Ser Gly Cys Arg Gly His Asp Gly Phe Thr Ser Ser Trp Arg Ser<br>105                     110                 115 | 432 |
| gta gcc gat acg tta agg cag aag gtg gag gat gct gtg agg gag cat<br>Val Ala Asp Thr Leu Arg Gln Lys Val Glu Asp Ala Val Arg Glu His<br>120                     125                 130                 135 | 480 |
| ccc gac tat cgc gtg gtg ttt acc gga cat agc ttg ggt ggt gca ttg<br>Pro Asp Tyr Arg Val Val Phe Thr Gly His Ser Leu Gly Gly Ala Leu<br>             140                    145                    150 | 528 |
| gca act gtt gcc gga gca gac ctg cgt gga aat ggg tat gat atc gac<br>Ala Thr Val Ala Gly Ala Asp Leu Arg Gly Asn Gly Tyr Asp Ile Asp<br>             155                    160                    165 | 576 |
| gtg ttt tca tat ggc gcc ccc cga gtc gga aac agg gct ttt gca gaa<br>Val Phe Ser Tyr Gly Ala Pro Arg Val Gly Asn Arg Ala Phe Ala Glu<br>     170                    175                 180 | 624 |
| ttc ctg acc gta cag acc ggc gga aca ctc tac cgc att acc cac acc<br>Phe Leu Thr Val Gln Thr Gly Gly Thr Leu Tyr Arg Ile Thr His Thr<br>185                     190                 195 | 672 |
| aat gat att gtc cct aga ctc ccg ccg cgc gaa ttc ggt tac agc cat<br>Asn Asp Ile Val Pro Arg Leu Pro Pro Arg Glu Phe Gly Tyr Ser His<br>200                     205                 210                 215 | 720 |
| tct agc cca gag tac tgg atc aaa tct gga acc ctt gtc ccc gtc acc<br>Ser Ser Pro Glu Tyr Trp Ile Lys Ser Gly Thr Leu Val Pro Val Thr<br>             220                    225                    230 | 768 |
| cga aac gat atc gtg aag ata gaa ggc atc gat gcc acc ggc ggc aat<br>Arg Asn Asp Ile Val Lys Ile Glu Gly Ile Asp Ala Thr Gly Gly Asn<br>             235                    240                    245 | 816 |
| aac cag cct aac att ccg gat atc cct gcg cac cta tgg tac ttc ggg<br>Asn Gln Pro Asn Ile Pro Asp Ile Pro Ala His Leu Trp Tyr Phe Gly<br>     250                    255                 260 | 864 |
| tta att ggg aca tgt ctt tag<br>Leu Ile Gly Thr Cys Leu<br>265 | 885 |

<210> SEQ ID NO 142

```
<211> LENGTH: 294
<212> TYPE: PRT
<213> ORGANISM: Humicola lanuginosa lipase

<400> SEQUENCE: 142

Met Lys Arg Ile Cys Gly Ser Leu Leu Leu Leu Gly Leu Ser Ile Ser
-25                 -20                 -15                 -10

Ala Ala Leu Ala Ser Pro Ile Arg Arg Glu Val Ser Gln Asp Leu Phe
                -5                  -1  1                   5

Asn Gln Phe Asn Leu Phe Ala Gln Tyr Ser Ala Ala Tyr Cys Gly
                10                  15                  20

Lys Asn Asn Asp Ala Pro Ala Gly Thr Asn Ile Thr Cys Thr Gly Asn
 25                 30                  35

Ala Cys Pro Glu Val Glu Lys Ala Asp Ala Thr Phe Leu Tyr Ser Phe
 40                  45                  50                  55

Glu Asp Ser Gly Val Gly Asp Val Thr Gly Phe Leu Ala Leu Asp Asn
                60                  65                  70

Thr Asn Lys Leu Ile Val Leu Ser Phe Arg Gly Ser Arg Ser Ile Glu
             75                  80                  85

Asn Trp Ile Gly Asn Leu Asn Phe Asp Leu Lys Glu Ile Asn Asp Ile
             90                  95                  100

Cys Ser Gly Cys Arg Gly His Asp Gly Phe Thr Ser Ser Trp Arg Ser
105                 110                 115

Val Ala Asp Thr Leu Arg Gln Lys Val Glu Asp Ala Val Arg Glu His
120                 125                 130                 135

Pro Asp Tyr Arg Val Val Phe Thr Gly His Ser Leu Gly Gly Ala Leu
                140                 145                 150

Ala Thr Val Ala Gly Ala Asp Leu Arg Gly Asn Gly Tyr Asp Ile Asp
                155                 160                 165

Val Phe Ser Tyr Gly Ala Pro Arg Val Gly Asn Arg Ala Phe Ala Glu
                170                 175                 180

Phe Leu Thr Val Gln Thr Gly Gly Thr Leu Tyr Arg Ile Thr His Thr
185                 190                 195

Asn Asp Ile Val Pro Arg Leu Pro Pro Arg Glu Phe Gly Tyr Ser His
200                 205                 210                 215

Ser Ser Pro Glu Tyr Trp Ile Lys Ser Gly Thr Leu Val Pro Val Thr
                220                 225                 230

Arg Asn Asp Ile Val Lys Ile Glu Gly Ile Asp Ala Thr Gly Gly Asn
                235                 240                 245

Asn Gln Pro Asn Ile Pro Asp Ile Pro Ala His Leu Trp Tyr Phe Gly
                250                 255                 260

Leu Ile Gly Thr Cys Leu
                265

<210> SEQ ID NO 143
<211> LENGTH: 294
<212> TYPE: PRT
<213> ORGANISM: Humicola lanuginose lipase

<400> SEQUENCE: 143

Met Lys Arg Ile Cys Gly Ser Leu Leu Leu Leu Gly Leu Ser Ile Ser
1               5                   10                  15

Ala Ala Leu Ala Ser Pro Ile Arg Arg Glu Val Ser Gln Asp Leu Phe
                20                  25                  30

Asn Gln Phe Asn Leu Phe Ala Gln Tyr Ser Ala Ala Tyr Cys Gly
                35                  40                  45
```

```
Lys Asn Asn Asp Ala Pro Ala Gly Thr Asn Ile Thr Cys Thr Gly Asn
    50                  55                  60

Ala Cys Pro Glu Val Glu Lys Ala Asp Ala Thr Phe Leu Tyr Ser Phe
 65                  70                  75                  80

Glu Asp Ser Gly Val Gly Asp Val Thr Gly Phe Leu Ala Leu Asp Asn
                85                  90                  95

Thr Asn Lys Leu Ile Val Leu Ser Phe Arg Gly Ser Arg Ser Ile Glu
            100                 105                 110

Asn Trp Ile Gly Asn Leu Asn Phe Asp Leu Lys Glu Ile Asn Asp Ile
            115                 120                 125

Cys Ser Gly Cys Arg Gly His Asp Gly Phe Thr Ser Ser Trp Arg Ser
    130                 135                 140

Val Ala Asp Thr Leu Arg Gln Lys Val Glu Asp Ala Val Arg Glu His
145                 150                 155                 160

Pro Asp Tyr Arg Val Val Phe Thr Gly His Ser Leu Gly Gly Ala Leu
                165                 170                 175

Ala Thr Val Ala Gly Ala Asp Leu Arg Gly Asn Gly Tyr Asp Ile Asp
            180                 185                 190

Val Phe Ser Tyr Gly Ala Pro Arg Val Gly Asn Arg Ala Phe Ala Glu
            195                 200                 205

Phe Leu Thr Val Gln Thr Gly Gly Thr Leu Tyr Arg Ile Thr His Thr
210                 215                 220

Asn Asp Ile Val Pro Arg Leu Pro Pro Arg Glu Phe Gly Tyr Ser His
225                 230                 235                 240

Ser Ser Pro Glu Tyr Trp Ile Lys Ser Gly Thr Leu Val Pro Val Thr
                245                 250                 255

Arg Asn Asp Ile Val Lys Ile Glu Gly Ile Asp Ala Thr Gly Gly Asn
            260                 265                 270

Asn Gln Pro Asn Ile Pro Asp Ile Pro Ala His Leu Trp Tyr Phe Gly
            275                 280                 285

Leu Ile Gly Thr Cys Leu
            290
```

<210> SEQ ID NO 144
<211> LENGTH: 870
<212> TYPE: DNA
<213> ORGANISM: Humicola lanuginosa lipase
<220> FEATURE:
<221> NAME/KEY: CDS
<222> LOCATION: (1)..(867)
<223> OTHER INFORMATION:
<220> FEATURE:
<221> NAME/KEY: mat_peptide
<222> LOCATION: (1)..()
<223> OTHER INFORMATION:
<220> FEATURE:
<221> NAME/KEY: sig_peptide
<222> LOCATION: (1)..(60)
<223> OTHER INFORMATION:

<400> SEQUENCE: 144

```
atg aaa cgc att tgt ggt tcc ctg ctg ttg ctc ggt ttg tcg atc agc      48
Met Lys Arg Ile Cys Gly Ser Leu Leu Leu Leu Gly Leu Ser Ile Ser
 1               5                  10                  15 gcc gcg ctc gcc gag gtc tcg cag gat ctg ttt aac cag ttc aat ctc      96
Ala Ala Leu Ala Glu Val Ser Gln Asp Leu Phe Asn Gln Phe Asn Leu
                20                  25                  30 ttt gca cag tat tct gca gcc gca tac tgc gga aaa aac aat gat gcc    144
Phe Ala Gln Tyr Ser Ala Ala Ala Tyr Cys Gly Lys Asn Asn Asp Ala
```

-continued

|  |  |  |  |
|---|---|---|---|
| cca gct ggt aca aac att acg tgc acg gga aat gcc tgc ccc gag gta | 192 |
| Pro Ala Gly Thr Asn Ile Thr Cys Thr Gly Asn Ala Cys Pro Glu Val |  |
| 50 55 60 |  |
| gag aag gcg gat gca acg ttt ctc tac tcg ttt gaa gac tct gga gtg | 240 |
| Glu Lys Ala Asp Ala Thr Phe Leu Tyr Ser Phe Glu Asp Ser Gly Val |  |
| 65 70 75 80 |  |
| ggc gat gtc acc ggc ttc ctt gct ctc gac aac acg aac aaa ttg atc | 288 |
| Gly Asp Val Thr Gly Phe Leu Ala Leu Asp Asn Thr Asn Lys Leu Ile |  |
| 85 90 95 |  |
| gtc ctc tct ttc cgt ggc tct cgt tcc ata gag aac tgg atc ggg aat | 336 |
| Val Leu Ser Phe Arg Gly Ser Arg Ser Ile Glu Asn Trp Ile Gly Asn |  |
| 100 105 110 |  |
| ctt aac ttc gac ttg aaa gaa ata aat gac att tgc tcc ggc tgc agg | 384 |
| Leu Asn Phe Asp Leu Lys Glu Ile Asn Asp Ile Cys Ser Gly Cys Arg |  |
| 115 120 125 |  |
| gga cat gac ggc ttc act tcg tcc tgg agg tct gta gcc gat acg tta | 432 |
| Gly His Asp Gly Phe Thr Ser Ser Trp Arg Ser Val Ala Asp Thr Leu |  |
| 130 135 140 |  |
| agg cag aag gtg gag gat gct gtg agg gag cat ccc gac tat cgc gtg | 480 |
| Arg Gln Lys Val Glu Asp Ala Val Arg Glu His Pro Asp Tyr Arg Val |  |
| 145 150 155 160 |  |
| gtg ttt acc gga cat agc ttg ggt ggt gca ttg gca act gtt gcc gga | 528 |
| Val Phe Thr Gly His Ser Leu Gly Gly Ala Leu Ala Thr Val Ala Gly |  |
| 165 170 175 |  |
| gca gac ctg cgt gga aat ggg tat gat atc gac gtg ttt tca tat ggc | 576 |
| Ala Asp Leu Arg Gly Asn Gly Tyr Asp Ile Asp Val Phe Ser Tyr Gly |  |
| 180 185 190 |  |
| gcc ccc cga gtc gga aac agg gct ttt gca gaa ttc ctg acc gta cag | 624 |
| Ala Pro Arg Val Gly Asn Arg Ala Phe Ala Glu Phe Leu Thr Val Gln |  |
| 195 200 205 |  |
| acc ggc gga aca ctc tac cgc att acc cac acc aat gat att gtc cct | 672 |
| Thr Gly Gly Thr Leu Tyr Arg Ile Thr His Thr Asn Asp Ile Val Pro |  |
| 210 215 220 |  |
| aga ctc ccg ccg cgc gaa ttc ggt tac agc cat tct agc cca gag tac | 720 |
| Arg Leu Pro Pro Arg Glu Phe Gly Tyr Ser His Ser Ser Pro Glu Tyr |  |
| 225 230 235 240 |  |
| tgg atc aaa tct gga acc ctt gtc ccc gtc acc cga aac gat atc gtg | 768 |
| Trp Ile Lys Ser Gly Thr Leu Val Pro Val Thr Arg Asn Asp Ile Val |  |
| 245 250 255 |  |
| aag ata gaa ggc atc gat gcc acc ggc ggc aat aac cag cct aac att | 816 |
| Lys Ile Glu Gly Ile Asp Ala Thr Gly Gly Asn Asn Gln Pro Asn Ile |  |
| 260 265 270 |  |
| ccg gat atc cct gcg cac cta tgg tac ttc ggg tta att ggg aca tgt | 864 |
| Pro Asp Ile Pro Ala His Leu Trp Tyr Phe Gly Leu Ile Gly Thr Cys |  |
| 275 280 285 |  |
| ctt tag | 870 |
| Leu |  |

<210> SEQ ID NO 145
<211> LENGTH: 289
<212> TYPE: PRT
<213> ORGANISM: Humicola lanuginosa lipase

<400> SEQUENCE: 145

Met Lys Arg Ile Cys Gly Ser Leu Leu Leu Gly Leu Ser Ile Ser
1               5                  10                  15

Ala Ala Leu Ala Glu Val Ser Gln Asp Leu Phe Asn Gln Phe Asn Leu
            20                  25                  30

```
Phe Ala Gln Tyr Ser Ala Ala Tyr Cys Gly Lys Asn Asn Asp Ala
            35                  40                  45

Pro Ala Gly Thr Asn Ile Thr Cys Thr Gly Asn Ala Cys Pro Glu Val
50                      55                  60

Glu Lys Ala Asp Ala Thr Phe Leu Tyr Ser Phe Glu Asp Ser Gly Val
65                  70                  75                  80

Gly Asp Val Thr Gly Phe Leu Ala Leu Asp Asn Thr Asn Lys Leu Ile
                85                  90                  95

Val Leu Ser Phe Arg Gly Ser Arg Ser Ile Glu Asn Trp Ile Gly Asn
            100                 105                 110

Leu Asn Phe Asp Leu Lys Glu Ile Asn Asp Ile Cys Ser Gly Cys Arg
            115                 120                 125

Gly His Asp Gly Phe Thr Ser Ser Trp Arg Ser Val Ala Asp Thr Leu
            130                 135                 140

Arg Gln Lys Val Glu Asp Ala Val Arg Glu His Pro Asp Tyr Arg Val
145                 150                 155                 160

Val Phe Thr Gly His Ser Leu Gly Gly Ala Leu Ala Thr Val Ala Gly
                165                 170                 175

Ala Asp Leu Arg Gly Asn Gly Tyr Asp Ile Asp Val Phe Ser Tyr Gly
            180                 185                 190

Ala Pro Arg Val Gly Asn Arg Ala Phe Ala Glu Phe Leu Thr Val Gln
            195                 200                 205

Thr Gly Gly Thr Leu Tyr Arg Ile Thr His Thr Asn Asp Ile Val Pro
210                 215                 220

Arg Leu Pro Pro Arg Glu Phe Gly Tyr Ser His Ser Ser Pro Glu Tyr
225                 230                 235                 240

Trp Ile Lys Ser Gly Thr Leu Val Pro Val Thr Arg Asn Asp Ile Val
                245                 250                 255

Lys Ile Glu Gly Ile Asp Ala Thr Gly Gly Asn Asn Gln Pro Asn Ile
            260                 265                 270

Pro Asp Ile Pro Ala His Leu Trp Tyr Phe Gly Leu Ile Gly Thr Cys
            275                 280                 285

Leu

<210> SEQ ID NO 146
<211> LENGTH: 7
<212> TYPE: PRT
<213> ORGANISM: Artificial Sequence
<220> FEATURE:
<223> OTHER INFORMATION: Peptide addition

<400> SEQUENCE: 146

Ser Arg Lys Arg Lys Arg Lys
1               5

<210> SEQ ID NO 147
<211> LENGTH: 9
<212> TYPE: PRT
<213> ORGANISM: Artificial Sequence
<220> FEATURE:
<223> OTHER INFORMATION: Peptide addition

<400> SEQUENCE: 147

Ser Pro Arg Ile Lys Pro Arg Ile Lys
1               5

<210> SEQ ID NO 148
<211> LENGTH: 7
```

```
<212> TYPE: PRT
<213> ORGANISM: Artificial Sequence
<220> FEATURE:
<223> OTHER INFORMATION: Peptide addition

<400> SEQUENCE: 148

Ser Pro Pro Arg Arg Pro Arg
1               5

<210> SEQ ID NO 149
<211> LENGTH: 8
<212> TYPE: PRT
<213> ORGANISM: Artificial Sequence
<220> FEATURE:
<223> OTHER INFORMATION: Peptide addition

<400> SEQUENCE: 149

Ser Pro Pro Cys Gly Arg Arg Pro
1               5

<210> SEQ ID NO 150
<211> LENGTH: 7
<212> TYPE: PRT
<213> ORGANISM: Artificial Sequence
<220> FEATURE:
<223> OTHER INFORMATION: Peptide addition

<400> SEQUENCE: 150

Ser Pro Cys Arg Pro Arg Pro
1               5

<210> SEQ ID NO 151
<211> LENGTH: 8
<212> TYPE: PRT
<213> ORGANISM: Artificial Sequence
<220> FEATURE:
<223> OTHER INFORMATION: Peptide addition

<400> SEQUENCE: 151

Ser Pro Pro Cys Arg Arg Arg Pro
1               5

<210> SEQ ID NO 152
<211> LENGTH: 7
<212> TYPE: PRT
<213> ORGANISM: Artificial Sequence
<220> FEATURE:
<223> OTHER INFORMATION: Synthetic

<400> SEQUENCE: 152

Ser Pro Pro Arg Pro Arg Pro
1               5

<210> SEQ ID NO 153
<211> LENGTH: 7
<212> TYPE: PRT
<213> ORGANISM: Artificial Sequence
<220> FEATURE:
<223> OTHER INFORMATION: Synthetic

<400> SEQUENCE: 153

Ser His Ser Arg His Asn Ala
1               5

<210> SEQ ID NO 154
<211> LENGTH: 7
<212> TYPE: PRT
```

```
<213> ORGANISM: Artificial sequence
<220> FEATURE:
<223> OTHER INFORMATION: Synthetic

<400> SEQUENCE: 154

Ser Ala Leu Arg Arg Arg Pro
1               5

<210> SEQ ID NO 155
<211> LENGTH: 7
<212> TYPE: PRT
<213> ORGANISM: Artificial Sequence
<220> FEATURE:
<223> OTHER INFORMATION: Synthetic

<400> SEQUENCE: 155

Ser Pro Ile Pro Pro Gly Pro
1               5

<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

Ser Ala Leu Arg Arg Pro
1               5

<210> SEQ ID NO 157
<211> LENGTH: 10
<212> TYPE: PRT
<213> ORGANISM: Artificial Sequence
<220> FEATURE:
<223> OTHER INFORMATION: Synthetic

<400> SEQUENCE: 157

Ser Pro Ile Arg Leu Ser Pro Ile Arg Arg
1               5                   10

<210> SEQ ID NO 158
<211> LENGTH: 6
<212> TYPE: PRT
<213> ORGANISM: Artificial Sequence
<220> FEATURE:
<223> OTHER INFORMATION: Synthetic

<400> SEQUENCE: 158

Pro Arg Pro Val Ser Gln
1               5

<210> SEQ ID NO 159
<211> LENGTH: 6
<212> TYPE: PRT
<213> ORGANISM: Artificial Sequence
<220> FEATURE:
<223> OTHER INFORMATION: Synthetic

<400> SEQUENCE: 159

Arg Pro Val Ser Gln Asp
1               5

<210> SEQ ID NO 160
<211> LENGTH: 6
<212> TYPE: PRT
<213> ORGANISM: Artificial Sequence
```

```
<220> FEATURE:
<223> OTHER INFORMATION: Synthetic

<400> SEQUENCE: 160

Pro Val Ser Gln Asp Leu
1               5

<210> SEQ ID NO 161
<211> LENGTH: 11
<212> TYPE: PRT
<213> ORGANISM: Artificial sequence
<220> FEATURE:
<223> OTHER INFORMATION: Synthetic

<400> SEQUENCE: 161

Ser Pro Ile Arg Pro Arg Pro Val Ser Gln Asp
1               5                   10

<210> SEQ ID NO 162
<211> LENGTH: 7
<212> TYPE: PRT
<213> ORGANISM: Artificial Sequence
<220> FEATURE:
<223> OTHER INFORMATION: Synthetic

<400> SEQUENCE: 162

Arg Pro Val Ser Gln Asp Leu
1               5
```